United States Patent
Cheruvallath et al.

(10) Patent No.: US 9,434,743 B2
(45) Date of Patent: Sep. 6, 2016

(54) INDAZOLE DERIVATIVES

(71) Applicant: TAKEDA PHARMACEUTICAL COMPANY LIMITED, San Diego, CA (US)

(72) Inventors: Zacharia Cheruvallath, San Diego, CA (US); Philip Erickson, San Diego, CA (US); Jun Feng, San Diego, CA (US); Mallareddy Komandla, San Diego, CA (US); John David Lawson, San Diego, CA (US); Christopher McBride, San Diego, CA (US); Joanne Miura, San Diego, CA (US); Sean Murphy, San Diego, CA (US); Mingnam Tang, San Diego, CA (US); Huong-Thu Ton-Nu, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 70 days.

(21) Appl. No.: 14/378,305

(22) PCT Filed: Feb. 28, 2013

(86) PCT No.: PCT/US2013/028386
§ 371 (c)(1),
(2) Date: Aug. 12, 2014

(87) PCT Pub. No.: WO2013/130855
PCT Pub. Date: Sep. 6, 2013

(65) Prior Publication Data
US 2015/0005232 A1    Jan. 1, 2015

Related U.S. Application Data

(60) Provisional application No. 61/606,243, filed on Mar. 2, 2012.

(51) Int. Cl.
| | | |
|---|---|---|
| C07D 498/04 | (2006.01) |
| C07D 401/04 | (2006.01) |
| C07D 471/04 | (2006.01) |
| C07D 403/04 | (2006.01) |
| C07D 405/04 | (2006.01) |
| C07D 417/04 | (2006.01) |
| C07D 487/04 | (2006.01) |
| C07D 401/14 | (2006.01) |
| C07D 413/14 | (2006.01) |
| C07D 231/56 | (2006.01) |
| C07D 403/10 | (2006.01) |
| C07D 407/14 | (2006.01) |
| C07D 413/04 | (2006.01) |
| C07D 413/10 | (2006.01) |
| A61K 31/416 | (2006.01) |
| A61K 31/4245 | (2006.01) |
| A61K 31/427 | (2006.01) |
| A61K 31/437 | (2006.01) |
| A61K 31/4439 | (2006.01) |
| A61K 31/506 | (2006.01) |
| A61K 31/53 | (2006.01) |
| A61K 31/5377 | (2006.01) |
| A61K 31/5383 | (2006.01) |
| A61K 45/06 | (2006.01) |

(52) U.S. Cl.
CPC .......... *C07D 498/04* (2013.01); *A61K 31/416* (2013.01); *A61K 31/427* (2013.01); *A61K 31/4245* (2013.01); *A61K 31/437* (2013.01); *A61K 31/4439* (2013.01); *A61K 31/506* (2013.01); *A61K 31/53* (2013.01); *A61K 31/5377* (2013.01); *A61K 31/5383* (2013.01); *A61K 45/06* (2013.01); *C07D 231/56* (2013.01); *C07D 401/04* (2013.01); *C07D 401/14* (2013.01); *C07D 403/04* (2013.01); *C07D 403/10* (2013.01); *C07D 405/04* (2013.01); *C07D 407/14* (2013.01); *C07D 413/04* (2013.01); *C07D 413/10* (2013.01); *C07D 413/14* (2013.01); *C07D 417/04* (2013.01); *C07D 471/04* (2013.01); *C07D 487/04* (2013.01)

(58) Field of Classification Search
None
See application file for complete search history.

(56) References Cited

U.S. PATENT DOCUMENTS

| 8,299,243 B2 * | 10/2012 | Dai | ...... C07D 403/12 544/115 |
|---|---|---|---|
| 2012/0004162 A1 | 1/2012 | Vath et al. | |
| 2012/0034233 A1 | 2/2012 | Hughes et al. | |

FOREIGN PATENT DOCUMENTS

| WO | WO/2010/065883 | 6/2010 |
| WO | WO/2011/150338 | 12/2011 |

OTHER PUBLICATIONS

ARFI et al PNAS 1995 pp. 7714-7718.
(Continued)

*Primary Examiner* — Kamal Saeed
(74) *Attorney, Agent, or Firm* — Matthew J. Russo

(57) ABSTRACT

Disclosed are compounds of Formula 1,

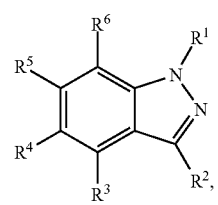

and pharmaceutically acceptable salts thereof, wherein $R^1$, $R^2$, $R^3$, $R^4$, $R^5$, and $R^6$ are defined in the specification. This disclosure also relates to materials and methods for preparing compounds of Formula 1, to pharmaceutical compositions which contain them, and to their use for treating obesity and related diseases, disorders, and conditions associated with MetAP2.

18 Claims, No Drawings

(56) References Cited

OTHER PUBLICATIONS

Bhargava et al Clin. Cancer Res. 1999 vol. 5 pp. 1989-1995.
Brakenhielm et al.—Circ. Res. 2004.
Griffith—Chemistry and Biology—1997, vol. 4, No. 6.
Herbst et al , J. of Clin. Oncology, 2002, vol. 20, No. 22, pp. 4440-4447.
Kim et al. J. of Mol. Endocrinology, 2007.
Kudelka et al, Clin. Cancer Res. 1997, vol. 3, pp. 1501-1505.
Kudelka et al, N. Engl. J. of. Med, 1998, vol. 338, pp. 991-992.
Leszczyniecka et al, Oncogene, 2006, vol. 25, pp. 3471-3478.
Lijnen, "Fumagillin Reduces Adipose", Obesity, 2010.
Logothetis et al, Clin Cancer Res, 2001, vol. 7, pp. 1198-1203.
The Practical Guide, Identification, evaluation, and Treatment of Overweight and Obesity in Adults, U.S. Department of Health and Human Services, NIH Publication No. 00-4084.
Rupnick et al, PNAS, 2002, vol. 99, pp. 10730-10735.
Scroyen et al., Biochimica et Biophysica Acta, vol. 1800, 2010, pp. 425-429.
Selvakumar et al., Biochimica et Biophysica Acta, vol. 765, 2006, pp. 148-154.
Stadler et al., J. Clin. Oncology, 1999, vol. 17, No. 8, pp. 2541-2545.
International Search Report and Written Opinion, International Patent Application No. PCT/US2013/028386 dated Apr. 15, 2013.

\* cited by examiner

INDAZOLE DERIVATIVES

CROSS-REFERENCE TO RELATED APPLICATIONS

This application is the U.S. National Stage entry under 35 U.S.C. §371(c) of International Application PCT/US2013/028386, filed Feb. 28, 2013, which claims the benefit of U.S. Provisional Application No. 61/606,243, filed Mar. 2, 2012, which is herein incorporated by reference.

FIELD OF THE INVENTION

This invention relates to substituted indazoles which are inhibitors of methionine aminopeptidase 2 (MetAP2), to pharmaceutical compositions which contain them, and to their use to treat diseases, disorders, and conditions associated with MetAP2, including obesity.

BACKGROUND OF THE INVENTION

Methionine aminopeptidases are enzymes that bind to cobalt and manganese ions. The metalloenzymes are widely found in prokaryotic and eukaryotic cells, and exist in three forms, MetAP1A, MetAP1D, and MetAP2. See M. Leszczyniecka et al., *Oncogene* 25:3471-78 (2006). They are responsible for the removal of the N-terminal methionine residue from nascent proteins, an important step in protein maturation and likely essential for proper functional regulation, intracellular targeting, and protein turnover. See S. M. Arfin et al., *Proc. Natl. Acad. Sci. USA* 92:7714-18 (1995). Known (irreversible) inhibitors of MetAP2 include the natural product fumagillin and its more potent semi-synthetic analog TNP-470 (AGM-1470). See D. Ingber et al., *Nature* 348:555-57 (1990); see also E. C. Griffith et al., *Chemistry & Biology* 4(6):461-471 (1997). Both compounds inhibit angiogenesis, and TNP-470 has been evaluated in numerous clinical trials as a treatment for cancer. See, e.g., R. S. Herbst et al., *J. Clin. Oncology* 20(22):4440-47 (2002) (non-small cell lung cancer); C. J. Logothetis et al., *Clin. Cancer Res.* 7:1198-1203 (2001) (progressive androgen-dependent prostate cancer); W. M. Stadler et al., *J. Clin. Oncology* 17(8):2541-45 (1999) (metastatic renal carcinoma); A. P. Kudelka et al, *N. Engl. J. Med.* 338:991-92 (1998) (metastatic cervical cancer); A. P. Kudelka et al., *Clin. Cancer Res.* 3:1501-05 (1997) (squamous cell cancer of the cervix); and P. Bhargava et al., *Clin. Cancer Res.* 5:1989-95 (1999) (sarcoma, colorectal cancer, and melanoma).

Numerous studies also suggest MetAP2 inhibitors may be used to treat obesity. For example, TNP-470 was tested in various mice obesity models and showed dose-dependent, reversible weight reduction and adipose tissue loss. See M. A. Rupnick et al., *Proc. Natl. Acad. Sci. USA* 99(16):10730-35 (2002). TNP-470 has also been shown to prevent diet-induced obesity in mice. See E. Bråkenhielm, et al., *Circulation Research* 94(12):1579-88 (2004). Treatment with fumagillin has been shown to impair diet-induced obesity in mice, as evidenced by adipocyte hypotrophy, but without significantly affecting adipose tissue angiogenesis. See H. R. Lijnen et al., *Obesity* 18(12):2241-46 (2010). Furthermore, a MetAP2 inhibitor, CKD-732, was found to decrease food intake, body weight, fat mass, and the size of adipocytes in genetically and diet-induced obese mice. See Y. M. Kim, et al., *J. Mol. Endocrinology*, 38:455-65 (2007). Recently, CKD-732 (beloranib hemioxalate) has undergone early-phase clinical testing in adult obese patients (e.g., 30≤BMI≤45 kg/m²).

Certain inhibitors of MetAP2 are described in US 2012/004162 A1 and WO 2010/065883 A2.

SUMMARY OF THE INVENTION

This invention provides substituted indazole derivatives and related compounds, and pharmaceutically acceptable salts thereof. This invention also provides pharmaceutical compositions that contain the substituted indazoles and provides for their use to treat diseases, disorders and conditions associated with MetAP2 inhibition, including obesity.

One aspect of the invention provides compounds of Formula 1:

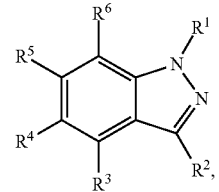

or a pharmaceutically acceptable salt thereof, wherein:
$R^1$ is hydrogen;
$R^2$ is selected from hydrogen, —OH, chloro, fluoro, —CN, methyl, and hydroxymethyl;
$R^3$ is selected from $C_{6-14}$ aryl, $C_{1-9}$ heteroaryl, and $C_{2-6}$ heterocyclyl, each optionally substituted with from one to five substituents independently selected from halo, oxo, —CN, $R^7$, and $R^8$;
$R^4$ is hydrogen;
$R^5$ is $C_{1-3}$ halo alkyl;
$R^6$ is selected from hydrogen, —OH, —NH$_2$, chloro, fluoro, and methyl;
each $R^7$ is independently selected from —OR$^9$, —N(R$^9$)R$^{10}$, —NR$^9$C(O)R$^{10}$, —NHC(O)NR$^9$R$^{10}$, —NR$^9$C(O)NHR$^{10}$, —C(O)R$^9$, —C(O)OR$^9$, —C(O)N(R$^9$)R$^{10}$, —C(O)N(R$^9$)OR$^{10}$, —C(O)N(R$^9$)S(O)$_2$R$^8$, —N(R$^9$)S(O)$_2$R$^8$, —SR$^9$, —S(O)R$^8$, —S(O)$_2$R$^8$, and —S(O)$_2$N(R$^9$)R$^{10}$;
each $R^8$ is independently selected from
  (a) $C_{1-6}$ alkyl, $C_{2-6}$ alkenyl, and $C_{2-6}$ alkynyl, each optionally substituted with from one to five substituents independently selected from halo, oxo, —CN, and R$^{11}$; and
  (b) $C_{3-8}$ cycloalkyl-(CH$_2$)$_m$—, $C_{2-6}$ heterocyclyl-(CH$_2$)$_m$—, $C_{6-14}$ aryl-(CH$_2$)$_m$—, and $C_{1-9}$ heteroaryl-(CH$_2$)$_m$—, each optionally substituted with from one to five substituents independently selected from halo, oxo, —CN, R$^{11}$, and $C_{1-6}$ alkyl optionally substituted with from one to five substituents independently selected from halo, oxo, —CN, and R$^{11}$;
each $R^9$ and $R^{10}$ is independently selected from
  (a) hydrogen;
  (b) $C_{1-6}$ alkyl, $C_{2-6}$ alkenyl, and $C_{2-6}$ alkynyl, each optionally substituted with from one to five substituents independently selected from halo, oxo, —CN, and R$^{11}$; and
  (c) $C_{3-8}$ cycloalkyl-(CH$_2$)$_m$—, $C_{2-6}$ heterocyclyl-(CH$_2$)$_m$—, $C_{6-14}$ aryl-(CH$_2$)$_m$—, and $C_{1-9}$ heteroaryl-(CH$_2$)$_m$—, each optionally substituted with from one to five substituents independently selected from halo, oxo, —CN, R$^{11}$, and $C_{1-6}$ alkyl optionally substituted with from one to five substituents independently selected from halo, oxo, —CN, and $R^{11}$;

each $R^{11}$ is independently selected from —$OR^{12}$, —$N(R^{12})R^{13}$, —$N(R^{12})C(O)R^{13}$, —$NHC(O)NR^{12}R^{13}$, —$NR^{12}C(O)NHR^{13}$, —$C(O)R^{12}$, —$C(O)OR^{12}$, —$C(O)N(R^{12})R^{13}$, —$C(O)N(R^{12})OR^{13}$, —$C(O)N(R^{12})S(O)_2R^{14}$, —$NR^{12}S(O)_2R^{14}$, —$SR^{12}$, —$S(O)R^{14}$, —$S(O)_2R^{14}$, and —$S(O)_2N(R^{12})R^{13}$;

each $R^{12}$ and $R^{13}$ is independently selected from
  (a) hydrogen; and
  (b) $C_{1-6}$ alkyl and $C_{3-8}$ cycloalkyl-$(CH_2)_m$—, each optionally substituted with from one to five substituents independently selected from halo, oxo, —CN, —OH, and —$NH_2$;

each $R^{14}$ is independently selected from $C_{1-6}$ alkyl and $C_{3-8}$ cycloalkyl-$(CH_2)_m$—, each optionally substituted with from one to five substituents independently selected from halo, oxo, —CN, —OH, and —$NH_2$; and each m is independently selected from 0, 1, 2, 3, and 4;

wherein each heteroaryl and heterocyclyl moiety has from one to four heteroatoms independently selected from N, O, and S.

Another aspect of the invention provides a compound which is selected from the group of compounds described in the examples, their pharmaceutically acceptable salts, and stereoisomers of any of the compounds in the examples and their pharmaceutically acceptable salts.

A further aspect of the invention provides a pharmaceutical composition which includes: a compound of Formula 1 or a pharmaceutically acceptable salt thereof or a compound selected from the group of compounds and their pharmaceutically acceptable salts as defined in the preceding paragraphs; and a pharmaceutically acceptable excipient.

An additional aspect of the invention provides a compound of Formula 1 or a pharmaceutically acceptable salt thereof or a compound selected from the group of compounds and their pharmaceutically acceptable salts as defined above, for use as a medicament.

Another aspect of the invention provides a compound of Formula 1 or pharmaceutically acceptable salt thereof or a compound selected from the group of compounds and their pharmaceutically acceptable salts as defined above, for treatment of a disease, disorder or condition selected from hyperglycemia, diabetes, dyslipidaemia, obesity, insulin resistance, metabolic syndrome X, impaired glucose tolerance, polycystic ovary syndrome, cardiovascular disease, non-alcoholic liver steatosis, and atherosclerosis.

A further aspect of the invention provides a use of a compound of Formula 1 or a pharmaceutically acceptable salt thereof or a compound selected from the group of compounds and their pharmaceutically acceptable salts as defined above, for the manufacture of a medicament for the treatment of a disease, disorder or condition associated with MetAP2.

An additional aspect of the invention provides a method of treating a disease, disorder or condition associated with MetAP2, the method comprising administering to the subject an effective amount of a compound of Formula 1 or a pharmaceutically acceptable salt thereof or a compound selected from the group of compounds and their pharmaceutically acceptable salts as defined above.

Another aspect of the invention provides a method of treating a disease, disorder or condition in a subject, the method comprising administering to the subject an effective amount of a compound of Formula 1 or a pharmaceutically acceptable salt thereof or a compound selected from the group of compounds and their pharmaceutically acceptable salts as defined above, wherein the disease, disorder or condition is selected from hyperglycemia, diabetes, dyslipidaemia, obesity, insulin resistance, metabolic syndrome X, impaired glucose tolerance, polycystic ovary syndrome, cardiovascular disease, non-alcoholic liver steatosis, and atherosclerosis.

A further aspect of the invention provides an effective amount of a compound of Formula 1 or a pharmaceutically acceptable salt thereof or a compound selected from the group of compounds and their pharmaceutically acceptable salts as defined above; and at least one additional pharmacologically active agent.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-3}$ alkyl refers to an alkyl group having 1 to 3 (i.e., 1, 2 or 3) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, 1-fluoroethyl, 1,1-difluoroethyl, 1-chloroethyl, 1,1-dichloroethyl, 1-fluoro-1-methylethyl, 1-chloro-1-methylethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no atoms), spiro rings (two rings sharing one atom), fused rings (two rings sharing two atoms and the bond between the two common atoms), and bridged rings (two rings sharing two atoms, but not a common bond). The cycloalkyl group may be attached through any ring atom unless such attachment would violate valence requirements. In addition, the cycloalkyl group may include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom and may include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom and may include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached through any ring atom and may include one or more non-hydrogen substituents unless such attachment or substitution would violate valence requirements or result in a chemically unstable compound. Examples of monocyclic heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, and 1,2-dihydropyrazolo[1,5-d][1,2,4]triazinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings) and may include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3- diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiopheneyl, benzo[c]thiopheneyl, 1H-indolyl, 3H-indolyl, isoindolyl, 1H-isoindolyl, indolinyl, isoindolinyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-c]pyrimidinyl, pyrido[4,3-c]pyrimidinyl, pyrido[3,4-d]pyrimidinyl, pyrido[2,3-c]pyrimidinyl, pyrido[2,3-b]pyrazinyl, pyrido[3,4-b]pyrazinyl, pyrimido[5,4-c]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[c]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-c]pyrimidinyl, 2,3,6,7-tetrahydro-1H-purinyl, 5H-pyrrolo[2,3-b]pyrazinyl, imidazo[1,2-a]pyrazinyl, and imidazo[1,2-b]pyridazinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and $OH^+$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with MetAP2" and similar phrases relate to a disease, disorder or condition in a subject for which inhibition of MetAP2 may provide a therapeutic or prophylactic benefit.

The following abbreviations may be used in the specification: Ac (acetyl); ACN (acetonitrile); AIBN (azo-bis-isobutyronitrile); API (active pharmaceutical ingredient); aq (aqueous); Boc (tert-butoxycarbonyl); Cbz (carbobenzyloxy); dba (dibenzylideneacetone); DCC (1,3-dicyclohexylcarbodiimide); DCM (dichloromethane); DIPEA (N,N-diisopropylethylamine, Hünig's Base); DMA (N,N- dimethylacetamide); DMAP (4-dimethylaminopyridine); DMARD (disease modifying antirheumatic drug); DME (1,2-dimethoxyethane); DMF (N,N-dimethylformamide); DMSO (dimethylsulfoxide); dppf (1,1'-bis(diphenylphosphino)ferrocene); DTT (dithiothreitol); $EC_{50}$ (half maximal effective concentration); EDA ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); $Et_3N$ (triethyl-amine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); AcOH (acetic acid); HOBt (1H-benzo[d][1,2,3]triazol-1-ol); $IC_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); PE (petroleum ether); Ph (phenyl); $pIC_{50}$ ($-\log_{10}(IC_{50})$, where $IC_{50}$ is given in molar (M) units); Pr (propyl); i-Pr (isopropyl); PTFE (polytetrafluoroethylene); RT (room temperature, approximately 20° C. to 25° C.); TCEP (tris(2-carboxyethyl)phosphine); TFA (trifluoroacetic acid); TFAA (2,2,2-trifluoroacetic anhydride); THF (tetrahydrofuran); TMS (trimethylsilyl); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating obesity and other diseases, disorders or conditions associated with MetAP2.

In addition to the specific compounds in the examples, compounds of Formula 1 include those in which (i) $R^3$ is $C_{6-14}$ aryl optionally substituted with from one to five substituents independently selected from halo, oxo, —CN, $R^7$, and $R^8$; (ii) $R^3$ is $C_{1-9}$ heteroaryl optionally substituted with from one to five substituents independently selected from halo, oxo, —CN, $R^7$, and $R^8$; or (iii) $R^3$ is $C_{2-6}$ heterocyclyl optionally substituted with from one to five substituents independently selected from halo, oxo, —CN, $R^7$, and $R^8$.

Compounds of Formula 1 also include those in which (iv) $R^3$ is selected from phenyl, naphthalenyl, fluorenyl, pyrrolyl, and furanyl, each optionally substituted with from one to five substituents independently selected from halo, —CN, $R^7$, and $R^8$; (v) $R^3$ is selected from phenyl and naphthalenyl, each optionally substituted with from one to five substituents independently selected from halo, —CN, $R^7$, and $R^8$; (vi) $R^3$ is phenyl optionally substituted with from one to five substituents independently selected from halo, —CN, $R^7$, and $R^8$; or (vii) $R^3$ is phenyl optionally substituted with from one to three substituents independently selected from halo, —CN, $R^7$, and $R^8$.

Compounds of Formula 1 also include those in which (viii) $R^3$ is selected from thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl, benzofuranyl, isobenzofuranyl, benzothiopheneyl, benzo[c]thiopheneyl, 1H-indolyl, isoindolyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-c]pyridinyl, imidazo[1,5-a]pyridinyl, pyrazolo[1,5-a]pyridinyl, pyrrolo[1,2-b]pyridazinyl, imidazo[1,2-a]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, benzo[d]thiazolyl, [1,2,4]triazolo[1,5-c]pyridinyl, tetrazolo[1,5-c]pyridinyl, 7H-pyrrolo[2,3-d]pyrimidinyl, pyrazolo[1,5-a]pyrimidinyl, imidazo[1,2-c]pyrimidinyl, 5H-pyrrolo[2,3-b]pyrazinyl, imidazo[1,2-c]pyrazinyl, and imidazo[1,2-b]pyridazinyl, each optionally substituted with from one to five substituents independently selected from halo, —CN, $R^7$, and $R^8$.

Compounds of Formula 1 also include those in which (ix) $R^3$ is selected from pyridinyl, pyrimidinyl, pyridazinyl, pyrazinyl, imidazolyl, pyrazolyl, tetrazolyl, thiazolyl, isoxazolyl, quinolinyl, isoquinolinyl, 1,7-naphthyridinyl, 1H-indolyl, benzimidazolyl, benzo[d]thiazolyl, 1H-pyrrolo[2,3-b]pyridinyl, 1H-pyrrolo[2,3-c]pyridinyl, imidazo[1,2-a]pyridinyl, pyrazolo[1,5-c]pyridinyl, 3H-imidazo[4,5-b]pyridinyl, [1,2,4]triazolo[1,5a]pyridinyl, tetrazolo[1,5-c]pyridinyl, 7H-pyrrolo[2,3-d]pyrimidinyl, pyrazolo[1,5-a]pyrimidinyl, imidazo[1,2-c]pyrimidinyl, imidazo[1,2-c]pyrazinyl, imidazo[1,2-b]pyridazinyl, and each optionally substituted with from one to five substituents independently selected from halo, —CN, $R^7$, and $R^8$; (x) $R^3$ is selected from pyridinyl, pyrimidinyl, pyrazolyl, and 3H-imidazo[4,5-b]pyridinyl, each optionally substituted with from one to three substituents independently selected from halo, —CN, $R^7$, and $R^8$; (xi) $R^3$ is pyridinyl optionally substituted with from one to three substituents independently selected from halo, —CN, $R^7$, and $R^8$; (xii) $R^3$ is pyrimidinyl optionally substituted with from one to three substituents independently selected from halo, —CN, $R^7$, and $R^8$; (xiii) $R^3$ is pyrazolyl optionally substituted with from one to three substituents independently selected from halo, —CN, $R^7$, and $R^8$; or (xiv) $R^3$ is 3H-imidazo[4,5-b]pyridinyl optionally substituted with from one to three substituents independently selected from halo, —CN, $R^7$, and $R^8$.

Compounds of Formula 1 also include those in which (xv) $R^3$ is selected from 3H-indolyl, 1H-isoindolyl, indolinyl, isoindolinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, 2,3-dihydro-1H-pyrrolo[2,3-b]pyridinyl, 2,3-dihydro-1H-imidazo[4,5-b]pyridinyl, 4,5-dihydro-1H-pyrazolo[3,4-c]pyrimidinyl, 2,3,6,7-tetrahydro-1H-purinyl, and 1,2-dihydropyrazolo[1,5-d][1,2,4]triazinyl, each optionally substituted with from one to five substituents independently selected from halo, oxo, —CN, $R^7$, and $R^8$.

Compounds of Formula 1 also include those in which: (xvi) $R^3$ is selected from 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, indolinyl, isoindolinyl, 2,3-dihydro-1H-benzo[d]imidazolyl, 2,3-dihydro-1H-pyrrolo[2,3-b]pyridinyl, 2,3-dihydro-1H-imidazo[4,5-b]pyridinyl, 4,5-dihydro-1H-pyrazolo[3,4-c]pyrimidinyl, 2,3,6,7-tetrahydro-1H-purinyl, 5H-pyrrolo[2,3-b]pyrazinyl, and 1,2-dihydropyrazolo[1,5-d][1,2,4]triazinyl, each optionally substituted with from one to five substituents independently selected from halo, oxo, —CN, $R^7$, and $R^8$.

Compounds of Formula 1 also include those in which (xvii) $R^3$ is selected from oxiranyl, thiiranyl, aziridinyl, oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, and 1,2,3,4-tetrahydropyrimidinyl, and, each optionally substituted with from one to five substituents independently selected from halo, oxo, —CN, $R^7$, and $R^8$.

Compounds of Formula 1 also include those in which (xviii) $R^3$ is selected from 1,2-dihydropyridinyl, 1,6-dihydropyrimidinyl, and 1,2,3,4-tetrahydropyrimidinyl, each optionally substituted with from one to five substituents independently selected from halo, oxo, —CN, $R^7$, and $R^8$; or (xix) $R^3$ is 1,2-dihydropyridinyl optionally substituted with from one to five substituents independently selected from halo, oxo, —CN, $R^7$, and $R^8$.

In addition, or as an alternative, to one of embodiments (i) through (xix) in the preceding paragraphs, compounds of Formula 1 include those in which (xx) $R^2$ is selected from hydrogen, —OH, chloro, and fluoro; (xxi) $R^2$ is selected from hydrogen, chloro, and fluoro; (xxii) $R^2$ is selected from hydrogen and fluoro; or (xxiii) $R^2$ is hydrogen.

In addition, or as an alternative, to one of embodiments (i) through (xix) in the preceding paragraphs, and one of embodiments (xx) through (xxiii) in the preceding paragraph, compounds of Formula 1 include those in which (xxiv) $R^6$ is selected from hydrogen, —OH, —NH$_2$, chloro, and fluoro; (xxv) $R^6$ is selected from hydrogen, chloro, and fluoro; (xxvi) $R^6$ is selected from hydrogen and fluoro; or (xxvii) $R^6$ is hydrogen.

In addition, or as an alternative, to one of embodiments (i) through (xix) in the preceding paragraphs, and one or more of embodiments (xx) through (xxvii) in the preceding paragraphs, compounds of Formula 1 include those in which (xxviii) $R^3$ is optionally substituted with from one to three substituents; (xxix) $R^3$ is optionally substituted with one or two substituents; (xxx) $R^3$ is optionally substituted with one substituent; or (xxxi) $R^3$ is unsubstituted (i.e., contains no optional substituents).

In addition, or as an alternative, to one of embodiments (i) through (xix) in the preceding paragraphs, and one or more of embodiments (xx) through (xxxi) in the preceding paragraphs, compounds of Formula 1 include those in which (xxxii) each $R^8$, $R^9$, and $R^{10}$ substituent is optionally substituted with one or two substituents; (xxxiii) each $R^8$, $R^9$, and $R^{10}$ substituent is optionally substituted with one substituent; or (xxxiv) each $R^8$, $R^9$, and $R^{10}$ substituent is unsubstituted (i.e., contains no optional substituents).

In addition, or as an alternative, to one of embodiments (i) through (xix) in the preceding paragraphs, and one or more of embodiments (xx) through (xxxiv) in the preceding paragraphs, compounds of Formula 1 include those in which (xxxv) each $R^{12}$, $R^{13}$, and $R^{14}$ substituent is optionally substituted with one or two substituents; (xxxvi) each $R^{12}$, $R^{13}$, and $R^{14}$ substituent is optionally substituted with one substituent; or (xxxvii) each $R^{12}$, $R^{13}$, and $R^{14}$ substituent is unsubstituted.

In addition, or as an alternative, to one of embodiments (i) through (xix) in the preceding paragraphs, and one or more of embodiments (xx) through (xxxvii) in the preceding paragraphs, compounds of Formula 1 include those in which (xxxviii) each m is independently selected from 0, 1, 2, and 3; (xxxix) each m is independently selected from 0, 1, and 2; (xxxx) each m is independently selected from 0 and 1; or (xxxxi) each m is 0.

In addition, or as an alternative, to one of embodiments (i) through (xix) in the preceding paragraphs, and one or more of embodiments (xx) through (xxxxi) in the preceding paragraphs, compounds of Formula 1 include those in which (xxxxii) $R^5$ is selected from fluoromethyl, difluoromethyl, and trifluoromethyl; or (xxxxiii) $R^5$ is trifluoromethyl.

In addition, or as an alternative, to one of embodiments (i) through (xix) in the preceding paragraphs, and one or more of embodiments (xxviii) through (xxxxi) in the preceding paragraphs, compounds of Formula 1 include those in which (xxxxiv) $R^2$ is hydrogen, $R^5$ is trifluoromethyl, and $R^6$ is hydrogen.

Compounds of Formula 1 include embodiments (i) through (xxxxiv) described in the preceding paragraphs and all compounds specifically named in the examples, and may exist as salts, complexes, solvates, hydrates, and liquid crystals. Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., $-COO^-Na^+$, $-COO^-K^+$, $-SO_3^-Na^+$) or polar non-ionic moiety (such as $-N^-N^+(CH_3)_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2$H and $^3$H; isotopes of carbon, such as $^{11}$C, $^{13}$C and $^{14}$C; isotopes of nitrogen, such as $^{13}$N and $^{15}$N; isotopes of oxygen, such as $^{15}$O, $^{17}$O and $^{18}$O; isotopes of sulfur, such as $^{35}$S; isotopes of fluorine, such as $^{18}$F; isotopes of chlorine, such as $^{36}$Cl, and isotopes of iodine, such as $^{123}$I and $^{125}$I. Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O, and $^{13}$N, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (e.g., $R^1$, $R^2$, $R^3$, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include an $R^2$ that is a moiety having a potentially reactive amine. In such cases, $R^2$ would include the moiety with or without, say, a Boc or Cbz group attached to the amine.

Scheme A shows a general method for preparing compounds of Formula 1 by reacting a halide or pseudohalide (A1, A4) with a boronic acid or ester (A2, A3) under Suzuki conditions. As shown in Scheme A, a halide or pseudohalide (A1 or A4, e.g. X is Br, Cl, I, or triflate) may be reacted with a boronic acid or ester (A2 or A3, e.g. Y is —B(OR')$_2$, where each R' is H or $C_{1-4}$ alkyl or each R' together forms a $C_{1-8}$ alkanediyl such as 2,3-dimethylbutan-2,3-diyl) in the presence of a palladium catalyst (e.g., Pd(PPh$_3$)$_4$, (PPh$_3$)$_2$PdCl$_2$, PdCl$_2$(dppf), etc.), a base (e.g., KF, Na$_2$CO$_3$, NaHCO$_3$, Cs$_2$CO$_3$), and one or more solvents (e.g., dioxane, DMF, H$_2$O, etc.) at elevated temperature (e.g., 90-145° C.). The method depicted in Scheme A may be varied as desired. For example, the halide or pseudohalide (A1, A4) may be reacted with the boronic acid or boronate ester (A2, A3) and the resulting intermediate (not shown) further elaborated via, for example, alkylation, acylation, hydrolysis, oxidation, reduction, amidation, sulfonation, alkynation, alkyenation, and the like, to give the compound of Formula 1.

Scheme A

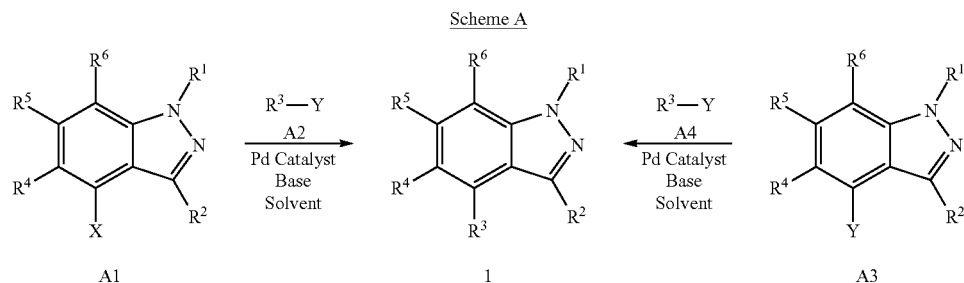

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more of these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10): 955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 µg to about 20 mg of the API per actuation and the actuation volume may vary from about 1 µL, to about 100 µL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders, and conditions for which inhibition of MetAP2 is indicated. Such diseases, disorders, and conditions generally relate to any unhealthy or abnormal state in a subject for which the inhibition of MetAP2 provides a therapeutic benefit. More particularly, the compounds of Formula 1 may be used to treat obesity or an overweight condition in a subject, or to treat diseases, disorders or conditions associated with obesity or an overweight condition, including cardiovascular disease, hypertension, diabetes, hyperglycemia, insulin resistance, metabolic syndrome X, impaired glucose tolerance, non-alcoholic liver steatosis, dyslipidemia (including high total cholesterol or high levels of triglycerides), atherosclerosis, stroke, sleep apnea, osteoarthritis, infertility, and polycystic ovary syndrome.

According to *The Practical Guide: Identification, Evaluation, and Treatment of Overweight and Obesity in Adults*, published in 2000 by the National Heart, Lung, and Blood Institute, a human adult may be classified as overweight or obese based upon the subject's body mass index (BMI). BMI is calculated by dividing a subject's mass (in kg) by the square of the subject's height (in meters). Under the Guide, a BMI of 25-29.9 $kg/m^2$ is classified as overweight, and body mass indices of 30-34.9 $kg/m^2$, 35-39.9 $kg/m^2$, and ≥40 $kg/m^2$ are classified as Class 1 obesity, Class 2 obesity, and Class 3 (extreme) obesity, respectively.

The claimed and disclosed compounds may be combined with one or more other pharmacologically active compounds or therapies to treat one or more disorders, diseases or conditions for which MetAP2 is indicated, including obesity.

For example, compounds of Formula 1, which include compounds specifically named above, and their pharmaceutically acceptable complexes, salts, solvates and hydrates, may be administered simultaneously, sequentially or separately in combination with one or more compounds or therapies for treating cardiovascular disease, hypertension, diabetes, hyperglycemia, insulin resistance, metabolic syndrome X, impaired glucose tolerance, non-alcoholic liver steatosis, dyslipidemia, atherosclerosis, stroke, sleep apnea, osteoarthritis, infertility, and polycystic ovary syndrome. Such combinations may offer significant therapeutic advantages, including fewer side effects, improved ability to treat underserved patient populations, or synergistic activity.

For example, the compounds of Formula 1 may be combined with one or more agents for treating obesity, diabetes, hyperglycemia, insulin resistance, metabolic syndrome X, impaired glucose tolerance, and non-alcoholic liver steatosis. These agents include pancreatic lipase inhibitors (e.g., orlistat); insulin; insulin sensitizers, including biguanides (e.g., buformin, metformin, and phenformin) and glitazones (e.g., pioglitazone and rosiglitazone); insulin secretagogues, including sulfonylureas (e.g., acetohexamide, chlorpropamide, tolazamide, tolbutamide, gliclazide, glimepiride, glipizide, and glyburide), and meglitinides (e.g., nateglinide and repaglinide); alpha-glucosidase inhibitors (e.g., acarbose and miglitol); glucagon-like peptide analogs and agonists (e.g., exenatide, liraglutide, and taspoglutide); dipeptidyl peptidase-4 inhibitors (e.g., alogliptin, linagliptin, saxagliptin, sitagliptin, and vildagliptin); and amylin analogs (e.g., pramlinitide).

In addition, the compounds of Formula 1 may be combined with one or more agents for treating osteoarthritis, including nonsteroidal anti-inflammatory drugs (NSAIDs) (e.g., apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac); analgesics (e.g., acetaminophen and morphine sulfate, as well as codeine, hydrocodone, oxycodone, propoxyphene, and tramadol, all with or without acetaminophen); corticosteroids (e.g., betamethasone, cortisone acetate, dexamethasone, hydrocortisone, methylprednisolone, prednisolone, and prednisone); and osteoporosis agents (e.g., alendronate, clodronate, etidronate, ibandronate, neridronate, olpadronate, pamidronate, risedronate, tiludronate, and zoledronate).

The compounds of Formula 1 may also be combined with one or more agents for treating cardiovascular disease, hypertension, dyslipidemia, atherosclerosis, and stroke, including calcium channel blockers (e.g., amlodipine, aranidipine, azelnidipine, barnidipine, bepridil, benidipine, cilnidipine, clevidipine, diltiazem, isradipine, efonidipine, felodipine, fendiline, fluspirilene, lacidipine, lercanidipine, manidipine, mibefradil, nicardipine, nifedipine, nilvadipine, nimodipine, nisoldipine, nitrendipine, pranidipine, and verapamil); statins (e.g., atorvastatin, fluvastatin, lovastatin, mevastatin, pitavastatin, pravastatin, rosuvastatin, and simvastatin); PPAR alpha activators (e.g., fibrates, such as bezafibrate, ciprofibrate, clofibrate, fenofibrate, and gemfibrozil); bile acid sequestrants (e.g., cholestyramine, colesevelam, and colestipol); other lipid-lowering agents (e.g., niacin and ezetimibe); beta-blockers (e.g., alprenolol, atenolol, betaxolol, bisoprolol, bucindolol, carteolol, carvedilol, celiprolol, esmolol, eucommia bark, labetalol, metoprolol, nadolol, nebivolol, oxprenolol, penbutolol, pindolol, propranolol, sotalol, and timolol); angeotensin-converting enzyme (ACE) inhibitors (benazepril, captopril, enalapril, imidapril, lisinopril, perindopril, quinapril, ramipril, trandolapril, and zofenopril); and platelet aggregation inhibitors (abciximab, aspirin, cilostazol, clopidogrel, dipyridamole, dipyridamole, eptifibatide, ifetroban, picotamide, prasugrel, terutroban, ticagrelor, ticlopidine, and tirofiban).

Biological Activity

The biological activity of the compound of Formula 1 may be determined using various in vitro and in vivo methods. The following in vitro assays measure a test compound's ability to inhibit MetAP2.

MetAP2 Protein Purification

DNA encoding the full-length sequence of human MetAP2 enzyme is amplified by PCR and cloned into a pFastBac expression vector (Invitrogen). Recombinant baculovirus incorporating the MetAP2 construct is generated by transposition using the Bac-to-Bac system (Invitrogen). The expression of recombinant protein is carried out by infection of *Spodoptera frugiperda* Sf9 cells (Invitrogen) in 5 L Wave Bioreactors (Wave Biotech). Recombinant protein is isolated from cellular extracts by binding to an SP Hitrap Fast Flow or SP Sepharose (Sigma) column, and the protein is eluted using a NaCl gradient. Partially purified extracts of MetAP2 are further purified by an AKTA FPLC over a Superdex-200 column (GE). The purity of MetAP2 protein is determined on denaturing SDS-PAGE gel. Purified MetAP2 protein is concentrated to a final concentration of 17 mg/mL or 2.5 mg/mL. The protein is stored at −78° C. in a buffer containing 10 mM HEPES pH 7.4, 150 mM NaCl, and 1 mM $CoCl_2$ or in a buffer containing 20 mM HEPES pH 7.4, 120 mM NaCl, and 5 mM $MnCl_2$.

Enzyme Assay

The inhibition of MetAP2 is determined using a black 384-well-plate format under the following reaction conditions: 50 mM Hepes pH 7.5, 100 mM NaCl, 10 µM $MnCl_2$ or 10 µM $CoCl_2$, 0.005% Brij35®, 1 mM TCEP, 1% DMSO. To initiate the assay, 4 µL, of 5 to 50 nM MetAP2 enzyme solution (enzyme final concentration is 2 to 20 nM) is added to each well, followed by the addition of 2 µL, of the test compound (2.5-fold serial dilutions for 11 data points for each test compound) in a buffer solution containing 5% DMSO. Next, 4 µL, of a substrate solution (2.5×$K_m$ of Met-AMC) is added to each well of the plate (final substrate concentration at $K_m$ value). The reaction rate is monitored by reading fluorescence at 460 nm with excitation wavelength at 330 nm for 10 to 30 minutes using a fluorescence plate reader. The results for each well are expressed as percent inhibition and calculated using the equation:

$$\text{Inhibition} = 1 - \left( \frac{x - \overline{\text{Positive}}}{\overline{\text{Negative}} - \overline{\text{Positive}}} \right),$$

where $\overline{\text{Negative}}$ is the average of all the rates on the plate in the presence of no test compound, $\overline{\text{Positive}}$ is the rate with a 10 µM tool compound (MetAP2 activity is 100% inhibited), and x is the rate (raw data) in the presence of the test compound. The $IC_{50}$ for each test compound is obtained by fitting the percent inhibition data with a standard 4-parameter equation and is reported as $pIC_{50}$, i.e., $-\log(IC_{50})$, where $IC_{50}$ is the molar concentration at 50% inhibition.

MetAP2 cellular activity: western blotting of NMet-14-3-3γ

HUVEC cells (Lonza) are seeded in 96-well tissue culture microplates and cultured for 24 hours prior to addition of test compounds (11 point range of serial dilutions) or DMSO vehicle. After 24 hours, whole cell extracts are prepared by lysing cells in cell extraction buffer (Cell Signaling) containing protease and phosphatase inhibitors (Calbiochem). Insoluble material is removed by centrifugation and samples are diluted and boiled in SDS-PAGE buffer. Proteins are resolved by SDS-PAGE and transferred to PVDF membranes. Membranes are blocked then incubated with the appropriate primary antibodies, NMet-14-3-3γ (Novus) and β-actin (Sigma), followed by incubation with secondary IRDye 680- or 800CW-conjugated antibodies (Li-Cor). Membranes are scanned on the Odyssey (Li-Cor) and signals corresponding to N-Met14-3-3γ and β-actin are quantified using LiCor software. Compound $EC_{50}$s are obtained by curve-fitting the ratios of unprocessed N-Met14-3-3γ protein signal over β-actin protein signal using XLfit4 Microsoft Excel curve-fitting software.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and THF-$d_8$ (deuterotetrahydrofuran). The mass spectra (m/z for [M+H]$^+$) were recorded using either electrospray ionization (ESI-MS) or atmospheric pressure chemical ionization (APCI-MS) mass spectrometry.

Where indicated, products of certain preparations and examples are purified by mass-triggered HPLC (Pump: Waters™ 2525; MS: ZQ™; Software: MassLynx™), flash chromatography or preparative thin layer chromatography (TLC). Reverse phase chromatography is typically carried out on a column (e.g., Gemini™ 5μ C18 110A, Axia™, 30×75 mm, 5μ) under acidic conditions ("acid mode") eluting with ACN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM $NH_4HCO_3$. Preparative TLC is typically carried out on silica gel 60 $F_{254}$ plates. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

PREPARATION x1: 4-(4,4,5,5-tetramethyl-1,3,2-dioxaborolan-2-yl)-6-(trifluoromethyl)-1H-indazole

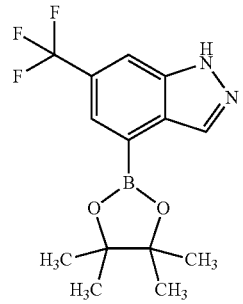 [SMILES: CC1(C)OB(c2cc(C(F)(F)F)cc3[nH]ncc23)OC1(C)C]

A mixture of 4-bromo-6-(trifluoromethyl)-1H-indazole (0.5 g, 1.887 mmol), bis(pinacolato)diboron (0.958 g, 3.77 mmol), $PdCl_2$(dppf) (0.028 g, 0.038 mmol), and potassium acetate (0.741 g, 7.55 mmol) in DMSO (10 mL) was charged to a microwave vial, which was sealed and heated at 100° C. in an oil bath for 13 hours. LCMS indicated the presence of bromide starting material, so the reaction mixture was heated for an additional 7 hours, after which LCMS showed the bromide starting material had been consumed. The reaction mixture was combined with product from an earlier run, and was subsequently partitioned between ethyl acetate (30 mL) and aqueous saturated $NH_4Cl$ (30 mL). The organic phase was washed sequentially with aqueous saturated $NH_4Cl$ (30 mL) and brine (30 mL) and was dried over anhydrous sodium sulfate. The solvents were removed in vacuo, and the resulting dark brown residue was purified by silica gel chromatography (Moritex size 60 silica gel column) eluting with a gradient of 5-30% ethyl acetate in hexanes to give the title compound as a pale yellow solid (468 mg, 72% for two runs). ESI-MS m/z [M+H]$^+$ calc'd for $C_{14}H_{16}BF_3N_2O_2$, 313.1. found 313.2.

PREPARATION x2:
(4-bromo-1-methyl-1H-pyrazol-5-yl)methanol

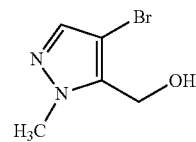

Methyl 4-bromo-1-methyl-1H-pyrazole-5-carboxylate (2 g, 9.13 mmol) in DCM (40 mL) was cooled to −78° C. Diisobutylaluminum hydride (36.5 mL, 36.5 mmol) in DCM was added, and the reaction mixture was stirred for 2 hours at the same temperature. The reaction mixture was subsequently quenched with aqueous saturated sodium potassium tartrate and was transferred to a reparatory funnel, where it was washed with water and brine, dried over $Na_2SO_4$, and concentrated to give the title compound as a white solid (0.76 g, 44%).

PREPARATION x3:
5-bromo-N-methylpyrimidine-4-carboxamide

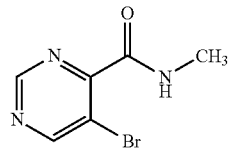

To a mixture of 5-bromopyrimidine-4-carboxylic acid (0.3 g, 1.478 mmol) in DMF (3 mL) were added HOBt (0.260 g, 1.921 mmol), EDC (0.397 g, 2.069 mmol), methanamine HCl (0.200 g, 2.96 mmol), followed by N-ethyl-N-isopropylpropan-2-amine (0.772 mL, 4.43 mmol). The reaction mixture was stirred for 18 hours at room temperature. The crude residue was purified by preparative HPLC (Waters SunFire C18, 5 µm, 30 mm ID×75 mm column) eluting with 5% ACN (containing 0.035% TFA) in water (containing 0.05% TFA) to give the title compound as a light brown solid (0.11 g, 35%). ESI-MS m/z [M+H]$^+$ calc'd for $C_6H_7BrN_3O$, 216.0. found 216.0.

PREPARATION x4:
N-(5-bromo-6-methylpyridin-2-yl)methanesulfonamide

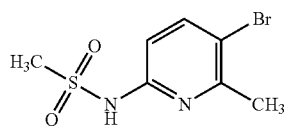

To a mixture of 5-bromo-6-methylpyridin-2-amine (0.3 g, 1.604 mmol) and N-ethyl-N-isopropylpropan-2-amine (0.559 mL, 3.21 mmol) in DCM (10 mL) was added methanesulfonyl chloride (0.137 mL, 1.764 mmol) at 0° C. The reaction mixture was stirred at room temperature for 48 hours and was subsequently concentrated in vacuo to give the title compound.

PREPARATION x5:
4-(6-(trifluoromethyl)-1H-indazol-4-yl)picolinic acid

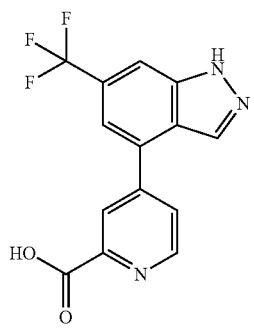 [SMILES: O=C(O)c1cc(-c2cc(C(F)(F)F)cc3[nH]ncc23)ccn1]

A mixture of 4-bromo-6-(trifluoromethyl)-1H-indazole (0.302 g, 1.140 mmol), methyl 4-(4,4,5,5-tetramethyl-1,3,2-dioxaborolan-2-yl)picolinate (0.3 g, 1.140 mmol), and PdCl$_2$(dppf) (0.042 g, 0.057 mmol) in dioxane (10 mL) was combined with aqueous saturated NaHCO$_3$ (3 mL) to give a light brown suspension. The reaction mixture was heated in a microwave reactor at 140° C. for 45 minutes and was then cooled, filtered, concentrated in vacuo, and purified by preparative HPLC (Waters SunFire C18, 5 µm, 30 mm ID×75 mm column) eluting with a gradient of 15-55% ACN (containing 0.035% TFA) in water (containing 0.05% TFA) to give a TFA salt of the title compound. ESI-MS m/z [M+H]$^+$ calc'd for $C_{14}H_8F_3N_3O_2$, 308.1. found 308.1.

PREPARATION x6: 4-(6-chloro-2-methylpyridin-3-yl)-6-(trifluoromethyl)-1H-indazole

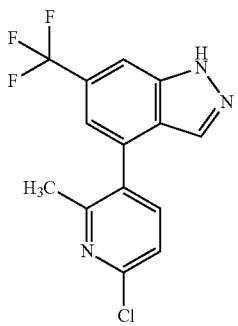 [SMILES: Cc1nc(Cl)ccc1-c1cc(C(F)(F)F)cc2[nH]ncc12]

A TFA salt of the title compound was prepared by a method similar to PREPARATION x5 using (6-chloro-2-methylpyridin-3-yl)boronic acid in place of methyl 4-(4,4,5,5-tetramethyl-1,3,2-dioxaborolan-2-yl)picolinate. ESI-MS m/z [M+H]$^+$ calc'd for $C_{14}H_9ClF_3N_3$, 312.1. found 312.1.

PREPARATION x7: 6-methyl-5-(6-(trifluoromethyl)-1H-indazol-4-yl)picolinic acid

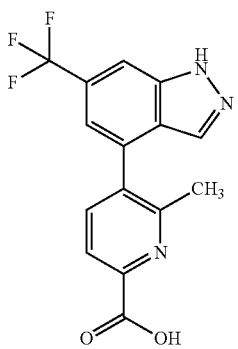 [SMILES: Cc1nc(C(=O)O)ccc1-c1cc(C(F)(F)F)cc2[nH]ncc12]

To 6-methyl-5-(6-(trifluoromethyl)-1H-indazol-4-yl)picolinonitrile (1.7 g, 5.62 mmol) in EtOH (20 mL) was added sodium hydroxide (14.06 mL, 28.1 mmol) and the resulting mixture was stirred for 16 hours at reflux. The mixture was subsequently cooled to room temperature and acidified with concentrated HCl. Volatiles were evaporated and the residue purified by CombiFlash® chromatography (5-40% MeOH in DCM over 120 minutes). The product-containing fractions were combined and concentrated in vacuo to give the title compound as a white solid (1.6 g, 89%). ESI-MS m/z [M+H]$^+$ calc'd for $C_{15}H_{10}F_3N_3O2$, 322.1. found 322.06.

PREPARATION x8: 3-bromo-5-(4-methylpiperazine-1-carbonyl)pyridin-2(1H)-one

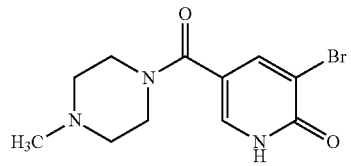 [SMILES: CN1CCN(C(=O)c2c[nH]c(=O)c(Br)c2)CC1]

To a mixture of 5-bromo-6-oxo-1,6-dihydropyridine-3-carboxylic acid (500 mg, 2.294 mmol) and 2-(1H-benzo[d][1,2,3]triazol-1-yl)-1,1,3,3-tetramethyluronium hexafluorophosphate(V) (1044 mg, 2.75 mmol) in DMF (6 mL) was added 1-methylpiperazine (0.382 mL, 3.44 mmol). The mixture was stirred at room temperature for 2 hours and was purified via preparative HPLC, eluting with a gradient of 10-50% ACN (containing 0.035% TFA) in $H_2O$ (containing 0.05% TFA). The product-containing fractions were dried under vacuum to give the title compound.

PREPARATION x9: 3-bromo-5-(morpholine-4-carbonyl)pyridin-2(1H)-one

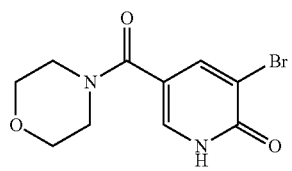 [SMILES: O=C(c1c[nH]c(=O)c(Br)c1)N1CCOCC1]

The title compound was prepared in a manner similar to PREPARATION x8 using morpholine in place of 1-methylpiperazine.

PREPARATION x10: 5-bromo-N-(2-hydroxyethyl)-6-oxo-1,6-dihydropyridine-3-carboxamide

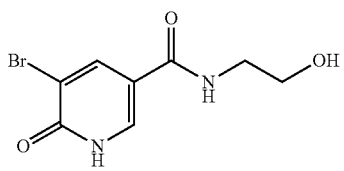 [SMILES: O=C(NCCO)c1c[nH]c(=O)c(Br)c1]

The title compound was prepared in a manner similar to PREPARATION x8 using 2-aminoethanol in place of 1-methylpiperazine.

PREPARATION x11: 2-(5-bromo-3-methyl-2,6-dioxo-2,3-dihydropyrimidin-1(6H)-yl)acetamide

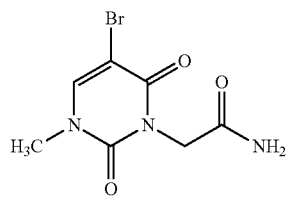

A mixture of 5-bromo-1-methylpyrimidine-2,4(1H,3H)-dione (200 mg, 0.976 mmol), 2-bromoacetamide (162 mg, 1.171 mmol) and $K_2CO_3$ (162 mg, 1.171 mmol) in DMSO (4 mL) was stirred at room temperature for 4 hours. The reaction mixture was subsequently filtered and purified via preparative HPLC, eluting with a gradient of 1-40% ACN (containing 0.035% TFA) in $H_2O$ (containing 0.05% TFA) to give the title compound.

PREPARATION x12: 2-(5-bromo-3-methyl-2,6-dioxo-2,3-dihydropyrimidin-1(6H)-yl)-N-methylacetamide

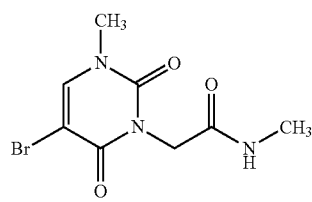

The title compound was prepared in a manner similar to PREPARATION x11 using 2-bromo-N-methylacetamide in place of 2-bromoacetamide.

PREPARATION x13: 2-(5-bromo-3-methyl-2,6-dioxo-2,3-dihydropyrimidin-1(6H)-yl)-N-ethylacetamide

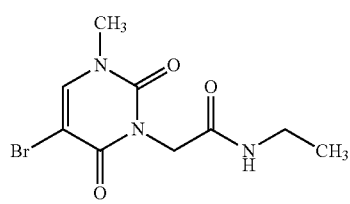 [SMILES: CCNC(=O)Cn1c(=O)c(Br)cn(C)c1=O]

The title compound was prepared in a manner similar to PREPARATION x11 using 2-bromo-N-ethylacetamide in place of 2-bromoacetamide.

PREPARATION x14: 5-bromo-3-(2-hydroxyethyl)-1-methylpyrimidine-2,4(1H,3H)-dione

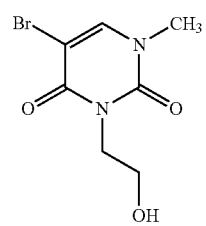

The title compound was prepared in a manner similar to PREPARATION x11 using 2-bromoethanol in place of 2-bromoacetamide.

PREPARATION x15: 2-(5-bromo-3-methyl-2,6-dioxo-2,3-dihydropyrimidin-1(6H)-yl)-N,N-dimethylacetamide

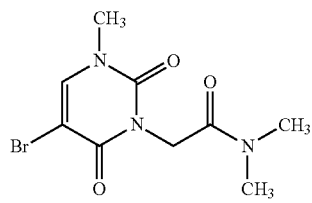

A mixture of 5-bromo-1-methylpyrimidine-2,4(1H,3H)-dione (80 mg, 0.390 mmol), 2-chloro-N,N-dimethylacetamide (47.4 mg, 0.390 mmol), and potassium carbonate (64.7 mg, 0.468 mmol) in DMSO (3 mL) was stirred at room temperature 2 hours. The reaction mixture was subsequently filtered and purified via preparative HPLC, eluting with a gradient of 5-70% ACN (containing 0.035% TFA) in $H_2O$ (containing 0.05% TFA) to give the title compound.

PREPARATION x16: 5-bromo-1-methyl-3-(2-morpholino-2-oxoethyl)pyrimidine-2,4(1H,3H)-dione

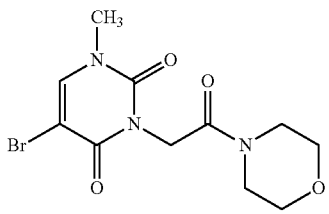 [SMILES: Cn1cc(Br)c(=O)n(CC(=O)N2CCOCC2)c1=O]

The title compound was prepared in a manner similar to PREPARATION x15 using 2-chloro-1-morpholinoethanone in place of 2-chloro-N,N-dimethylacetamide.

PREPARATION x17: 5-bromo-3-(4-fluorobenzyl)-1-methylpyrimidine-2,4(1H,3H)-dione

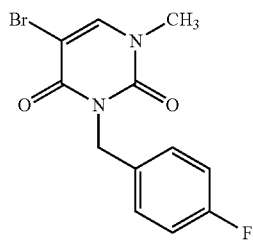 [SMILES: Cn1cc(Br)c(=O)n(Cc2ccc(F)cc2)c1=O]

The title compound was prepared in a manner similar to PREPARATION x15 using 1-(bromomethyl)-4-fluorobenzene in place of 2-chloro-N,N-dimethylacetamide.

PREPARATION x18: 2-(5-bromo-3-methyl-2,6-dioxo-2,3-dihydropyrimidin-1(6H)-yl)acetonitrile

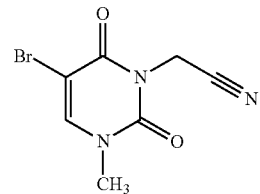

The title compound was prepared in a manner similar to PREPARATION x15 using 2-bromoacetonitrile in place of 2-chloro-N,N-dimethylacetamide.

PREPARATION x19: 5-bromo-1-methyl-3-(2-morpholinoethyl)pyrimidine-2,4(1H,3H)-dione

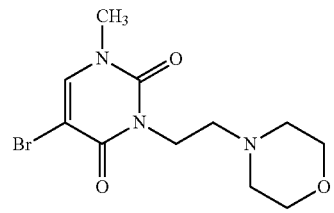 [SMILES: Cn1cc(Br)c(=O)n(CCN2CCOCC2)c1=O]

The title compound was prepared in a manner similar to PREPARATION x15 using 4-(2-chloroethyl)morpholine hydrochloride in place of 2-chloro-N,N-dimethylacetamide.

PREPARATION x20: 5-bromo-3-(2-(dimethylamino)ethyl)-1-methylpyrimidine-2,4(1H,3H)-dione

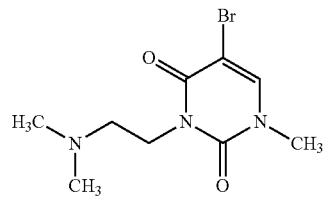

The title compound was prepared in a manner similar to PREPARATION x15 using 2-chloro-N,N-dimethylethanamine hydrochloride in place of 2-chloro-N,N-dimethylacetamide.

PREPARATION x21: 3-bromo-1-methyl-5-(morpholine-4-carbonyl)pyridin-2(1H)-one

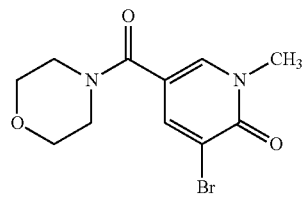 [SMILES: Cn1cc(C(=O)N2CCOCC2)cc(Br)c1=O]

A mixture of 3-bromo-5-(morpholine-4-carbonyl)pyridin-2(1H)-one (430 mg, 1.498 mmol), iodomethane (0.112 mL, 1.797 mmol), and potassium carbonate (207 mg, 1.498 mmol) in DMSO (5 mL) was stirred at room temperature overnight. The reaction mixture was subsequently filtered and purified via preparative HPLC, eluting with a gradient of 30-70% ACN in H$_2$O (containing 10 mM NH$_4$HCO$_3$) to give the title compound.

PREPARATION x22: 5-bromo-N-(2-hydroxyethyl)-1-methyl-6-oxo-1,6-dihydropyridine-3-carboxamide

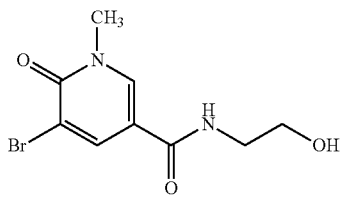

A mixture of 5-bromo-N-(2-hydroxyethyl)-6-oxo-1,6-dihydropyridine-3-carboxamide (400 mg, 1.532 mmol), iodomethane (0.114 mL, 1.839 mmol), and potassium carbonate (212 mg, 1.532 mmol) in DMSO (5 mL) was stirred at room temperature overnight. The reaction mixture was subsequently filtered and purified via preparative HPLC, eluting with a gradient of 1-30% ACN in H$_2$O (containing 10 mM NH$_4$HCO$_3$) to give the title compound.

PREPARATION x23: 5-bromo-N-cyclopropyl-6-oxo-1,6-dihydropyridine-3-carboxamide

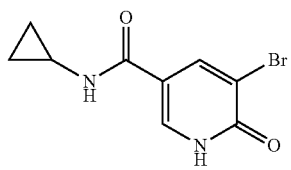 [SMILES: O=C(NC1CC1)c1c[nH]c(=O)c(Br)c1]

To a mixture of 5-bromo-6-oxo-1,6-dihydropyridine-3-carboxylic acid (200 mg, 0.917 mmol), Et$_3$N (0.1 mL), and 2-(1H-benzo[d][1,2,3]triazol-1-yl)-1,1,3,3-tetramethyluronium hexafluorophosphate(V) (348 mg, 0.917 mmol) in DMF (5 mL) was added cyclopropanamine (52.4 mg, 0.917 mmol). The mixture was stirred at room temperature for 2 hours and purified via preparative HPLC, eluting with a gradient of 1-50% ACN (containing 0.035% TFA) in H$_2$O (containing 0.05% TFA). The product was dried under vacuum to give the title compound.

PREPARATION x24: 5-bromo-N-(cyanomethyl)-6-oxo-1,6-dihydropyridine-3-carboxamide

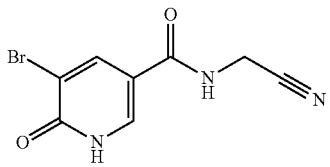 [SMILES: N#CCNC(=O)c1c[nH]c(=O)c(Br)c1]

The title compound was prepared in a manner similar to PREPARATION x23 using 2-aminoacetonitrile hydrochloride in place of cyclopropanamine.

PREPARATION x25: 5-bromo-N,N-dimethyl-6-oxo-1,6-dihydropyridine-3-carboxamide

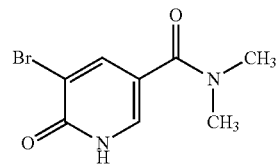

The title compound was prepared in a manner similar to PREPARATION x23 using dimethylamine in place of cyclopropanamine.

PREPARATION x26: (S)-5-bromo-N-(2-hydroxypropyl)-6-oxo-1,6-dihydropyridine-3-carboxamide

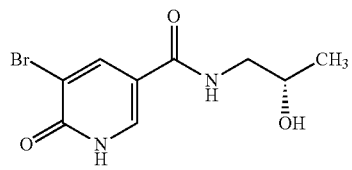

The title compound was prepared in a manner similar to PREPARATION x23 using (S)-1-aminopropan-2-ol in place of cyclopropanamine.

PREPARATION x27: (R)-5-bromo-N-(2-hydroxypropyl)-6-oxo-1,6-dihydropyridine-3-carboxamide

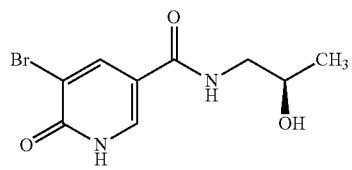

The title compound was prepared in a manner similar to PREPARATION x23 using (R)-1-aminopropan-2-ol in place of cyclopropanamine.

PREPARATION x28: 5-bromo-N-(2,3-dihydroxypropyl)-6-oxo-1,6-dihydropyridine-3-carboxamide

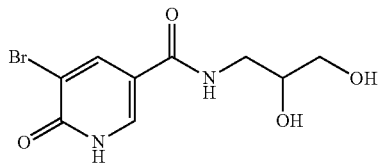 [SMILES: O=C(NCC(O)CO)c1c[nH]c(=O)c(Br)c1]

The title compound was prepared in a manner similar to PREPARATION x23 using 3-aminopropane-1,2-diol in place of cyclopropanamine.

PREPARATION x29: 5-bromo-N-(2,2-difluoro-ethyl)-6-oxo-1,6-dihydropyridine-3-carboxamide

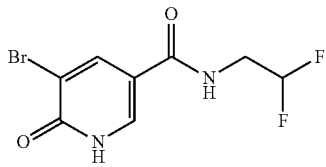 [SMILES: O=C(NCC(F)F)c1c[nH]c(=O)c(Br)c1]

The title compound was prepared in a manner similar to PREPARATION x23 using 2,2-difluoroethanamine in place of cyclopropanamine.

PREPARATION x30: 5-bromo-N,N,1-trimethyl-6-oxo-1,6-dihydropyridine-3-carboxamide

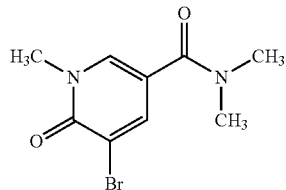

To a solution of 5-bromo-N,N-dimethyl-6-oxo-1,6-dihydropyridine-3-carboxamide (100 mg, 0.408 mmol) and iodomethane (57.9 mg, 0.408 mmol) in DMSO (3 mL) was added potassium carbonate (56.4 mg, 0.408 mmol). The mixture was stirred at room temperature overnight, filtered, and purified via preparative HPLC, eluting with a gradient of 10-90% ACN (containing 0.035% TFA) in $H_2O$ (containing 0.05% TFA). The product was dried under vacuum to give the title compound.

PREPARATION x31: 5-bromo-N-(cyanomethyl)-1-methyl-6-oxo-1,6-dihydropyridine-3-carboxamide

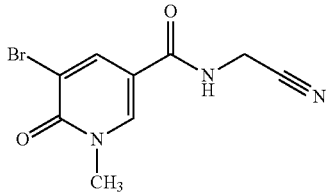

The title compound was prepared in a manner similar to PREPARATION x30 using 5-bromo-N-(cyanomethyl)-6-oxo-1,6-dihydropyridine-3-carboxamide in place of 5-bromo-N,N-dimethyl-6-oxo-1,6-dihydropyridine-3-carboxamide.

PREPARATION x32: 5-bromo-N-(2,2-difluoro-ethyl)-1-methyl-6-oxo-1,6-dihydropyridine-3-carboxamide

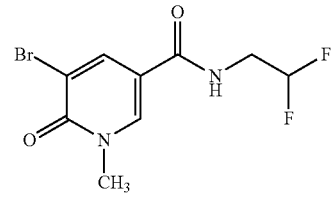

The title compound was prepared in a manner similar to PREPARATION x30 using 5-bromo-N-(2,2-difluoroethyl)-6-oxo-1,6-dihydropyridine-3-carboxamide in place of 5-bromo-N,N-dimethyl-6-oxo-1,6-dihydropyridine-3-carboxamide.

PREPARATION x33: 5-bromo-N-(2,3-dihydroxy-propyl)-1-methyl-6-oxo-1,6-dihydropyridine-3-carboxamide

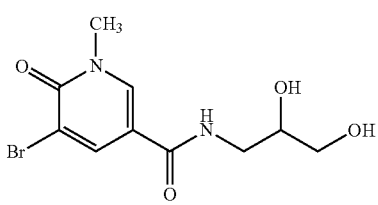 [SMILES: Cn1cc(C(=O)NCC(O)CO)cc(Br)c1=O]

The title compound was prepared in a manner similar to PREPARATION x30 using 5-bromo-N-(2,3-dihydroxypropyl)-6-oxo-1,6-dihydropyridine-3-carboxamide in place of 5-bromo-N,N-dimethyl-6-oxo-1,6-dihydropyridine-3-carboxamide.

PREPARATION x34: 5-bromo-N-cyclopropyl-1-methyl-6-oxo-1,6-dihydropyridine-3-carboxamide

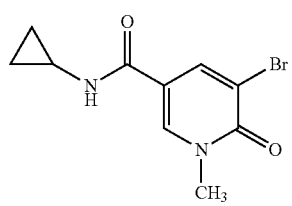

The title compound was prepared in a manner similar to PREPARATION x30 using 5-bromo-N-cyclopropyl-6-oxo-1,6-dihydropyridine-3-carboxamide in place of 5-bromo-N,N-dimethyl-6-oxo-1,6-dihydropyridine-3-carboxamide.

PREPARATION x35: (R)-5-bromo-N-(2-hydroxypropyl)-1-methyl-6-oxo-1,6-dihydropyridine-3-carboxamide

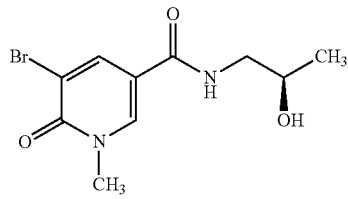

The title compound was prepared in a manner similar to PREPARATION x30 using (R)-5-bromo-N-(2-hydroxypropyl)-6-oxo-1,6-dihydropyridine-3-carboxamide in place of 5-bromo-N,N-dimethyl-6-oxo-1,6-dihydropyridine-3-carboxamide.

PREPARATION x36: (S)-5-bromo-N-(2-hydroxypropyl)-1-methyl-6-oxo-1,6-dihydropyridine-3-carboxamide

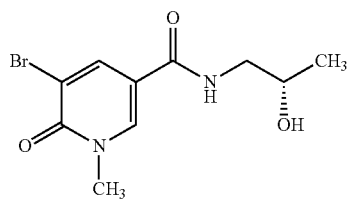 [SMILES: C[C@H](O)CNC(=O)c1cc(Br)c(=O)n(C)c1]

The title compound was prepared in a manner similar to PREPARATION x30 using (S)-5-bromo-N-(2-hydroxypropyl)-6-oxo-1,6-dihydropyridine-3-carboxamide in place of 5-bromo-N,N-dimethyl-6-oxo-1,6-dihydropyridine-3-carboxamide.

PREPARATION x37: methyl 2-(5-bromo-2-oxopyridin-1(2H)-yl)acetate

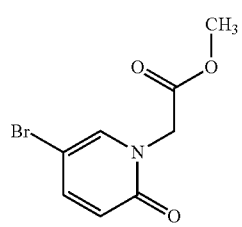

To solution of 5-bromopyridin-2(1H)-one (2.5 g, 14.37 mmol) and methyl 2-bromoacetate (2.418 g, 15.81 mmol) in DMSO (12 mL) was added $K_2CO_3$ (2.383 g, 17.24 mmol). The mixture was stirred at 60° C. for 4 hours, filtered, and purified via preparative HPLC, eluting with a gradient of 10-90% ACN (containing 0.035% TFA) in $H_2O$ (containing 0.05% TFA) to give the title compound.

PREPARATION x38: 3-bromo-1-methyl-5-(4-methylpiperazine-1-carbonyl)pyridin-2(1H)-one

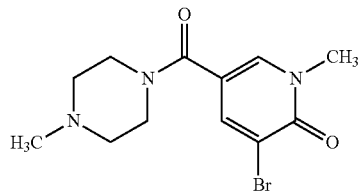 [SMILES: CN1CCN(C(=O)c2cc(Br)c(=O)n(C)c2)CC1]

A mixture of 5-iodo-1-methyl-6-oxo-1,6-dihydropyridine-3-carboxylic acid (80 mg, 0.287 mmol), 1-methylpiperazine (28.7 mg, 0.287 mmol), and 2-(1H-benzo[d][1,2,3]triazol-1-yl)-1,1,3,3-tetramethyluronium hexafluorophosphate(V) (109 mg, 0.287 mmol) in DMF (3 mL) was stirred at room temperature for 2 hours. The reaction mixture was subsequently filtered and purified via preparative HPLC, eluting with a gradient of 10-50% ACN in $H_2O$ (containing 10 mM $NH_4HCO_3$) to give the title compound.

PREPARATION x39: 1-(5-bromo-6-methylpyridin-2-yl)-4-methylpiperazine

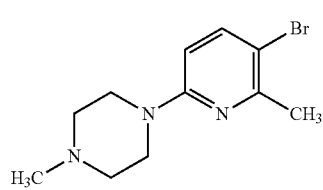

A solution of 3-bromo-6-chloro-2-methylpyridine (700 mg, 3.39 mmol) and 1-methylpiperazine (0.753 mL, 6.78 mmol) in DMF (4 mL) was heated in microwave reactor at 150° C. for 50 minutes. The mixture was subsequently purified via preparative HPLC, eluting with a gradient of 10-70% ACN (containing 0.035% TFA) in $H_2O$ (containing 0.05% TFA) to give the title compound.

PREPARATION x40: 3-bromo-1,6-dimethyl-5-(4-methylpiperazine-1-carbonyl)pyridin-2(1H)-one

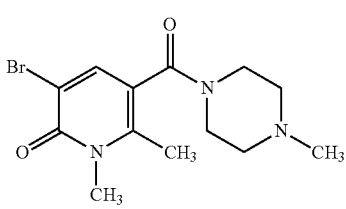 [SMILES: Cc1c(C(=O)N2CCN(C)CC2)cc(Br)c(=O)n1C]

A mixture of 5-bromo-1,2-dimethyl-6-oxo-1,6-dihydropyridine-3-carboxylic acid (70 mg, 0.284 mmol), 1-methylpiperazine (28.5 mg, 0.284 mmol), $Et_3N$ (0.1 mL) and 2-(1H-benzo[d][1,2,3]triazol-1-yl)-1,1,3,3-tetramethyluronium hexafluorophosphate(V) (108 mg, 0.284 mmol) in DMF (3 mL) was stirred at room temperature for 2 hours.

The reaction mixture was subsequently purified via preparative HPLC, eluting with a gradient of 20-70% ACN in H$_2$O (containing 10 mM NH$_4$HCO$_3$) to give the title compound.

PREPARATION x41: 5-bromo-N-(2-hydroxyethyl)-1,2-dimethyl-6-oxo-1,6-dihydropyridine-3-carboxamide

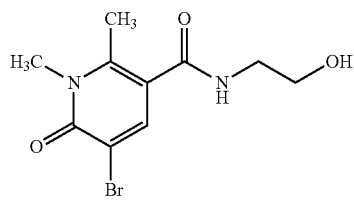 [SMILES: Cc1c(C(=O)NCCO)cc(Br)c(=O)n1C]

The title compound was prepared in a manner similar to PREPARATION x40 using 2-aminoethanol in place of 1-methylpiperazine.

PREPARATION x42: 5-bromo-1,6-dimethylpyridin-2(1H)-one

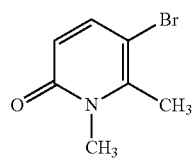

To a solution of 5-bromo-6-methylpyridin-2(1H)-one (164 mg, 0.872 mmol) and iodomethane (0.065 mL, 1.047 mmol) in DMSO (3 mL) was added K$_2$CO$_3$ (145 mg, 1.047 mmol). The mixture was stirred at 60° C. overnight, filtered, and purified via preparative HPLC, eluting with a gradient of 20-70% ACN (containing 0.035% TFA) in H$_2$O (containing 0.05% TFA) to give the title compound.

PREPARATION x43: 2-(5-bromo-6-methyl-2-oxopyridin-1(2H)-yl)acetonitrile

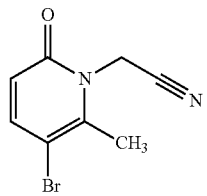

The title compound was prepared in a manner similar to PREPARATION x42 using 2-bromoacetonitrile in place of iodomethane.

PREPARATION x44: 5-bromo-6-methyl-1-(pyridin-2-ylmethyl)pyridin-2(1H)-one

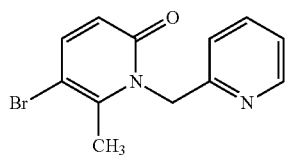 [SMILES: Cc1c(Br)ccc(=O)n1Cc1ccccn1]

The title compound was prepared in a manner similar to PREPARATION x42 using 2-(chloromethyl)pyridine hydrochloride in place of iodomethane.

PREPARATION x45: 5-bromo-1,4-dimethylpyridin-2(1H)-one

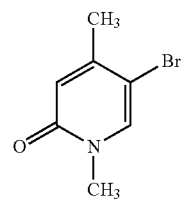

To a solution of 5-bromo-4-methylpyridin-2(1H)-one (164 mg, 0.872 mmol) and iodomethane (124 mg, 0.872 mmol) in DMSO (3 mL) was added potassium carbonate (121 mg, 0.872 mmol). The mixture was stirred at 60° C. overnight, filtered, and purified via preparative HPLC, eluting with a gradient of 20-70% ACN (containing 0.035% TFA) in H$_2$O (containing 0.05% TFA) to give the title compound.

PREPARATION x46: 5-bromo-4-methyl-1-(pyridin-2-ylmethyl)pyridin-2(1H)-one

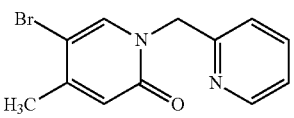 [SMILES: Cc1cc(=O)n(Cc2ccccn2)cc1Br]

The title compound was prepared in a manner similar to PREPARATION x45 using 2-(chloromethyl)pyridine hydrochloride in place of iodomethane.

PREPARATION x47: 2-(5-bromo-4-methyl-2-oxopyridin-1 (2H)-yl)acetonitrile

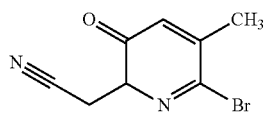

The title compound was prepared in a manner similar to PREPARATION x45 using 2-bromoacetonitrile in place of iodomethane.

PREPARATION x48: 5-bromopyridine-2-sulfonamide

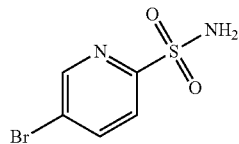 [SMILES: NS(=O)(=O)c1ccc(Br)cn1]

To a 4 mL vial equipped with a magnetic stir bar were added 5-bromopyridine-2-sulfonyl chloride hydrochloride (250 mg, 0.853 mmol) and ammonium hydroxide (1329 μL, 34.1 mmol) to give a white suspension, which was heated to 70° C. in a sand bath overnight. The solvent was subsequently evaporated to give the title compound, which was used without further purification.

PREPARATION x49: 2-(4-bromo-3,5-dimethyl-1H-pyrazol-1-yl)-N-isopropylacetamide

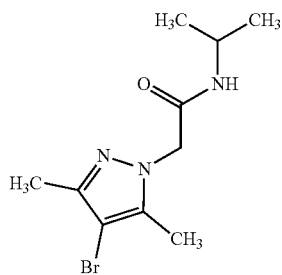

To a 4 mL vial equipped with a magnetic stir bar were added 4-bromo-3,5-dimethyl-1H-pyrazole (50 mg, 0.286 mmol), 2-bromo-N-isopropylacetamide (51.4 mg, 0.286 mmol), K$_2$CO$_3$ (118 mg, 0.857 mmol), and acetonitrile (2 mL). The contents of the vial were stirred to give a white suspension. The vial was heated in a sand bath to 70° C. for 24 hours. The reaction mixture was subsequently partitioned between water (10 mL) and ethyl acetate (15 mL). The layers were separated, and the aqueous layer was back-extracted with ethyl acetate (15 mL). The combined organic layers were concentrated to give the title compound as a white solid, which was used without further purification (80 mg).

PREPARATION x50: (S)-5-((4-bromo-3,5-dimethyl-1H-pyrazol-1-yl)methyl)pyrrolidin-2-one

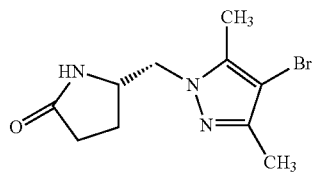

The title compound was prepared in a manner similar to PREPARATION x49 using (S)-5-(bromomethyl)pyrrolidin-2-one in place of 2-bromo-N-isopropylacetamide.

PREPARATION x51: 5-bromo-N-(2-hydroxyethyl)pyridine-2-sulfonamide

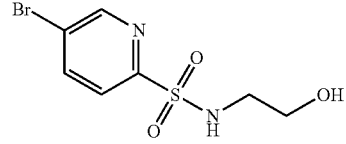 [SMILES: O=S(=O)(NCCO)c1ccc(Br)cn1]

In a 4 mL vial equipped with a magnetic stir bar were combined 5-bromopyridine-2-sulfonyl chloride hydrochloride (50 mg, 0.171 mmol), 2-aminoethanol (0.015 mL, 0.256 mmol), Et$_3$N (0.071 mL, 0.512 mmol), and acetonitrile (1 mL). The resulting yellow solution stirred at room temperature overnight. The reaction mixture was subsequently partitioned between water (10 mL) and ethyl acetate (15 mL). The layers were separated and the aqueous layer was back-extracted with ethyl acetate (15 mL). The combined organic layers were concentrated to give the title compound as a clear liquid, which was used without further purification (55 mg).

PREPARATION x52: 4-bromo-3,5-dimethyl-1-((3-methyloxetan-3-yl)methyl)-1H-pyrazole

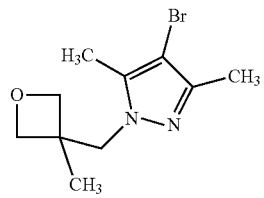

To a 4 mL vial equipped with a magnetic stir bar were added 4-bromo-3,5-dimethyl-1H-pyrazole (150 mg, 0.857 mmol), 3-(bromomethyl)-3-methyloxetane (283 mg, 1.714 mmol), K$_2$CO$_3$ (355 mg, 2.57 mmol), and acetonitrile (2 mL). The contents of the vial were stirred to give a white suspension. The vial was heated in a sand bath to 70° C. for 24 hours, and the reaction mixture was subsequently partitioned between water (15 mL) and ethyl acetate (20 mL). The layers were separated and the aqueous layer was back-extracted with ethyl acetate (20 mL). The combined organic layers were concentrated and the residue was purified via flash chromatography (4 g column) eluting with a gradient of 0-70% EtOAc in heptanes. The pure fractions were combined and concentrated to give the title compound as a clear liquid (110 mg, 49.5%).

PREPARATION x53: 3-(6-(trifluoromethyl)-1H-indazol-4-yl)imidazo[1,2-b]pyridazine-6-carboxylic acid

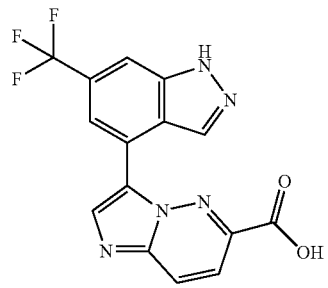 [SMILES: O=C(O)c1ccc2ncc(-c3cc(C(F)(F)F)cc4[nH]ncc34)n2n1]

To a 10 mL vial was added a mixture of 4-(4,4,5,5-tetramethyl-1,3,2-dioxaborolan-2-yl)-6-(trifluoromethyl)-1H-indazole (0.066 g, 0.211 mmol), methyl 3-bromoimidazo[1,2-b]pyridazine-6-carboxylate (0.054 g, 0.211 mmol) and PdCl₂(dppf) (7.74 mg, 10.57 µmol) in dioxane (2 mL) and aqueous saturated NaHCO₃ (1 mL). The resulting orange suspension was heated at 140° C. for 30 minutes in a microwave reactor. The major peak by LCMS was the decarboxylated product. The reaction mixture was extracted into EtOAc and the water layer was separated and acidified with concentrated HCl to pH 2. The water layer was extracted with EtOAc. The organic layers were combined, dried over Na₂SO₄, filtered, and concentrated to give an oil, which was used without further purification (36 mg).

PREPARATION x54: (5-bromopyridin-3-yl)(4-methylpiperazin-1-yl)methanone

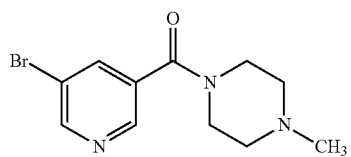 [SMILES: CN1CCN(C(=O)c2cncc(Br)c2)CC1]

5-Bromonicotinic acid (0.020 g, 0.10 mmol), 1-methylpiperazine (0.015 g, 0.15 mmol), HATU (0.046 g, 0.12 mmol), DIPEA (0.052 g, 0.40 mmol), and dioxane (2 mL) were added to a 20 mL vial. The vial was sealed and placed on a heater/shaker for 3 days at 40° C. The reaction mixture, containing the title compound, was used without purification.

PREPARATION x55: (5-bromo-2-methoxypyridin-3-yl)(4-methylpiperazin-1-yl)methanone

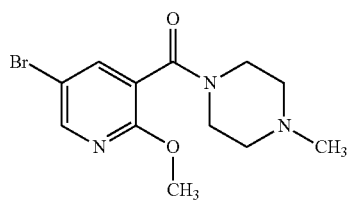 [SMILES: COc1ncc(Br)cc1C(=O)N1CCN(C)CC1]

The title compound was prepared in a manner similar to PREPARATION x54 using 5-bromo-2-methoxynicotinic acid in place of 5-bromonicotinic acid.

PREPARATION x56: (2-amino-5-bromopyridin-3-yl)(4-methylpiperazin-1-yl)methanone

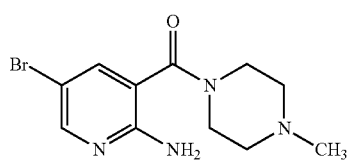 [SMILES: CN1CCN(C(=O)c2cc(Br)cnc2N)CC1]

The title compound was prepared in a manner similar to PREPARATION x54 using 2-amino-5-bromonicotinic acid in place of 5-bromonicotinic acid.

PREPARATION x57: (5-bromo-2-fluoropyridin-3-yl)(4-methylpiperazin-1-yl)methanone

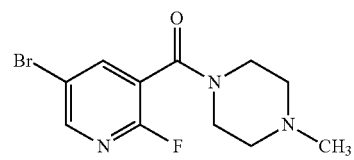 [SMILES: CN1CCN(C(=O)c2cc(Br)cnc2F)CC1]

The title compound was prepared in a manner similar to PREPARATION x54 using 5-bromo-2-fluoronicotinic acid in place of 5-bromonicotinic acid.

PREPARATION x58: 5-bromo-N-(2-hydroxyethyl)nicotinamide

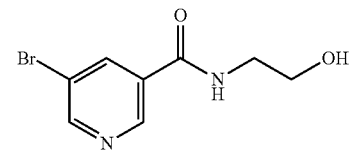 [SMILES: O=C(NCCO)c1cncc(Br)c1]

5-Bromonicotinic acid (0.020 g, 0.10 mmol), 2-aminoethanol (9.16 mg, 0.15 mmol), HATU (0.046 g, 0.12 mmol), DIPEA (0.052 g, 0.40 mmol), and dioxane (2 mL) were added to a 20 mL vial. The vial was sealed and placed on a heater/shaker for 3 days at 40° C. The reaction mixture, containing the title compound, was used without purification.

PREPARATION x59: 5-bromo-N-(2-hydroxyethyl)-2-methoxynicotinamide

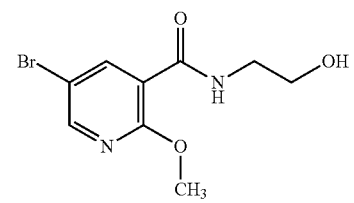

The title compound was prepared in a manner similar to PREPARATION x58 using 5-bromo-2-methoxynicotinic acid in place of 5-bromonicotinic acid.

PREPARATION x60: 4-bromo-N-(2-hydroxyethyl)picolinamide

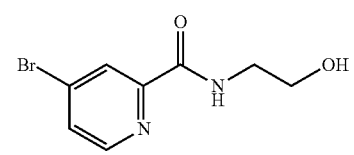 [SMILES: O=C(NCCO)c1cc(Br)ccn1]

To 4-bromopicolinic acid (0.3 g, 1.485 mmol) in DMF (4 mL) were added 2-aminoethanol (0.181 g, 2.97 mmol), HOBt (0.301 g, 2.228 mmol), and EDC (0.456 g, 2.376 mmol), followed by N-ethyl-N-isopropylpropan-2-amine (1.293 mL, 7.43 mmol). The reaction mixture was stirred for 18 hours at room temperature. The reaction mixture was diluted with DCM, washed with brine, and concentrated to give the title compound, which was used without further purification.

PREPARATION x61:
4-bromo-1,3-dimethyl-1H-pyrazole-5-carboxamide

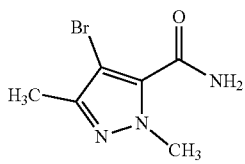

To 4-bromo-1,3-dimethyl-1H-pyrazole-5-carboxylic acid (0.3 g, 1.370 mmol) in DMF (5 mL) were added ammonium chloride (0.293 g, 5.48 mmol), HOBt (0.222 g, 1.644 mmol), and EDC (0.368 g, 1.917 mmol), followed by N-ethyl-N-isopropylpropan-2-amine (1.193 mL, 6.85 mmol). The reaction mixture was stirred for 18 hours at room temperature. The reaction mixture was subsequently diluted with EtOAc, washed with brine, dried over $Na_2SO_4$, and concentrated to give the title compound, which was used without further purification (0.28 g).

PREPARATION x62: 3-methoxy-4-(6-(trifluoromethyl)-1H-indazol-4-yl)benzoic acid

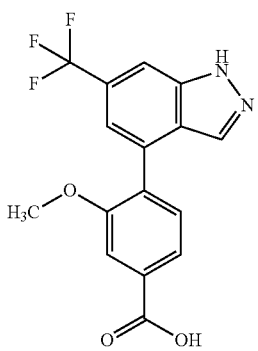 [SMILES: COc1cc(C(=O)O)ccc1-c1cc(C(F)(F)F)cc2[nH]ncc12]

To a mixture of 4-bromo-6-(trifluoromethyl)-1H-indazole (0.5 g, 1.887 mmol), 5-borono-4-methoxypyrimidine-2-carboxylic acid (0.560 g, 2.83 mmol) and $PdCl_2(dppf)$ (0.014 g, 0.019 mmol) in dioxane (10 mL) was added 2N sodium carbonate (1.887 mL, 3.77 mmol). The reaction mixture was heated in a microwave reactor at 130° C. for 1 hour. A white precipitate was subsequently filtered off, rinsing with methanol. The solvents were removed in vacuo. The residue was taken up in DMSO/methanol (1:1) and purified via preparative HPLC, eluting with a gradient of 40-50% acetonitrile (containing 0.035% TFA) in $H_2O$ (containing 0.05% TFA). The product fractions were collected and dried to give a TFA salt of the title compound as an off-white solid (153 mg, 24%). ESI-MS m/z $[M+H]^+$ calc'd for $C_{16}H_{11}F_3N_2O_3$, 337.1. found 337.2.

PREPARATION x63: 2-(3,5-dimethyl-4-(6-(trifluoromethyl)-1H-indazol-4-yl)-1H-pyrazol-1-yl)acetic acid

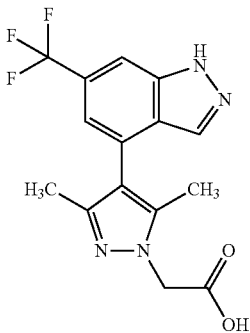 [SMILES: Cc1nn(CC(=O)O)c(C)c1-c1cc(C(F)(F)F)cc2[nH]ncc12]

To a microwave vial were added a mixture of 4-(4,4,5,5-tetramethyl-1,3,2-dioxaborolan-2-yl)-6-(trifluoromethyl)-1H-indazole (0.3 g, 0.961 mmol), ethyl 2-(4-bromo-3,5-dimethyl-1H-pyrazol-1-yl)acetate (0.351 g, 1.346 mmol) and $PdCl_2(dppf)$ (0.035 g, 0.048 mmol) in dioxane (10 mL) and aqueous saturated $NaHCO_3$ (3 mL). The resulting light yellow suspension was heated at 140° C. for 45 minutes in a microwave reactor. The reaction mixture was subsequently concentrated and the residue was purified by preparative HPLC, eluting with a gradient of 40-50% acetonitrile (containing 0.035% TFA) in $H_2O$ (containing 0.05% TFA) over a period of 6 minutes. Two products were separated. The product-containing fractions were combined and the volatiles removed in vacuo to give the title compound as the major product. ESI-MS m/z $[M+H]^+$ calc'd for $C_{15}H_{13}F_3N_4O_2$, 339.1. found 339.2.

PREPARATION x64: methyl 2-(4-methoxy-3-(6-(trifluoromethyl)-1H-indazol-4-yl)phenyl)acetate

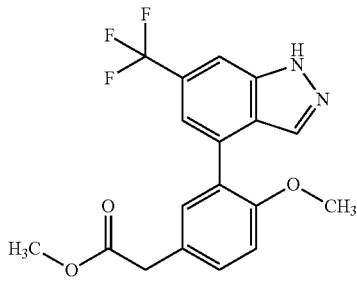

A vial was charged with a mixture of 4-bromo-6-(trifluoromethyl)-1H-indazole (0.433 g, 1.633 mmol), methyl 2-(4-methoxy-3-(4,4,5,5-tetramethyl-1,3,2-dioxaborolan-2-yl)phenyl)acetate (0.5 g, 1.633 mmol) and $PdCl_2(dppf)$ (0.060 g, 0.082 mmol) in dioxane (10 mL) and aqueous saturated $NaHCO_3$ (3 mL). The resulting light brown suspension was heated at 140° C. for 45 minutes in a microwave reactor. The reaction mixture was subsequently concentrated. The crude residue was dissolved in EtOAc and was washed with water and brine, concentrated, and purified by CombiFlash® chromatography (0-35% MeOH in DCM). The product-containing fractions were combined and concentrated by rotary evaporation to give the title compound (0.47 g, 79%). ESI-MS m/z [M+H]+ calc'd for $C_{18}H_{15}F_3N_2O_3$, 365.1. found 365.2.

PREPARATION x65: methyl 3-fluoro-4-(6-(trifluoromethyl)-1H-indazol-4-yl)benzoate

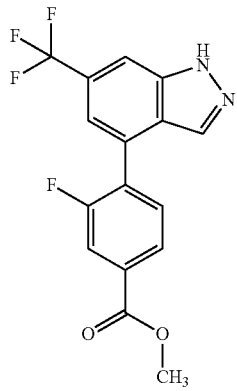 [SMILES: COC(=O)c1ccc(-c2cc(C(F)(F)F)cc3[nH]ncc23)c(F)c1]

A vial was charged with a mixture of 4-bromo-6-(trifluoromethyl)-1H-indazole (0.402 g, 1.515 mmol), (2-fluoro-4-(methoxycarbonyl)phenyl)boronic acid (0.3 g, 1.515 mmol) and PdCl$_2$(dppf) (0.055 g, 0.076 mmol) in dioxane (10 mL) and aqueous saturated NaHCO$_3$ (3 mL). The resulting light yellow suspension was heated at 140° C. for 45 minutes in a microwave reactor. The reaction mixture was subsequently concentrated. The crude residue was diluted with EtOAc and washed with water, dried over Na$_2$SO$_4$, and the volatiles were removed via rotary evaporation to give the title compound, which was used without further purification (0.4 g, 78%). ESI-MS m/z [M+H]+ calc'd for $C_{16}H_{10}F_4N_2O_2$, 339.1. found 339.1.

PREPARATION x66: methyl 3-methyl-4-(6-(trifluoromethyl)-1H-indazol-4-yl)benzoate

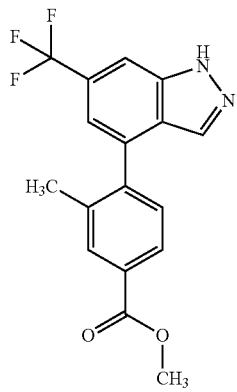 [SMILES: COC(=O)c1ccc(-c2cc(C(F)(F)F)cc3[nH]ncc23)c(C)c1]

To a microwave vial was added a mixture 4-bromo-6-(trifluoromethyl)-1H-indazole (0.478 g, 1.804 mmol), (4-(methoxycarbonyl)-2-methylphenyl)boronic acid (0.35 g, 1.804 mmol) and PdCl$_2$(dppf) (0.066 g, 0.090 mmol) in dioxane (10 mL) and aqueous saturated NaHCO$_3$ (3 mL). The resulting light yellow suspension was heated at 140° C. for 60 minutes in a microwave reactor. The reaction mixture was subsequently concentrated and the residue was diluted with EtOAc and washed with water. The volatiles were removed via rotary evaporation to give the title compound, which was used without further purification (0.53 g). ESI-MS m/z [M+H]+ calc'd for $C_{17}H_{13}F_3N_2O_2$, 335.1. found 335.2.

PREPARATION x67: ethyl 4-fluoro-3-(6-(trifluoromethyl)-1H-indazol-4-yl)benzoate

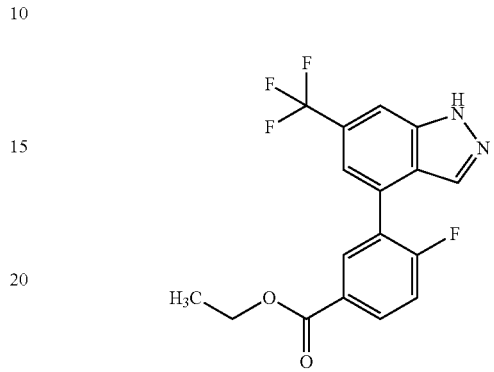

The title compound was prepared in a manner similar to PREPARATION x66 using (5-(ethoxycarbonyl)-2-fluorophenyl)boronic acid in place of (4-(methoxycarbonyl)-2-methylphenyl)boronic acid. ESI-MS m/z [M+H]+ calc'd for $C_{17}H_{12}F_4N_2O_2$, 353.1. found 353.2.

PREPARATION x68: methyl 4-methyl-3-(6-(trifluoromethyl)-1H-indazol-4-yl)benzoate

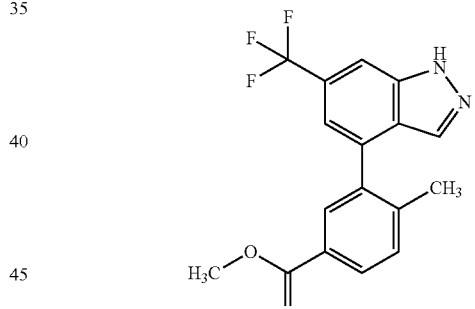

The title compound was prepared in a manner similar to PREPARATION x66 using (5-(methoxycarbonyl)-2-methylphenyl)boronic acid in place of (4-(methoxycarbonyl)-2-methylphenyl)boronic acid. ESI-MS m/z [M+H]+ calc'd for $C_{17}H_{13}F_3N_2O_2$, 335.1. found 335.1.

PREPARATION x69: 1-(2-methyl-6-(4,4,5,5-tetramethyl-1,3,2-dioxaborolan-2-yl)-1H-imidazo[4,5-b]pyridin-1-yl)ethanone

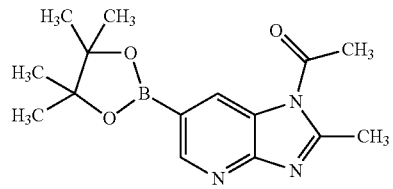

To a 250 mL round bottom flask were added 1-(6-bromo-2-methyl-1H-imidazo[4,5-b]pyridin-1-yl)ethanone (1.032 g, 4.06 mmol), 4,4,4',4',5,5,5',5'-octamethyl-2,2'-bi(1,3,2-dioxaborolane) (1.547 g, 6.09 mmol), PdCl₂(dppf) (0.149 g, 0.203 mmol), potassium acetate (0.797 g, 8.12 mmol) and dioxane (40 mL). The resulting brown suspension was purged with nitrogen for 5 minutes and then heated to reflux under nitrogen for 12 hours. The reaction mixture was treated with water and filtered. The filtrate was extracted with EtOAc. The combined organic layers were dried over MgSO₄, filtered, and concentrated to give the title compound as brown solid (1.82 g). The crude product was used without further purification.

PREPARATION x70: 2-(4-bromo-3,5-dimethyl-1H-pyrazol-1-yl)-1-(3-hydroxyazetidin-1-yl)ethanone

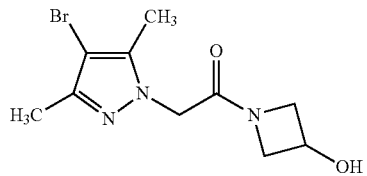 [SMILES: Cc1nn(CC(=O)N2CC(O)C2)c(C)c1Br]

To 2-(4-bromo-3,5-dimethyl-1H-pyrazol-1-yl)acetic acid (0.4 g, 1.716 mmol) in DMF (6 mL) were added azetidin-3-ol (0.151 g, 2.060 mmol), HOBt (0.301 g, 2.231 mmol), and EDC (0.461 g, 2.403 mmol), followed by N-ethyl-N-isopropylpropan-2-amine (1.495 mL, 8.58 mmol). The reaction mixture was stirred for 18 hours at room temperature. The crude reaction mixture was subsequently diluted with EtOAc, washed with brine, dried over Na₂SO₄, and concentrated to give the title compound, which was used without further purification.

PREPARATION x71: 2-(4-bromo-3,5-dimethyl-1H-pyrazol-1-yl)-N-methylacetamide

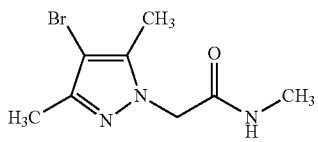

The title compound was prepared in a manner similar to PREPARATION x70 using methanamine HCl in place of azetidin-3-ol.

PREPARATION x72: 2-(4-bromo-3,5-dimethyl-1H-pyrazol-1-yl)-N-(2-hydroxyethyl)acetamide

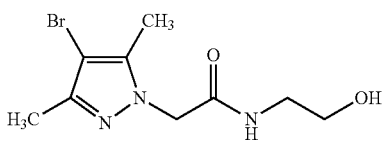

The title compound was prepared in a manner similar to PREPARATION x70 using 2-aminoethanol in place of azetidin-3-ol.

PREPARATION x73: (5-bromo-6-methyl-2-(methylamino)pyridin-3-yl)(3-hydroxyazetidin-1-yl)methanone

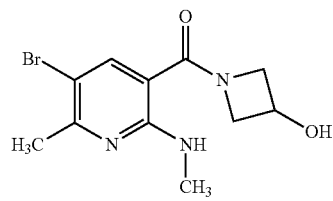 [SMILES: CNc1nc(C)c(Br)cc1C(=O)N1CC(O)C1]

To 5-bromo-6-methyl-2-(methylamino)nicotinic acid (0.2 g, 0.816 mmol) in DMF (3 mL) were added azetidin-3-ol (0.119 g, 1.632 mmol), HOBt (0.154 g, 1.143 mmol), and EDC (0.235 g, 1.224 mmol), followed by N-ethyl-N-isopropylpropan-2-amine (0.426 mL, 2.448 mmol). The reaction mixture was stirred for 18 hours at room temperature. The crude reaction mixture was subsequently diluted with EtOAc, washed with brine, dried over Na₂SO₄, and concentrated by rotary evaporation to give the title compound, which was used without further purification (0.15 g).

PREPARATION x74: 6-methoxy-5-(6-(trifluoromethyl)-1H-indazol-4-yl)picolinic acid

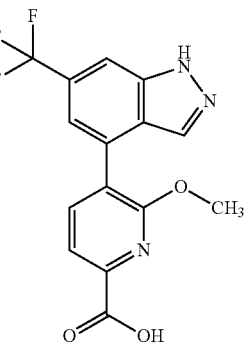

To 6-methoxy-5-(6-(trifluoromethyl)-1H-indazol-4-yl)picolinonitrile (0.5 g, 1.571 mmol) in EtOH (20 mL) was added sodium hydroxide (3.93 mL, 7.86 mmol). The reaction mixture was stirred for 50 minutes at reflux and was subsequently diluted with water and acidified with concentrated HCl. The volatiles were evaporated and the residue was purified by preparative HPLC, eluting with 45% acetonitrile (containing 0.035% TFA) in H₂O (containing 0.05% TFA) over a period of 4 minutes. The product-containing fractions were combined and the volatiles removed by rotary evaporation to give the title compound.

Example 1

4-phenyl-6-(trifluoromethyl)-1H-indazole

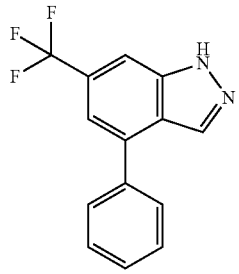 [SMILES: FC(F)(F)c1cc(-c2ccccc2)c2cn[nH]c2c1]

A vessel was charged with 4-bromo-6-(trifluoromethyl)-1H-indazole (0.1 g, 0.377 mmol), phenylboronic acid (0.069 g, 0.566 mmol), PdCl$_2$(dppf) (0.014 g, 0.019 mmol), and dioxane (3 mL). To the resulting slurry was added 2N aqueous sodium carbonate (0.377 mL, 0.755 mmol). The mixture was purged with nitrogen, heated in a microwave reactor at 120° C. for 30 minutes, and then filtered through a pad of Celite, which was rinsed with methanol. The solvent was removed in vacuo, and the resulting residue was taken up in DMSO and methanol (1:1) and was purified via acidic preparative HPLC (Waters SunFire C18, 5 µm, 30 mm ID×75 mm column), eluting with a gradient of 55-80% ACN (containing 0.035% TFA) in H$_2$O (containing 0.05% TFA). The collected fractions were dried in vacuo to give a TFA salt of the title compound as a tan solid (35 mg, 35%). $^1$H NMR (400 MHz, CDCl$_3$) δ ppm 7.43-7.62 (m, 4H), 7.71 (d, J=7.07 Hz, 2H), 7.83 (s, 1H), 8.23-8.38 (m, 1H), 8.47 (br s, 1H); ESI-MS m/z [M+H]$^+$ calc'd for C$_{14}$H$_9$F$_3$N$_2$, 263.1. found 263.1.

The compounds of EXAMPLES 2 through 52, below, were prepared in accordance with Scheme B using procedures similar to the method in EXAMPLE 1.

Scheme B

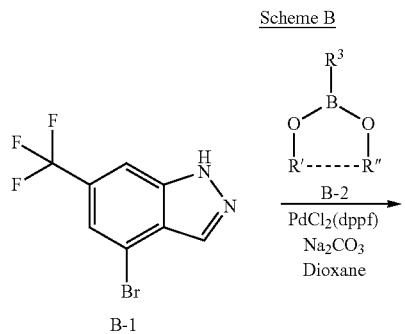

Reaction conditions: 4-bromo-6-(trifluoromethyl)-1H-indazole (B-1) (40 mg, 0.151 mmol), boronic acid (B-2, R' and R"=H) or ester (B-2, R' and R" together=2,3-dimethylbutan-2,3-diyl) (1.5 eq), PdCl$_2$(dppf) (0.1 eq), aqueous Na$_2$CO$_3$ (2N, 2-3 eq), dioxane (1.2-1.5 mL) at 130° C. for 30 minutes to 1 hour. Unless stated otherwise, the title compounds were isolated as TFA salts.

Example 2

4-(3-methylpyridin-4-yl)-6-(trifluoromethyl)-1H-indazole

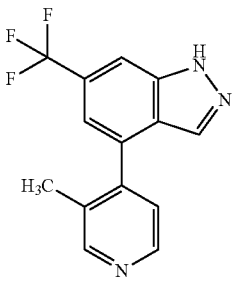 [SMILES: Cc1cnccc1-c1cc(C(F)(F)F)cc2[nH]ncc12]

ESI-MS m/z [M+H]$^+$ calc'd for C$_{14}$H$_{10}$F$_3$N$_3$, 278.1. found 278.1.

Example 3

4-(imidazo[1,2-a]pyridin-6-yl)-6-(trifluoromethyl)-1H-indazole

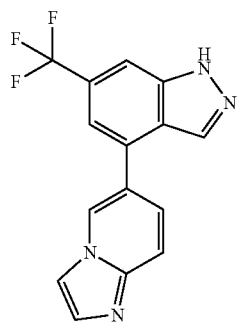 [SMILES: FC(F)(F)c1cc(-c2ccc3nccn3c2)c2cn[nH]c2c1]

ESI-MS m/z [M+H]$^+$ calc'd for C$_{15}$H$_9$F$_3$N$_4$, 303.1. found 303.1.

Example 4

7-(6-(trifluoromethyl)-1H-indazol-4-yl)-3,4-dihydro-2H-pyrido[3,2-b][1,4]oxazine

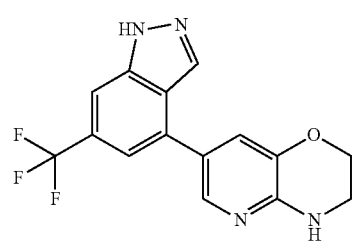 [SMILES: FC(F)(F)c1cc(-c2cnc3c(c2)OCCN3)c2cn[nH]c2c1]

ESI-MS m/z [M+H]+ calc'd for $C_{15}H_{11}F_3N_4O$, 321.1. found 321.2.

Example 5

5-(6-(trifluoromethyl)-1H-indazol-4-yl)nicotinonitrile

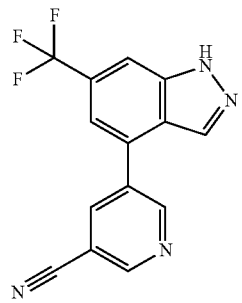 [SMILES: N#Cc1cncc(-c2cc(C(F)(F)F)cc3[nH]ncc23)c1]

$^1$H NMR (400 MHz, DMSO-$d_6$) δ ppm 7.71 (d, J=1.01 Hz, 1H), 8.06 (s, 1H), 8.48 (t, J=1.26 Hz, 1H), 8.78 (t, J=2.15 Hz, 1H), 9.15 (d, J=2.02 Hz, 1H), 9.29 (d, J=2.27 Hz, 1H), 13.83 (s, 1H); ESI-MS m/z [M+H]+ calc'd for $C_{14}H_7F_3N_4$, 289.1. found 289.1.

Example 6

4-(pyrimidin-5-yl)-6-(trifluoromethyl)-1H-indazole

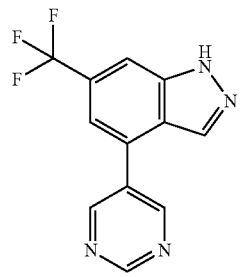 [SMILES: FC(F)(F)c1cc(-c2cncnc2)c2cn[nH]c2c1]

ESI-MS m/z [M+H]+ calc'd for $C_{12}H_7F_3N_4$, 265.1. found 265.1.

Example 7

4-(6-(trifluoromethyl)-1H-indazol-4-yl)benzamide

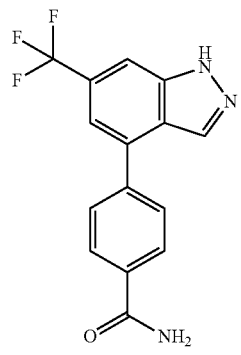

$^1$H NMR (400 MHz, DMSO-$d_6$) δ ppm 7.47 (s, 1H), 7.53 (d, J=1.01 Hz, 1H), 7.89 (d, J=8.59 Hz, 2H), 7.98 (s, 1H), 8.07 (d, J=8.34 Hz, 2H), 8.12 (s, 1H), 8.37 (s, 1H), 13.76 (s, 1H); ESI-MS m/z [M+H]+ calc'd for $C_{15}H_{10}F_3N_3O$, 306.1. found 306.1.

Example 8

(3-(6-(trifluoromethyl)-1H-indazol-4-yl)phenyl)methanol

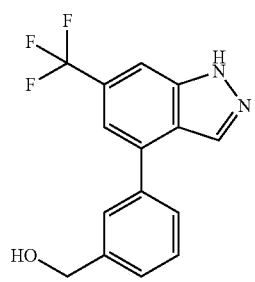 [SMILES: OCc1cccc(-c2cc(C(F)(F)F)cc3[nH]ncc23)c1]

ESI-MS m/z [M+H]+ calc'd for $C_{15}H_{11}F_3N_2O$, 293.1. found 293.1.

Example 9

5-(6-(trifluoromethyl)-1H-indazol-4-yl)pyrimidin-2-amine

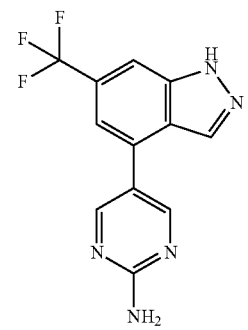 [SMILES: Nc1ncc(-c2cc(C(F)(F)F)cc3[nH]ncc23)cn1]

$^1$H NMR (400 MHz, DMSO-$d_6$) δ ppm 7.08 (br s, 2H), 7.47 (s, 1H), 7.88 (s, 1H), 8.39 (s, 1H), 8.71 (s, 2H), 13.33-14.00 (m, 1H); ESI-MS m/z [M+H]+ calc'd for $C_{12}H_8F_3N_5$, 280.1. found 280.1.

Example 10

2-(6-(trifluoromethyl)-1H-indazol-4-yl)benzamide

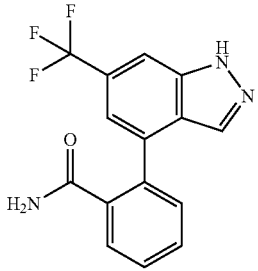 [SMILES: NC(=O)c1ccccc1-c1cc(C(F)(F)F)cc2[nH]ncc12]

ESI-MS m/z [M+H]+ calc'd for $C_{15}H_{10}F_3N_3O$, 306.1. found 306.1.

Example 11

(4-(6-(trifluoromethyl)-1H-indazol-4-yl)phenyl) methanol

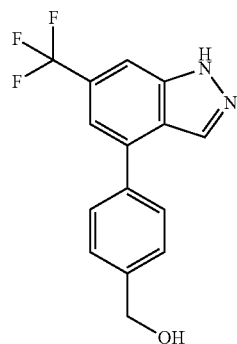 [SMILES: OCc1ccc(-c2cc(C(F)(F)F)cc3[nH]ncc23)cc1]

ESI-MS m/z [M+H]+ calc'd for $C_{15}H_{11}F_3N_2O$, 293.1. found 293.1.

Example 12

(2-(6-(trifluoromethyl)-1H-indazol-4-yl)phenyl) methanol

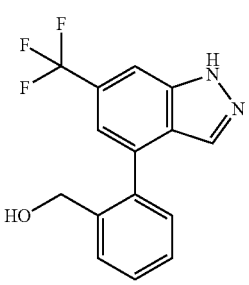 [SMILES: OCc1ccccc1-c1cc(C(F)(F)F)cc2[nH]ncc12]

ESI-MS m/z [M+H]+ calc'd for $C_{15}H_{11}F_3N_2O$, 293.1. found 293.

Example 13

4-(1H-pyrazol-3-yl)-6-(trifluoromethyl)-1H-indazole

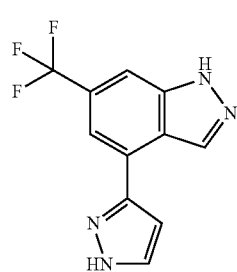 [SMILES: FC(F)(F)c1cc(-c2cc[nH]n2)c2cn[nH]c2c1]

ESI-MS m/z [M+H]+ calc'd for $C_{11}H_7F_3N_4$, 253.1. found 253.1.

Example 14

4-(pyridin-4-yl)-6-(trifluoromethyl)-1H-indazole

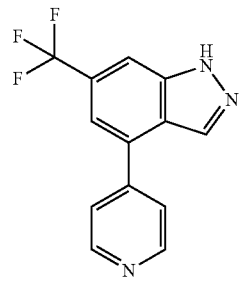 [SMILES: FC(F)(F)c1cc(-c2ccncc2)c2cn[nH]c2c1]

ESI-MS m/z [M+H]+ calc'd for $C_{13}H_8F_3N_3$, 264.1. found 264.1.

Example 15

2'-methyl-6-(trifluoromethyl)-1H,2'H-4,4'-biindazole

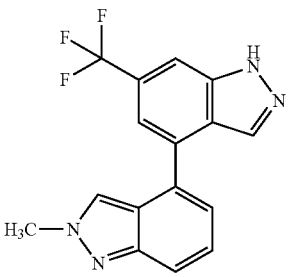 [SMILES: Cn1cc2c(-c3cc(C(F)(F)F)cc4[nH]ncc34)cccc2n1]

ESI-MS m/z [M+H]+ calc'd for $C_{16}H_{11}F_3N_4$, 317.1. found 317.2.

Example 16

5-(6-(trifluoromethyl)-1H-indazol-4-yl)pyridin-2-amine

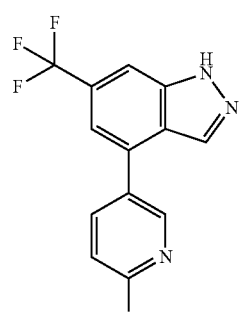

ESI-MS m/z [M+H]+ calc'd for $C_{13}H_9F_3N_4$, 279.1. found 279.1.

Example 17

4-(1H-benzo[d]imidazol-5-yl)-6-(trifluoromethyl)-1H-indazole

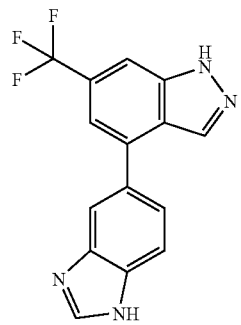 [SMILES: FC(F)(F)c1cc(-c2ccc3[nH]cnc3c2)c2cn[nH]c2c1]

¹H NMR (400 MHz, DMSO-d₆) δ ppm 7.52 (s, 1H), 7.77-7.85 (m, 1H), 7.85-7.94 (m, 1H), 7.96 (s, 1H), 8.10 (s, 1H), 8.36 (s, 1H), 8.98 (br s, 1H), 13.76 (br s, 1H); ESI-MS m/z [M+H]⁺ calc'd for $C_{15}H_9F_3N_4$, 303.1. found 303.1.

Example 18

3-(6-(trifluoromethyl)-1H-indazol-4-yl)benzamide

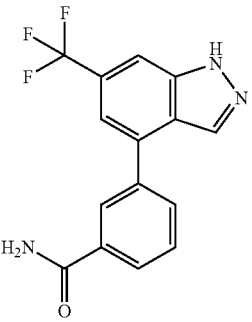 [SMILES: NC(=O)c1cccc(-c2cc(C(F)(F)F)cc3[nH]ncc23)c1]

¹H NMR (400 MHz, DMSO-d₆) δ ppm 7.51 (br s, 1H), 7.56 (d, J=1.01 Hz, 1H), 7.66 (t, J=7.83 Hz, 1H), 7.93-8.03 (m, 3H), 8.18 (s, 1H), 8.23 (s, 1H), 8.36 (s, 1H), 13.75 (s, 1H); ESI-MS m/z [M+H]⁺ calc'd for $C_{15}H_{10}F_3N_3O$, 306.1. found 306.2.

Example 19

4-(pyridin-3-yl)-6-(trifluoromethyl)-1H-indazole

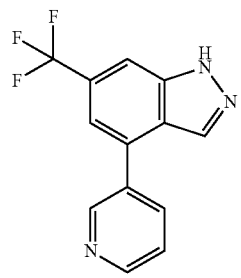 [SMILES: FC(F)(F)c1cc(-c2cccnc2)c2cn[nH]c2c1]

ESI-MS m/z [M+H]⁺ calc'd for $C_{13}H_8F_3N_3$, 264.1. found 264.1.

Example 20

4-(1-methyl-1H-pyrazol-5-yl)-6-(trifluoromethyl)-1H-indazole

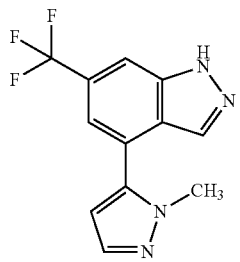 [SMILES: Cn1nccc1-c1cc(C(F)(F)F)cc2[nH]ncc12]

ESI-MS m/z [M+H]⁺ calc'd for $C_{12}H_9F_3N_4$, 267.1. found 267.1.

Example 21

4-(1-methyl-1H-pyrazol-5-yl)-6-(trifluoromethyl)-1H-indazole

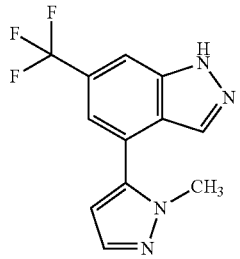 [SMILES: Cn1nccc1-c1cc(C(F)(F)F)cc2[nH]ncc12]

The title compound was isolated as the free base. ¹H NMR (400 MHz, DMSO-d₆) δ ppm 3.87 (s, 3H), 6.67 (d, J=1.77 Hz, 1H), 7.51 (s, 1H), 7.63 (d, J=1.77 Hz, 1H), 8.03 (s, 1H), 8.19 (s, 1H), 13.81 (s, 1H); ESI-MS m/z [M+H]⁺ calc'd for $C_{12}H_9F_3N_4$, 267.1. found 267.1.

Example 22

4-(3-methyl-1H-pyrazol-4-yl)-6-(trifluoromethyl)-1H-indazole

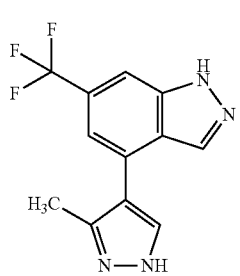 [SMILES: Cc1n[nH]cc1-c1cc(C(F)(F)F)cc2[nH]ncc12]

ESI-MS m/z [M+H]$^+$ calc'd for $C_{12}H_9F_3N_4$, 267.1. found 267.1.

Example 23

4-(1H-pyrazol-4-yl)-6-(trifluoromethyl)-1H-indazole

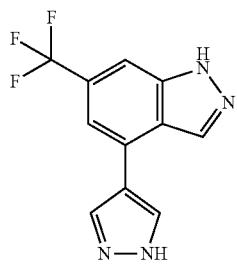 [SMILES: FC(F)(F)c1cc(-c2cn[nH]c2)c2cn[nH]c2c1]

ESI-MS m/z [M+H]$^+$ calc'd for $C_{11}H_7F_3N_4$, 253.1. found 253.1.

Example 24

1'-methyl-6-(trifluoromethyl)-1H,1'H-4,6'-biindazole

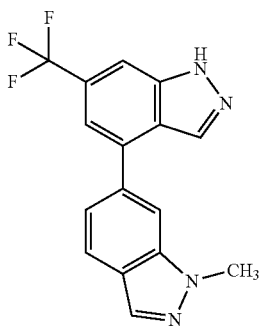 [SMILES: Cn1ncc2ccc(-c3cc(C(F)(F)F)cc4[nH]ncc34)cc21]

ESI-MS m/z [M+H]$^+$ calc'd for $C_{16}H_{11}F_3N_4$, 317.1. found 317.2.

Example 25

4-(6-(trifluoromethyl)-1H-indazol-4-yl)benzenesulfonamide

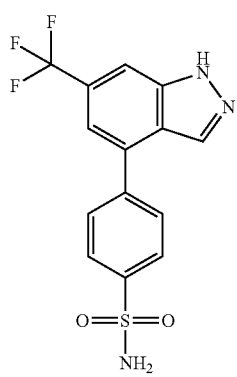

ESI-MS m/z [M+H]$^+$ calc'd for $C_{14}H_{10}F_3N_3O_2S$, 342.0. found 342.1.

Example 26

7-(6-(trifluoromethyl)-1H-indazol-4-yl)isoquinoline

ESI-MS m/z [M+H]$^+$ calc'd for $C_{17}H_{10}F_3N_3$, 314.1. found 314.2.

Example 27

4-(benzo[d][1,3]dioxol-4-yl)-6-(trifluoromethyl)-1H-indazole

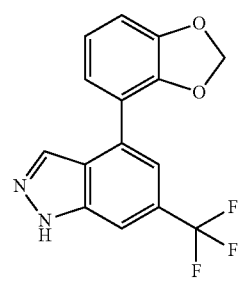 [SMILES: FC(F)(F)c1cc(-c2cccc3c2OCO3)c2cn[nH]c2c1]

ESI-MS m/z [M+H]$^+$ calc'd for $C_{15}H_9F_3N_2O_2$, 307.1. found 307.1.

Example 28

N-isobutyl-3-(6-(trifluoromethyl)-1H-indazol-4-yl)benzamide

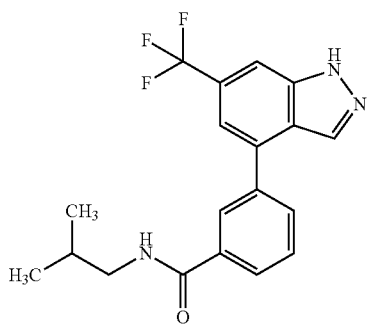 [SMILES: CC(C)CNC(=O)c1cccc(-c2cc(C(F)(F)F)cc3[nH]ncc23)c1]

ESI-MS m/z [M+H]+ calc'd for C19H18F3N3O, 362.1. found 362.3.

Example 29

(5-(6-(trifluoromethyl)-1H-indazol-4-yl)pyridin-3-yl)methanol

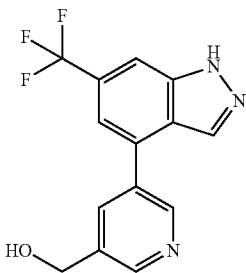 [SMILES: OCc1cncc(-c2cc(C(F)(F)F)cc3[nH]ncc23)c1]

ESI-MS m/z [M+H]+ calc'd for C14H10F3N3O, 294.1. found 294.1.

Example 30

4-(4-methoxypyridin-3-yl)-6-(trifluoromethyl)-1H-indazole

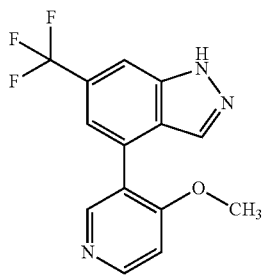 [SMILES: COc1ccncc1-c1cc(C(F)(F)F)cc2[nH]ncc12]

ESI-MS m/z [M+H]+ calc'd for C14H10F3N3O, 294.1. found 294.2.

Example 31

8-(6-(trifluoromethyl)-1H-indazol-4-yl)quinoline

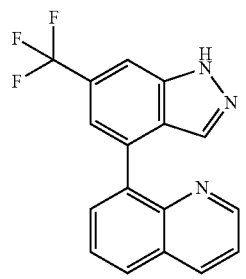 [SMILES: FC(F)(F)c1cc(-c2cccc3cccnc23)c2cn[nH]c2c1]

$^1$H NMR (400 MHz, DMSO-d$_6$) δ ppm 7.51 (d, J=1.01 Hz, 1H), 7.61 (dd, J=8.34, 4.29 Hz, 1H), 7.71-7.77 (m, 1H), 7.76-7.83 (m, 1H), 7.94 (dd, J=7.20, 1.39 Hz, 1H), 7.98 (s, 1H), 8.15 (dd, J=8.21, 1.39 Hz, 1H), 8.52 (dd, J=8.59, 1.77 Hz, 1H), 8.83 (dd, J=4.29, 1.77 Hz, 1H), 13.62 (s, 1H); ESI-MS m/z [M+H]+ calc'd for C17H10F3N3, 314.1. found 314.1.

Example 32

N,N-diethyl-3-(6-(trifluoromethyl)-1H-indazol-4-yl)benzamide

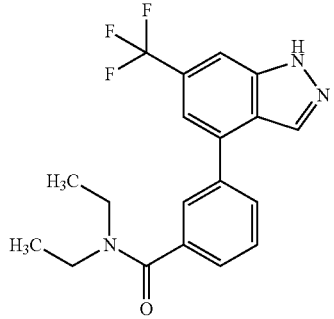 [SMILES: CCN(CC)C(=O)c1cccc(-c2cc(C(F)(F)F)cc3[nH]ncc23)c1]

ESI-MS m/z [M+H]+ calc'd for C19H18F3N3O, 362.1. found 362.3.

Example 33

3-(6-(trifluoromethyl)-1H-indazol-4-yl)benzonitrile

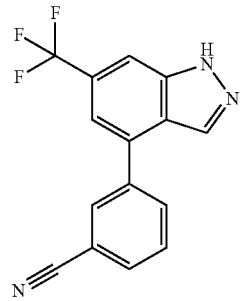 [SMILES: N#Cc1cccc(-c2cc(C(F)(F)F)cc3[nH]ncc23)c1]

ESI-MS m/z [M+H]+ calc'd for C15H8F3N3, 288.1. found 288.1.

Example 34

N-benzyl-3-(6-(trifluoromethyl)-1H-indazol-4-yl)benzamide

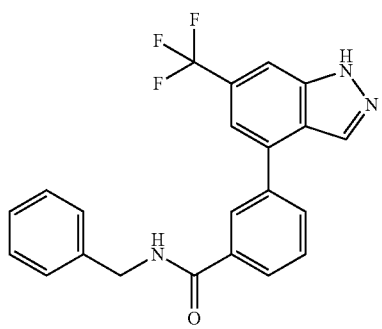 [SMILES: O=C(NCc1ccccc1)c1cccc(-c2cc(C(F)(F)F)cc3[nH]ncc23)c1]

ESI-MS m/z [M+H]+ calc'd for $C_{22}H_{16}F_3N_3O$, 396.1. found 396.3.

Example 35

N-cyclopropyl-4-(6-(trifluoromethyl)-1H-indazol-4-yl)benzamide

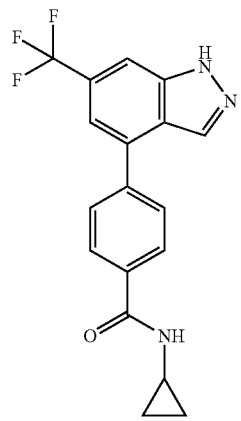 [SMILES: O=C(NC1CC1)c1ccc(-c2cc(C(F)(F)F)cc3[nH]ncc23)cc1]

ESI-MS m/z [M+H]+ calc'd for $C_{18}H_{14}F_3N_3O$, 346.1. found 346.2.

Example 36

1'-methyl-6-(trifluoromethyl)-1H,1'H-4,5'-biindazole

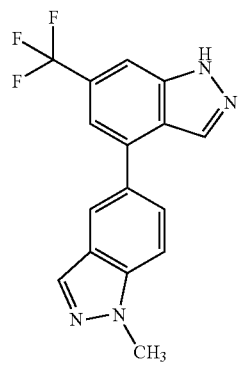 [SMILES: Cn1ncc2cc(-c3cc(C(F)(F)F)cc4[nH]ncc34)ccc21]

$^1$H NMR (400 MHz, CD$_3$OD) δ ppm 4.14 (s, 3H), 7.47 (d, J=1.26 Hz, 1H), 7.74 (d, J=8.59 Hz, 1H), 7.80-7.85 (m, 1H), 7.87 (s, 1H), 8.11-8.16 (m, 2H), 8.29 (d, J=1.01 Hz, 1H); ESI-MS m/z [M+H]+ calc'd for $C_{16}H_{11}F_3N_4$, 317.1. found 317.2.

Example 37

2-methyl-5-(3-(6-(trifluoromethyl)-1H-indazol-4-yl)phenyl)-1,3,4-oxadiazole

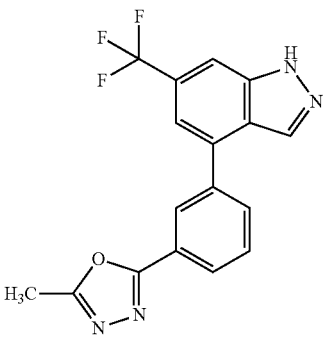 [SMILES: Cc1nnc(-c2cccc(-c3cc(C(F)(F)F)cc4[nH]ncc34)c2)o1]

$^1$H NMR (400 MHz, DMSO-d$_6$) δ ppm 2.62 (s, 3H), 7.58 (s, 1H), 7.80 (t, J=7.83 Hz, 1H), 8.01 (s, 1H), 8.03-8.08 (m, 1H), 8.11 (d, J=7.58 Hz, 1H), 8.29 (t, J=1.52 Hz, 1H), 8.37 (s, 1H), 13.81 (s, 1H); ESI-MS m/z [M+H]+ calc'd for $C_{17}H_{11}F_3N_4O$, 345.1. found 345.2.

Example 38

2-(3-(6-(trifluoromethyl)-1H-indazol-4-yl)phenyl)acetamide

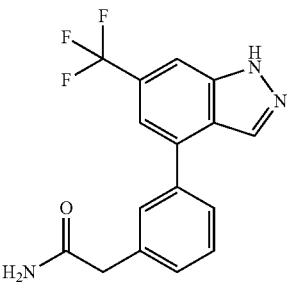 [SMILES: NC(=O)Cc1cccc(-c2cc(C(F)(F)F)cc3[nH]ncc23)c1]

ESI-MS m/z [M+H]+ calc'd for $C_{16}H_{12}F_3N_3O$, 320.1. found 320.2.

Example 39

4-(1,3-dimethyl-1H-pyrazol-4-yl)-6-(trifluoromethyl)-1H-indazole

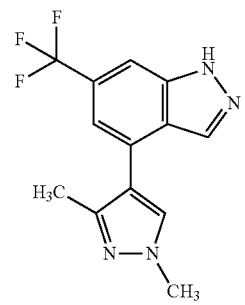 [SMILES: Cc1nn(C)cc1-c1cc(C(F)(F)F)cc2[nH]ncc12]

ESI-MS m/z [M+H]+ calc'd for $C_{13}H_{11}F_3N_4$, 281.1. found 281.2.

Example 40

2,4-dimethyl-5-(6-(trifluoromethyl)-1H-indazol-4-yl)thiazole

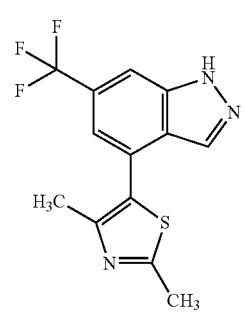 [SMILES: Cc1nc(C)c(-c2cc(C(F)(F)F)cc3[nH]ncc23)s1]

ESI-MS m/z [M+H]+ calc'd for $C_{13}H_{10}F_3N_3S$, 298.1. found 298.1.

Example 41

4-(pyrazolo[1,5-a]pyridin-3-yl)-6-(trifluoromethyl)-1H-indazole

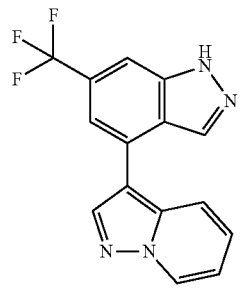 [SMILES: FC(F)(F)c1cc(-c2cnn3ccccc23)c2cn[nH]c2c1]

ESI-MS m/z [M+H]+ calc'd for $C_{15}H_9F_3N_4$, 303.1. found 303.1.

Example 42

4-(5-methoxypyridin-3-yl)-6-(trifluoromethyl)-1H-indazole

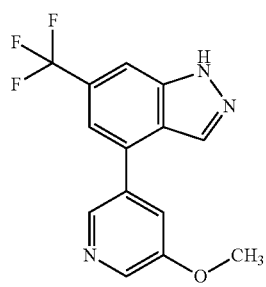

$^1$H NMR (400 MHz, DMSO-d$_6$) δ ppm 3.97 (s, 3H), 7.61 (s, 1H), 7.83 (d, J=2.02 Hz, 1H), 8.02 (s, 1H), 8.42 (d, J=0.76 Hz, 1H), 8.46 (d, J=2.53 Hz, 1H), 8.62 (d, J=1.01 Hz, 1H), 13.81 (s, 1H); ESI-MS m/z [M+H]+ calc'd for $C_{14}H_{10}F_3N_3O$, 294.1. found 294.1.

Example 43

4-(1-(pyridin-4-ylmethyl)-1H-pyrazol-4-yl)-6-(trifluoromethyl)-1H-indazole

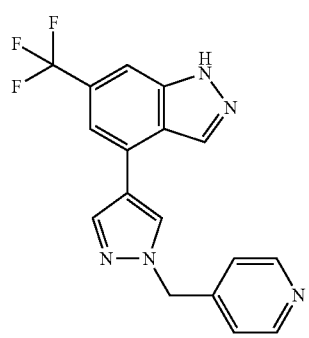 [SMILES: FC(F)(F)c1cc(-c2cnn(Cc3ccncc3)c2)c2cn[nH]c2c1]

ESI-MS m/z [M+H]+ calc'd for $C_{17}H_{12}F_3N_5$, 344.1. found 344.2.

Example 44

N-(2-(6-(trifluoromethyl)-1H-indazol-4-yl)phenyl)methanesulfonamide

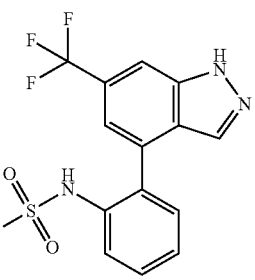

$^1$H NMR (400 MHz, DMSO-d$_6$) δ ppm 2.79 (s, 3H), 7.34-7.45 (m, 2H), 7.45-7.60 (m, 3H), 7.89-7.97 (m, 2H), 9.08 (s, 1H), 13.61 (s, 1H); ESI-MS m/z [M+H]+ calc'd for $C_{15}H_{12}F_3N_3O_2S$, 356.1. found 356.2.

Example 45

4-(3-methoxypyridin-4-yl)-6-(trifluoromethyl)-1H-indazole

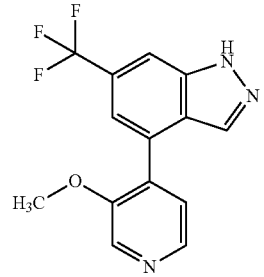 [SMILES: COc1cnccc1-c1cc(C(F)(F)F)cc2[nH]ncc12]

ESI-MS m/z [M+H]+ calc'd for $C_{14}H_{10}F_3N_3O$, 294.1. found 294.2.

Example 46

4-(3-fluoropyridin-4-yl)-6-(trifluoromethyl)-1H-indazole

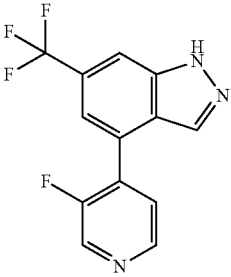

ESI-MS m/z [M+H]+ calc'd for $C_{13}H_7F_4N_3$, 282.1. found 282.1.

Example 47

N,N-dimethyl-2-(6-(trifluoromethyl)-1H-indazol-4-yl)benzamide

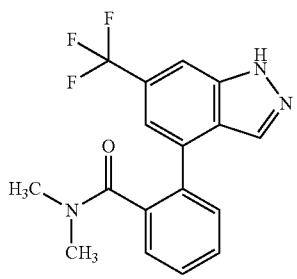 [SMILES: CN(C)C(=O)c1ccccc1-c1cc(C(F)(F)F)cc2[nH]ncc12]

ESI-MS m/z [M+H]+ calc'd for $C_{17}H_{14}F_3N_3O$, 334.1. found 334.2.

Example 48

4-(4-(methoxymethyl)phenyl)-6-(trifluoromethyl)-1H-indazole

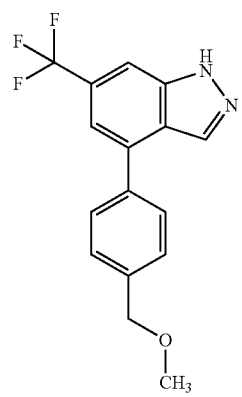 [SMILES: COCc1ccc(-c2cc(C(F)(F)F)cc3[nH]ncc23)cc1]

ESI-MS m/z [M+H]+ calc'd for $C_{16}H_{13}F_3N_2O$, 307.1. found 307.2.

Example 49

4-(3-chloropyridin-4-yl)-6-(trifluoromethyl)-1H-indazole

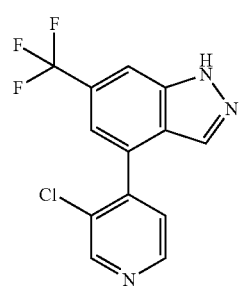

ESI-MS m/z [M+H]+ calc'd for $C_{13}H_7ClF_3N_3$, 298.0. found 298.1.

Example 50

4-(2-methylpyridin-3-yl)-6-(trifluoromethyl)-1H-indazole

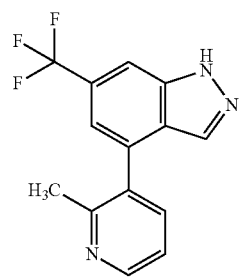 [SMILES: Cc1ncccc1-c1cc(C(F)(F)F)cc2[nH]ncc12]

ESI-MS m/z [M+H]+ calc'd for $C_{14}H_{10}F_3N_3$, 278.1. found 278.1.

Example 51

4-(1-methyl-1H-indol-2-yl)-6-(trifluoromethyl)-1H-indazole

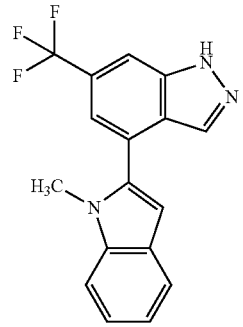 [SMILES: Cn1c(-c2cc(C(F)(F)F)cc3[nH]ncc23)cc2ccccc21]

ESI-MS m/z [M+H]+ calc'd for $C_{17}H_{12}F_3N_3$, 316.1. found 316.2.

Example 52

2-(6-(trifluoromethyl)-1H-indazol-4-yl)benzonitrile

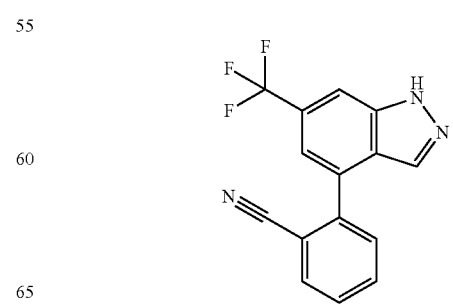

ESI-MS m/z [M+H]+ calc'd for $C_{15}H_8F_3N_3$, 288.1. found 288.1.

Example 53

4-(2-methoxypyridin-3-yl)-6-(trifluoromethyl)-1H-indazole

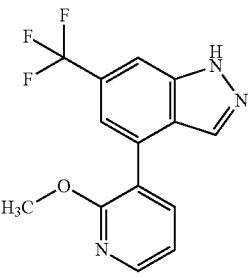 [SMILES: COc1ncccc1-c1cc(C(F)(F)F)cc2[nH]ncc12]

ESI-MS m/z [M+H]+ calc'd for $C_{14}H_{10}F_3N_3O$, 294.1. found 294.2.

Example 54

5-(6-(trifluoromethyl)-1H-indazol-4-yl)pyrimidine-2,4(1H,3H)-dione

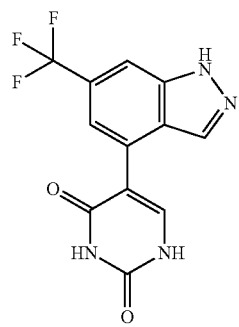 [SMILES: O=c1[nH]cc(-c2cc(C(F)(F)F)cc3[nH]ncc23)c(=O)[nH]1]

ESI-MS m/z [M+H]+ calc'd for $C_{12}H_7F_3N_4O_2$, 297.1. found 297.1.

Example 55

4-(2,6-dimethoxypyridin-3-yl)-6-(trifluoromethyl)-1H-indazole

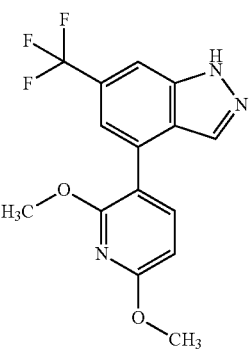 [SMILES: COc1ccc(-c2cc(C(F)(F)F)cc3[nH]ncc23)c(OC)n1]

$^1$H NMR (400 MHz, DMSO-$d_6$) δ ppm 3.91 (s, 3H), 3.96 (s, 3H), 6.57 (d, J=8.08 Hz, 1H), 7.36 (s, 1H), 7.79-7.96 (m, 2H), 8.04 (s, 1H), 13.58 (s, 1H); ESI-MS m/z [M+H]+ calc'd for $C_{15}H_{12}F_3N_3O_2$, 324.1. found 324.2.

Example 56

N-(4-(6-(trifluoromethyl)-1H-indazol-4-yl)phenyl)methanesulfonamide

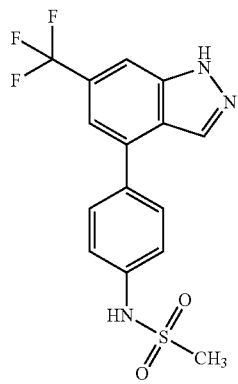 [SMILES: CS(=O)(=O)Nc1ccc(-c2cc(C(F)(F)F)cc3[nH]ncc23)cc1]

$^1$H NMR (400 MHz, CD$_3$OD) δ ppm 3.05 (s, 3H), 7.43 (d, J=1.26 Hz, 1H), 7.43-7.48 (m, 2H), 7.71-7.78 (m, 2H), 7.87 (s, 1H), 8.29 (d, J=1.01 Hz, 1H); ESI-MS m/z [M+H]+ calc'd for $C_{15}H_{12}F_3N_3O_2S$, 356.1. found 356.2.

Example 57

4-(3-(6-(trifluoromethyl)-1H-indazol-4-yl)phenyl)morpholine

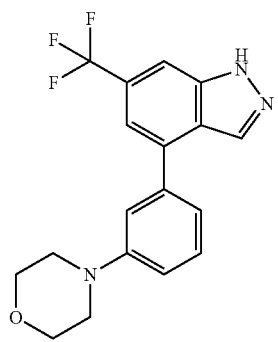 [SMILES: FC(F)(F)c1cc(-c2cccc(N3CCOCC3)c2)c2cn[nH]c2c1]

$^1$H NMR (400 MHz, CD$_3$OD) δ ppm 3.39-3.47 (m, 4H), 3.91-3.98 (m, 4H), 7.32 (ddd, J=8.34, 2.53, 1.01 Hz, 1H), 7.42-7.48 (m, 2H), 7.49-7.52 (m, 1H), 7.53-7.60 (m, 1H), 7.88-7.92 (m, 1H), 8.26 (d, J=1.01 Hz, 1H); ESI-MS m/z [M+H]+ calc'd for $C_{18}H_{16}F_3N_3O$, 348.1. found 348.2.

Example 58

4-(6-(cyclopropylmethoxy)pyridin-3-yl)-6-(trifluoromethyl)-1H-indazole

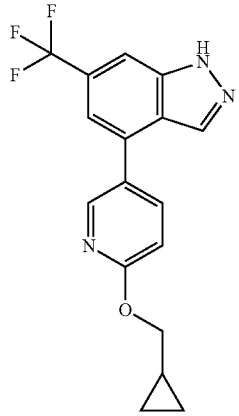 [SMILES: FC(F)(F)c1cc(-c2ccc(OCC3CC3)nc2)c2cn[nH]c2c1]

$^{1}$H NMR (400 MHz, CD$_3$OD) δ ppm 0.34-0.44 (m, 2H), 0.56-0.71 (m, 2H), 1.24-1.44 (m, 1H), 4.22 (d, J=7.07 Hz, 2H), 6.99-7.08 (m, 1H), 7.43 (d, J=1.01 Hz, 1H), 7.90 (s, 1H), 8.12 (dd, J=8.72, 2.65 Hz, 1H), 8.27 (d, J=1.01 Hz, 1H), 8.50 (d, J=2.02 Hz, 1H); ESI-MS m/z [M+H]$^+$ calc'd for C$_{17}$H$_{14}$F$_3$N$_3$O, 334.1. found 334.2.

Example 59

4-(1H-pyrrolo[2,3-b]pyridin-5-yl)-6-(trifluoromethyl)-1H-indazole

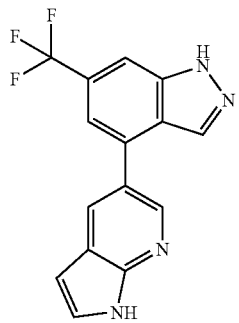 [SMILES: FC(F)(F)c1cc(-c2cnc3[nH]ccc3c2)c2cn[nH]c2c1]

$^{1}$H NMR (400 MHz, CD$_3$OD) δ ppm 6.80 (d, J=3.54 Hz, 1H), 7.50-7.60 (m, 1H), 7.64 (d, J=3.54 Hz, 1H), 7.96 (s, 1H), 8.33 (d, J=1.01 Hz, 1H), 8.67 (s, 2H); ESI-MS m/z [M+H]$^+$ calc'd for C$_{15}$H$_9$F$_3$N$_4$, 303.1. found 303.2.

Example 60

4-(4-(6-(trifluoromethyl)-1H-indazol-4-yl)thiazol-2-yl)morpholine

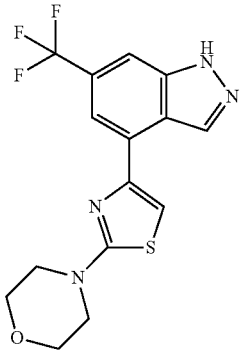 [SMILES: FC(F)(F)c1cc(-c2csc(N3CCOCC3)n2)c2cn[nH]c2c1]

$^{1}$H NMR (400 MHz, CD$_3$OD) δ ppm 3.55-3.63 (m, 4H), 3.81-3.91 (m, 4H), 7.42 (s, 1H), 7.84 (d, J=9.60 Hz, 2H), 8.68 (s, 1H); ESI-MS m/z [M+H]$^+$ calc'd for C$_{15}$H$_{13}$F$_3$N$_4$OS, 355.1. found 355.2.

Example 61

4-(3-(1H-pyrazol-3-yl)phenyl)-6-(trifluoromethyl)-1H-indazole

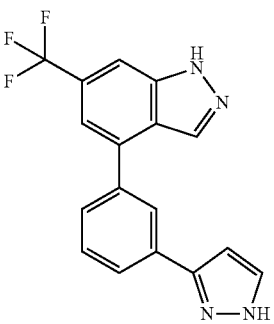 [SMILES: FC(F)(F)c1cc(-c2cccc(-c3cc[nH]n3)c2)c2cn[nH]c2c1]

$^{1}$H NMR (400 MHz, CD$_3$OD) δ ppm 6.83 (d, J=2.53 Hz, 1H), 7.52 (d, J=1.01 Hz, 1H), 7.61-7.68 (m, 1H), 7.72-7.76 (m, 1H), 7.77 (d, J=2.27 Hz, 1H), 7.87-7.91 (m, 1H), 7.92 (s, 1H), 8.17 (t, J=1.52 Hz, 1H), 8.33 (d, J=1.01 Hz, 1H); ESI-MS m/z [M+H]$^+$ calc'd for C$_{17}$H$_{11}$F$_3$N$_4$, 329.1. found 329.2.

Example 62

4-(4-(1H-pyrazol-5-yl)phenyl)-6-(trifluoromethyl)-1H-indazole

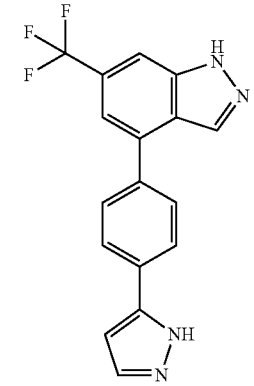 [SMILES: FC(F)(F)c1cc(-c2ccc(-c3ccn[nH]3)cc2)c2cn[nH]c2c1]

$^{1}$H NMR (400 MHz, CD$_3$OD) δ ppm 6.81 (d, J=2.27 Hz, 1H), 7.49 (d, J=1.01 Hz, 1H), 7.76 (d, J=2.27 Hz, 1H), 7.81-7.83 (m, 1H), 7.83-7.86 (m, 1H), 7.89-7.91 (m, 1H), 7.97-7.99 (m, 1H), 7.99-8.01 (m, 1H), 8.32 (d, J=1.01 Hz, 1H); ESI-MS m/z [M+H]$^+$ calc'd for C$_{17}$H$_{11}$F$_3$N$_4$, 329.1. found 329.2.

Example 63

2-chloro-5-(6-(trifluoromethyl)-1H-indazol-4-yl)benzamide

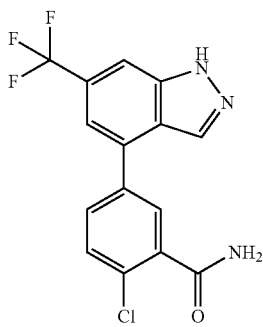 [SMILES: NC(=O)c1cc(-c2cc(C(F)(F)F)cc3[nH]ncc23)ccc1Cl]

The title compound was isolated as the free base. $^1$H NMR (400 MHz, CD$_3$OD) δ ppm 7.50 (s, 1H), 7.68 (d, J=8.34 Hz, 1H), 7.80-7.85 (m, 1H), 7.86 (d, J=2.27 Hz, 1H), 7.94 (s, 1H), 8.31-8.36 (m, 1H); ESI-MS m/z [M+H]$^+$ calc'd for C$_{15}$H$_9$ClF$_3$N$_3$O, 340.0. found 340.1.

Example 64

4-(1-methyl-1H-benzo[d]imidazol-6-yl)-6-(trifluoromethyl)-1H-indazole

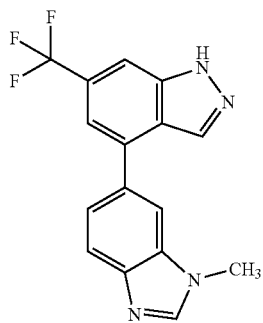 [SMILES: Cn1cnc2ccc(-c3cc(C(F)(F)F)cc4[nH]ncc34)cc21]

$^1$H NMR (400 MHz, CD$_3$OD) δ ppm 4.21 (s, 3H), 7.60 (d, J=1.26 Hz, 1H), 7.98 (s, 1H), 7.99-8.06 (m, 2H), 8.26 (s, 1H), 8.35 (d, J=1.01 Hz, 1H), 9.32 (s, 1H); ESI-MS m/z [M+H]$^+$ calc'd for C$_{16}$H$_{11}$F$_3$N$_4$, 317.1. found 317.2.

Example 65

4-(3-fluoro-4-(6-(trifluoromethyl)-1H-indazol-4-yl)pyridin-2-yl)morpholine

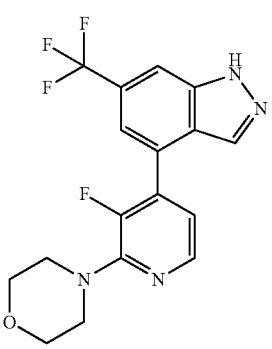 [SMILES: Fc1c(-c2cc(C(F)(F)F)cc3[nH]ncc23)ccnc1N1CCOCC1]

$^1$H NMR (400 MHz, CD$_3$OD) δ ppm 3.51-3.57 (m, 4H), 3.83-3.89 (m, 4H), 7.11-7.15 (m, 1H), 7.51 (s, 1H), 8.02 (d, J=1.26 Hz, 1H), 8.10 (dd, J=2.27, 1.01 Hz, 1H), 8.13 (d, J=5.05 Hz, 1H); ESI-MS m/z [M+H]$^+$ calc'd for C$_{17}$H$_{14}$F$_4$N$_4$O, 367.1. found 367.2.

Example 66

4-(5-fluoro-1H-pyrrolo[2,3-b]pyridin-4-yl)-6-(trifluoromethyl)-1H-indazole

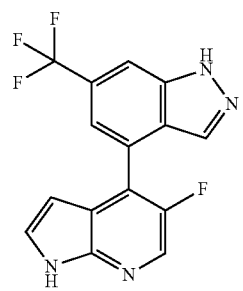 [SMILES: Fc1cnc2[nH]ccc2c1-c1cc(C(F)(F)F)cc2[nH]ncc12]

$^1$H NMR (400 MHz, CD$_3$OD) δ ppm 6.32 (d, J=3.54 Hz, 1H), 7.55 (d, J=3.54 Hz, 1H), 7.61 (s, 1H), 7.97 (dd, J=2.27, 1.01 Hz, 1H), 8.05 (s, 1H), 8.33 (d, J=3.03 Hz, 1H); ESI-MS m/z [M+H]$^+$ calc'd for C$_{15}$H$_8$F$_4$N$_4$, 321.1. found 321.1.

Example 67

1',3'-dimethyl-6-(trifluoromethyl)-1H,1'H-4,6'-biindazole

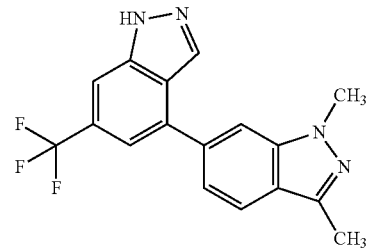 [SMILES: Cc1nn(C)c2cc(-c3cc(C(F)(F)F)cc4[nH]ncc34)ccc12]

$^1$H NMR (400 MHz, CD$_3$OD) δ ppm 2.60 (s, 3H), 4.07 (s, 3H), 7.52 (dd, J=8.46, 1.39 Hz, 1H), 7.54 (d, J=1.01 Hz, 1H), 7.80-7.82 (m, 1H), 7.88 (dd, J=8.34, 0.76 Hz, 1H), 7.92 (s, 1H), 8.32 (d, J=1.01 Hz, 1H); ESI-MS m/z [M+H]$^+$ calc'd for C$_{17}$H$_{13}$F$_3$N$_4$, 331.1. found 331.2.

Example 68

1',3'-dimethyl-6-(trifluoromethyl)-1H,1'H-4,6'-biindazole

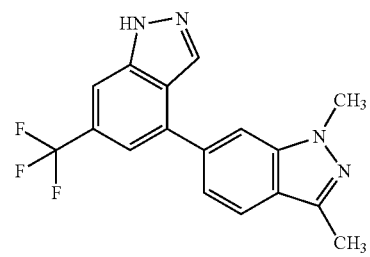 [SMILES: Cc1nn(C)c2cc(-c3cc(C(F)(F)F)cc4[nH]ncc34)ccc12]

The title compound was isolated as the free base. ¹H NMR (400 MHz, DMSO-d₆) δ ppm 2.54 (s, 3H), 4.06 (s, 3H), 7.52 (d, J=8.34 Hz, 1H), 7.58 (s, 1H), 7.88 (d, J=8.08 Hz, 1H), 7.96 (br s, 2H), 8.43 (s, 1H); ESI-MS m/z [M+H]⁺ calc'd for $C_{17}H_{13}F_3N_4$, 331.1. found 331.2.

Example 69

4-(3-(1H-pyrazol-1-yl)phenyl)-6-(trifluoromethyl)-1H-indazole

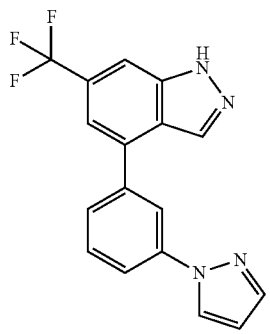 [SMILES: FC(F)(F)c1cc(-c2cccc(-n3cccn3)c2)c2cn[nH]c2c1]

¹H NMR (400 MHz, CD₃OD) δ ppm 6.56 (dd, J=2.40, 1.89 Hz, 1H), 7.54 (d, J=1.01 Hz, 1H), 7.64-7.74 (m, 2H), 7.77 (d, J=1.77 Hz, 1H), 7.83 (dt, J=7.45, 1.96 Hz, 1H), 7.92 (s, 1H), 8.11 (t, J=1.64 Hz, 1H), 8.34 (td, J=3.03, 0.76 Hz, 2H); ESI-MS m/z [M+H]⁺ calc'd for $C_{17}H_{11}F_3N_4$, 329.1. found 329.2.

Example 70

4-(5-methyl-1-phenyl-1H-pyrazol-4-yl)-6-(trifluoromethyl)-1H-indazole

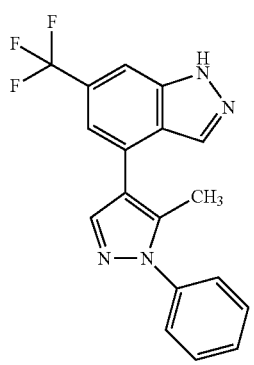 [SMILES: Cc1c(-c2cc(C(F)(F)F)cc3[nH]ncc23)cnn1-c1ccccc1]

The title compound was isolated as the free base. ¹H NMR (400 MHz, CD₃OD) δ ppm 2.41 (s, 3H), 7.36 (s, 1H), 7.53 (dt, J=6.19, 2.59 Hz, 1H), 7.56-7.66 (m, 4H), 7.86 (s, 1H), 8.00 (s, 1H), 8.25 (s, 1H); ESI-MS m/z [M+H]⁺ calc'd for $C_{18}H_{13}F_3N_4$, 343.1. found 343.2.

Example 71

4-(5-methyl-1-phenyl-1H-pyrazol-4-yl)-6-(trifluoromethyl)-1H-indazole

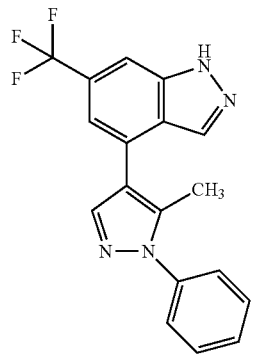

ESI-MS m/z [M+H]⁺ calc'd for $C_{18}H_{13}F_3N_4$, 343.1. found 343.2.

Example 72

4-(1-(pyridin-2-ylmethyl)-1H-pyrazol-4-yl)-6-(trifluoromethyl)-1H-indazole

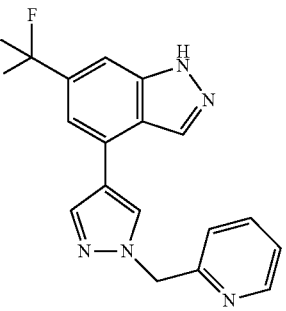

¹H NMR (400 MHz, CD₃OD) δ ppm 5.68 (s, 2H), 7.44 (d, J=7.83 Hz, 1H), 7.55-7.61 (m, 2H), 7.76-7.81 (m, 1H), 8.08 (td, J=7.77, 1.64 Hz, 1H), 8.18 (d, J=0.76 Hz, 1H), 8.47 (d, J=1.01 Hz, 1H), 8.53 (d, J=0.76 Hz, 1H), 8.63-8.69 (m, 1H); ESI-MS m/z [M+H]⁺ calc'd for $C_{17}H_{12}F_3N_5$, 344.1. found 344.2.

Example 73

N-(3-(6-(trifluoromethyl)-1H-indazol-4-yl)pyridin-2-yl)pivalamide

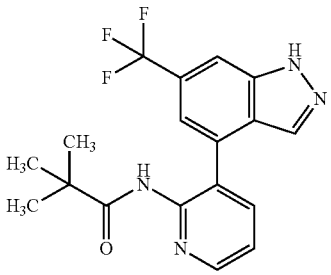 [SMILES: CC(C)(C)C(=O)Nc1ncccc1-c1cc(C(F)(F)F)cc2[nH]ncc12]

ESI-MS m/z [M+H]⁺ calc'd for $C_{18}H_{17}F_3N_4O$, 363.1. found 363.3.

Example 74

4-(2-(4-(6-(trifluoromethyl)-1H-indazol-4-yl)-1H-pyrazol-1-yl)ethyl)morpholine

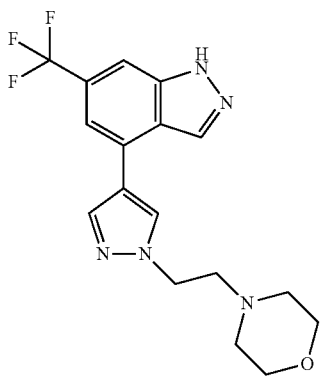 [SMILES: FC(F)(F)c1cc(-c2cnn(CCN3CCOCC3)c2)c2cn[nH]c2c1]

ESI-MS m/z [M+H]+ calc'd for C17H18F3N5O, 366.1. found 366.3.

Example 75

5-fluoro-2-(6-(trifluoromethyl)-1H-indazol-4-yl)benzonitrile

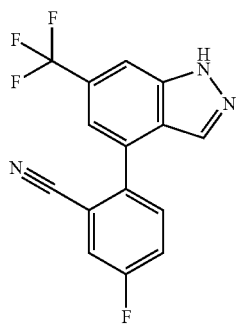 [SMILES: N#Cc1cc(F)ccc1-c1cc(C(F)(F)F)cc2[nH]ncc12]

The title compound was isolated as the free base. ESI-MS m/z [M+H]+ calc'd for C15H7F4N3, 306.1. found 306.1.

Example 76

4-(1H-indol-7-yl)-6-(trifluoromethyl)-1H-indazole

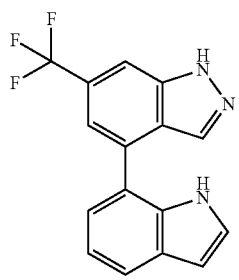 [SMILES: FC(F)(F)c1cc(-c2cccc3cc[nH]c23)c2cn[nH]c2c1]

ESI-MS m/z [M+H]+ calc'd for C16H10F3N3, 302.1. found 302.2.

Example 77

4-(1-methyl-1H-indol-4-yl)-6-(trifluoromethyl)-1H-indazole

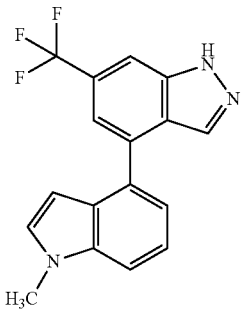 [SMILES: Cn1ccc2c(-c3cc(C(F)(F)F)cc4[nH]ncc34)cccc21]

ESI-MS m/z [M+H]+ calc'd for C17H12F3N3, 316.1. found 316.2.

Example 78

3-(6-(trifluoromethyl)-1H-indazol-4-yl)pyridin-2-amine

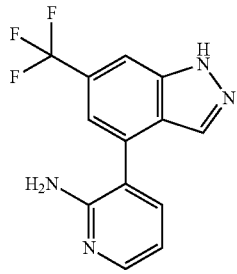 [SMILES: Nc1ncccc1-c1cc(C(F)(F)F)cc2[nH]ncc12]

ESI-MS m/z [M+H]+ calc'd for C13H9F3N4, 279.1. found 279.1.

Example 79

4-(1,5-dimethyl-1H-pyrazol-4-yl)-6-(trifluoromethyl)-1H-indazole

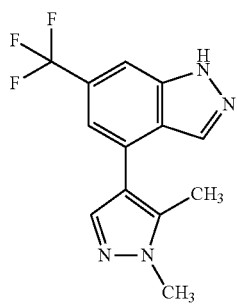

The title compound was isolated as the free base. ESI-MS m/z [M+H]+ calc'd for $C_{13}H_{11}F_3N_4$, 281.1. found 281.2.

Example 80

3,5-dimethyl-4-(6-(trifluoromethyl)-1H-indazol-4-yl)isoxazole

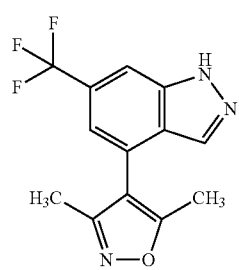

ESI-MS m/z [M+H]+ calc'd for $C_{13}H_{10}F_3N_3O$, 282.1. found 282.1.

Example 81

4-(1H-indol-4-yl)-6-(trifluoromethyl)-1H-indazole

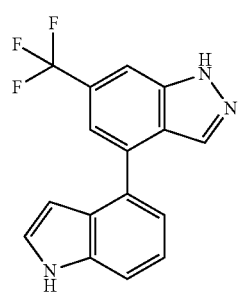 [SMILES: FC(F)(F)c1cc(-c2cccc3[nH]ccc23)c2cn[nH]c2c1]

ESI-MS m/z [M+H]+ calc'd for $C_{16}H_{10}F_3N_3$, 302.1. found 302.2.

Example 82

1,3-dimethyl-5-(6-(trifluoromethyl)-1H-indazol-4-yl)pyrimidine-2,4(1H,3H)-dione

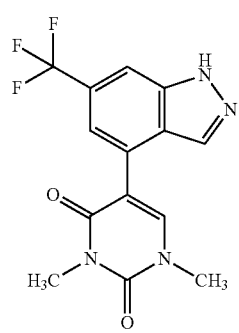 [SMILES: Cn1cc(-c2cc(C(F)(F)F)cc3[nH]ncc23)c(=O)n(C)c1=O]

$^1$H NMR (400 MHz, DMSO-$d_6$) δ ppm 3.30 (s, 3H), 3.45 (s, 3H), 7.48 (s, 1H), 7.89 (s, 1H), 8.17 (s, 1H), 8.21 (s, 1H), 13.55 (s, 1H); ESI-MS m/z [M+H]+ calc'd for $C_{14}H_{11}F_3N_4O_2$, 325.1. found 325.2.

Example 83

4-(3,5-dimethyl-1H-pyrazol-4-yl)-6-(trifluoromethyl)-1H-indazole

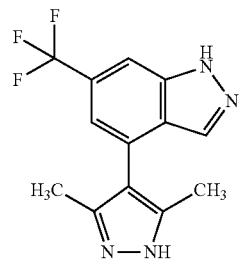 [SMILES: Cc1n[nH]c(C)c1-c1cc(C(F)(F)F)cc2[nH]ncc12]

The title compound was isolated as the free base. ESI-MS m/z [M+H]+ calc'd for $C_{13}H_{11}F_3N_4$, 281.1. found 281.2.

Example 84

(4-methylpiperazin-1-yl)(3-(6-(trifluoromethyl)-1H-indazol-4-yl)phenyl)methanone

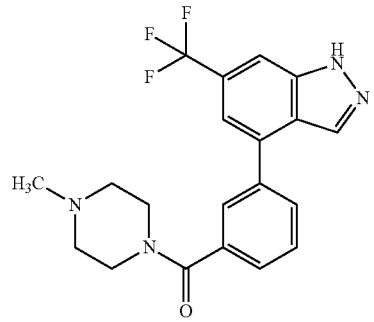 [SMILES: CN1CCN(C(=O)c2cccc(-c3cc(C(F)(F)F)cc4[nH]ncc34)c2)CC1]

$^1$H NMR (400 MHz, CD$_3$OD) δ ppm 2.96 (s, 3H), 3.13-3.29 (m, 4H), 3.33-3.44 (m, 1H), 3.44-3.72 (m, 3H), 7.48-7.51 (m, 1H), 7.59-7.64 (m, 1H), 7.69-7.75 (m, 1H), 7.85-7.89 (m, 1H), 7.91-7.96 (m, 2H), 8.30 (d, J=1.01 Hz, 1H); ESI-MS m/z [M+H]+ calc'd for $C_{20}H_{19}F_3N_4O$, 389.2. found 389.3.

Example 85 pyrrolidin-1-yl(3-(6-(trifluoromethyl)-1H-indazol-4-yl)phenyl)methanone

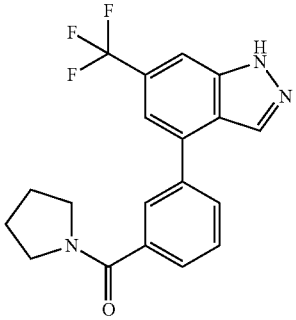 [SMILES: O=C(c1cccc(-c2cc(C(F)(F)F)cc3[nH]ncc23)c1)N1CCCC1]

¹H NMR (400 MHz, CD₃OD) δ ppm 1.89-1.98 (m, 2H), 1.98-2.08 (m, 2H), 3.55 (t, J=6.69 Hz, 2H), 3.64 (t, J=6.95 Hz, 2H), 7.47 (d, J=1.01 Hz, 1H), 7.62-7.70 (m, 2H), 7.83-7.89 (m, 2H), 7.92 (d, J=0.76 Hz, 1H), 8.31 (d, J=1.01 Hz, 1H); ESI-MS m/z [M+H]⁺ calc'd for C₁₉H₁₆F₃N₃O, 360.1. found 360.3.

Example 86

4-(2,5-dimethoxyphenyl)-6-(trifluoromethyl)-1H-indazole

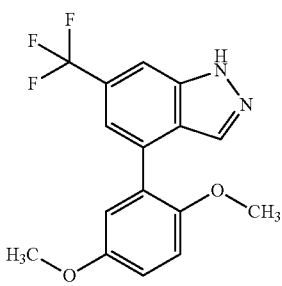 [SMILES: COc1ccc(OC)c(-c2cc(C(F)(F)F)cc3[nH]ncc23)c1]

¹H NMR (400 MHz, CD₃OD) δ ppm 3.73 (s, 3H), 3.81 (s, 3H), 6.97 (d, J=2.78 Hz, 1H), 7.02 (dd, J=8.84, 3.03 Hz, 1H), 7.11 (d, J=8.84 Hz, 1H), 7.34 (d, J=1.77 Hz, 1H), 7.84-7.87 (m, 1H), 7.92 (d, J=1.01 Hz, 1H); ESI-MS m/z [M+H]⁺ calc'd for C₁₆H₁₃F₃N₂O₂, 323.1. found 323.2.

Example 87

4-(2,3-dimethoxyphenyl)-6-(trifluoromethyl)-1H-indazole

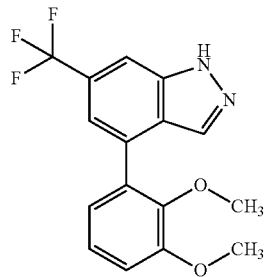 [SMILES: COc1cccc(-c2cc(C(F)(F)F)cc3[nH]ncc23)c1OC]

¹H NMR (400 MHz, CD₃OD) δ ppm 3.49 (s, 3H), 3.94 (s, 3H), 7.04 (dd, J=7.45, 1.64 Hz, 1H), 7.16 (dd, J=8.34, 1.52 Hz, 1H), 7.23 (dd, J=8.34, 7.58 Hz, 1H), 7.39 (d, J=1.26 Hz, 1H), 7.87-7.90 (m, 1H), 7.97 (d, J=0.76 Hz, 1H); ESI-MS m/z [M+H]⁺ calc'd for C₁₆H₁₃F₃N₂O₂, 323.1. found 323.2.

Example 88

N-ethyl-3-(6-(trifluoromethyl)-1H-indazol-4-yl)benzamide

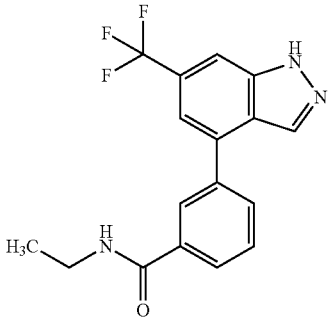 [SMILES: CCNC(=O)c1cccc(-c2cc(C(F)(F)F)cc3[nH]ncc23)c1]

¹H NMR (400 MHz, CD₃OD) δ ppm 1.20-1.33 (m, 3H), 3.46 (q, J=7.33 Hz, 2H), 7.52-7.55 (m, 1H), 7.65-7.70 (m, 1H), 7.91-7.94 (m, 2H), 7.94-7.96 (m, 1H), 8.17-8.21 (m, 1H), 8.32 (d, J=1.01 Hz, 1H); ESI-MS m/z [M+H]⁺ calc'd for C₁₇H₁₄F₃N₃O, 334.1. found 334.2.

Example 89

4-(5-(6-(trifluoromethyl)-1H-indazol-4-yl)pyridin-2-yl)morpholine

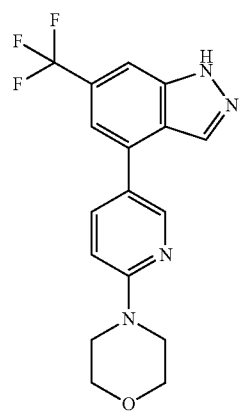 [SMILES: FC(F)(F)c1cc(-c2ccc(N3CCOCC3)nc2)c2cn[nH]c2c1]

¹H NMR (400 MHz, CD₃OD) δ ppm 3.68-3.78 (m, 4H), 3.86-3.94 (m, 4H), 7.43 (dd, J=9.35, 0.76 Hz, 1H), 7.51 (d, J=1.01 Hz, 1H), 7.93-7.99 (m, 1H), 8.31 (d, J=1.01 Hz, 1H), 8.34 (dd, J=9.35, 2.53 Hz, 1H), 8.38 (dd, J=2.53, 0.76 Hz, 1H); ESI-MS m/z [M+H]⁺ calc'd for C₁₇H₁₅F₃N₄O, 349.1. found 349.2.

Example 90

2-(3-(6-(trifluoromethyl)-1H-indazol-4-yl)phenyl)acetonitrile

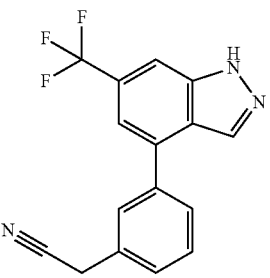 [SMILES: N#CCc1cccc(-c2cc(C(F)(F)F)cc3[nH]ncc23)c1]

¹H NMR (400 MHz, CD₃OD) δ ppm 4.05 (s, 2H), 7.45 (d, J=1.01 Hz, 1H), 7.48-7.53 (m, 1H), 7.60 (t, J=7.71 Hz, 1H), 7.69-7.74 (m, 1H), 7.74-7.77 (m, 1H), 7.91 (s, 1H), 8.28 (d, J=1.01 Hz, 1H); ESI-MS m/z [M+H]⁺ calc'd for C₁₆H₁₀F₃N₃, 302.1. found 302.2.

Example 91

4-(6-methoxypyridin-2-yl)-6-(trifluoromethyl)-1H-indazole

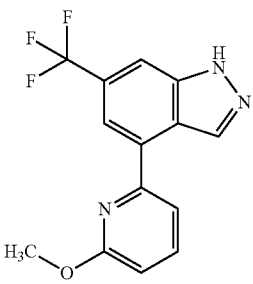 [SMILES: COc1cccc(-c2cc(C(F)(F)F)cc3[nH]ncc23)n1]

$^1$H NMR (400 MHz, CD$_3$OD) δ ppm 4.08 (s, 3H), 6.85 (d, J=8.34 Hz, 1H), 7.63 (d, J=7.33 Hz, 1H), 7.83 (t, J=7.83 Hz, 1H), 7.90 (s, 1H), 7.94 (s, 1H), 8.80 (s, 1H); ESI-MS m/z [M+H]$^+$ calc'd for C$_{14}$H$_{10}$F$_3$N$_3$O, 294.1. found 294.2.

Example 92

2-fluoro-N-methyl-4-(6-(trifluoromethyl)-1H-indazol-4-yl)benzamide

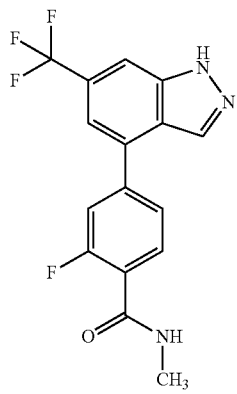 [SMILES: CNC(=O)c1ccc(-c2cc(C(F)(F)F)cc3[nH]ncc23)cc1F]

The title compound was isolated as the free base. $^1$H NMR (400 MHz, CD$_3$OD) δ ppm 2.98 (s, 3H), 7.52 (d, J=1.01 Hz, 1H), 7.62 (dd, J=11.87, 1.52 Hz, 1H), 7.69 (dd, J=8.08, 1.77 Hz, 1H), 7.91-7.95 (m, 1H), 7.96 (s, 1H), 8.31 (s, 1H); ESI-MS m/z [M+H]$^+$ calc'd for C$_{16}$H$_{11}$F$_4$N$_3$O, 338.1. found 338.2.

Example 93

2-(2-(6-(trifluoromethyl)-1H-indazol-4-yl)phenoxy)acetonitrile

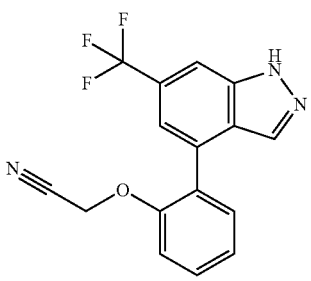 [SMILES: N#CCOc1ccccc1-c1cc(C(F)(F)F)cc2[nH]ncc12]

$^1$H NMR (400 MHz, CD$_3$OD) δ ppm 4.94 (s, 2H), 7.27 (td, J=7.45, 1.01 Hz, 1H), 7.32 (dd, J=8.34, 0.76 Hz, 1H), 7.35 (d, J=1.01 Hz, 1H), 7.50 (dd, J=7.58, 1.52 Hz, 1H), 7.51-7.57 (m, 1H), 7.89 (s, 1H), 7.94 (d, J=1.01 Hz, 1H); ESI-MS m/z [M+H]$^+$ calc'd for C$_{16}$H$_{10}$F$_3$N$_3$O, 318.1. found 318.2.

Example 94

4-(5-(6-(trifluoromethyl)-1H-indazol-4-yl)pyrazin-2-yl)morpholine

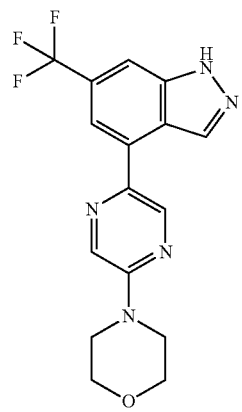 [SMILES: FC(F)(F)c1cc(-c2cnc(N3CCOCC3)cn2)c2cn[nH]c2c1]

$^1$H NMR (400 MHz, CD$_3$OD) δ ppm 3.68-3.74 (m, 4H), 3.82-3.88 (m, 4H), 7.79-7.83 (m, 1H), 7.88 (s, 1H), 8.43 (d, J=1.52 Hz, 1H), 8.68 (d, J=1.01 Hz, 1H), 8.78 (d, J=1.52 Hz, 1H); ESI-MS m/z [M+H]$^+$ calc'd for C$_{16}$H$_{14}$F$_3$N$_5$O, 350.1. found 350.2.

Example 95

N-(4-(6-(trifluoromethyl)-1H-indazol-4-yl)benzyl)methanesulfonamide

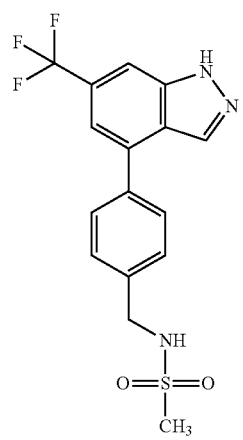 [SMILES: CS(=O)(=O)NCc1ccc(-c2cc(C(F)(F)F)cc3[nH]ncc23)cc1]

¹H NMR (400 MHz, CD₃OD) δ ppm 2.92 (s, 3H), 4.36 (s, 2H), 7.40-7.46 (m, 1H), 7.56-7.62 (m, 2H), 7.72-7.79 (m, 2H), 7.88 (s, 1H), 8.26 (s, 1H); ESI-MS m/z [M+H]⁺ calc'd for $C_{16}H_{14}F_3N_3O_2S$, 370.1. found 370.2.

Example 96

4-(1-(pyridin-3-ylmethyl)-1H-pyrazol-4-yl)-6-(trifluoromethyl)-1H-indazole

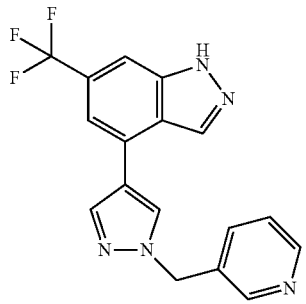 [SMILES: FC(F)(F)c1cc(-c2cnn(Cc3cccnc3)c2)c2cn[nH]c2c1]

¹H NMR (400 MHz, CD₃OD) δ ppm 5.67 (s, 2H), 7.55 (dd, J=1.26, 0.51 Hz, 1H), 7.77-7.80 (m, 1H), 7.84-7.91 (m, 1H), 8.19 (d, J=0.76 Hz, 1H), 8.29-8.34 (m, 1H), 8.45 (d, J=1.01 Hz, 1H), 8.54 (d, J=0.76 Hz, 1H), 8.72 (d, J=5.05 Hz, 1H), 8.77 (s, 1H); ESI-MS m/z [M+H]⁺ calc'd for $C_{17}H_{12}F_3N_5$, 344.1. found 344.2.

Example 97

N-methyl-5-(6-(trifluoromethyl)-1H-indazol-4-yl)picolinamide

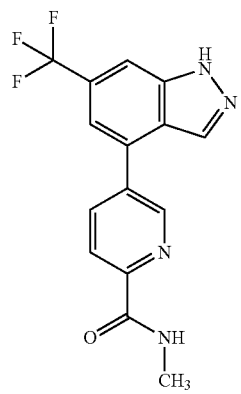

The title compound was isolated as the free base. ESI-MS m/z [M+H]⁺ calc'd for $C_{15}H_{11}F_3N_4O$, 321.1. found 321.2.

Example 98

4-(2-(cyclopentyloxy)pyridin-3-yl)-6-(trifluoromethyl)-1H-indazole

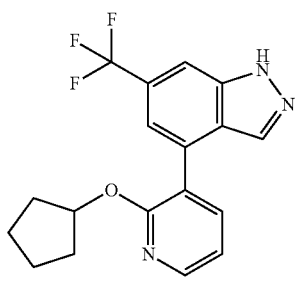 [SMILES: FC(F)(F)c1cc(-c2cccnc2OC2CCCC2)c2cn[nH]c2c1]

ESI-MS m/z [M+H]⁺ calc'd for $C_{18}H_{16}F_3N_3O$, 348.1. found 348.2.

Example 99

4-(2-(benzyloxy)pyridin-3-yl)-6-(trifluoromethyl)-1H-indazole

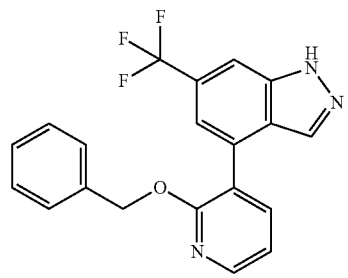 [SMILES: FC(F)(F)c1cc(-c2cccnc2OCc2ccccc2)c2cn[nH]c2c1]

ESI-MS m/z [M+H]⁺ calc'd for $C_{20}H_{14}F_3N_3O$, 370.1. found 370.2.

Example 100

4-(2-(2,2,2-trifluoroethoxy)pyridin-3-yl)-6-(trifluoromethyl)-1H-indazole

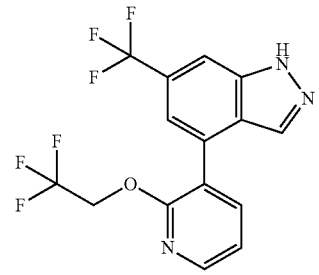 [SMILES: FC(F)(F)COc1ncccc1-c1cc(C(F)(F)F)cc2[nH]ncc12]

ESI-MS m/z [M+H]⁺ calc'd for $C_{15}H_9F_6N_3O$, 362.1. found 362.2.

Example 101

5-(6-(trifluoromethyl)-1H-indazol-4-yl)quinoline

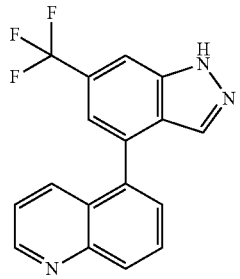 [SMILES: FC(F)(F)c1cc(-c2cccc3ncccc23)c2cn[nH]c2c1]

ESI-MS m/z [M+H]⁺ calc'd for $C_{17}H_{10}F_3N_3$, 314.1. found 314.2.

Example 102

4-fluoro-N-methyl-2-(6-(trifluoromethyl)-1H-indazol-4-yl)benzamide

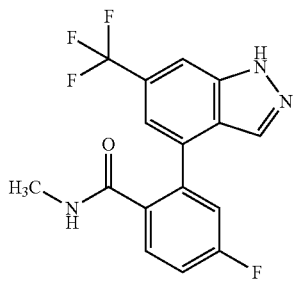 [SMILES: CNC(=O)c1ccc(F)cc1-c1cc(C(F)(F)F)cc2[nH]ncc12]

The title compound was isolated as the free base. ¹H NMR (400 MHz, DMSO-d₆) δ ppm 2.48 (s, 2H), 3.17 (d, J=5.31 Hz, 1H), 7.31 (s, 1H), 7.33-7.49 (m, 2H), 7.61 (dd, J=8.46, 5.94 Hz, 1H), 7.93 (s, 1H), 8.05 (s, 1H), 8.32 (d, J=4.55 Hz, 1H), 13.64 (br s, 1H); ESI-MS m/z [M+H]⁺ calc'd for $C_{16}H_{11}F_4N_3O$, 338.1. found 338.2.

Example 103

4-(3-(methylsulfonyl)phenyl)-6-(trifluoromethyl)-1H-indazole

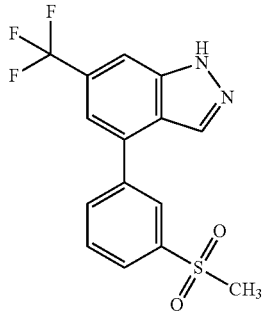 [SMILES: CS(=O)(=O)c1cccc(-c2cc(C(F)(F)F)cc3[nH]ncc23)c1]

¹H NMR (400 MHz, CD₃OD) δ ppm 3.23 (s, 3H), 7.54 (d, J=1.26 Hz, 1H), 7.82-7.88 (m, 1H), 7.96-7.99 (m, 1H), 8.08 (ddd, J=7.89, 1.83, 1.14 Hz, 1H), 8.12 (dq, J=7.71, 0.97 Hz, 1H), 8.27-8.31 (m, 2H); ESI-MS m/z [M+H]⁺ calc'd for $C_{15}H_{11}F_3N_2O_2S$, 341.0. found 341.2.

Example 104

N-methyl-3-(6-(trifluoromethyl)-1H-indazol-4-yl)benzenesulfonamide

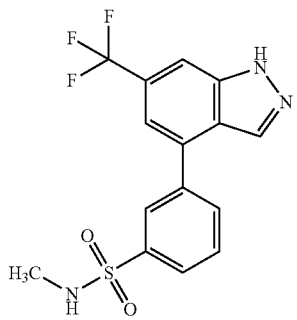 [SMILES: CNS(=O)(=O)c1cccc(-c2cc(C(F)(F)F)cc3[nH]ncc23)c1]

¹H NMR (400 MHz, CD₃OD) δ ppm 2.60 (s, 3H), 7.51 (d, J=1.01 Hz, 1H), 7.75-7.83 (m, 1H), 7.93-7.99 (m, 2H), 8.03 (dq, J=7.71, 0.97 Hz, 1H), 8.17-8.21 (m, 1H), 8.28 (d, J=1.01 Hz, 1H); ESI-MS m/z [M+H]⁺ calc'd for $C_{15}H_{12}F_3N_3O_2S$, 356.1. found 356.2.

Example 105

4-(5-(methylsulfonyl)pyridin-3-yl)-6-(trifluoromethyl)-1H-indazole

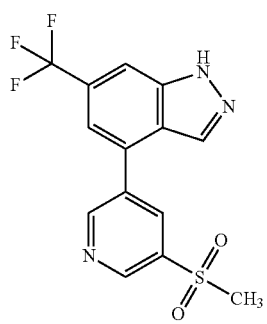 [SMILES: CS(=O)(=O)c1cncc(-c2cc(C(F)(F)F)cc3[nH]ncc23)c1]

The title compound was isolated as the free base. ¹H NMR (400 MHz, CD₃OD) δ ppm 3.33 (s, 3H), 7.65 (d, J=1.01 Hz, 1H), 8.05 (d, J=1.01 Hz, 1H), 8.33 (d, J=1.01 Hz, 1H), 8.68 (t, J=2.15 Hz, 1H), 9.20 (d, J=2.02 Hz, 1H), 9.27 (d, J=2.02 Hz, 1H); ESI-MS m/z [M+H]⁺ calc'd for $C_{14}H_{10}F_3N_3O_2S$, 342.0. found 342.1.

Example 106

2-(3-(6-(trifluoromethyl)-1H-indazol-4-yl)phenyl)ethanol

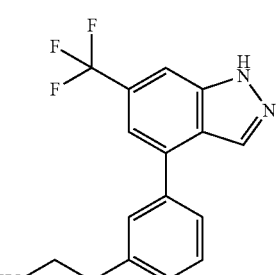

The title compound was isolated as the free base. ¹H NMR (400 MHz, CD₃OD) δ ppm 2.95 (t, J=6.82 Hz, 2H), 3.85 (t, J=6.69 Hz, 2H), 7.37 (d, J=7.33 Hz, 1H), 7.43 (s, 1H), 7.49 (t, J=7.58 Hz, 1H), 7.55-7.60 (m, 1H), 7.62 (s, 1H), 7.87 (s, 1H), 8.26 (s, 1H); ESI-MS m/z [M+H]⁺ calc'd for $C_{16}H_{13}F_3N_2O$, 307.1. found 307.2.

Example 107

5-(6-(trifluoromethyl)-1H-indazol-4-yl)benzo[d]thiazole

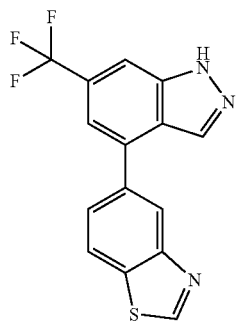 [SMILES: FC(F)(F)c1cc(-c2ccc3scnc3c2)c2cn[nH]c2c1]

$^1$H NMR (400 MHz, CD$_3$OD) δ ppm 7.55 (d, J=1.01 Hz, 1H), 7.87-7.92 (m, 1H), 7.92-7.96 (m, 1H), 8.27 (dd, J=8.34, 0.51 Hz, 1H), 8.32 (d, J=1.01 Hz, 1H), 8.42 (dd, J=1.77, 0.51 Hz, 1H), 9.36 (s, 1H); ESI-MS m/z [M+H]$^+$ calc'd for C$_{15}$H$_8$F$_3$N$_3$S, 320.0. found 320.1.

Example 108

N,N-dimethyl-3-(6-(trifluoromethyl)-1H-indazol-4-yl)benzenesulfonamide

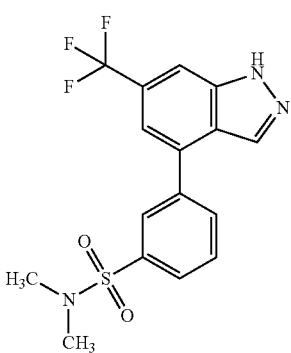 [SMILES: CN(C)S(=O)(=O)c1cccc(-c2cc(C(F)(F)F)cc3[nH]ncc23)c1]

$^1$H NMR (400 MHz, CD$_3$OD) δ ppm 2.76 (s, 6H), 7.48-7.51 (m, 1H), 7.80-7.87 (m, 1H), 7.89-7.94 (m, 1H), 7.96-7.99 (m, 1H), 8.05-8.10 (m, 2H), 8.25 (d, J=1.01 Hz, 1H); ESI-MS m/z [M+H]$^+$ calc'd for C$_{16}$H$_{14}$F$_3$N$_3$O$_2$S, 370.1. found 370.2.

Example 109

2-fluoro-N-(2-hydroxyethyl)-4-(6-(trifluoromethyl)-1H-indazol-4-yl)benzamide

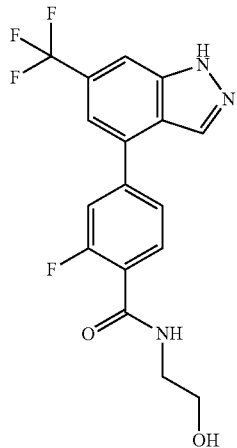 [SMILES: O=C(NCCO)c1ccc(-c2cc(C(F)(F)F)cc3[nH]ncc23)cc1F]

$^1$H NMR (400 MHz, CD$_3$OD) δ ppm 3.57 (t, J=5.81 Hz, 2H), 3.75 (t, J=5.81 Hz, 2H), 7.52 (d, J=1.01 Hz, 1H), 7.62 (dd, J=11.75, 1.64 Hz, 1H), 7.69 (dd, J=7.96, 1.64 Hz, 1H), 7.94-8.00 (m, 2H), 8.31 (d, J=1.01 Hz, 1H); ESI-MS m/z [M+H]$^+$ calc'd for C$_{17}$H$_{13}$F$_4$N$_3$O$_2$, 368.1. found 368.2.

Example 110

2-fluoro-5-(6-(trifluoromethyl)-1H-indazol-4-yl)benzamide

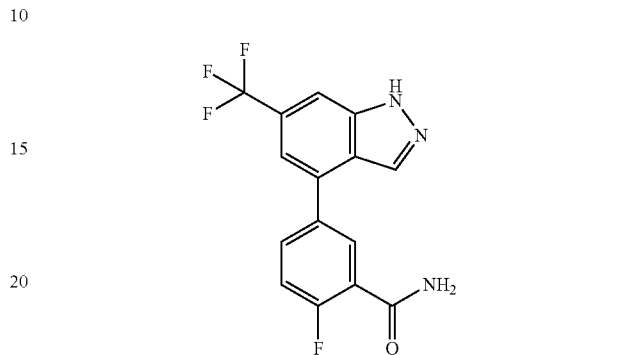

The title compound was isolated as the free base. $^1$H NMR (400 MHz, CD$_3$OD) δ ppm 7.44 (dd, J=10.61, 8.59 Hz, 1H), 7.48 (d, J=1.26 Hz, 1H), 7.93 (s, 1H), 7.93-7.97 (m, 1H), 8.17 (dd, J=6.95, 2.40 Hz, 1H), 8.31 (d, J=1.01 Hz, 1H); ESI-MS m/z [M+H]$^+$ calc'd for C$_{15}$H$_9$F$_4$N$_3$O, 324.1. found 324.2.

Example 111

4-(6-(trifluoromethyl)-1H-indazol-4-yl)isoquinoline

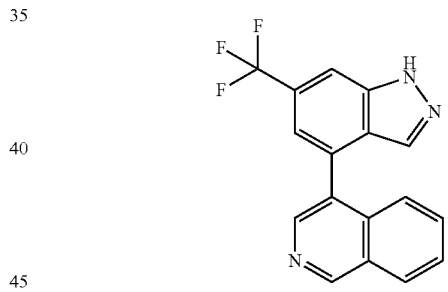

The title compound was isolated as the free base. ESI-MS m/z [M+H]$^+$ calc'd for C$_{17}$H$_{10}$F$_3$N$_3$, 314.1. found 314.2.

Example 112

4-(6-(trifluoromethyl)-1H-indazol-4-yl)quinoline

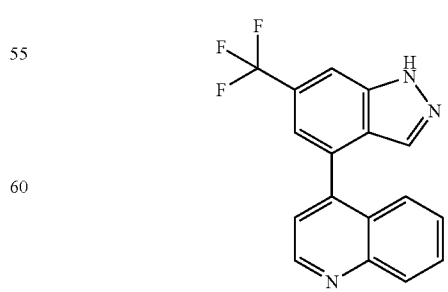

ESI-MS m/z [M+H]$^+$ calc'd for C$_{17}$H$_{10}$F$_3$N$_3$, 314.1. found 314.2.

Example 113

8-methoxy-5-(6-(trifluoromethyl)-1H-indazol-4-yl)quinoline

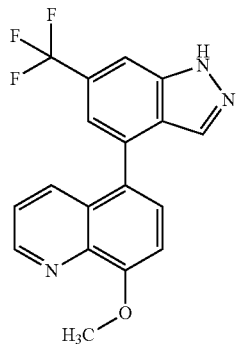 [SMILES: COc1ccc(-c2cc(C(F)(F)F)cc3[nH]ncc23)c2cccnc12]

$^1$H NMR (400 MHz, DMSO-d$_6$) δ ppm 4.11 (s, 3H), 7.34-7.51 (m, 2H), 7.63 (dd, J=8.46, 4.17 Hz, 1H), 7.69-7.86 (m, 2H), 8.06 (s, 1H), 8.12 (d, J=8.59 Hz, 1H), 8.91-9.06 (m, 1H); ESI-MS m/z [M+H]$^+$ calc'd for C$_{18}$H$_{12}$F$_3$N$_3$O, 344.1. found 344.2.

Example 114

4-fluoro-N-methyl-3-(6-(trifluoromethyl)-1H-indazol-4-yl)benzamide

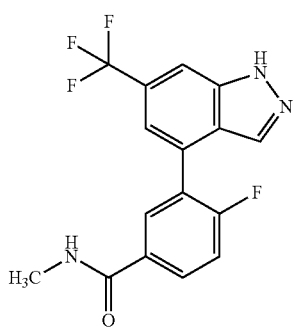 [SMILES: CNC(=O)c1ccc(F)c(-c2cc(C(F)(F)F)cc3[nH]ncc23)c1]

ESI-MS m/z [M+H]$^+$ calc'd for C$_{16}$H$_{11}$F$_4$N$_3$O, 338.1. found 338.2.

Example 115

3-fluoro-N,N-dimethyl-5-(6-(trifluoromethyl)-1H-indazol-4-yl)benzamide

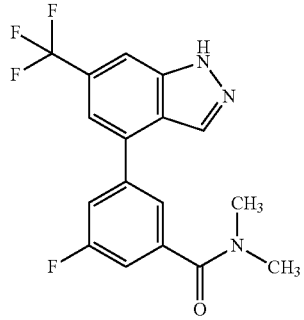 [SMILES: CN(C)C(=O)c1cc(F)cc(-c2cc(C(F)(F)F)cc3[nH]ncc23)c1]

$^1$H NMR (400 MHz, DMSO-d$_6$) δ ppm 3.01 (d, J=13.39 Hz, 6H), 7.41 (d, J=9.09 Hz, 1H), 7.57 (s, 1H), 7.64 (s, 1H), 7.74 (d, J=9.35 Hz, 1H), 8.01 (s, 1H), 8.36 (s, 1H), 13.80 (s, 1H); ESI-MS m/z [M+H]$^+$ calc'd for C$_{17}$H$_{13}$F$_4$N$_3$O, 352.1. found 352.2.

Example 116

4-(2-(pyrrolidin-1-yl)pyrimidin-5-yl)-6-(trifluoromethyl)-1H-indazole

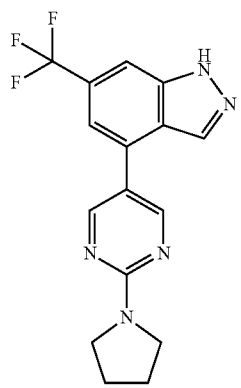 [SMILES: FC(F)(F)c1cc(-c2cnc(N3CCCC3)nc2)c2cn[nH]c2c1]

ESI-MS m/z [M+H]$^+$ calc'd for C$_{16}$H$_{14}$F$_3$N$_5$, 334.1. found 334.2.

Example 117

N-methyl-4-(6-(trifluoromethyl)-1H-indazol-4-yl)benzamide

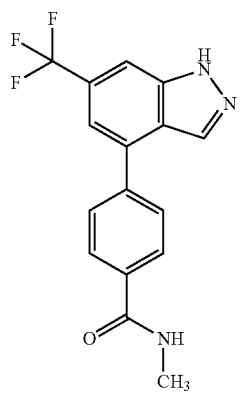 [SMILES: CNC(=O)c1ccc(-c2cc(C(F)(F)F)cc3[nH]ncc23)cc1]

$^1$H NMR (400 MHz, DMSO-d$_6$) δ ppm 2.83 (d, J=4.55 Hz, 3H), 7.54 (s, 1H), 7.90 (d, J=8.34 Hz, 2H), 7.98 (s, 1H), 8.03 (d, J=8.08 Hz, 2H), 8.37 (s, 1H), 13.76 (s, 1H); ESI-MS m/z [M+H]$^+$ calc'd for C$_{16}$H$_{12}$F$_3$N$_3$O, 320.1. found 320.2.

Example 118

4-(5-(6-(trifluoromethyl)-1H-indazol-4-yl)pyrimidin-2-yl)morpholine

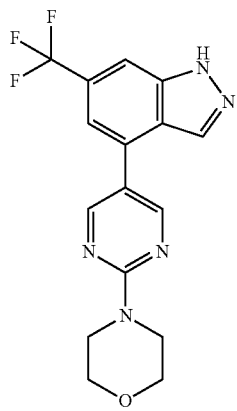

ESI-MS m/z [M+H]$^+$ calc'd for $C_{16}H_{14}F_3N_5O$, 350.1. found 350.3.

Example 119

N,N-dimethyl-4-(6-(trifluoromethyl)-1H-indazol-4-yl)benzamide

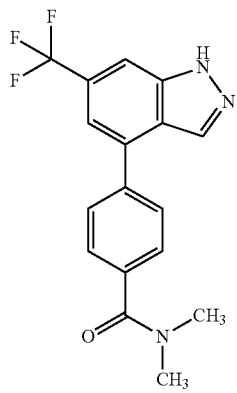 [SMILES: CN(C)C(=O)c1ccc(-c2cc(C(F)(F)F)cc3[nH]ncc23)cc1]

ESI-MS m/z [M+H]$^+$ calc'd for $C_{17}H_{14}F_3N_3O$, 334.1. found 334.2.

Example 120

2-methyl-5-(4-(6-(trifluoromethyl)-1H-indazol-4-yl)phenyl)-1,3,4-oxadiazole

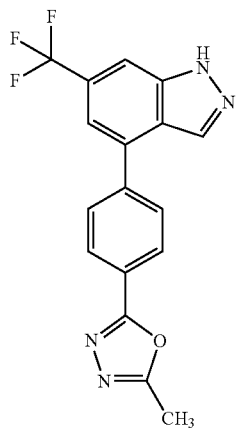 [SMILES: Cc1nnc(-c2ccc(-c3cc(C(F)(F)F)cc4[nH]ncc34)cc2)o1]

ESI-MS m/z [M+H]$^+$ calc'd for $C_{17}H_{11}F_3N_4O$, 345.1. found 345.2.

Example 121

N,N-dimethyl-3-(6-(trifluoromethyl)-1H-indazol-4-yl)benzamide

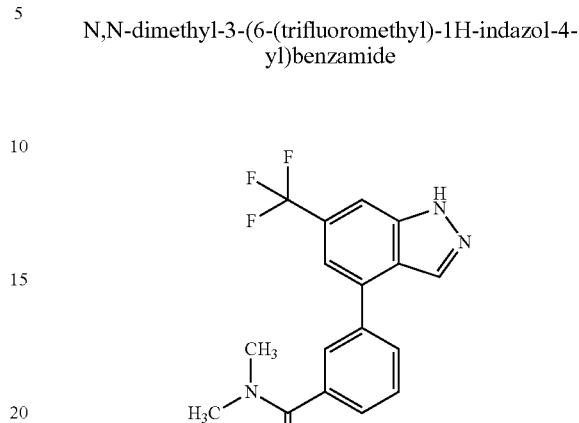

ESI-MS m/z [M+H]$^+$ calc'd for $C_{17}H_{14}F_3N_3O$, 334.1. found 334.2.

Example 122

4-methyl-7-(6-(trifluoromethyl)-1H-indazol-4-yl)-3,4-dihydro-2H-pyrido[3,2-b][1,4]oxazine

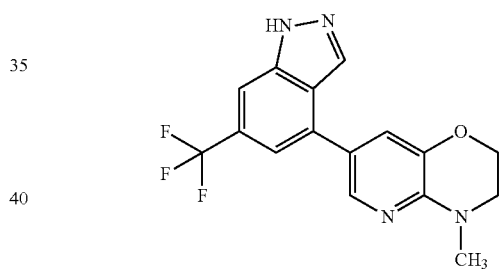

ESI-MS m/z [M+H]$^+$ calc'd for $C_{16}H_{13}F_3N_4O$, 335.1. found 335.2.

Example 123

4-(2-methoxy-4-methylpyridin-3-yl)-6-(trifluoromethyl)-1H-indazole

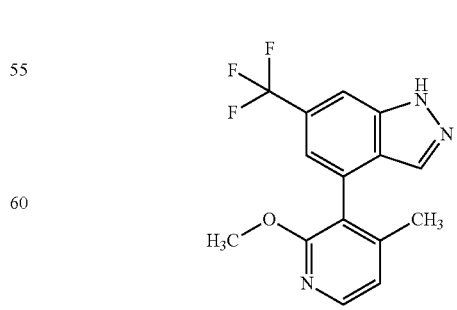

ESI-MS m/z [M+H]$^+$ calc'd for $C_{15}H_{12}F_3N_3O$, 308.1. found 308.2.

Example 124

4-(3-chloro-2-methoxypyridin-4-yl)-6-(trifluoromethyl)-1H-indazole

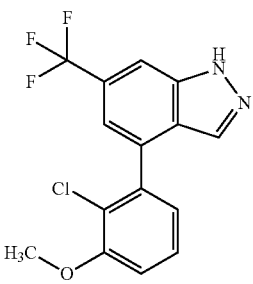 [SMILES: COc1cccc(-c2cc(C(F)(F)F)cc3[nH]ncc23)c1Cl]

ESI-MS m/z [M+H]$^+$ calc'd for $C_{14}H_9ClF_3N_3O$, 328.1. found 328.1.

Example 125

N,N,3-trimethyl-4-(6-(trifluoromethyl)-1H-indazol-4-yl)benzenesulfonamide

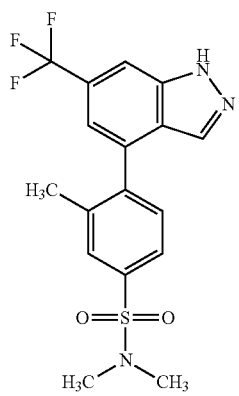 [SMILES: Cc1cc(S(=O)(=O)N(C)C)ccc1-c1cc(C(F)(F)F)cc2[nH]ncc12]

$^1$H NMR (400 MHz, DMSO-d$_6$) δ ppm 2.26 (s, 3H), 2.70 (s, 6H), 7.35 (s, 1H), 7.58-7.65 (m, 1H), 7.66-7.73 (m, 1H), 7.79 (s, 1H), 7.96 (s, 1H), 8.01 (s, 1H), 13.75 (s, 1H); ESI-MS m/z [M+H]$^+$ calc'd for $C_{17}H_{16}F_3N_3O_2S$, 384.1. found 384.2.

Example 126

4-(1,3-dimethyl-1H-pyrazol-5-yl)-6-(trifluoromethyl)-1H-indazole

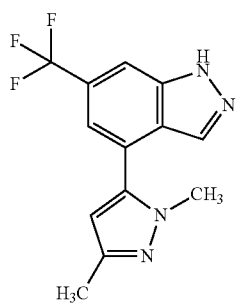 [SMILES: Cc1cc(-c2cc(C(F)(F)F)cc3[nH]ncc23)n(C)n1]

ESI-MS m/z [M+H]$^+$ calc'd for $C_{13}H_{11}F_3N_4$, 281.1. found 281.2.

Example 127

N,N,4-trimethyl-3-(6-(trifluoromethyl)-1H-indazol-4-yl)benzenesulfonamide

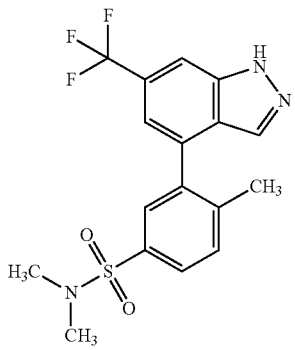 [SMILES: Cc1ccc(S(=O)(=O)N(C)C)cc1-c1cc(C(F)(F)F)cc2[nH]ncc12]

ESI-MS m/z [M+H]$^+$ calc'd for $C_{17}H_{16}F_3N_3O_2S$, 384.1. found 384.2.

Example 128

(4-chloro-3-(6-(trifluoromethyl)-1H-indazol-4-yl)phenyl)methanol

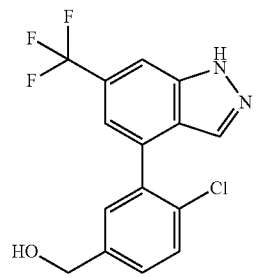 [SMILES: OCc1ccc(Cl)c(-c2cc(C(F)(F)F)cc3[nH]ncc23)c1]

ESI-MS m/z [M+H]$^+$ calc'd for $C_{15}H_{10}ClF_3N_2O$, 327.0. found 327.1.

Example 129

4-(6-(trifluoromethyl)-1H-indazol-4-yl)indolin-2-one

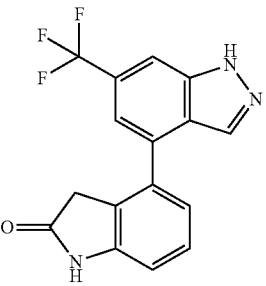 [SMILES: O=C1Cc2c(cccc2-c2cc(C(F)(F)F)cc3[nH]ncc23)N1]

A vial was charged with a mixture of 4-bromo-6-(trifluoromethyl)-1H-indazole (0.026 g, 0.096 mmol), 4-(4,4,5,5-tetramethyl-1,3,2-dioxaborolan-2-yl)indolin-2-one (0.025 g, 0.096 mmol) and PdCl$_2$(dppf) (3.53 mg, 4.82 µmol) in dioxane (4 mL) and aqueous saturated NaHCO$_3$ (3 mL). The resulting light brown suspension was heated at 140° C. for 45 minutes in a microwave reactor. The reaction mixture was subsequently concentrated and the crude residue was purified by preparative HPLC, eluting with 30% ACN (containing 0.035% TFA) in H$_2$O (containing 0.05% TFA) over a period of 10 minutes. The product-containing fractions were combined and volatiles evaporated in vacuo to give a TFA salt of the title compound as a light brown solid (0.014 g, 0.044 mmol, 46%). $^1$H NMR (400 MHz, DMSO-d$_6$) δ ppm 3.50 (s, 2H), 6.94 (d, J=7.58 Hz, 1H), 7.17 (dd, J=7.96, 0.88 Hz, 1H), 7.29-7.44 (m, 1H), 7.46-7.53 (m, 1H), 7.94 (s, 1H), 8.15 (s, 1H), 10.55 (s, 1H), 13.70 (s, 1H); ESI-MS m/z [M+H]$^+$ calc'd for C$_{16}$H$_{10}$F$_3$N$_3$O, 318.1. found 318.15.

Example 130

N-(2-hydroxyethyl)-4-(6-(trifluoromethyl)-1H-indazol-4-yl)benzamide

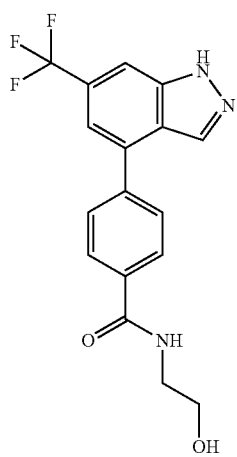

A vial was charged with a mixture of 4-bromo-6-(trifluoromethyl)-1H-indazole (0.300 g, 1.132 mmol), (4-((2-hydroxyethyl)carbamoyl)phenyl)boronic acid (0.237 g, 1.132 mmol) and PdCl$_2$(dppf) (0.041 g, 0.057 mmol) in dioxane (10 mL) and aqueous saturated NaHCO$_3$ (3 mL). The resulting yellow suspension was heated at 140° C. for 60 minutes in a microwave reactor. The reaction mixture was subsequently concentrated and the crude residue was purified by preparative HPLC, eluting with 40% ACN (containing 0.035% TFA) in H$_2$O (containing 0.05% TFA) over a period of 4.5 minutes. The product-containing fractions were combined and volatiles removed in vacuo to give a TFA salt of the title compound as white solid (0.12 g, 30%). $^1$H NMR (400 MHz, CD$_3$OD) δ ppm 3.56 (t, J=5.81 Hz, 2H), 3.75 (t, J=5.81 Hz, 2H), 7.49 (d, J=1.01 Hz, 1H), 7.78-7.89 (m, 2H), 7.93 (s, 1H), 8.00-8.10 (m, 2H), 8.21-8.32 (m, 1H); ESI-MS m/z [M+H]$^+$ calc'd for C$_{17}$H$_{14}$F$_3$N$_3$O$_2$, 350.1. found 350.1.

Example 131

4(2,4-dimethoxypyrimidin-5-yl)-6-(trifluoromethyl)-1H-indazole

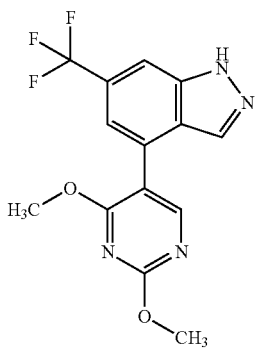 [SMILES: COc1ncc(-c2cc(C(F)(F)F)cc3[nH]ncc23)c(OC)n1]

4-(4,4,5,5-Tetramethyl-1,3,2-dioxaborolan-2-yl)-6-(trifluoromethyl)-1H-indazole (35 mg, 0.112 mmol), 5-bromo-2,4-dimethoxypyrimidine (24.56 mg, 0.112 mmol), and PdCl$_2$(dppf) (8.21 mg, 0.011 mmol) were dispersed in dioxane (1.5 mL). To the resulting slurry was added 2N aqueous sodium carbonate (0.112 mL, 0.224 mmol). The mixture was purged with nitrogen, heated in a microwave reactor at 130° C. for 50 minutes, and then filtered through a microfiltration frit. Dioxane was stripped with nitrogen. The resulting residue was taken up in DMSO and methanol (1:1) and was purified via preparative HPLC, eluting with a gradient of ACN (containing 0.035% TFA) in H$_2$O (containing 0.05% TFA). The purified fractions were collected to give a TFA salt of the title compound (8.2 mg, 23%). ESI-MS m/z [M+H]$^+$ calc'd for C$_{14}$H$_{11}$F$_3$N$_4$O$_2$, 325.1. found 325.2.

Example 132

4-(2,4-dimethoxypyrimidin-5-yl)-6-(trifluoromethyl)-1H-indazole

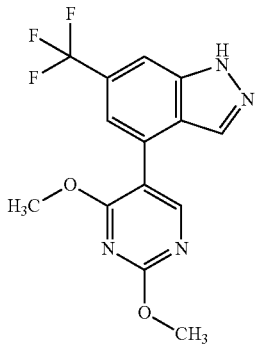 [SMILES: COc1ncc(-c2cc(C(F)(F)F)cc3[nH]ncc23)c(OC)n1]

4-(4,4,5,5-Tetramethyl-1,3,2-dioxaborolan-2-yl)-6-(trifluoromethyl)-1H-indazole (100 mg, 0.320 mmol), 5-iodo-2,4-dimethoxypyrimidine (57 mg, 0.215 mmol), and PdCl$_2$(dppf) (23 mg, 0.032 mmol) were dispersed in dioxane (3 mL). To the resulting slurry was added 2N aqueous sodium carbonate (0.320 mL, 0.641 mmol). The mixture was heated in a microwave reactor at 130° C. for 1 hour, and then filtered through a microfiltration frit, which was rinsed with methanol. The solvents were removed in vacuo and the resulting residue was taken up in DMSO and methanol (1:1) and was purified via preparative HPLC, eluting with a gradient of 40-45% ACN (containing 0.1% formic acid) in H$_2$O (containing 0.1% formic acid). The purified fractions were collected to give a formic acid salt of the title compound (33.5 mg, 32.2%). $^1$H NMR (400 MHz, DMSO-d$_6$) δ ppm 3.95 (s, 3H), 4.00 (s, 3 H), 7.43 (s, 1H), 7.95 (s, 1H), 8.12 (s, 1H), 8.52 (s, 1H), 13.64 (br s, 1H); ESI-MS m/z [M+H]$^+$ calc'd for C$_{14}$H$_{11}$F$_3$N$_4$O$_2$, 325.1. found 325.2.

The compounds of EXAMPLES 133 through 244, below, were prepared in accordance with Scheme C using procedures similar to the method in EXAMPLE 131.

Scheme C

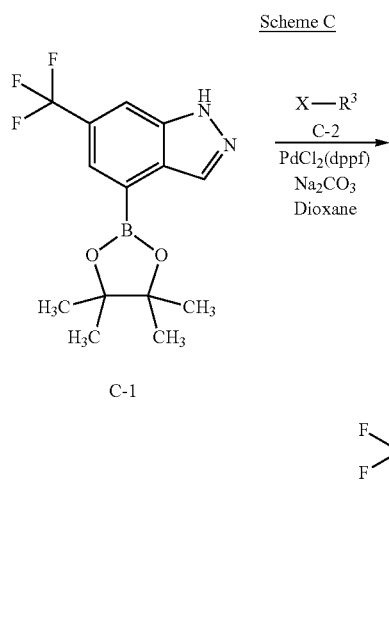

Reaction conditions: 4-(4,4,5,5-tetramethyl-1,3,2-dioxaborolan-2-yl)-6-(trifluoromethyl)-1H-indazole (C–1) (19-40 mg, 0.061-0.128 mmol), halide (C-2, X=Br, Cl or I) (0.67-1.5 eq), PdCl$_2$(dppf) or PdCl$_2$(dppf)CH$_2$Cl$_2$ (0.1 eq), aqueous Na$_2$CO$_3$ (2N, 2-4 eq), dioxane (1.5-2.0 mL) at 130-135° C. for 30-60 minutes (except for EXAMPLES 144-158, 90° C. for 60 minutes). Unless stated otherwise, the title compounds were isolated as TFA salts.

Example 133

4-(2-ethoxypyridin-3-yl)-6-(trifluoromethyl)-1H-indazole

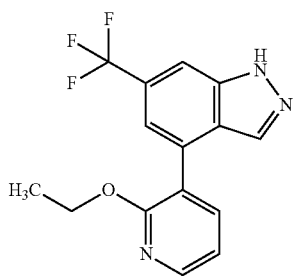 [SMILES: CCOc1ncccc1-c1cc(C(F)(F)F)cc2[nH]ncc12]

$^1$H NMR (400 MHz, DMSO-d$_6$) δ ppm 1.20 (t, J=6.95 Hz, 3H), 4.38 (q, J=6.99 Hz, 2H), 7.16 (dd, J=7.33, 5.05 Hz, 1H), 7.46 (s, 1H), 7.88-7.99 (m, 2H), 8.07 (s, 1H), 8.28 (dd, J=4.93, 1.89 Hz, 1H), 13.61 (br s, 1H); ESI-MS m/z [M+H]$^+$ calc'd for C$_{15}$H$_{12}$F$_3$N$_3$O, 308.1. found 308.2.

Example 134

4-(2-propoxypyridin-3-yl)-6-(trifluoromethyl)-1H-indazole

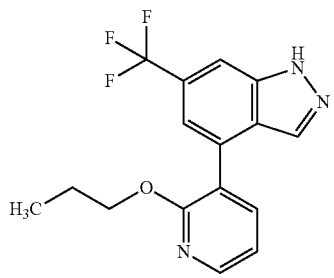 [SMILES: CCCOc1ncccc1-c1cc(C(F)(F)F)cc2[nH]ncc12]

$^1$H NMR (400 MHz, DMSO-d$_6$) δ ppm 0.83 (t, J=7.33 Hz, 3H), 1.60 (q, J=6.82 Hz, 2H), 4.28 (t, J=6.44 Hz, 2H), 7.16 (dd, J=7.33, 5.05 Hz, 1H), 7.48 (s, 1H), 7.89-8.00 (m, 2H), 8.08 (s, 1H), 8.28 (dd, J=4.80, 1.77 Hz, 1H), 13.63 (s, 1H); ESI-MS m/z [M+H]$^+$ calc'd for C$_{16}$H$_{14}$F$_3$N$_3$O, 322.1. found 322.2.

Example 135

4-(3-methylpyridin-2-yl)-6-(trifluoromethyl)-1H-indazole

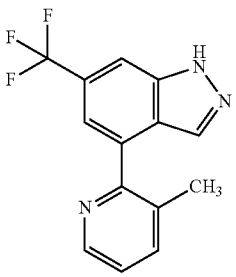 [SMILES: Cc1cccnc1-c1cc(C(F)(F)F)cc2[nH]ncc12]

$^1$H NMR (400 MHz, DMSO-d$_6$) δ ppm 2.28 (s, 3H), 7.48 (s, 1H), 7.49-7.56 (m, 1H), 7.94 (d, J=7.58 Hz, 1H), 8.03 (s, 2H), 8.62 (d, J=4.29 Hz, 1H); ESI-MS m/z [M+H]$^+$ calc'd for C$_{14}$H$_{10}$F$_3$N$_3$, 278.1. found 278.2.

Example 136

7-(6-(trifluoromethyl)-1H-indazol-4-yl)indolin-2-one

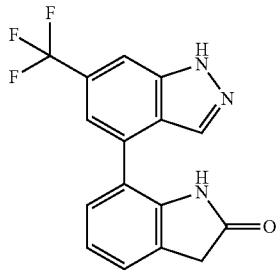 [SMILES: O=C1Cc2cccc(-c3cc(C(F)(F)F)cc4[nH]ncc34)c2N1]

ESI-MS m/z [M+H]+ calc'd for $C_{16}H_{10}F_3N_3O$, 318.1. found 318.2.

Example 137

5-chloro-3-(6-(trifluoromethyl)-1H-indazol-4-yl)pyridin-2-amine

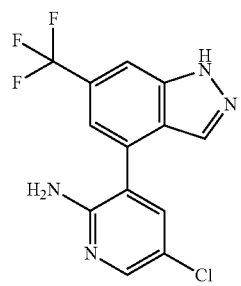

ESI-MS m/z [M+H]+ calc'd for $C_{13}H_8ClF_3N_4$, 313.0. found 313.1.

Example 138

4-methoxy-5-(6-(trifluoromethyl)-1H-indazol-4-yl)pyrimidin-2-amine

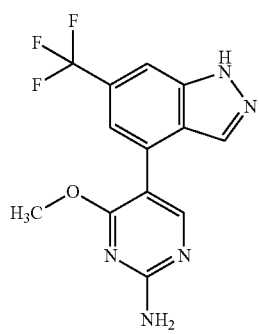 [SMILES: COc1nc(N)ncc1-c1cc(C(F)(F)F)cc2[nH]ncc12]

ESI-MS m/z [M+H]+ calc'd for $C_{13}H_{10}F_3N_5O$, 310.1. found 310.2.

Example 139

8-(6-(trifluoromethyl)-1H-indazol-4-yl)-2H-benzo[b][1,4]oxazin-3(4H)-one

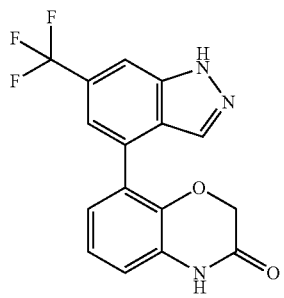 [SMILES: O=C1COc2c(cccc2-c2cc(C(F)(F)F)cc3[nH]ncc23)N1]

ESI-MS m/z [M+H]+ calc'd for $C_{16}H_{10}F_3N_3O_2$, 334.1. found 334.2.

Example 140

4-(hydroxymethyl)-3-(6-(trifluoromethyl)-1H-indazol-4-yl)benzonitrile

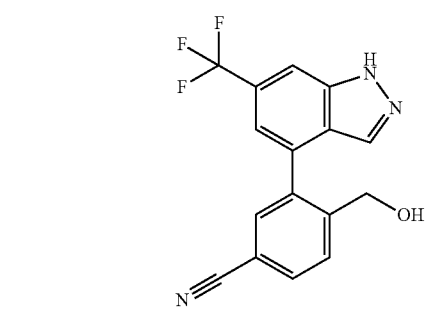 [SMILES: N#Cc1ccc(CO)c(-c2cc(C(F)(F)F)cc3[nH]ncc23)c1]

$^1$H NMR (400 MHz, DMSO-d$_6$) δ ppm 4.36 (s, 2H), 7.39 (s, 1H), 7.83-7.92 (m, 2H), 7.93-8.06 (m, 3H), 13.76 (br s, 1H); ESI-MS m/z [M+H]+ calc'd for $C_{16}H_{10}F_3N_3O$, 318.1. found 318.2.

Example 141

4-(6-(trifluoromethyl)-1H-indazol-4-yl)isoindolin-1-one

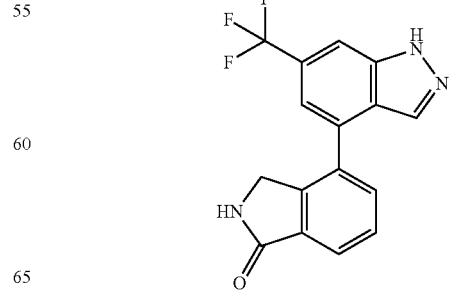

¹H NMR (400 MHz, DMSO-d₆) δ ppm 4.41 (s, 2H), 7.59 (s, 1H), 7.64-7.75 (m, 1H), 7.77-7.89 (m, 2H), 8.00 (s, 1H), 8.16 (s, 1H), 8.67 (s, 1H), 13.76 (s, 1H); ESI-MS m/z [M+H]⁺ calc'd for $C_{16}H_{10}F_3N_3O$, 318.1. found 318.2.

Example 142

5-(6-(trifluoromethyl)-1H-indazol-4-yl)-1,7-naphthyridin-8-amine

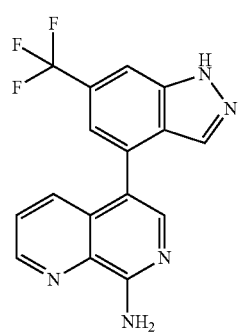 [SMILES: Nc1ncc(-c2cc(C(F)(F)F)cc3[nH]ncc23)c2cccnc12]

ESI-MS m/z [M+H]⁺ calc'd for $C_{16}H_{10}F_3N_5$, 330.1. found 330.2.

Example 143

4-(2-isopropoxypyridin-3-yl)-6-(trifluoromethyl)-1H-indazole

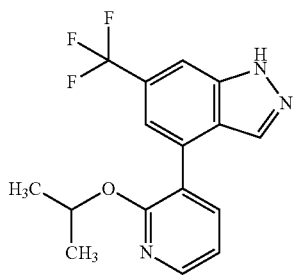 [SMILES: CC(C)Oc1ncccc1-c1cc(C(F)(F)F)cc2[nH]ncc12]

ESI-MS m/z [M+H]⁺ calc'd for $C_{16}H_{14}F_3N_3O$, 322.1. found 322.2.

Example 144

1-methyl-4-(6-(trifluoromethyl)-1H-indazol-4-yl)-1H-pyrazol-3-amine

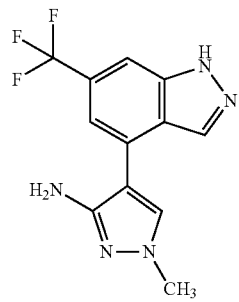

ESI-MS m/z [M+H]⁺ calc'd for $C_{12}H_{10}F_3N_5$, 282.1. found 282.1.

Example 145

4-(1-(ethoxymethyl)-1H-imidazol-2-yl)-6-(trifluoromethyl)-1H-indazole

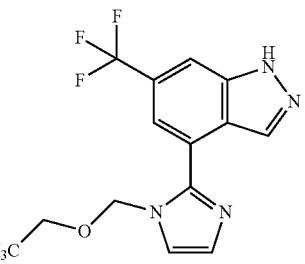

ESI-MS m/z [M+H]⁺ calc'd for $C_{14}H_{13}F_3N_4O$, 311.1. found 311.2.

Example 146

4-(1,2-dimethyl-1H-imidazol-5-yl)-6-(trifluoromethyl)-1H-indazole

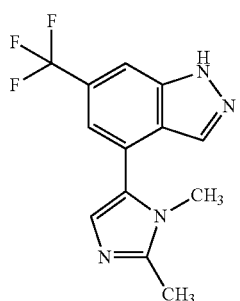

¹H NMR (400 MHz, DMSO-d₆) δ ppm 2.70 (s, 3H), 3.63 (s, 3H), 7.56 (s, 1H), 7.97 (s, 1H), 8.17 (s, 1H), 8.30 (s, 1H); ESI-MS m/z [M+H]⁺ calc'd for $C_{13}H_{11}F_3N_4$, 281.1. found 281.2.

Example 147

4-(1-methyl-1H-imidazol-2-yl)-6-(trifluoromethyl)-1H-indazole

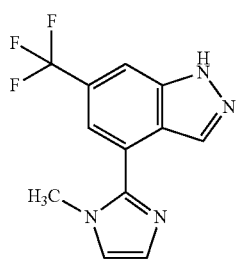 [SMILES: Cn1ccnc1-c1cc(C(F)(F)F)cc2[nH]ncc12]

ESI-MS m/z [M+H]⁺ calc'd for $C_{12}H_9F_3N_4$, 267.1. found 267.2.

Example 148

4-(6-(trifluoromethyl)-1H-indazol-4-yl)-1H-pyrazole-3-carbonitrile

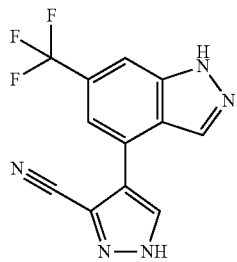 [SMILES: N#Cc1n[nH]cc1-c1cc(C(F)(F)F)cc2[nH]ncc12]

ESI-MS m/z [M+H]+ calc'd for $C_{12}H_6F_3N_5$, 278.1. found 278.2.

Example 149

4-(imidazo[1,2-a]pyridin-3-yl)-6-(trifluoromethyl)-1H-indazole

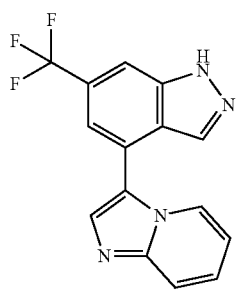 [SMILES: FC(F)(F)c1cc(-c2cnc3ccccn23)c2cn[nH]c2c1]

ESI-MS m/z [M+H]+ calc'd for $C_{15}H_9F_3N_4$, 303.1. found 303.2.

Example 150

4-(2-methylimidazo[1,2-a]pyridin-3-yl)-6-(trifluoromethyl)-1H-indazole

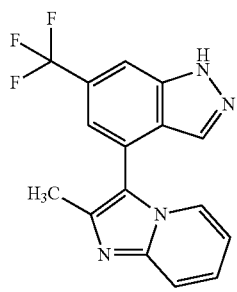 [SMILES: Cc1nc2ccccn2c1-c1cc(C(F)(F)F)cc2[nH]ncc12]

ESI-MS m/z [M+H]+ calc'd for $C_{16}H_{11}F_3N_4$, 317.1. found 317.2.

Example 151

3-(6-(trifluoromethyl)-1H-indazol-4-yl)imidazo[1,2-a]pyrimidine

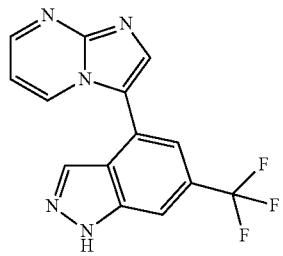 [SMILES: FC(F)(F)c1cc(-c2cnc3ncccn23)c2cn[nH]c2c1]

ESI-MS m/z [M+H]+ calc'd for $C_{14}H_8F_3N_5$, 304.1. found 304.2.

Example 152

3-(6-(trifluoromethyl)-1H-indazol-4-yl)imidazo[1,2-a]pyrazine

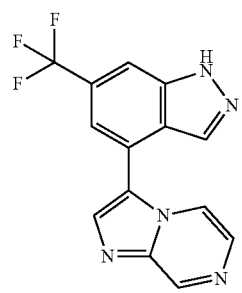 [SMILES: FC(F)(F)c1cc(-c2cnc3cnccn23)c2cn[nH]c2c1]

$^1$H NMR (400 MHz, DMSO-d$_6$) δ ppm 7.74 (s, 1H), 8.01 (d, J=4.80 Hz, 1H), 8.10 (s, 1H), 8.25 (s, 1H), 8.32 (s, 1H), 8.49 (dd, J=4.80, 1.26 Hz, 1H), 9.26 (d, J=1.26 Hz, 1H); ESI-MS m/z [M+H]+ calc'd for $C_{14}H_8F_3N_5$, 304.1. found 304.2.

Example 153

3-(6-(trifluoromethyl)-1H-indazol-4-yl)imidazo[1,2-a]pyridine-6-carbonitrile

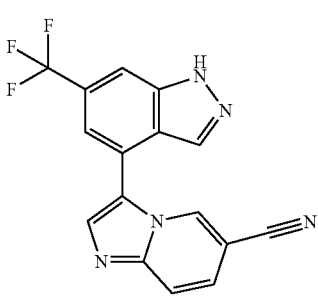 [SMILES: N#Cc1ccc2ncc(-c3cc(C(F)(F)F)cc4[nH]ncc34)n2c1]

ESI-MS m/z [M+H]+ calc'd for $C_{16}H_8F_3N_5$, 328.1. found 328.2.

Example 154

4-(imidazo[1,5-a]pyridin-1-yl)-6-(trifluoromethyl)-1H-indazole

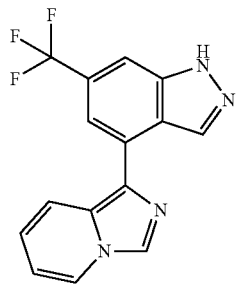 [SMILES: FC(F)(F)c1cc(-c2ncn3ccccc23)c2cn[nH]c2c1]

¹H NMR (400 MHz, DMSO-d₆) δ ppm 6.86 (t, J=6.69 Hz, 1H), 7.08 (dd, J=9.09, 6.32 Hz, 1H), 7.62 (s, 1H), 7.81 (s, 1H), 7.90 (d, J=9.09 Hz, 1H), 8.51 (d, J=7.07 Hz, 1H), 8.70 (d, J=8.08 Hz, 2H); ESI-MS m/z [M+H]⁺ calc'd for $C_{15}H_9F_3N_4$, 303.1. found 303.2.

Example 155

5-(6-(trifluoromethyl)-1H-indazol-4-yl)-7H-pyrrolo[2,3-d]pyrimidine

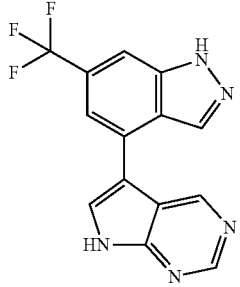 [SMILES: FC(F)(F)c1cc(-c2c[nH]c3ncncc23)c2cn[nH]c2c1]

ESI-MS m/z [M+H]⁺ calc'd for $C_{14}H_8F_3N_5$, 304.1. found 304.1.

Example 156

3-(6-(trifluoromethyl)-1H-indazol-4-yl)-1H-pyrazolo[3,4-d]pyrimidin-4(5H)-one

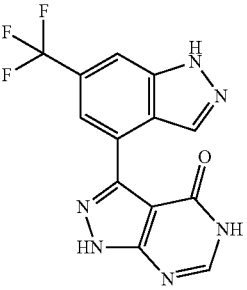 [SMILES: O=c1[nH]cnc2[nH]nc(-c3cc(C(F)(F)F)cc4[nH]ncc34)c12]

ESI-MS m/z [M+H]⁺ calc'd for $C_{13}H_7F_3N_6O$, 321.1. found 321.2.

Example 157

7-(6-(trifluoromethyl)-1H-indazol-4-yl)-5H-pyrrolo[2,3-b]pyrazine

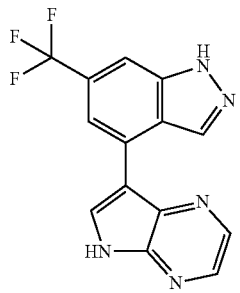 [SMILES: FC(F)(F)c1cc(-c2c[nH]c3nccnc23)c2cn[nH]c2c1]

ESI-MS m/z [M+H]⁺ calc'd for $C_{14}H_8F_3N_5$, 304.1. found 304.2.

Example 158

4-(6-(trifluoromethyl)-1H-indazol-4-yl)-1H-pyrazole-5-carbonitrile

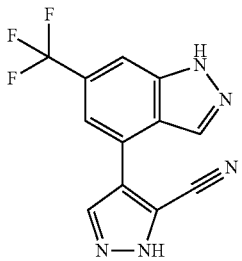 [SMILES: N#Cc1[nH]ncc1-c1cc(C(F)(F)F)cc2[nH]ncc12]

ESI-MS m/z [M+H]⁺ calc'd for $C_{12}H_6F_3N_5$, 278.1. found 278.1.

Example 159

7-amino-3-(6-(trifluoromethyl)-1H-indazol-4-yl)pyrazolo[1,5-a]pyrimidine-6-carbonitrile

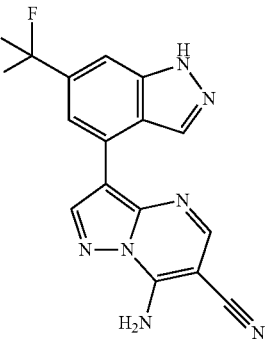

ESI-MS m/z [M+H]+ calc'd for C15H8F3N7, 344.1. found 344.1.

Example 160

7-methoxy-3-(6-(trifluoromethyl)-1H-indazol-4-yl) imidazo[1,2-a]pyridine-8-carbonitrile

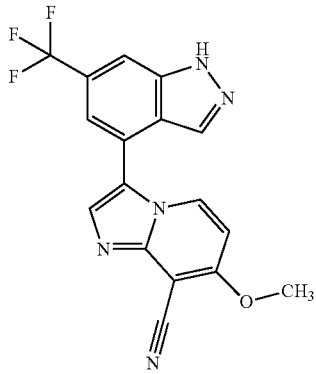 [SMILES: COc1ccn2c(-c3cc(C(F)(F)F)cc4[nH]ncc34)cnc2c1C#N]

ESI-MS m/z [M+H]+ calc'd for C17H10F3N5O, 358.1. found 358.2.

Example 161

4-(5-methyl-1H-imidazol-4-yl)-6-(trifluoromethyl)-1H-indazole

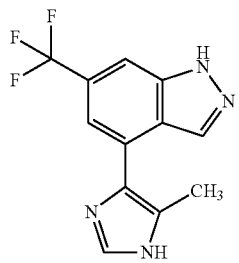 [SMILES: Cc1[nH]cnc1-c1cc(C(F)(F)F)cc2[nH]ncc12]

ESI-MS m/z [M+H]+ calc'd for C12H9F3N4, 267.1. found 267.1.

Example 162

4-(1,5-dimethyl-1H-imidazol-2-yl)-6-(trifluoromethyl)-1H-indazole

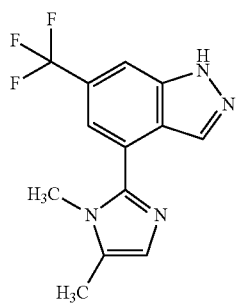 [SMILES: Cc1cnc(-c2cc(C(F)(F)F)cc3[nH]ncc23)n1C]

ESI-MS m/z [M+H]+ calc'd for C13H11F3N4, 281.1. found 281.1.

Example 163

4-(1,4-dimethyl-1H-imidazol-2-yl)-6-(trifluoromethyl)-1H-indazole

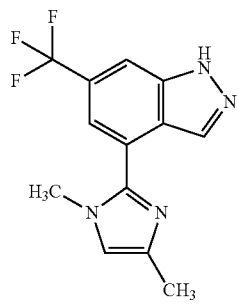 [SMILES: Cc1cn(C)c(-c2cc(C(F)(F)F)cc3[nH]ncc23)n1]

ESI-MS m/z [M+H]+ calc'd for C13H11F3N4, 281.1. found 281.1.

Example 164

6-(trifluoromethyl)-4-(1,3,5-trimethyl-1H-pyrazol-4-yl)-1H-indazole

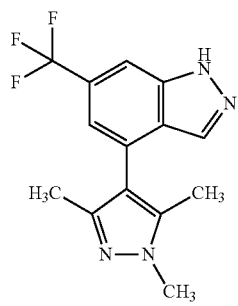 [SMILES: Cc1nn(C)c(C)c1-c1cc(C(F)(F)F)cc2[nH]ncc12]

ESI-MS m/z [M+H]+ calc'd for C14H13F3N4, 295.1. found 295.2.

Example 165

1-methyl-4-(6-(trifluoromethyl)-1H-indazol-4-yl)-1H-pyrazol-5-amine

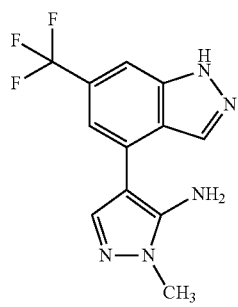 [SMILES: Cn1ncc(-c2cc(C(F)(F)F)cc3[nH]ncc23)c1N]

ESI-MS m/z [M+H]+ calc'd for $C_{12}H_{10}F_3N_5$, 282.1. found 282.1.

Example 166

5-methyl-4-(6-(trifluoromethyl)-1H-indazol-4-yl)isoxazol-3-amine

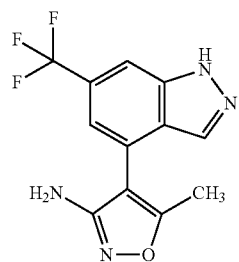 [SMILES: Cc1onc(N)c1-c1cc(C(F)(F)F)cc2[nH]ncc12]

ESI-MS m/z [M+H]+ calc'd for $C_{12}H_9F_3N_4O$, 283.1. found 283.1.

Example 167

3,7-dimethyl-8-(6-(trifluoromethyl)-1H-indazol-4-yl)-1H-purine-2,6(3H,7H)-dione

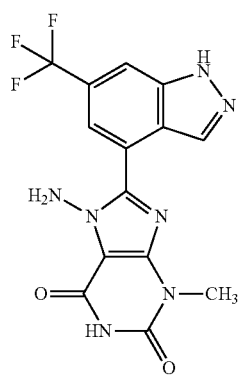 [SMILES: Cn1c(=O)[nH]c(=O)c2c1nc(-c1cc(C(F)(F)F)cc3[nH]ncc13)n2N]

ESI-MS m/z [M+H]+ calc'd for $C_{15}H_{11}F_3N_6O_2$, 365.1. found 365.2.

Example 168

4-(1-ethyl-3,5-dimethyl-1H-pyrazol-4-yl)-6-(trifluoromethyl)-1H-indazole

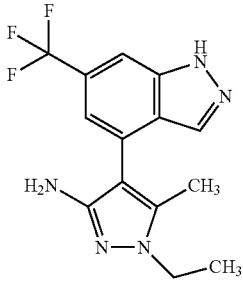 [SMILES: CCn1nc(N)c(-c2cc(C(F)(F)F)cc3[nH]ncc23)c1C]

1H NMR (400 MHz, DMSO-$d_6$) δ ppm 1.37 (t, J=7.20 Hz, 3H), 2.09 (s, 3H), 2.19 (s, 3H), 4.08 (q, J=7.07 Hz, 2H), 7.14 (s, 1H), 7.85 (s, 1H), 8.00 (s, 1H); ESI-MS m/z [M+H]+ calc'd for $C_{15}H_{15}F_3N_4$, 309.1. found 309.3.

Example 169

4-(3,5-dimethyl-1-(1H-tetrazol-5-yl)-1H-pyrazol-4-yl)-6-(trifluoromethyl)-1H-indazole

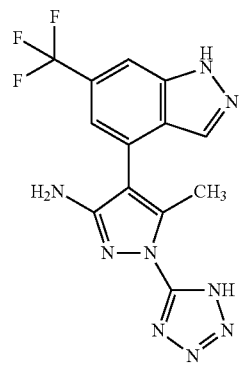 [SMILES: Cc1c(-c2cc(C(F)(F)F)cc3[nH]ncc23)c(N)nn1-c1nnn[nH]1]

ESI-MS m/z [M+H]+ calc'd for $C_{14}H_{11}F_3N_8$, 349.1. found 349.2.

Example 170

2-(3,5-dimethyl-4-(6-(trifluoromethyl)-1H-indazol-4-yl)-1H-pyrazol-1-yl)acetonitrile

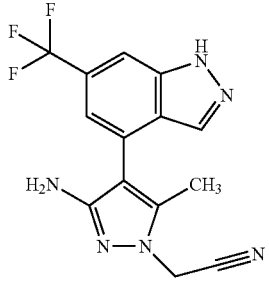 [SMILES: Cc1c(-c2cc(C(F)(F)F)cc3[nH]ncc23)c(N)nn1CC#N]

ESI-MS m/z [M+H]+ calc'd for $C_{15}H_{12}F_3N_5$, 320.1. found 320.1.

Example 171

4-(1-ethyl-3-methyl-1H-pyrazol-4-yl)-6-(trifluoromethyl)-1H-indazole

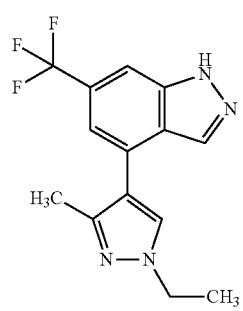 [SMILES: CCn1cc(-c2cc(C(F)(F)F)cc3[nH]ncc23)c(C)n1]

ESI-MS m/z [M+H]+ calc'd for $C_{14}H_{13}F_3N_4$, 295.1. found 295.2.

Example 172

3-(3,5-dimethyl-4-(6-(trifluoromethyl)-1H-indazol-4-yl)-1H-pyrazol-1-yl)propanamide

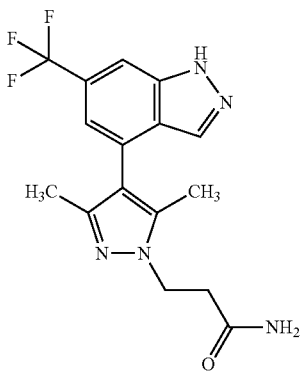 [SMILES: Cc1nn(CCC(N)=O)c(C)c1-c1cc(C(F)(F)F)cc2[nH]ncc12]

ESI-MS m/z [M+H]+ calc'd for $C_{16}H_{16}F_3N_5O$, 352.1. found 352.1.

Example 173

2-(3,5-dimethyl-4-(6-(trifluoromethyl)-1H-indazol-4-yl)-1H-pyrazol-1-yl)acetamide

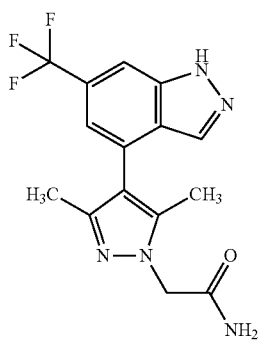 [SMILES: Cc1nn(CC(N)=O)c(C)c1-c1cc(C(F)(F)F)cc2[nH]ncc12]

$^1$H NMR (400 MHz, DMSO-d$_6$) δ ppm 2.09 (s, 3H), 2.14 (s, 3H), 4.73 (s, 2H), 7.15 (d, J=1.01 Hz, 1H), 7.30 (s, 1H), 7.52 (br s, 1H), 7.87 (s, 1H), 7.98 (d, J=1.01 Hz, 1H); ESI-MS m/z [M+H]+ calc'd for $C_{15}H_{14}F_3N_5O$, 338.1. found 338.2.

Example 174

3-(3,5-dimethyl-4-(6-(trifluoromethyl)-1H-indazol-4-yl)-1H-pyrazol-1-yl)propanenitrile

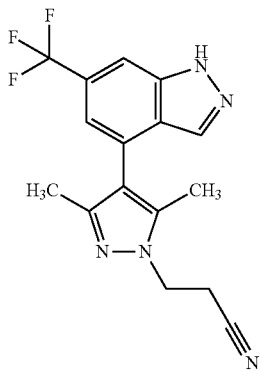 [SMILES: Cc1nn(CCC#N)c(C)c1-c1cc(C(F)(F)F)cc2[nH]ncc12]

$^1$H NMR (400 MHz, DMSO-d$_6$) δ ppm 2.11 (s, 3H), 2.23 (s, 3H), 3.08 (t, J=6.44 Hz, 2H), 4.36 (t, J=6.44 Hz, 2H), 7.16 (s, 1H), 7.88 (s, 1H), 7.97 (s, 1H); ESI-MS m/z [M+H]+ calc'd for $C_{16}H_{14}F_3N_5$, 334.1. found 334.1.

Example 175

4-(1-ethyl-5-methyl-1H-pyrazol-4-yl)-6-(trifluoromethyl)-1H-indazole

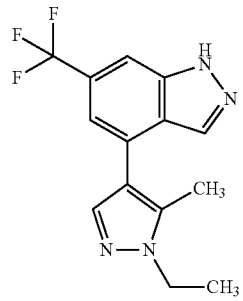

ESI-MS m/z [M+H]+ calc'd for $C_{14}H_{13}F_3N_4$, 295.1. found 295.1.

Example 176

2-(3,5-dimethyl-4-(6-(trifluoromethyl)-1H-indazol-4-yl)-1H-pyrazol-1-yl)ethanamine

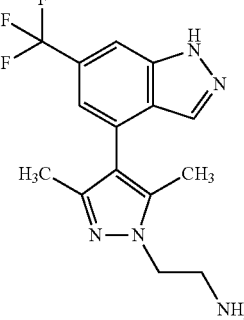

$^1$H NMR (400 MHz, DMSO-d$_6$) δ ppm 2.09-2.16 (m, 3H), 2.17-2.24 (m, 3H), 3.27-3.36 (m, 2H), 4.28 (t, J=6.19 Hz, 2H), 7.15 (s, 1H), 7.89 (s, 1H), 7.93 (br s, 2H), 8.03 (s, 1H), 13.64 (br s, 1H); ESI-MS m/z [M+H]+ calc'd for $C_{15}H_{16}F_3N_5$, 324.1. found 324.1.

Example 177

4-methyl-5-(6-(trifluoromethyl)-1H-indazol-4-yl)thiazole

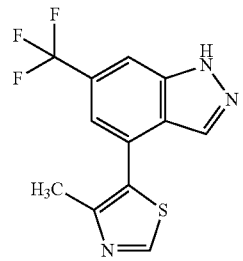 [SMILES: Cc1ncsc1-c1cc(C(F)(F)F)cc2[nH]ncc12]

ESI-MS m/z [M+H]+ calc'd for $C_{12}H_8F_3N_3S$, 284.1. found 284.1.

Example 178

N-(6-methyl-5-(6-(trifluoromethyl)-1H-indazol-4-yl)pyridin-2-yl)acetamide

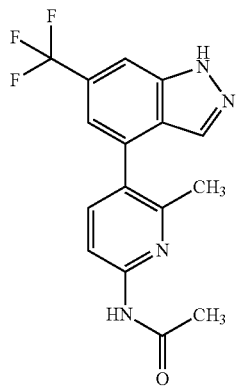 [SMILES: CC(=O)Nc1ccc(-c2cc(C(F)(F)F)cc3[nH]ncc23)c(C)n1]

$^1$H NMR (400 MHz, DMSO-d$_6$) δ ppm 2.13 (s, 3H), 2.31 (s, 3H), 7.33 (s, 1H), 7.77 (d, J=8.59 Hz, 1H), 7.99 (d, J=13.89 Hz, 2H), 8.07 (d, J=8.34 Hz, 1H), 10.66 (s, 1H); ESI-MS m/z [M+H]$^+$ calc'd for C$_{16}$H$_{13}$F$_3$N$_4$O, 335.1. found 335.2.

Example 179

N-(4-methyl-5-(6-(trifluoromethyl)-1H-indazol-4-yl)pyridin-2-yl)acetamide

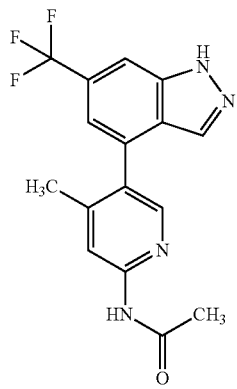 [SMILES: CC(=O)Nc1cc(C)c(-c2cc(C(F)(F)F)cc3[nH]ncc23)cn1]

ESI-MS m/z [M+H]$^+$ calc'd for C$_{16}$H$_{13}$F$_3$N$_4$O, 335.1. found 335.2.

Example 180

1-morpholino-3-(2-(6-(trifluoromethyl)-1H-indazol-4-yl)phenoxy)propan-2-ol

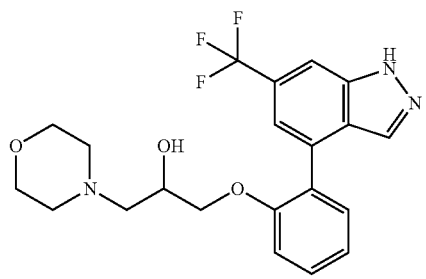 [SMILES: OC(COc1ccccc1-c1cc(C(F)(F)F)cc2[nH]ncc12)CN1CCOCC1]

ESI-MS m/z [M+H]$^+$ calc'd for C$_{21}$H$_{22}$F$_3$N$_3$O$_3$, 422.2. found 422.3.

Example 181

4-methoxy-N-methyl-3-(6-(trifluoromethyl)-1H-indazol-4-yl)benzamide

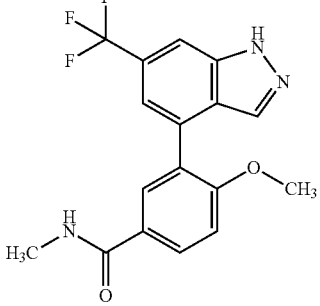

$^1$H NMR (400 MHz, DMSO-d$_6$) δ ppm 2.78 (d, J=4.29 Hz, 3H), 3.82 (s, 3H), 7.30 (d, J=8.84 Hz, 1H), 7.38 (s, 1H), 7.88-8.05 (m, 4H), 8.41 (d, J=4.55 Hz, 1H), 13.59 (s, 1H); ESI-MS m/z [M+H]$^+$ calc'd for C$_{17}$H$_{14}$F$_3$N$_3$O$_2$, 350.1. found 350.2.

Example 182

2-(2-(6-(trifluoromethyl)-1H-indazol-4-yl)phenylsulfonyl)ethanol

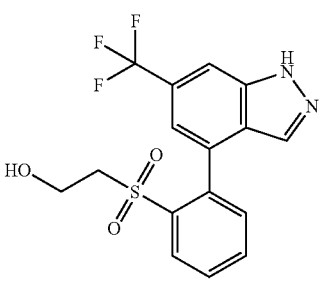 [SMILES: O=S(=O)(CCO)c1ccccc1-c1cc(C(F)(F)F)cc2[nH]ncc12]

$^1$H NMR (400 MHz, DMSO-d$_6$) δ ppm 3.54 (t, J=6.19 Hz, 2H), 3.57-3.62 (m, 2H), 7.43 (s, 1H), 7.53 (dd, J=7.33, 1.26 Hz, 1H), 7.72-7.89 (m, 3H), 8.01 (s, 1H), 8.15 (dd, J=7.71, 1.14 Hz, 1H); ESI-MS m/z [M+H]$^+$ calc'd for C$_{16}$H$_{13}$F$_3$N$_2$O$_3$S, 371.1. found 371.1.

Example 183

N,N-dimethyl-2-(6-(trifluoromethyl)-1H-indazol-4-yl)benzenesulfonamide

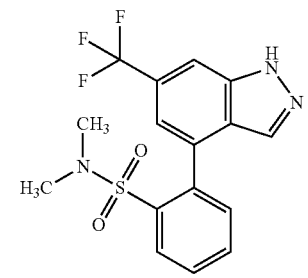 [SMILES: CN(C)S(=O)(=O)c1ccccc1-c1cc(C(F)(F)F)cc2[nH]ncc12]

ESI-MS m/z [M+H]$^+$ calc'd for C$_{16}$H$_{14}$F$_3$N$_3$O$_2$S, 370.1. found 370.2.

Example 184

6-methoxy-2-(6-(trifluoromethyl)-1H-indazol-4-yl)pyridin-3-amine

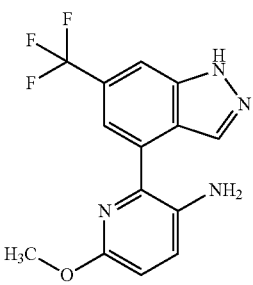 [SMILES: COc1ccc(N)c(-c2cc(C(F)(F)F)cc3[nH]ncc23)n1]

ESI-MS m/z [M+H]$^+$ calc'd for $C_{14}H_{11}F_3N_4O$, 309.1. found 309.2.

Example 185

(4-methoxy-3-(6-(trifluoromethyl)-1H-indazol-4-yl)phenyl)methanol

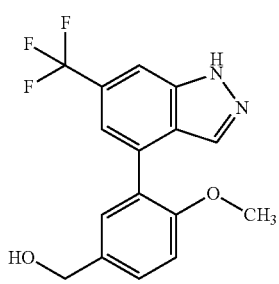 [SMILES: COc1ccc(CO)cc1-c1cc(C(F)(F)F)cc2[nH]ncc12]

ESI-MS m/z [M+H]$^+$ calc'd for $C_{16}H_{13}F_3N_2O_2$, 323.1. found 323.2.

Example 186

3-methyl-4-(6-(trifluoromethyl)-1H-indazol-4-yl)benzenesulfonamide

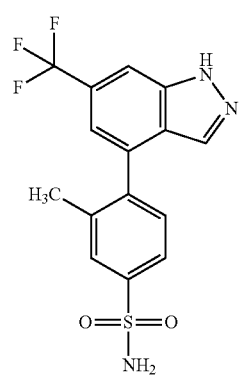 [SMILES: Cc1cc(S(N)(=O)=O)ccc1-c1cc(C(F)(F)F)cc2[nH]ncc12]

ESI-MS m/z [M+H]$^+$ calc'd for $C_{15}H_{12}F_3N_3O_2S$, 356.1. found 356.1.

Example 187

6-methoxy-5-(6-(trifluoromethyl)-1H-indazol-4-yl)pyridin-3-amine

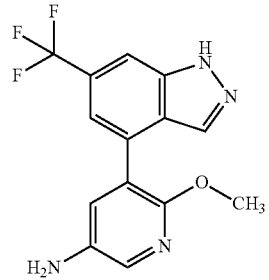 [SMILES: COc1ncc(N)cc1-c1cc(C(F)(F)F)cc2[nH]ncc12]

ESI-MS m/z [M+H]$^+$ calc'd for $C_{14}H_{11}F_3N_4O$, 309.1. found 309.1.

Example 188

6-methyl-2-(6-(trifluoromethyl)-1H-indazol-4-yl)pyridin-3-amine

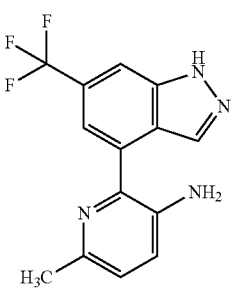 [SMILES: Cc1ccc(N)c(-c2cc(C(F)(F)F)cc3[nH]ncc23)n1]

ESI-MS m/z [M+H]$^+$ calc'd for $C_{14}H_{11}F_3N_4$, 293.1. found 293.1.

Example 189

(5-methoxy-2-(6-(trifluoromethyl)-1H-indazol-4-yl)phenyl)methanol

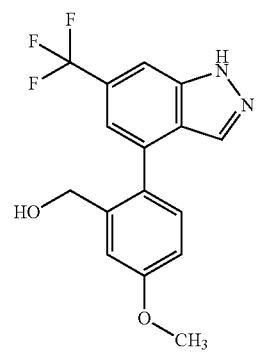 [SMILES: COc1ccc(-c2cc(C(F)(F)F)cc3[nH]ncc23)c(CO)c1]

ESI-MS m/z [M+H]+ calc'd for $C_{16}H_{13}F_3N_2O_2$, 323.1. found 323.1.

Example 190

4,6-dimethyl-5-(6-(trifluoromethyl)-1H-indazol-4-yl)pyrimidin-2-amine

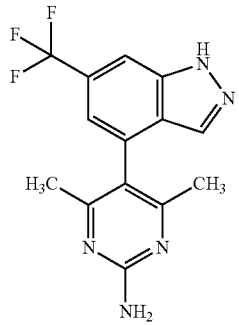 [SMILES: Cc1nc(N)nc(C)c1-c1cc(C(F)(F)F)cc2[nH]ncc12]

$^1$H NMR (400 MHz, DMSO-d$_6$) δ ppm 2.00 (s, 6H), 7.31 (s, 1H), 7.98 (d, J=10.11 Hz, 2H), 8.03 (s, 1H); ESI-MS m/z [M+H]+ calc'd for $C_{14}H_{12}F_3N_5$, 308.1. found 308.2.

Example 191

2-chloro-5-(6-(trifluoromethyl)-1H-indazol-4-yl)pyrimidin-4-amine

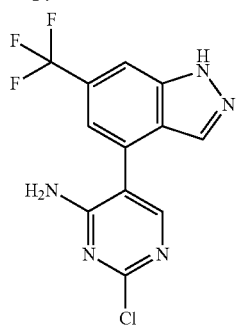

$^1$H NMR (400 MHz, CD$_3$OD) δ ppm 7.42 (d, J=1.01 Hz, 1H), 7.99 (s, 1H), 8.03-8.09 (m, 2H); ESI-MS m/z [M+H]+ calc'd for $C_{12}H_7ClF_3N_5$, 314.0. found 314.09.

Example 192

5-(6-(trifluoromethyl)-1H-indazol-4-yl)pyrimidine-4-carboxylic acid

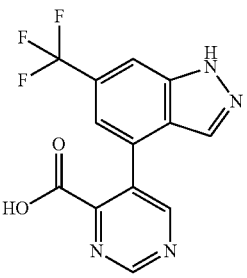 [SMILES: O=C(O)c1ncncc1-c1cc(C(F)(F)F)cc2[nH]ncc12]

$^1$H NMR (400 MHz, CD$_3$OD) δ ppm 7.43 (d, J=1.01 Hz, 1H), 7.94-8.11 (m, 2H), 9.10 (s, 1H), 9.35 (s, 1H); ESI-MS m/z [M+H]+ calc'd for $C_{13}H_7F_3N_4O_2$, 309.1. found 309.12.

Example 193

5-methyl-3-(6-(trifluoromethyl)-1H-indazol-4-yl)pyridin-2-amine

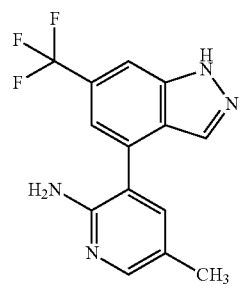 [SMILES: Cc1cnc(N)c(-c2cc(C(F)(F)F)cc3[nH]ncc23)c1]

ESI-MS m/z [M+H]+ calc'd for $C_{14}H_{11}F_3N_4$, 293.1. found 293.2.

Example 194

5-fluoro-3-(6-(trifluoromethyl)-1H-indazol-4-yl)pyridin-2-amine

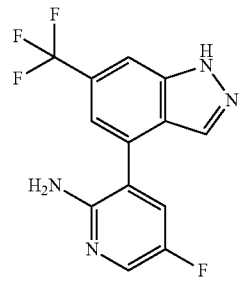 [SMILES: Nc1ncc(F)cc1-c1cc(C(F)(F)F)cc2[nH]ncc12]

ESI-MS m/z [M+H]+ calc'd for $C_{13}H_8F_4N_4$, 297.1. found 297.2.

Example 195

5-methyl-6-(6-(trifluoromethyl)-1H-indazol-4-yl)-3H-imidazo[4,5-b]pyridine

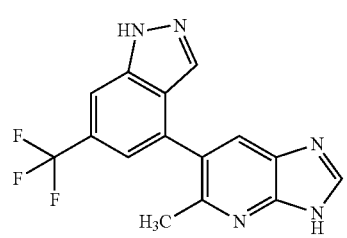 [SMILES: Cc1nc2[nH]cnc2cc1-c1cc(C(F)(F)F)cc2[nH]ncc12]

ESI-MS m/z [M+H]+ calc'd for $C_{15}H_{10}F_3N_5$, 318.1. found 318.2.

Example 196

N-methyl-5-(6-(trifluoromethyl)-1H-indazol-4-yl)pyrimidin-2-amine

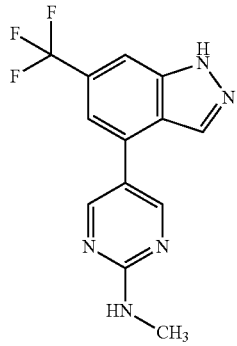 [SMILES: CNc1ncc(-c2cc(C(F)(F)F)cc3[nH]ncc23)cn1]

ESI-MS m/z [M+H]$^+$ calc'd for $C_{13}H_{10}F_3N_5$, 294.1. found 294.2.

Example 197

N-cyclopropyl-5-(6-(trifluoromethyl)-1H-indazol-4-yl)pyrimidin-2-amine

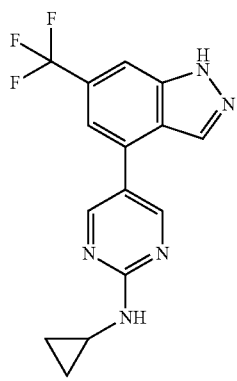 [SMILES: FC(F)(F)c1cc(-c2cnc(NC3CC3)nc2)c2cn[nH]c2c1]

ESI-MS m/z [M+H]$^+$ calc'd for $C_{15}H_{12}F_3N_5$, 320.1. found 320.2.

Example 198

5-(6-(trifluoromethyl)-1H-indazol-4-yl)pyrimidine-2-carbonitrile

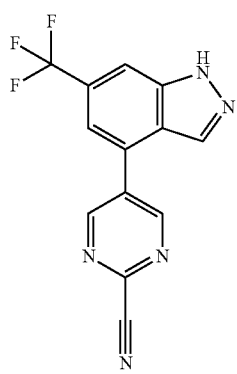 [SMILES: N#Cc1ncc(-c2cc(C(F)(F)F)cc3[nH]ncc23)cn1]

ESI-MS m/z [M+H]$^+$ calc'd for $C_{13}H_6F_3N_5$, 290.1. found 290.2.

Example 199

1-ethyl-5-methyl-7-(6-(trifluoromethyl)-1H-indazol-4-yl)indoline-2,3-dione

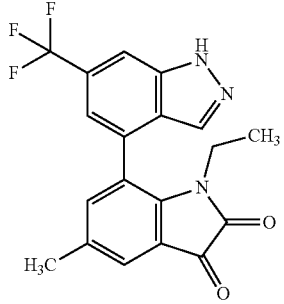 [SMILES: CCN1C(=O)C(=O)c2cc(C)cc(-c3cc(C(F)(F)F)cc4[nH]ncc34)c21]

$^1$H NMR (400 MHz, DMSO-d$_6$) δ ppm 0.56 (t, J=6.95 Hz, 3H), 2.34 (s, 3H), 3.4 (m, 2H), 7.43 (s, 1H), 7.51 (s, 1H), 7.54 (s, 1H), 8.06 (s, 1H), 8.13 (s, 1H); ESI-MS m/z [M+H]$^+$ calc'd for $C_{19}H_{14}F_3N_3O_2$, 374.1. found 374.3.

Example 200

4-(3-methoxy-6-methylpyridin-2-yl)-6-(trifluoromethyl)-1H-indazole

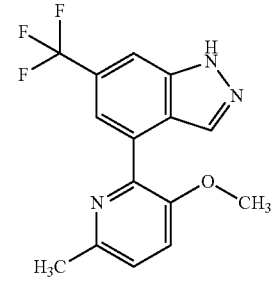 [SMILES: COc1ccc(C)nc1-c1cc(C(F)(F)F)cc2[nH]ncc12]

ESI-MS m/z [M+H]$^+$ calc'd for $C_{15}H_{12}F_3N_3O$, 308.1. found 308.2.

Example 201

6-methoxy-3-(6-(trifluoromethyl)-1H-indazol-4-yl)picolinamide

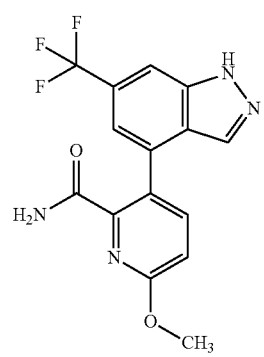 [SMILES: COc1ccc(-c2cc(C(F)(F)F)cc3[nH]ncc23)c(C(N)=O)n1]

ESI-MS m/z [M+H]$^+$ calc'd for $C_{15}H_{11}F_3N_4O_2$, 337.1. found 337.2.

Example 202

2-(1H-1,2,4-triazol-1-yl)-N-(2-(6-(trifluoromethyl)-1H-indazol-4-yl)benzyl)acetamide

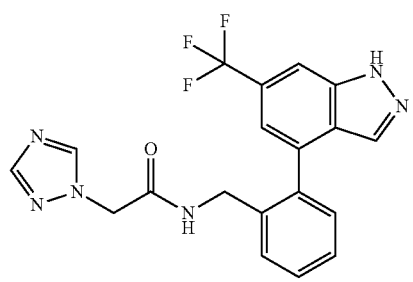 [SMILES: O=C(Cn1cncn1)NCc1ccccc1-c1cc(C(F)(F)F)cc2[nH]ncc12]

ESI-MS m/z [M+H]+ calc'd for $C_{19}H_{15}F_3N_6O$, 401.1. found 401.3.

Example 203

5-fluoro-2-(6-(trifluoromethyl)-1H-indazol-4-yl)benzamide

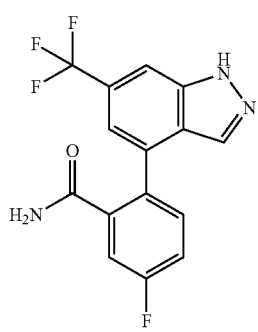 [SMILES: NC(=O)c1cc(F)ccc1-c1cc(C(F)(F)F)cc2[nH]ncc12]

ESI-MS m/z [M+H]+ calc'd for $C_{15}H_9F_4N_3O$, 324.1. found 324.1.

Example 204

6-methyl-5-(6-(trifluoromethyl)-1H-indazol-4-yl)pyrimidine-2,4(1H,3H)-dione

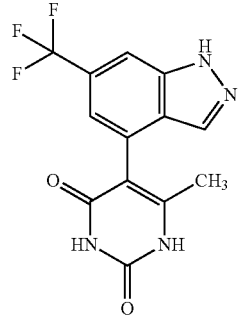 [SMILES: Cc1[nH]c(=O)[nH]c(=O)c1-c1cc(C(F)(F)F)cc2[nH]ncc12]

ESI-MS m/z [M+H]+ calc'd for $C_{13}H_9F_3N_4O_2$, 311.1. found 311.1.

Example 205

2-amino-1-(2-(6-(trifluoromethyl)-1H-indazol-4-yl)phenyl)ethanol

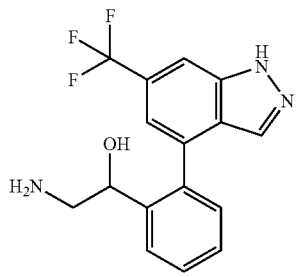 [SMILES: NCC(O)c1ccccc1-c1cc(C(F)(F)F)cc2[nH]ncc12]

$^1$H NMR (400 MHz, DMSO-d$_6$) δ ppm 3.50 (s, 2H), 6.01 (d, J=2.78 Hz, 1H), 7.40 (t, J=7.58 Hz, 1H), 7.51 (t, J=7.20 Hz, 2H), 7.59 (br s, 3H), 7.68 (br s, 1H), 7.93 (s, 1H), 13.67 (br s, 1H); ESI-MS m/z [M+H]+ calc'd for $C_{16}H_{14}F_3N_3O$, 322.1. found 322.1.

Example 206

(R)-2-(5-(6-(trifluoromethyl)-1H-indazol-4-yl)pyrimidin-2-ylamino)propan-1-ol

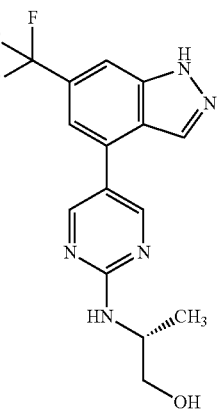

ESI-MS m/z [M+H]+ calc'd for $C_{15}H_{14}F_3N_5O$, 338.1. found 338.1.

Example 207

(R)-1-(5-(6-(trifluoromethyl)-1H-indazol-4-yl)pyrimidin-2-ylamino)propan-2-ol

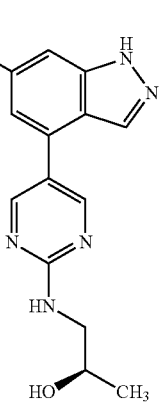

$^1$H NMR (400 MHz, DMSO-d$_6$) δ ppm 1.11 (d, J=6.06 Hz, 3H), 1.74-2.11 (m, 1H), 3.32 (br s, 2H), 3.86 (sxt, J=6.21 Hz, 1H), 7.48 (s, 2H), 7.89 (s, 1H), 8.40 (s, 1H), 8.75 (s, 2H); ESI-MS m/z [M+H]$^+$ calc'd for C$_{15}$H$_{14}$F$_3$N$_5$O, 338.1. found 338.1.

Example 208

(S)-1-(5-(6-(trifluoromethyl)-1H-indazol-4-yl)pyrimidin-2-ylamino)propan-2-ol

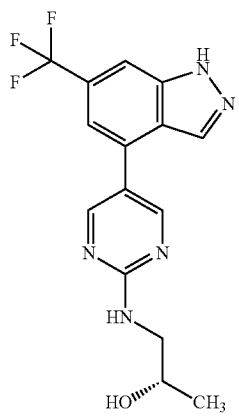 [SMILES: C[C@H](O)CNc1ncc(-c2cc(C(F)(F)F)cc3[nH]ncc23)cn1]

ESI-MS m/z [M+H]$^+$ calc'd for C$_{15}$H$_{14}$F$_3$N$_5$O, 338.1. found 338.1.

Example 209

2-(5-(6-(trifluoromethyl)-1H-indazol-4-yl)pyrimidin-2-ylamino)ethanol

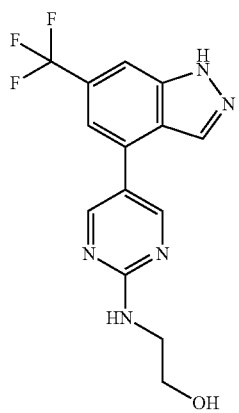 [SMILES: OCCNc1ncc(-c2cc(C(F)(F)F)cc3[nH]ncc23)cn1]

ESI-MS m/z [M+H]$^+$ calc'd for C$_{14}$H$_{12}$F$_3$N$_5$O, 324.1. found 324.4.

Example 210

3-(6-(trifluoromethyl)-1H-indazol-4-yl)pyridin-2-ol

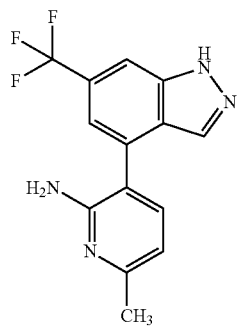 [SMILES: Cc1ccc(-c2cc(C(F)(F)F)cc3[nH]ncc23)c(N)n1]

ESI-MS m/z [M+H]$^+$ calc'd for C$_{13}$H$_8$F$_3$N$_3$O, 280.1. found 280.1.

Example 211

6-methyl-3-(6-(trifluoromethyl)-1H-indazol-4-yl)pyridin-2-amine

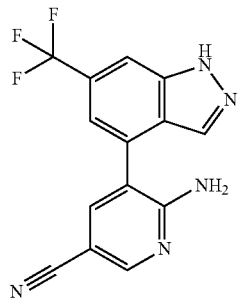 [SMILES: N#Cc1cnc(N)c(-c2cc(C(F)(F)F)cc3[nH]ncc23)c1]

ESI-MS m/z [M+H]$^+$ calc'd for C$_{14}$H$_{11}$F$_3$N$_4$, 293.1. found 293.1.

Example 212

6-amino-5-(6-(trifluoromethyl)-1H-indazol-4-yl)nicotinonitrile

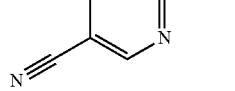

ESI-MS m/z [M+H]$^+$ calc'd for $C_{14}H_8F_3N_5$, 304.1. found 304.1.

Example 213

4-(3-methoxypyridin-2-yl)-6-(trifluoromethyl)-1H-indazole

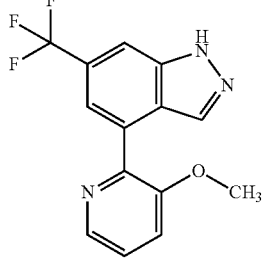

ESI-MS m/z [M+H]$^+$ calc'd for $C_{14}H_{10}F_3N_3O$, 294.1. found 294.1.

Example 214

2-(6-(trifluoromethyl)-1H-indazol-4-yl)pyridin-3-ol

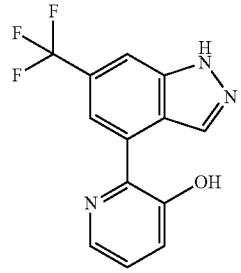 [SMILES: Oc1cccnc1-c1cc(C(F)(F)F)cc2[nH]ncc12]

ESI-MS m/z [M+H]$^+$ calc'd for $C_{13}H_8F_3N_3O$, 280.1. found 280.0.

Example 215

4-(2,6-dimethylpyridin-3-yl)-6-(trifluoromethyl)-1H-indazole

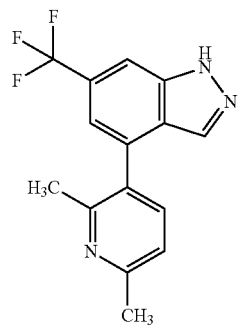

ESI-MS m/z [M+H]$^+$ calc'd for $C_{15}H_{12}F_3N_3$, 292.1. found 292.1.

Example 216

5-chloro-2-(6-(trifluoromethyl)-1H-indazol-4-yl)pyridin-3-amine

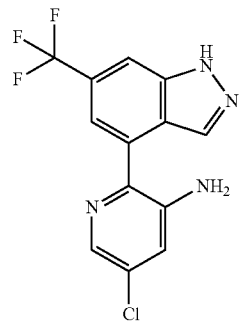 [SMILES: Nc1cc(Cl)cnc1-c1cc(C(F)(F)F)cc2[nH]ncc12]

ESI-MS m/z [M+H]$^+$ calc'd for $C_{13}H_8ClF_3N_4$, 313.0. found 313.0.

Example 217

4-(2-(1H-imidazol-1-yl)pyrimidin-5-yl)-6-(trifluoromethyl)-1H-indazole

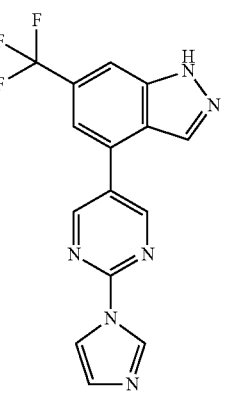

ESI-MS m/z [M+H]$^+$ calc'd for $C_{15}H_9F_3N_6$, 331.1. found 331.1.

Example 218

N-(2-(6-(trifluoromethyl)-1H-indazol-4-yl)pyridin-3-yl)acetamide

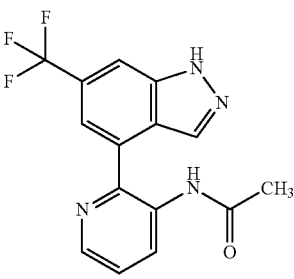 [SMILES: CC(=O)Nc1cccnc1-c1cc(C(F)(F)F)cc2[nH]ncc12]

ESI-MS m/z [M+H]$^+$ calc'd for $C_{15}H_{11}F_3N_4O$, 321.1. found 321.1.

Example 219

2-(3,5-dimethyl-4-(6-(trifluoromethyl)-1H-indazol-4-yl)-1H-pyrazol-1-yl)-N,N-dimethylethanamine

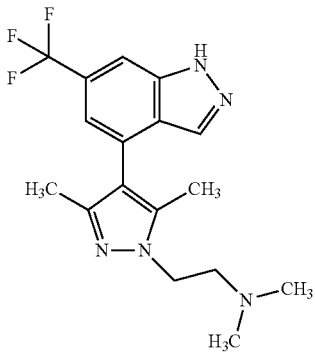 [SMILES: Cc1nn(CCN(C)C)c(C)c1-c1cc(C(F)(F)F)cc2[nH]ncc12]

ESI-MS m/z [M+H]$^+$ calc'd for $C_{17}H_{20}F_3N_5$, 352.2. found 352.2.

Example 220

(1-methyl-4-(6-(trifluoromethyl)-1H-indazol-4-yl)-1H-pyrazol-3-yl)methanol

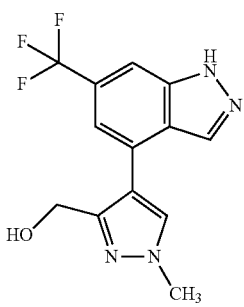 [SMILES: Cn1cc(-c2cc(C(F)(F)F)cc3[nH]ncc23)c(CO)n1]

ESI-MS m/z [M+H]$^+$ calc'd for $C_{13}H_{11}F_3N_4O$, 297.1. found 297.1.

Example 221

(6-amino-5-(6-(trifluoromethyl)-1H-indazol-4-yl)pyridin-3-yl)(4-methylpiperazin-1-yl)methanone

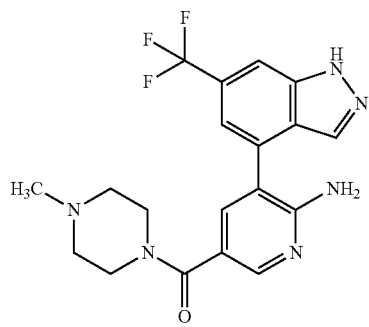 [SMILES: CN1CCN(C(=O)c2cnc(N)c(-c3cc(C(F)(F)F)cc4[nH]ncc34)c2)CC1]

ESI-MS m/z [M+H]$^+$ calc'd for $C_{19}H_{19}F_3N_6O$, 405.2. found 405.3.

Example 222

2-methyl-3-(6-(trifluoromethyl)-1H-indazol-4-yl)pyrazolo[1,5-d][1,2,4]triazin-7(6H)-one

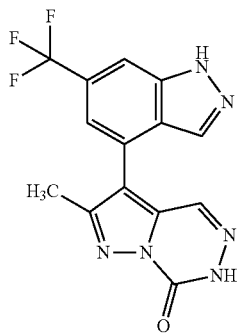 [SMILES: Cc1nn2c(=O)[nH]ncc2c1-c1cc(C(F)(F)F)cc2[nH]ncc12]

ESI-MS m/z [M+H]$^+$ calc'd for $C_{14}H_9F_3N_6O$, 335.1. found 335.2.

Example 223

4-(4-(1H-pyrazol-1-ylsulfonyl)phenyl)-6-(trifluoromethyl)-1H-indazole

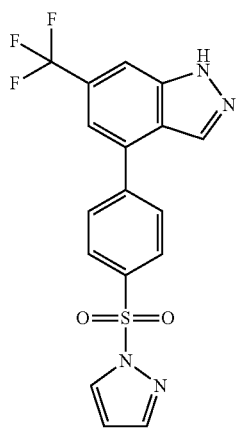 [SMILES: O=S(=O)(c1ccc(-c2cc(C(F)(F)F)cc3[nH]ncc23)cc1)n1cccn1]

$^1$H NMR (400 MHz, DMSO-d$_6$) δ ppm 6.67 (dd, J=2.65, 1.64 Hz, 1H), 7.61 (s, 1H), 7.97 (d, J=1.26 Hz, 1H), 8.04 (s, 1H), 8.08-8.21 (m, 4H), 8.40 (s, 1H), 8.59 (d, J=2.78 Hz, 1H), 13.84 (s, 1H); ESI-MS m/z [M+H]$^+$ calc'd for $C_{17}H_{11}F_3N_4O_2S$, 393.1. found 393.2.

Example 224

N-(2-hydroxyethyl)-4-(6-(trifluoromethyl)-1H-indazol-4-yl)benzenesulfonamide

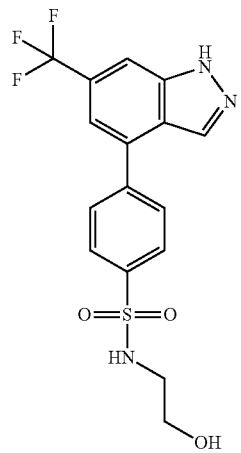

ESI-MS m/z [M+H]$^+$ calc'd for $C_{16}H_{14}F_3N_3O_3S$, 386.1. found 386.2.

Example 225

4-(4-(6-(trifluoromethyl)-1H-indazol-4-yl)phenylsulfonyl)morpholine

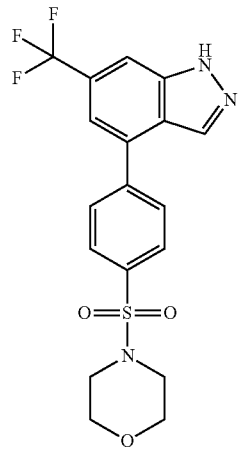 [SMILES: O=S(=O)(c1ccc(-c2cc(C(F)(F)F)cc3[nH]ncc23)cc1)N1CCOCC1]

ESI-MS m/z [M+H]$^+$ calc'd for $C_{18}H_{16}F_3N_3O_3S$, 412.1. found 412.3.

Example 226

4-(3-methyl-4-(6-(trifluoromethyl)-1H-indazol-4-yl)phenylsulfonyl)morpholine

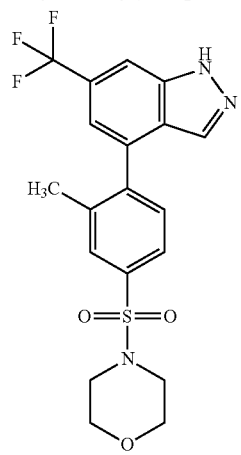 [SMILES: Cc1cc(S(=O)(=O)N2CCOCC2)ccc1-c1cc(C(F)(F)F)cc2[nH]ncc12]

$^1$H NMR (400 MHz, DMSO-d$_6$) δ ppm 2.27 (s, 3H), 2.92-3.03 (m, 4H), 3.63-3.75 (m, 4H), 7.38 (s, 1H), 7.59-7.73 (m, 2H), 7.77 (s, 1H), 8.00 (d, J=13.39 Hz, 2H), 13.76 (br s, 1H); ESI-MS m/z [M+H]$^+$ calc'd for $C_{19}H_{18}F_3N_3O_3S$, 426.1. found 426.3.

Example 227

3-(4-methylpiperazine-1-carbonyl)-5-(6-(trifluoromethyl)-1H-indazol-4-yl)pyridin-2(1H)-one

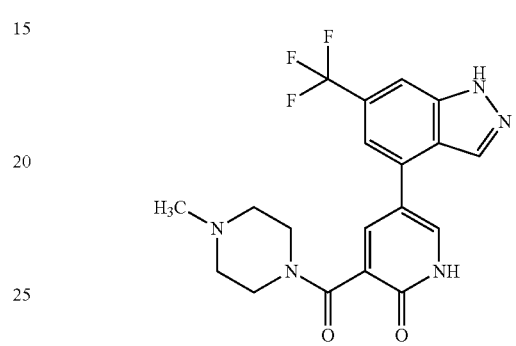

The title compound was isolated as the free base. ESI-MS m/z [M+H]$^+$ calc'd for $C_{19}H_{18}F_3N_5O_2$, 406.1. found 406.2.

Example 228

N-(2-hydroxyethyl)-2-oxo-5-(6-(trifluoromethyl)-1H-indazol-4-yl)-1,2-dihydropyridine-3-carboxamide

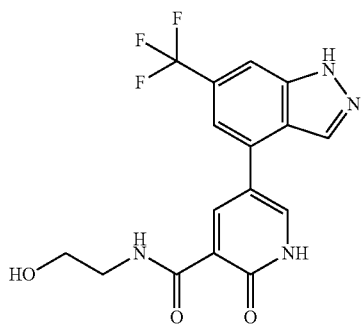 [SMILES: O=C(NCCO)c1cc(-c2cc(C(F)(F)F)cc3[nH]ncc23)c[nH]c1=O]

The title compound was isolated as the free base. $^1$H NMR (400 MHz, DMSO-d$_6$) δ ppm 3.35 (q, J=5.56 Hz, 2H), 3.43-3.51 (m, 2H), 7.42 (s, 1H), 7.85 (s, 1H), 8.11 (dd, J=6.57, 2.78 Hz, 1H), 8.24 (s, 1H), 8.60-8.66 (m, 1H), 9.81 (t, J=5.56 Hz, 1H), 12.89 (d, J=6.32 Hz, 1H), 13.68 (br s, 1H); ESI-MS m/z [M+H]$^+$ calc'd for $C_{16}H_{13}F_3N_4O_3$, 367.1. found 367.2.

Example 229

N-(2-hydroxyethyl)-2-methoxy-5-(6-(trifluoromethyl)-1H-indazol-4-yl)nicotinamide

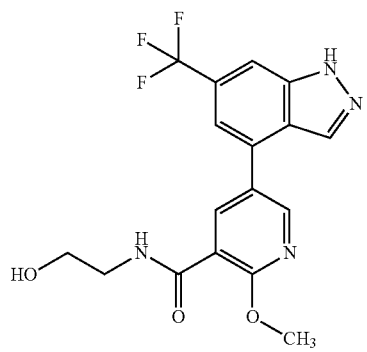 [SMILES: COc1ncc(-c2cc(C(F)(F)F)cc3[nH]ncc23)cc1C(=O)NCCO]

The title compound was isolated as the free base. ESI-MS m/z [M+H]$^+$ calc'd for $C_{17}H_{15}F_3N_4O_3$, 381.1. found 381.2.

Example 230

2-amino-N-(2-hydroxyethyl)-5-(6-(trifluoromethyl)-1H-indazol-4-yl)nicotinamide

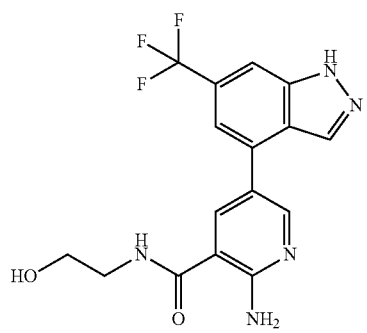 [SMILES: Nc1ncc(-c2cc(C(F)(F)F)cc3[nH]ncc23)cc1C(=O)NCCO]

The title compound was isolated as the free base. ESI-MS m/z [M+H]$^+$ calc'd for $C_{16}H_{14}F_3N_5O_2$, 366.1. found 366.2.

Example 231

2-oxo-5-(6-(trifluoromethyl)-1H-indazol-4-yl)-1,2-dihydropyridine-3-carboxamide

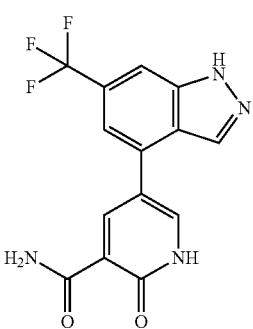 [SMILES: NC(=O)c1cc(-c2cc(C(F)(F)F)cc3[nH]ncc23)c[nH]c1=O]

The title compound was isolated as the free base. ESI-MS m/z [M+H]$^+$ calc'd for $C_{14}H_9F_3N_4O_2$, 323.1. found 323.1.

Example 232

2-methoxy-5-(6-(trifluoromethyl)-1H-indazol-4-yl)nicotinamide

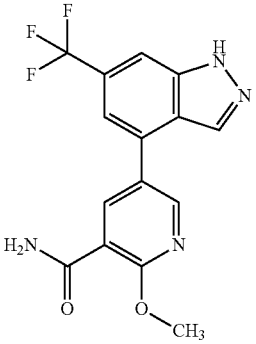 [SMILES: COc1ncc(-c2cc(C(F)(F)F)cc3[nH]ncc23)cc1C(N)=O]

The title compound was isolated as the free base. ESI-MS m/z [M+H]$^+$ calc'd for $C_{15}H_{11}F_3N_4O_2$, 337.1. found 337.1.

Example 233

2-amino-5-(6-(trifluoromethyl)-1H-indazol-4-yl)nicotinamide

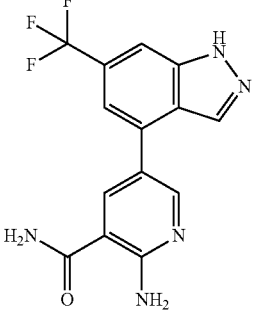

The title compound was isolated as the free base. ESI-MS m/z [M+H]$^+$ calc'd for $C_{14}H_{10}F_3N_5O$, 322.1. found 322.1.

Example 234

1-methyl-5-(6-(trifluoromethyl)-1H-indazol-4-yl)indolin-2-one

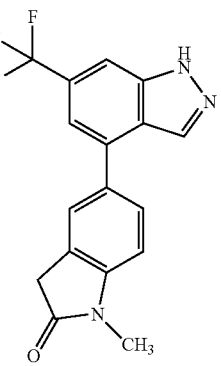

¹H NMR (400 MHz, DMSO-d₆) δ ppm 3.20 (s, 3H), 3.68 (s, 2H), 7.17 (d, J=8.08 Hz, 1H), 7.43 (s, 1H), 7.71-7.76 (m, 2H), 7.89 (s, 1H), 8.35 (s, 1H), 13.69 (s, 1H); ESI-MS m/z [M+H]⁺ calc'd for $C_{17}H_{12}F_3N_3O$, 332.1. found 332.2.

Example 235

5-(6-(trifluoromethyl)-1H-indazol-4-yl)indolin-2-one

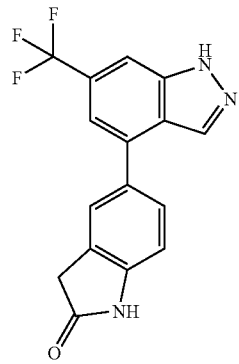 [SMILES: O=C1Cc2cc(-c3cc(C(F)(F)F)cc4[nH]ncc34)ccc2N1]

ESI-MS m/z [M+H]⁺ calc'd for $C_{16}H_{10}F_3N_3O$, 318.1. found 318.1.

Example 236

6-(trifluoromethyl)-1H,1'H-4,5'-biindazole

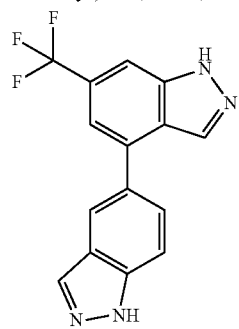

ESI-MS m/z [M+H]⁺ calc'd for $C_{15}H_9F_3N_4$, 303.1. found 303.1.

Example 237

5-(6-(trifluoromethyl)-1H-indazol-4-yl)-1H-benzo[d]imidazol-2(3H)-one

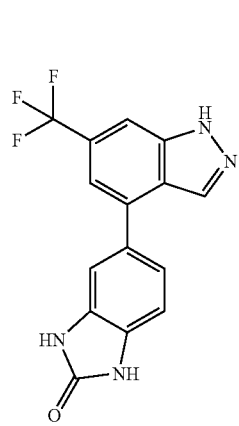 [SMILES: O=c1[nH]c2ccc(-c3cc(C(F)(F)F)cc4[nH]ncc34)cc2[nH]1]

ESI-MS m/z [M+H]⁺ calc'd for $C_{15}H_9F_3N_4O$, 319.1. found 319.1.

Example 238

5-(6-(trifluoromethyl)-1H-indazol-4-yl)-1H-pyrrolo[2,3-b]pyridin-2(3H)-one

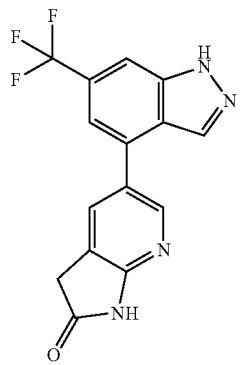 [SMILES: O=C1Cc2cc(-c3cc(C(F)(F)F)cc4[nH]ncc34)cnc2N1]

ESI-MS m/z [M+H]⁺ calc'd for $C_{15}H_9F_3N_4O$, 319.1. found 319.1.

Example 239

6-(6-(trifluoromethyl)-1H-indazol-4-yl)indolin-2-one

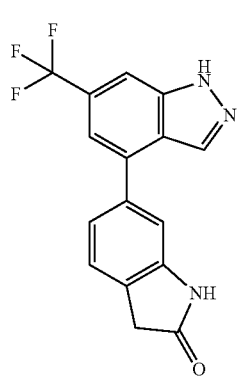 [SMILES: O=C1Cc2ccc(-c3cc(C(F)(F)F)cc4[nH]ncc34)cc2N1]

¹H NMR (400 MHz, DMSO-d₆) δ ppm 3.59 (s, 2H), 7.17 (s, 1H), 7.33-7.45 (m, 3H), 7.93 (s, 1H), 8.30 (s, 1H), 10.47 (s, 1H), 13.73 (s, 1H); ESI-MS m/z [M+H]⁺ calc'd for $C_{16}H_{10}F_3N_3O$, 318.1. found 318.1.

Example 240

2-(6-(trifluoromethyl)-1H-indazol-4-yl)-5H-pyrrolo[2,3-b]pyrazine

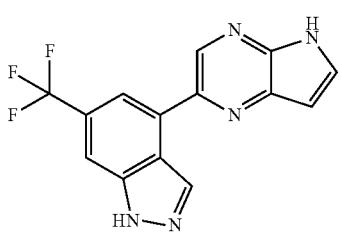 [SMILES: FC(F)(F)c1cc(-c2cnc3[nH]ccc3n2)c2cn[nH]c2c1]

ESI-MS m/z [M+H]⁺ calc'd for $C_{14}H_8F_3N_5$, 304.1. found 304.1.

Example 241

6-(6-(trifluoromethyl)-1H-indazol-4-yl)-1H-imidazo[4,5-b]pyridin-2(3H)-one

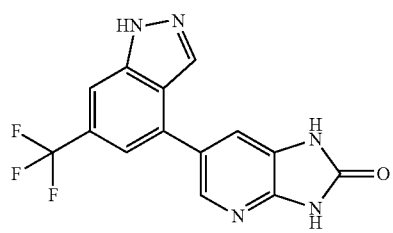 [SMILES: O=c1[nH]c2cc(-c3cc(C(F)(F)F)cc4[nH]ncc34)cnc2[nH]1]

ESI-MS m/z [M+H]$^+$ calc'd for $C_{14}H_8F_3N_5O$, 320.1. found 320.1.

Example 242

2-(trifluoromethyl)-6-(6-(trifluoromethyl)-1H-indazol-4-yl)-3H-imidazo[4,5-b]pyridine

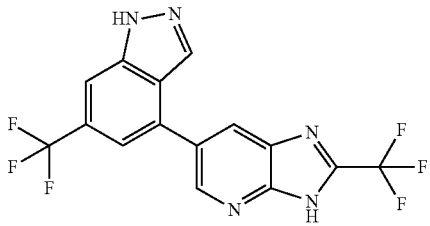 [SMILES: FC(F)(F)c1cc(-c2cnc3[nH]c(C(F)(F)F)nc3c2)c2cn[nH]c2c1]

ESI-MS m/z [M+H]$^+$ calc'd for $C_{15}H_7F_6N_5$, 372.1. found 372.1.

Example 243

5-(6-(trifluoromethyl)-1H-indazol-4-yl)-1H-pyrazolo[3,4-b]pyridine

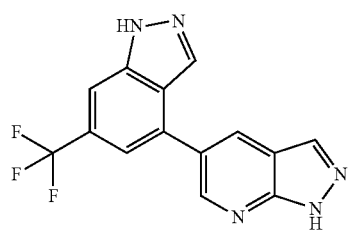 [SMILES: FC(F)(F)c1cc(-c2cnc3[nH]ncc3c2)c2cn[nH]c2c1]

ESI-MS m/z [M+H]$^+$ calc'd for $C_{14}H_8F_3N_5$, 304.1. found 304.1.

Example 244

7-(6-(trifluoromethyl)-1H-indazol-4-yl)-3,4-dihydropyrido[2,3-b]pyrazin-2(1H)-one

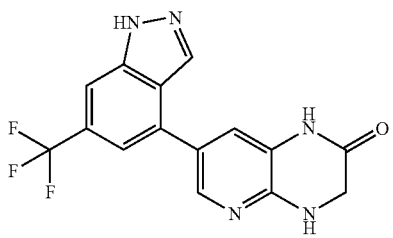 [SMILES: O=C1CNc2ncc(-c3cc(C(F)(F)F)cc4[nH]ncc34)cc2N1]

ESI-MS m/z [M+H]$^+$ calc'd for $C_{15}H_{10}F_3N_5O$, 334.1. found 334.1.

Example 245

6-amino-3-methyl-5-(6-(trifluoromethyl)-1H-indazol-4-yl)pyrimidin-4(3H)-one

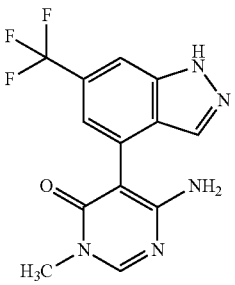 [SMILES: Cn1cnc(N)c(-c2cc(C(F)(F)F)cc3[nH]ncc23)c1=O]

A vial was charged with a mixture of 4-(4,4,5,5-tetramethyl-1,3,2-dioxaborolan-2-yl)-6-(trifluoromethyl)-1H-indazole (0.05 g, 0.160 mmol), 6-amino-5-bromo-3-methylpyrimidin-4(3H)-one (0.042 g, 0.208 mmol) and PdCl$_2$(dppf) (5.86 mg, 8.01 μmol) in dioxane (8 mL) and aqueous saturated NaHCO$_3$ (2 mL). The resulting light brown suspension was heated at 140° C. for 45 minutes in a microwave reactor. The reaction mixture was subsequently concentrated and the crude residue was purified by preparative HPLC, eluting with a gradient of 25-35% ACN (containing 0.035% TFA) in H$_2$O (containing 0.05% TFA) over a period of 4 minutes. The product-containing fractions were combined and the volatiles removed in vacuo to give a TFA salt of the title compound (8 mg, 16%). $^1$H NMR (400 MHz, CD$_3$OD) δ ppm 3.45 (s, 3H), 7.33 (d, J=1.01 Hz, 1H), 7.83 (s, 1H), 7.89 (d, J=0.76 Hz, 1H), 8.19 (s, 1H); ESI-MS m/z [M+H]$^+$ calc'd for $C_{13}H_{10}F_3N_5O$, 310.1. found 310.2.

Example 246

4-(2-methoxypyrimidin-5-yl)-6-(trifluoromethyl)-1H-indazole

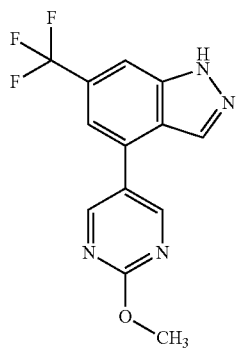 [SMILES: COc1ncc(-c2cc(C(F)(F)F)cc3[nH]ncc23)cn1]

A vial was charged with a mixture of 4-bromo-6-(trifluoromethyl)-1H-indazole (0.1 g, 0.377 mmol), (2-methoxypyrimidin-5-yl)boronic acid (0.076 g, 0.491 mmol) and PdCl$_2$(dppf) (0.014 g, 0.019 mmol) in dioxane (8 mL) and aqueous saturated NaHCO$_3$ (2 mL). The resulting light brown suspension was heated at 140° C. for 45 minutes in a microwave reactor. The reaction mixture was subsequently concentrated and the crude residue was purified by preparative HPLC, eluting with a gradient of 35-40% ACN (containing 0.035% TFA) in H$_2$O (containing 0.05% TFA) over a period of 8 minutes. The volatiles were removed in vacuo to give a TFA salt of the title compound as white solid (0.043 g, 39%). $^1$H NMR (400 MHz, DMSO-d$_6$) δ ppm 4.03 (s, 3H), 7.60 (d, J=1.01 Hz, 1H), 8.00 (s, 1H), 8.34-8.52 (m, 1H), 9.06 (s, 2H); ESI-MS m/z [M+1-1]' calc'd for C$_{13}$H$_9$F$_3$N$_4$O, 295.1. found 295.15.

Example 247

N,N-dimethyl-5-(6-(trifluoromethyl)-1H-indazol-4-yl)pyrimidin-2-amine

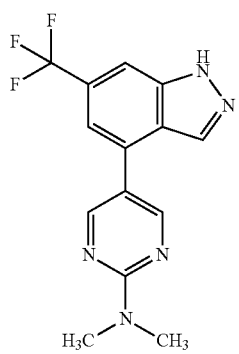 [SMILES: CN(C)c1ncc(-c2cc(C(F)(F)F)cc3[nH]ncc23)cn1]

A vial was charged with a mixture of 4-bromo-6-(trifluoromethyl)-1H-indazole (0.1 g, 0.377 mmol), N,N-dimethyl-5-(4,4,5,5-tetramethyl-1,3,2-dioxaborolan-2-yl)pyrimidin-2-amine (0.122 g, 0.491 mmol) and PdCl$_2$(dppf) (0.014 g, 0.019 mmol) in dioxane (8 mL) and aqueous saturated NaHCO$_3$ (2 mL). The resulting light brown suspension was heated at 140° C. for 45 minutes in a microwave reactor. The reaction mixture was subsequently concentrated and the crude residue was purified by preparative HPLC, eluting with a gradient of 30-40% ACN (containing 0.035% TFA) in H$_2$O (containing 0.05% TFA) over a period of 8 minutes. The product-containing fractions were combined and the volatiles removed in vacuo to give a TFA salt of the title compound as a light brown solid (68 mg, 59%). $^1$H NMR (400 MHz, DMSO-d$_6$) δ ppm 3.23 (s, 6H), 7.48 (d, J=1.01 Hz, 1H), 7.89 (s, 1H), 8.40 (d, J=0.76 Hz, 1H), 8.82 (s, 2H); ESI-MS m/z [M+H]$^+$ calc'd for C$_{14}$H$_{12}$F$_3$N$_5$, 308.1. found 308.15.

Example 248

4-(3,6-dimethoxypyridazin-4-yl)-6-(trifluoromethyl)-1H-indazole

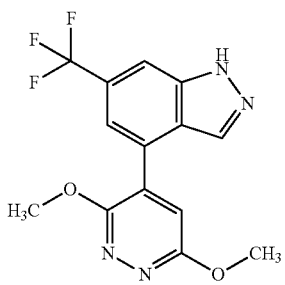 [SMILES: COc1cc(-c2cc(C(F)(F)F)cc3[nH]ncc23)c(OC)nn1]

A vial was charged with a mixture of 4-bromo-6-(trifluoromethyl)-1H-indazole (0.15 g, 0.566 mmol), (3,6-dimethoxypyridazin-4-yl)boronic acid (0.135 g, 0.736 mmol) and PdCl$_2$(dppf) (0.021 g, 0.028 mmol) in dioxane (10 mL) and aqueous saturated NaHCO$_3$ (3 mL). The resulting light brown suspension was heated at 140° C. for 45 minutes in a microwave reactor. The reaction mixture was subsequently concentrated and the crude residue was purified by preparative HPLC, eluting with a gradient of 40-45% ACN (containing 0.035% TFA) in H$_2$O (containing 0.05% TFA) over a period of 6.5 minutes. The volatiles were removed in vacuo to give a TFA salt of the title compound as a light brown solid (8 mg, 4%). $^1$H NMR (400 MHz, DMSO-d$_6$) δ ppm 3.97 (s, 3H), 4.03 (s, 3H), 7.42 (s, 1H), 7.55 (d, J=1.01 Hz, 1H), 8.05 (s, 1H), 8.14 (s, 1H), 13.74 (s, 1H); ESI-MS m/z [M+H]$^+$ calc'd for C$_{14}$H$_{11}$F$_3$N$_4$O$_2$, 325.1. found 325.16.

Example 249

4-(6-methoxy-2-methylpyridin-3-yl)-6-(trifluoromethyl)-1H-indazole

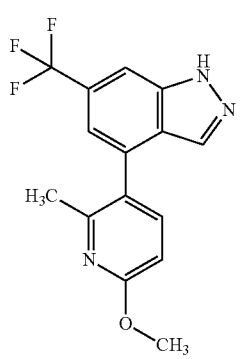 [SMILES: COc1ccc(-c2cc(C(F)(F)F)cc3[nH]ncc23)c(C)n1]

A vial was charged with a mixture of 4-bromo-6-(trifluoromethyl)-1H-indazole (0.15 g, 0.566 mmol), (6-methoxy-2-methylpyridin-3-yl)boronic acid (0.123 g, 0.736 mmol) and PdCl₂(dppf) (0.021 g, 0.028 mmol) in dioxane (10 mL) and aqueous saturated NaHCO₃ (3 mL). The resulting light brown suspension was heated at 140° C. for 45 minutes in microwave reactor. The reaction mixture was subsequently concentrated and the crude residue was purified by preparative HPLC, eluting with 45% ACN (containing 0.035% TFA) in H₂O (containing 0.05% TFA) over a period of 6.5 minutes. The volatiles were removed in vacuo to give a TFA salt of the title compound as a light brown oil (82 mg, 47%). ¹H NMR (400 MHz, DMSO-d₆) δ ppm 2.30 (s, 3H), 3.93 (s, 3H), 6.75-6.86 (m, 1H), 7.29 (d, J=1.26 Hz, 1H), 7.72 (d, J=8.34 Hz, 1H), 7.90-8.03 (m, 2H); ESI-MS m/z [M+H]⁺ calc'd for C₁₅H₁₂F₃N₃O, 308.1. found 308.15.

Example 250

(1-methyl-4-(6-(trifluoromethyl)-1H-indazol-4-yl)-1H-pyrazol-5-yl)methanol

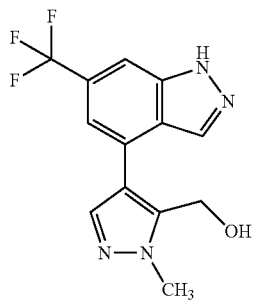 [SMILES: Cn1ncc(-c2cc(C(F)(F)F)cc3[nH]ncc23)c1CO]

A vial was charged with a mixture of 4-(4,4,5,5-tetramethyl-1,3,2-dioxaborolan-2-yl)-6-(trifluoromethyl)-1H-indazole (0.1 g, 0.320 mmol), (4-bromo-1-methyl-1H-pyrazol-5-yl)methanol (0.086 g, 0.449 mmol) and PdCl₂(dppf) (0.012 g, 0.016 mmol) in dioxane (8 mL) and aqueous saturated NaHCO₃ (2 mL). The resulting light brown suspension was heated at 140° C. for 45 minutes in a microwave reactor. The reaction mixture was subsequently concentrated and the crude residue was purified by preparative HPLC, eluting with 30% ACN (containing 0.035% TFA) in H₂O (containing 0.05% TFA) over a period of 6 minutes. The product-containing fractions were combined and volatiles removed in vacuo to give a TFA salt of the title compound as an off white solid (8 mg, 8%). ¹H NMR (400 MHz, DMSO-d₆) δ ppm 3.96 (s, 3H), 4.56 (d, J=4.80 Hz, 2H), 5.53 (t, J=4.93 Hz, 1H), 7.43 (s, 1H), 7.78-7.92 (m, 2H), 8.30 (s, 1H), 13.62 (s, 1H); ESI-MS m/z [M+H]⁺ calc'd for C₁₃H₁₁F₃N₄O, 297.1. found 297.14.

Example 251

5-(6-(trifluoromethyl)-1H-indazol-4-yl)picolinamide

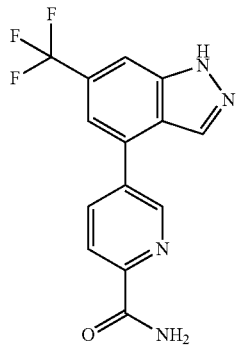

A vial was charged with a mixture of 4-(4,4,5,5-tetramethyl-1,3,2-dioxaborolan-2-yl)-6-(trifluoromethyl)-1H-indazole (0.05 g, 0.160 mmol), 5-bromopicolinamide (0.042 g, 0.208 mmol) and PdCl₂(dppf) (5.86 mg, 8.01 μmol) in dioxane (8 mL) and aqueous saturated NaHCO₃ (2 mL). The resulting light brown suspension was heated at 140° C. for 45 minutes in a microwave reactor. The reaction mixture was subsequently concentrated and the crude residue was purified by preparative HPLC, eluting with a gradient of 25-45% ACN (containing 0.035% TFA) in H₂O (containing 0.05% TFA) over a period of 6 minutes. The volatiles were removed in vacuo to give a TFA salt of the title compound as an off white solid (19 mg, 0.062 mmol, 39%). ¹H NMR (400 MHz, DMSO-d₆) δ ppm 7.66 (s, 1H), 7.77 (br s, 1H), 8.06 (s, 1H), 8.14-8.33 (m, 1H), 8.37-8.49 (m, 1H), 9.00-9.08 (m, 1H), 13.84 (br s, 1H); ESI-MS m/z [M+H]⁺ calc'd for C₁₄H₉F₃N₄O, 307.1. found 307.15.

Example 252

2-methyl-3-(6-(trifluoromethyl)-1H-indazol-4-yl)pyridin-4-amine

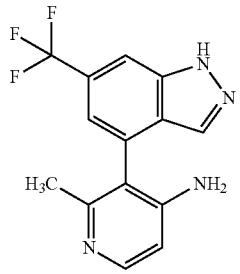 [SMILES: Cc1nccc(N)c1-c1cc(C(F)(F)F)cc2[nH]ncc12]

A vial was charged with a mixture of 4-(4,4,5,5-tetramethyl-1,3,2-dioxaborolan-2-yl)-6-(trifluoromethyl)-1H-indazole (0.1 g, 0.320 mmol), 3-bromo-2-methylpyridin-4-amine (0.078 g, 0.417 mmol) and PdCl₂(dppf) (0.012 g, 0.016 mmol) in dioxane (8 mL) and aqueous saturated NaHCO₃ (2 mL). The resulting light brown suspension was heated at 140° C. for 45 minutes in a microwave reactor. The reaction mixture was subsequently concentrated and the crude residue was purified by preparative HPLC, eluting with 20% ACN (containing 0.035% TFA) in H₂O (containing 0.05% TFA) over a period of 5 minutes. The volatiles were removed in vacuo to give a TFA salt of the title compound as clear oil (12 mg, 13%). ¹H NMR (400 MHz, DMSO-d₆) δ ppm 2.11 (s, 3H), 6.69 (br s, 1H), 6.90 (d, J=7.07 Hz, 1H), 7.38 (s, 1H), 8.01 (s, 1H), 8.08 (s, 1H), 8.17 (t, J=6.44 Hz, 1H), 13.51 (br s, 1H); ESI-MS m/z [M+H]⁺ calc'd for C₁₄H₁₁F₃N₄, 293.1. found 293.14.

Example 253

4-(6-methoxy-4-methylpyridin-3-yl)-6-(trifluoromethyl)-1H-indazole

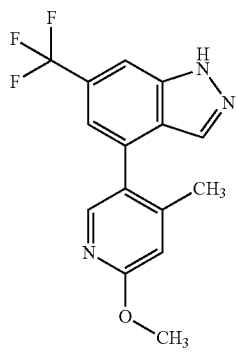 [SMILES: COc1cc(C)c(-c2cc(C(F)(F)F)cc3[nH]ncc23)cn1]

A vial was charged with a mixture of 4-bromo-6-(trifluoromethyl)-1H-indazole (0.1 g, 0.377 mmol), (6-methoxy-4-methylpyridin-3-yl)boronic acid (0.082 g, 0.491 mmol) and PdCl$_2$(dppf) (0.014 g, 0.019 mmol) in dioxane (8 mL) and aqueous saturated NaHCO$_3$ (2 mL). The resulting light brown suspension was heated at 140° C. for 45 minutes in a microwave reactor. The reaction mixture was subsequently concentrated and the crude residue was purified by preparative HPLC, eluting with a gradient of 40-45% ACN (containing 0.035% TFA) in H$_2$O (containing 0.05% TFA) over a period of 6.5 minutes. The product-containing fractions were combined and solvent was removed on a rotary evaporator. The crude product was extracted into DCM, was washed sequentially with aqueous saturated NaHCO$_3$, water, and brine, and was dried over Na$_2$SO$_4$. The volatiles were removed in vacuo to give the title compound as a white solid (0.053 g, 0.172 mmol, 46%). $^1$H NMR (400 MHz, DMSO-d$_6$) δ ppm 2.14 (s, 3H), 3.91 (s, 3H), 6.88 (s, 1H), 7.29 (s, 1H), 7.97 (s, 2H), 8.12 (s, 1H), 13.71 (s, 1H); ESI-MS m/z [M+H]$^+$ calc'd for C$_{15}$H$_{12}$F$_3$N$_3$O, 308.1. found 308.15.

Example 254

N-methyl-5-(6-(trifluoromethyl)-1H-indazol-4-yl)pyrimidine-4-carboxamide

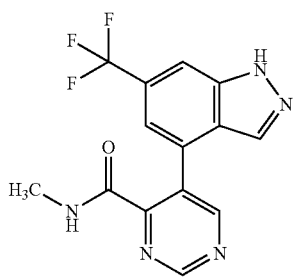 [SMILES: CNC(=O)c1ncncc1-c1cc(C(F)(F)F)cc2[nH]ncc12]

A vial was charged with a mixture of 4-(4,4,5,5-tetramethyl-1,3,2-dioxaborolan-2-yl)-6-(trifluoromethyl)-1H-indazole (0.144 g, 0.463 mmol), 5-bromo-N-methylpyrimidine-4-carboxamide (0.1 g, 0.463 mmol) and PdCl$_2$(dppf) (0.017 g, 0.023 mmol) in dioxane (8 mL) and aqueous saturated NaHCO$_3$ (2 mL). The resulting light brown suspension was heated at 140° C. for 45 minutes in a microwave reactor. The reaction mixture was subsequently concentrated and the crude residue was purified by preparative HPLC, eluting with a gradient of 25-30% ACN in H$_2$O (containing 10 mMol NH$_4$HCO$_3$) over a period of 8 minutes. The product-containing fractions were combined and the solvent was removed via rotary evaporation. The crude product was extracted into DCM and was washed with water. The volatiles were removed in vacuo to give the title compound as a white solid (0.018 g, 0.056 mmol, 12%). $^1$H NMR (400 MHz, DMSO-d$_6$) δ ppm 2.62 (d, J=4.80 Hz, 3H), 7.43 (s, 1H), 8.04 (s, 1H), 8.01 (s, 1H), 8.89 (d, J=4.29 Hz, 1H), 9.09 (s, 1H), 9.38 (s, 1H), 13.72 (br s, 1H); ESI-MS m/z [M+H]$^+$ calc'd for C$_{14}$H$_{10}$F$_3$N$_5$O, 322.1. found 322.2.

Example 255

6-methyl-5-(6-(trifluoromethyl)-1H-indazol-4-yl)pyridin-2-amine

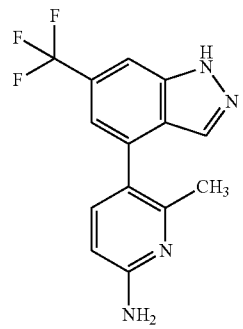 [SMILES: Cc1nc(N)ccc1-c1cc(C(F)(F)F)cc2[nH]ncc12]

To a mixture of 4-(4,4,5,5-tetramethyl-1,3,2-dioxaborolan-2-yl)-6-(trifluoromethyl)-1H-indazole (0.05 g, 0.160 mmol), 5-iodo-6-methylpyridin-2-amine (0.025 g, 0.107 mmol) and PdCl$_2$(dppf) (0.012 g, 0.016 mmol) in dioxane (1.5 mL) was added 2N sodium carbonate (0.160 mL, 0.320 mmol). The reaction mixture was heated in a microwave reactor at 130° C. for 50 minutes. LCMS showed incomplete conversion of the starting material, so the reaction mixture was heated at 130° C. for an additional 50 minutes. LCMS again showed incomplete conversion. More catalyst was added, and the reaction mixture was again heated at 130° C. for 50 minutes. The reaction mixture was subsequently filtered through a microfiltration frit, which was rinsed with methanol. The solvents were removed in vacuo. The residue was taken up in DMSO and methanol (1:1) and was purified by preparative HPLC, eluting with 25% ACN (containing 0.035% TFA) in H$_2$O (containing 0.05% TFA). The product-containing fractions were dried under vacuum to give a TFA salt of the title compound as a tan film (12 mg, 26%). $^1$H NMR (400 MHz, DMSO-d$_6$) δ ppm 2.32 (s, 3H), 6.94 (d, J=9.35 Hz, 1H), 7.37 (s, 1H), 7.97 (d, J=8.84 Hz, 1H), 8.02 (s, 1H), 8.14 (s, 1H); ESI-MS m/z [M+H]$^+$ calc'd for C$_{14}$H$_{11}$F$_3$N$_4$, 293.1. found 293.2.

Example 256

2-methoxy-5-(6-(trifluoromethyl)-1H-indazol-4-yl)pyrimidin-4-amine

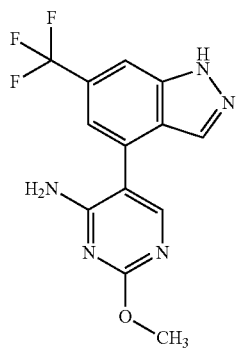

A vial was charged with a mixture of 4-(4,4,5,5-tetramethyl-1,3,2-dioxaborolan-2-yl)-6-(trifluoromethyl)-1H-indazole (0.1 g, 0.320 mmol), 5-bromo-2-methoxypyrimidin-4-amine (0.131 g, 0.641 mmol) and PdCl$_2$(dppf) (0.012 g, 0.016 mmol) in dioxane (8 mL) and aqueous saturated NaHCO$_3$ (2 mL). The resulting light brown suspension was heated at 140° C. for 45 minutes in a microwave reactor. The reaction mixture was subsequently concentrated and the crude residue was purified by preparative HPLC, eluting with a gradient of 15-25% ACN (containing 0.035% TFA) in H$_2$O (containing 0.05% TFA) over a period of 5 minutes. The product-containing fractions were combined and volatiles were removed in vacuo to give a TFA salt of the title compound as light brown solid (0.029 g, 29%). $^1$H NMR (400 MHz, DMSO-d$_6$) δ ppm 4.04 (s, 3H), 7.35-7.41 (m, 1H), 8.03 (s, 1H), 8.06-8.15 (m, 1H), 8.21 (s, 1H); ESI-MS m/z [M+H]$^+$ calc'd for C$_{13}$H$_{10}$F$_3$N$_5$O, 310.1. found 310.13.

Example 257

N-(6-methyl-5-(6-(trifluoromethyl)-1H-indazol-4-yl)pyridin-2-yl)methanesulfonamide

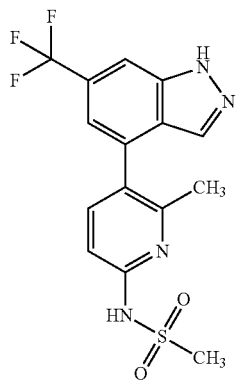 [SMILES: Cc1nc(NS(C)(=O)=O)ccc1-c1cc(C(F)(F)F)cc2[nH]ncc12]

A vial was charged with a mixture of 4-(4,4,5,5-tetramethyl-1,3,2-dioxaborolan-2-yl)-6-(trifluoromethyl)-1H-indazole (0.1 g, 0.320 mmol), N-(5-bromo-6-methylpyridin-2-yl)methanesulfonamide (0.170 g, 0.641 mmol) and PdCl$_2$(dppf) (0.012 g, 0.016 mmol) in dioxane (8 mL) and aqueous saturated NaHCO$_3$ (2 mL). The resulting light brown suspension was heated at 140° C. for 45 minutes in a microwave reactor. The reaction mixture was subsequently concentrated and the crude residue was purified by preparative HPLC, eluting with 30% ACN (containing 0.035% TFA) in H$_2$O (containing 0.05% TFA) over a period of 8 minutes. The product-containing fractions were combined and the volatiles were removed in vacuo to give a TFA salt of the title compound as an off white solid (0.039 g, 33%). $^1$H NMR (400 MHz, DMSO-d$_6$) δ ppm 2.30 (s, 3H), 3.31 (br s, 3H), 7.02 (d, J=8.08 Hz, 1H), 7.32 (d, J=1.01 Hz, 1H), 7.76 (d, J=8.34 Hz, 1H), 7.97 (s, 1H), 8.02 (s, 1H); ESI-MS m/z [M+H]$^+$ calc'd for C$_{15}$H$_{13}$F$_3$N$_4$O$_2$S, 371.1. found 371.17.

Example 258

2-methoxy-N-(6-methyl-5-(6-(trifluoromethyl)-1H-indazol-4-yl)pyridin-2-yl)acetamide

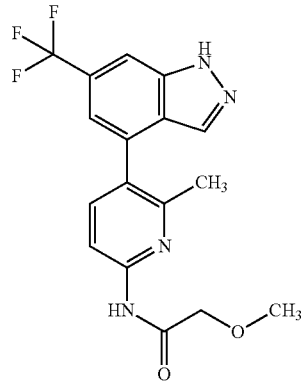 [SMILES: COCC(=O)Nc1ccc(-c2cc(C(F)(F)F)cc3[nH]ncc23)c(C)n1]

A TFA salt of the title compound was prepared in a manner similar to EXAMPLE 257 using N-(5-bromo-6-methylpyridin-2-yl)-2-methoxyacetamide in place of N-(5-bromo-6-methylpyridin-2-yl)methanesulfonamide. $^1$H NMR (400 MHz, DMSO-d$_6$) δ ppm 2.31 (s, 3H), 3.39 (s, 3H), 4.11 (s, 2H), 7.34 (d, J=1.26 Hz, 1H), 7.82 (d, J=8.34 Hz, 1H), 7.93-8.02 (m, 2H), 8.07 (d, J=8.59 Hz, 1H), 10.19 (s, 1H); ESI-MS m/z [M+H]$^+$ calc'd for C$_{17}$H$_{15}$F$_3$N$_4$O$_2$, 365.1. found 365.2.

Example 259

1-methyl-N-(6-methyl-5-(6-(trifluoromethyl)-1H-indazol-4-yl)pyridin-2-yl)-1H-pyrazole-4-sulfonamide

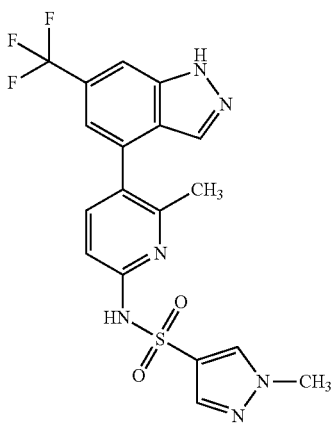 [SMILES: Cc1nc(NS(=O)(=O)c2cnn(C)c2)ccc1-c1cc(C(F)(F)F)cc2[nH]ncc12]

A TFA salt of the title compound was prepared in a manner similar to EXAMPLE 257 using N-(5-bromo-6-methylpyridin-2-yl)-1-methyl-1H-pyrazole-4-sulfonamide in place of N-(5-bromo-6-methylpyridin-2-yl)methanesulfonamide. $^1$H NMR (400 MHz, CD$_3$OD) δ ppm 2.31 (s, 3H), 3.92 (s, 3H), 7.15-7.32 (m, 2H), 7.72 (d, J=8.84 Hz, 1H), 7.86 (d, J=0.51 Hz, 1H), 7.89-7.99 (m, 2H), 8.20 (s, 1H); ESI-MS m/z [M+H]$^+$ calc'd for C$_{18}$H$_{15}$F$_3$N$_6$O$_2$S, 437.1. found 437.18.

Example 260 ethyl 2-(4-(6-(trifluoromethyl)-1H-indazol-4-yl)-1H-pyrazol-1-yl)acetate

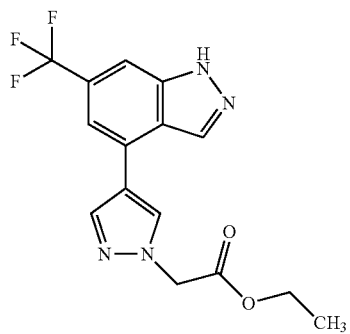 [SMILES: CCOC(=O)Cn1cc(-c2cc(C(F)(F)F)cc3[nH]ncc23)cn1]

A vial was charged with a mixture of 4-bromo-6-(trifluoromethyl)-1H-indazole (0.3 g, 1.132 mmol), ethyl 2-(4-(4,4,5,5-tetramethyl-1,3,2-dioxaborolan-2-yl)-1H-pyrazol-1-yl)acetate (0.349 g, 1.245 mmol) and PdCl$_2$(dppf) (0.041 g, 0.057 mmol) in dioxane (10 mL) and aqueous saturated NaHCO$_3$ (3 mL). The resulting light brown suspension was heated at 140° C. for 45 minutes in a microwave reactor. The reaction mixture was subsequently concentrated and the crude residue was purified by preparative HPLC, eluting with a gradient of 40-45% ACN (containing 0.035% TFA) in H$_2$O (containing 0.05% TFA) over a period of 6.5 minutes. The product-containing fractions were combined and the volatiles were removed via rotary evaporation to give a TFA salt of the title compound as a light brown solid (0.14 g, 37%). $^1$H NMR (400 MHz, DMSO-d$_6$) δ ppm 1.24 (t, J=7.07 Hz, 3H), 4.19 (q, J=7.16 Hz, 2H), 5.15 (s, 2H), 7.60 (d, J=1.01 Hz, 1H), 7.77 (s, 1H), 8.27 (d, J=0.76 Hz, 1H), 8.53 (s, 1H), 8.63 (s, 1H), 13.64 (s, 1H); ESI-MS m/z [M+H]$^+$ calc'd for C$_{15}$H$_{13}$F$_3$N$_4$O$_2$, 339.1. found 339.

Example 261

2-(4-(6-(trifluoromethyl)-1H-indazol-4-yl)-1H-pyrazol-1-yl)acetic acid

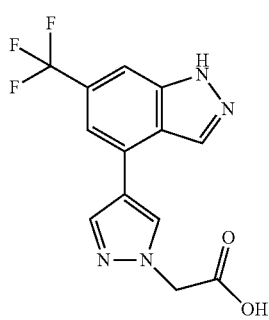 [SMILES: O=C(O)Cn1cc(-c2cc(C(F)(F)F)cc3[nH]ncc23)cn1]

To a mixture of ethyl 2-(4-(6-(trifluoromethyl)-1H-indazol-4-yl)-1H-pyrazol-1-yl)acetate (0.14 g, 0.414 mmol) and THF—H$_2$O (5:1, 4 mL) was added lithium hydroxide (0.621 mL, 1.242 mmol) at room temperature. The reaction mixture was stirred for 1 hour, then acidified with concentrated HCl, and concentrated in vacuo to give an HCl salt of the title compound as a light brown solid (0.12 g, 93%). $^1$H NMR (400 MHz, DMSO-d$_6$) δ ppm 4.97 (s, 2H), 7.58 (s, 1H), 7.76 (s, 1H), 8.22 (s, 1H), 8.54 (s, 1H), 8.59 (s, 1H), 13.70 (br s, 1H); ESI-MS m/z [M+H]$^+$ calc'd for C$_{13}$H$_9$F$_3$N$_4$O$_2$, 311.1. found 311.15.

Example 262 morpholino(5-(6-(trifluoromethyl)-1H-indazol-4-yl)pyridin-2-yl)methanone

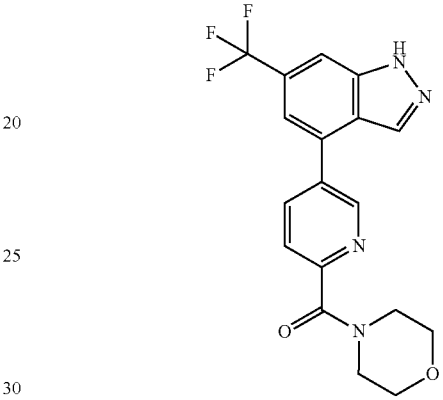

A vial was charged with a mixture of 4-(4,4,5,5-tetramethyl-1,3,2-dioxaborolan-2-yl)-6-(trifluoromethyl)-1H-indazole (0.1 g, 0.320 mmol), (5-bromopyridin-2-yl)(morpholino)methanone (0.174 g, 0.641 mmol) and PdCl$_2$(dppf) (0.012 g, 0.016 mmol) in dioxane (10 mL) and aqueous saturated NaHCO$_3$ (3 mL). The resulting light brown suspension was heated at 140° C. for 45 minutes in a microwave reactor. The reaction mixture was subsequently concentrated and the crude residue was purified by preparative HPLC, eluting with a gradient of 35-45% ACN (containing 0.035% TFA) in H$_2$O (containing 0.05% TFA) over a period of 5 minutes. The product-containing fractions were combined and the volatiles were removed in vacuo to give a TFA salt of the title compound as a light brown solid (0.053 g, 44%). $^1$H NMR (400 MHz, DMSO-d$_6$) δ ppm 3.49-3.67 (m, 4H), 3.71 (s, 4H), 7.63 (s, 1H), 7.80 (dd, J=8.08, 0.76 Hz, 1H), 8.03 (s, 1H), 8.28-8.48 (m, 2H), 9.01 (dd, J=2.40, 0.88 Hz, 1H), 13.82 (br s, 1H); ESI-MS m/z [M+H]$^+$ calc'd for C$_{15}$H$_{15}$F$_3$N$_4$O$_2$, 377.1. found 377.

Example 263 methyl 4-methoxy-3-(6-(trifluoromethyl)-1H-indazol-4-yl)benzoate

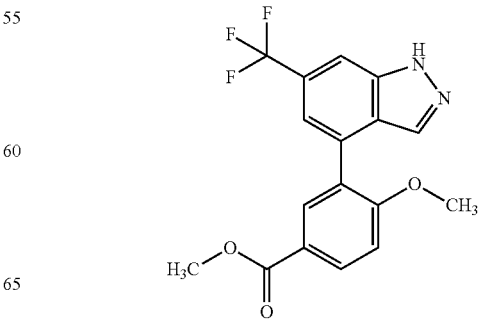

A vial was charged with a mixture of 4-bromo-6-(trifluoromethyl)-1H-indazole (0.631 g, 2.381 mmol), (2-methoxy-5-(methoxycarbonyl)phenyl)boronic acid (0.5 g, 2.381 mmol) and PdCl₂(dppf) (0.087 g, 0.119 mmol) in dioxane (10 mL) and aqueous saturated NaHCO₃ (3 mL). The resulting light brown suspension was heated at 140° C. for 45 minutes in a microwave reactor. The reaction mixture was subsequently concentrated and the crude residue was diluted with DCM and washed with water, concentrated, and then purified by CombiFlash® chromatography, eluting with a gradient of 0-40% MeOH in DCM over a period of 200 minutes. The product-containing fractions were combined and concentrated to give the title compound as a light brown solid (0.592 g, 71.0%). $^1$H NMR (400 MHz, DMSO-d$_6$) δ ppm 3.85 (s, 3H), 3.84 (s, 3H), 7.21-7.46 (m, 2H), 7.89-7.99 (m, 3H), 8.10 (dd, J=8.59, 2.27 Hz, 1H), 13.62 (s, 1H); ESI-MS m/z [M+H]$^+$ calc'd for C$_{17}$H$_{13}$F$_3$N$_2$O$_3$, 351.1. found 351.16.

Example 264

2-(4-(6-(trifluoromethyl)-1H-indazol-4-yl)-1H-pyrazol-1-yl)acetamide

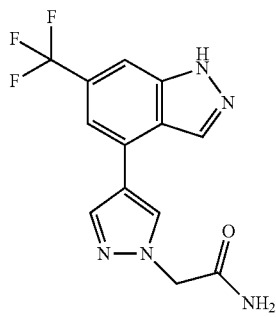 [SMILES: NC(=O)Cn1cc(-c2cc(C(F)(F)F)cc3[nH]ncc23)cn1]

To 2-(4-(6-(trifluoromethyl)-1H-indazol-4-yl)-1H-pyrazol-1-yl)acetic acid (0.052 g, 0.168 mmol) in DMF (3 mL) were added HOBt (0.029 g, 0.218 mmol), EDC (0.045 g, 0.235 mmol), ammonium chloride (0.045 g, 0.838 mmol), followed by N-ethyl-N-isopropylpropan-2-amine (0.146 mL, 0.838 mmol). The reaction mixture was stirred for 18 hours at room temperature. The crude mixture was subsequently purified by preparative HPLC (Waters SunFire C18, 5 μm, 30 mm ID×75 mm column) eluting with a gradient of 20-30% ACN (containing 0.035% TFA) in water (containing 0.05% TFA) to give the title compound as white solid (0.016 g, 31%). $^1$H NMR (400 MHz, DMSO-d$_6$) δ ppm 4.84 (s, 2H), 7.33 (br s, 1 H), 7.51-7.68 (m, 2H), 7.75 (s, 1H), 8.23 (d, J=0.76 Hz, 1H), 8.56 (d, J=4.29 Hz, 2H), 13.62 (s, 1H); ESI-MS m/z [M+H]$^+$ calc'd for C$_{13}$H$_{10}$F$_3$N$_5$O, 310.1. found 310.

Example 265 methyl 6-oxo-5-(6-(trifluoromethyl)-1H-indazol-4-yl)-1,6-dihydropyridine-3-carboxylate

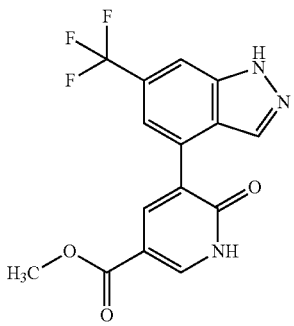 [SMILES: COC(=O)c1c[nH]c(=O)c(-c2cc(C(F)(F)F)cc3[nH]ncc23)c1]

A mixture of 4-(4,4,5,5-tetramethyl-1,3,2-dioxaborolan-2-yl)-6-(trifluoromethyl)-1H-indazole (43 mg, 0.138 mmol), methyl 5-iodo-6-oxo-1,6-dihydropyridine-3-carboxylate (38.4 mg, 0.138 mmol) and PdCl₂(dppf) (5.04 mg, 6.89 μmol) in dioxane (2 mL) and aqueous saturated NaHCO₃ solution (0.5 mL) was heated in a microwave reactor at 140° C. for 30 minutes. The reaction mixture was subsequently filtered and purified via preparative HPLC, eluting with a gradient of 20-90% ACN (containing 0.035% TFA) in H₂O (containing 0.05% TFA) to give the title compound as a white solid (7 mg, 15%). $^1$H NMR (400 MHz, DMSO-d$_6$) δ ppm 8.19 (s, 1H), 8.09-8.14 (m, 2H), 7.94 (s, 1H), 7.62 (s, 1H), 3.82 (s, 3H); ESI-MS m/z [M+H]$^+$ calc'd for C$_{15}$H$_{10}$F$_3$N$_3$O$_3$, 338.1. found 338.2.

Example 266

(4-methoxy-3-(6-(trifluoromethyl)-1H-indazol-4-yl)phenyl)(4-methylpiperazin-1-yl)methanone

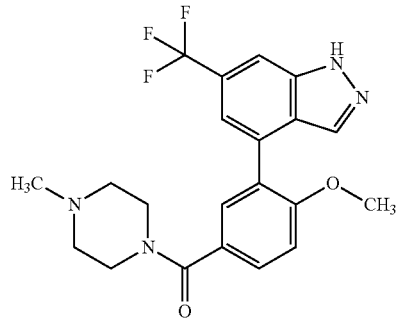

To a 10 mL microwave vial charged with a solution of 1-methylpiperazine (0.029 g, 0.285 mmol) in dioxane (2 mL) was added, dropwise and at room temperature, trimethylaluminum (0.428 mL, 0.856 mmol) in toluene. After stirring for 15 minutes at room temperature, methyl 4-methoxy-3-(6-(trifluoromethyl)-1H-indazol-4-yl)benzoate (0.1 g, 0.285 mmol) was added. The reaction mixture was heated at 110° C. for 1 hour in a microwave reactor and was subsequently transferred to a round bottom flask, where it was quenched with concentrated HCl. The reaction mixture was concentrated, and the crude residue was purified by preparative HPLC (Waters SunFire C18, 5 μm, 30 mm ID×75 mm column) eluting with a gradient of 25-30% ACN (containing 0.035% TFA) in water (containing 0.05% TFA) to give a TFA salt of the title compound (0.051 g, 43%). $^1$H NMR (400 MHz, DMSO-d$_6$) δ ppm 2.83 (s, 3H), 3.11 (br s, 2H), 3.33 (br s, 2H), 3.45 (br s, 2H), 3.83 (s, 3H), 4.27 (br s, 2H), 7.32 (d, J=8.59 Hz, 1H), 7.37-7.44 (m, 1H), 7.54 (d, J=2.02 Hz, 1H), 7.62 (dd, J=8.59, 2.02 Hz, 1H), 7.93-8.05 (m, 2H), 10.29 (br s, 1H); ESI-MS m/z [M+H]$^+$ calc'd for C$_{21}$H$_{21}$F$_3$N$_4$O$_2$, 419.2. found 419.21.

Example 267

(4-methoxy-3-(6-(trifluoromethyl)-1H-indazol-4-yl)phenyl)(morpholino)methanone

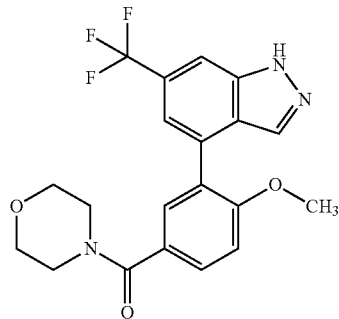 [SMILES: COc1ccc(C(=O)N2CCOCC2)cc1-c1cc(C(F)(F)F)cc2[nH]ncc12]

A TFA salt of the title compound was prepared in a manner similar to EXAMPLE 266 using morpholine in place of 1-methylpiperazine. $^1$H NMR (400 MHz, DMSO-d$_6$) δ ppm 3.55 (br s, 4H), 3.72 (br s, 4H), 3.81 (s, 3H), 7.28 (d, J=8.59 Hz, 1H), 7.35 (d, J=1.01 Hz, 1H), 7.47 (d, J=2.27 Hz, 1H), 7.56 (dd, J=8.46, 2.15 Hz, 1H), 7.87-8.02 (m, 2H); ESI-MS m/z [M+H]$^+$ calc'd for C$_{20}$H$_{18}$F$_3$N$_3$O$_3$, 406.1. found 406.22.

Example 268

N-(2-hydroxyethyl)-4-methoxy-3-(6-(trifluoromethyl)-1H-indazol-4-yl)benzamide

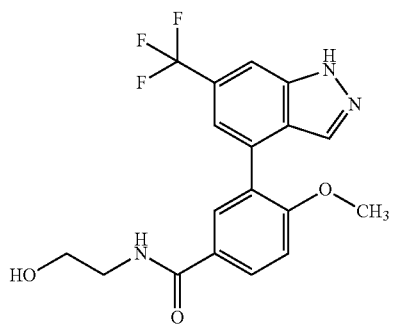 [SMILES: COc1ccc(C(=O)NCCO)cc1-c1cc(C(F)(F)F)cc2[nH]ncc12]

A TFA salt of the title compound was prepared in a manner similar to EXAMPLE 266 using 2-aminoethanol in place of 1-methylpiperazine. $^1$H NMR (400 MHz, CD$_3$OD) δ ppm 3.44-3.55 (m, 2H), 3.65-3.75 (m, 2H), 3.83-3.92 (m, 3H), 7.19-7.33 (m, 1H), 7.39 (s, 1H), 7.85-7.97 (m, 3H), 8.01 (dd, J=8.72, 2.40 Hz, 1H); ESI-MS m/z [M+H]$^+$ calc'd for C$_{18}$H$_{16}$F$_3$N$_3$O$_3$, 380.1. found 380.16.

Example 269 methyl 5-(6-(trifluoromethyl)-1H-indazol-4-yl)picolinate

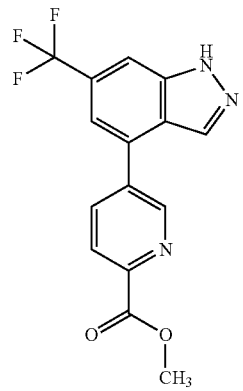 [SMILES: COC(=O)c1ccc(-c2cc(C(F)(F)F)cc3[nH]ncc23)cn1]

A vial was charged with a mixture of 4-bromo-6-(trifluoromethyl)-1H-indazole (0.732 g, 2.76 mmol), (6-(methoxycarbonyl)pyridin-3-yl)boronic acid (0.5 g, 2.76 mmol) and PdCl$_2$(dppf) (0.101 g, 0.138 mmol) in dioxane (10 mL) and aqueous saturated NaHCO$_3$ (3 mL). The resulting light brown suspension was heated at 140° C. for 45 minutes in a microwave reactor. The reaction mixture was subsequently concentrated. The residue was diluted with DCM, washed with water, and the volatiles removed via rotary evaporation. The crude product was purified by CombiFlash® chromatography (0-30% MeOH in DCM over 180 minutes). The product-containing fractions were combined and concentrated by rotary evaporation to give product with some impurities (0.28 g). A portion of the product (20 mg) was re-purified by preparative HPLC, eluting with 40% ACN (containing 0.035% TFA) in H$_2$O (containing 0.05% TFA) over a period of 6.5 minutes to give a TFA salt of the title compound. $^1$H NMR (400 MHz, DMSO-d$_6$) δ ppm 3.95 (s, 3H), 7.69 (s, 1H), 8.07 (s, 1H), 8.23 (dd, J=8.21, 0.63 Hz, 1H), 8.39-8.57 (m, 2H), 9.10-9.26 (m, 1H), 13.86 (br s, 1H); ESI-MS m/z [M+H]$^+$ calc'd for C$_{15}$H$_{10}$F$_3$N$_3$O$_2$, 322.1. found 322.11.

Example 270

N-(2-hydroxyethyl)-5-(6-(trifluoromethyl)-1H-indazol-4-yl)picolinamide

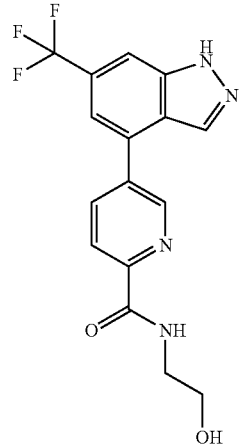 [SMILES: O=C(NCCO)c1ccc(-c2cc(C(F)(F)F)cc3[nH]ncc23)cn1]

To a 10 mL vial charged with 2-aminoethanol (0.057 g, 0.934 mmol) in dioxane (2 mL) was added dropwise trimethylaluminum (0.467 mL, 0.934 mmol) in toluene at room temperature. The mixture was stirred for 15 minutes at room temperature. Methyl 5-(6-(trifluoromethyl)-1H-indazol-4-yl)picolinate (0.1 g, 0.285 mmol) was added, and the reaction mixture was heated at 110° C. for 1 hour in a microwave reactor. The reaction mixture was transferred to a round bottom flask, quenched with concentrated HCl, and then concentrated. The crude residue was purified by preparative HPLC, eluting with a gradient of 30-35% ACN (containing 0.035% TFA) in H$_2$O (containing 0.05% TFA) over a period of 6 minutes. The product-containing fractions were combined and the volatiles were removed in vacuo to give a TFA salt of the title compound (0.023 g, 42%) $^1$H NMR (400 MHz, DMSO-d$_6$) δ ppm 3.44 (q, J=5.98 Hz, 2H), 3.57 (d, J=4.80 Hz, 2H), 4.86 (br s, 1H), 7.66 (s, 1H), 8.06 (s, 1H), 8.21 (d, J=8.08 Hz, 1H), 8.37-8.51 (m, 2H), 8.79 (t, J=5.81 Hz, 1H), 9.06 (dd, J=2.27, 0.76 Hz, 1H), 13.85 (s, 1H); ESI-MS m/z [M+H]$^+$ calc'd for C$_{16}$H$_{13}$F$_3$N$_4$O$_2$, 351.1. found 351.16.

Example 271

(4-methylpiperazin-1-yl)(5-(6-(trifluoromethyl)-1H-indazol-4-yl)pyridin-2-yl)methanone

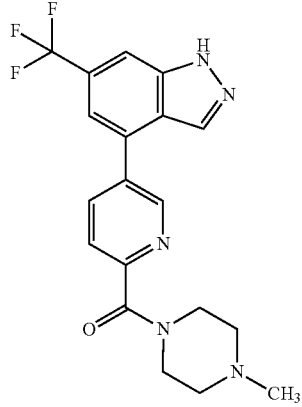 [SMILES: CN1CCN(C(=O)c2ccc(-c3cc(C(F)(F)F)cc4[nH]ncc34)cn2)CC1]

A TFA salt of the title compound was prepared in a manner similar to EXAMPLE 270 using 1-methylpiperazine in place of 2-aminoethanol. $^1$H NMR (400 MHz, DMSO-d$_6$) δ ppm 2.81-2.90 (m, 3H), 3.17 (br s, 3H), 3.42 (br s, 1H), 3.54 (d, J=16.17 Hz, 2H), 4.25 (br s, 1H), 4.64 (br s, 1H), 7.63 (d, J=1.01 Hz, 1H), 7.86 (dd, J=8.08, 0.76 Hz, 1H), 8.06 (s, 1H), 8.38-8.49 (m, 2H), 9.03 (d, J=1.77 Hz, 1H), 10.27 (br s, 1H); ESI-MS m/z [M+H]$^+$ calc'd for C$_{19}$H$_{18}$F$_3$N$_5$O, 390.1. found 390.25.

Example 272

4-methoxy-N,N-dimethyl-3-(6-(trifluoromethyl)-1H-indazol-4-yl)benzamide

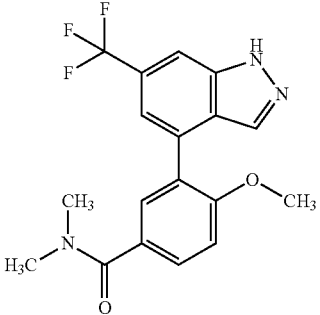

A TFA salt of the title compound was prepared in a manner similar to EXAMPLE 266 using dimethylamine HCl in place of 1-methylpiperazine. $^1$H NMR (400 MHz, DMSO-d$_6$) δ ppm 3.00 (br s, 6H), 3.81 (s, 3H), 7.26 (d, J=8.59 Hz, 1H), 7.35 (d, J=1.01 Hz, 1H), 7.47 (d, J=2.02 Hz, 1H), 7.56 (dd, J=8.46, 2.15 Hz, 1H), 7.96 (s, 1H), 7.93 (s, 1H), 13.59 (br s, 1H); ESI-MS m/z [M+H]$^+$ calc'd for C$_{18}$H$_{16}$F$_3$N$_3$O$_2$, 364.1. found 364.2.

Example 273

4-methoxy-3-(6-(trifluoromethyl)-1H-indazol-4-yl)benzamide

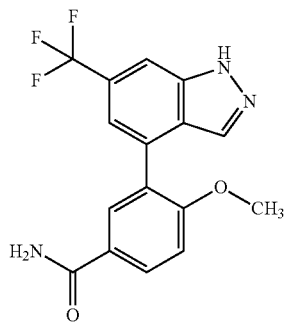 [SMILES: COc1ccc(C(N)=O)cc1-c1cc(C(F)(F)F)cc2[nH]ncc12]

A TFA salt of the title compound was prepared in a manner similar to EXAMPLE 266 using ammonium chloride in place of 1-methylpiperazine. $^1$H NMR (400 MHz, DMSO-d$_6$) δ ppm 3.82 (s, 3H), 7.28 (d, J=8.59 Hz, 2H), 7.37 (d, J=1.26 Hz, 1H), 7.83-8.11 (m, 5H), 13.58 (s, 1H); ESI-MS m/z [M+H]$^+$ calc'd for C$_{16}$H$_{12}$F$_3$N$_3$O$_2$, 336.1. found 336.16.

Example 274

2-(3-methyl-4-(6-(trifluoromethyl)-1H-indazol-4-yl)-1H-pyrazol-1-yl)acetamide

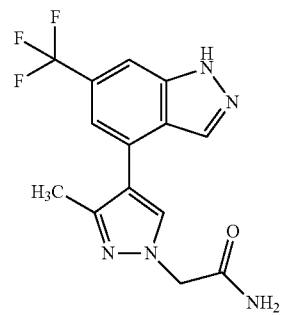 [SMILES: Cc1nn(CC(N)=O)cc1-c1cc(C(F)(F)F)cc2[nH]ncc12]

A TFA salt of the title compound was prepared in a manner similar to EXAMPLE 257 using 2-(4-bromo-3-methyl-1H-pyrazol-1-yl)acetamide in place of N-(5-bromo-6-methylpyridin-2-yl)methanesulfonamide. $^1$H NMR (400 MHz, DMSO-d$_6$) δ ppm 2.32 (s, 3H), 4.77 (s, 2H), 7.21-7.37 (m, 2H), 7.52 (br s, 1H), 7.81 (s, 1H), 8.16-8.33 (m, 2H), 13.62 (s, 1H); ESI-MS m/z [M+H]$^+$ calc'd for C$_{14}$H$_{12}$F$_3$N$_5$O, 324.1. found 324.1.

Example 275

6-(6-(trifluoromethyl)-1H-indazol-4-yl)pyrazolo[1,5-a]pyrimidine

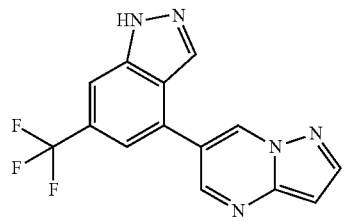 [SMILES: FC(F)(F)c1cc(-c2cnc3ccnn3c2)c2cn[nH]c2c1]

A TFA salt of the title compound was prepared in a manner similar to EXAMPLE 257 using 6-bromopyrazolo[1,5-a]pyrimidine in place of N-(5-bromo-6-methylpyridin-2-yl)methanesulfonamide. $^1$H NMR (400 MHz, DMSO-d$_6$) δ ppm 6.86 (dd, J=2.40, 0.88 Hz, 1H), 7.73 (d, J=1.01 Hz, 1H), 8.03 (s, 1H), 8.35 (d, J=2.53 Hz, 1H), 8.49 (t, J=1.26 Hz, 1H), 8.98 (d, J=2.27 Hz, 1H), 9.57 (dd, J=2.27, 0.76 Hz, 1H), 13.80 (s, 1H); ESI-MS m/z [M+H]$^+$ calc'd for C$_{14}$H$_8$F$_3$N$_5$, 304.1. found 304.2.

Example 276

3-(6-(trifluoromethyl)-1H-indazol-4-yl)imidazo[1,2-b]pyridazine-6-carboxamide

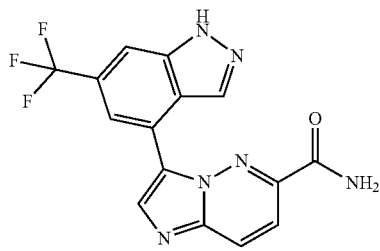 [SMILES: NC(=O)c1ccc2ncc(-c3cc(C(F)(F)F)cc4[nH]ncc34)n2n1]

To 3-(6-(trifluoromethyl)-1H-indazol-4-yl)imidazo[1,2-b]pyridazine-6-carboxylic acid (0.036 g, 0.104 mmol) in DMF (3 mL) was added O-(benzotriazol-1-yl)-N,N,N',N'-tetramethyluronium tetrafluoroborate (0.028 g, 0.073 mmol), ammonium chloride (8.32 mg, 0.156 mmol), and Et$_3$N (0.013 g, 0.124 mmol). The reaction mixture was stirred at room temperature overnight and was subsequently filtered and purified by preparative HPLC, eluting with a gradient of 25-50% ACN (containing 0.035% TFA) in H$_2$O (containing 0.05% TFA) to give a TFA salt of the title compound. $^1$H NMR (400 MHz, DMSO-d$_6$) δ ppm 7.35-7.46 (m, 1H), 7.53 (t, J=7.58 Hz, 1H), 7.71 (d, J=8.59 Hz, 1H), 7.82 (dd, J=18.32, 9.47 Hz, 1H), 7.95-8.05 (m, 2H), 8.40 (t, J=9.35 Hz, 1H), 8.50 (br s, 1H), 8.57-8.66 (m, 1H), 8.70 (s, 1H); ESI-MS m/z [M+H]$^+$ calc'd for C$_{15}$H$_9$F$_3$N$_6$O, 347.1. found 347.2.

Example 277

2-(3-methyl-4-(6-(trifluoromethyl)-1H-indazol-4-yl)-1H-pyrazol-1-yl)-1-morpholinoethanone

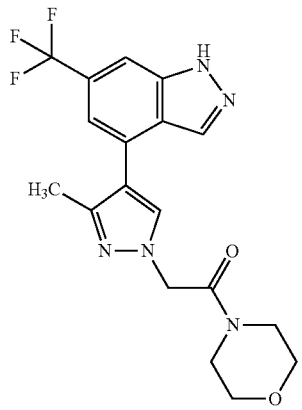 [SMILES: Cc1nn(CC(=O)N2CCOCC2)cc1-c1cc(C(F)(F)F)cc2[nH]ncc12]

A TFA salt of the title compound was prepared in a manner similar to EXAMPLE 257 using 2-(4-bromo-3-methyl-1H-pyrazol-1-yl)-1-morpholinoethanone in place of N-(5-bromo-6-methylpyridin-2-yl)methanesulfonamide. $^1$H NMR (400 MHz, DMSO-d$_6$) δ ppm 2.32 (s, 3H), 3.48 (d, J=4.55 Hz, 2H), 3.52-3.69 (m, 6H), 5.16 (s, 2H), 7.28 (d, J=1.01 Hz, 1H), 7.82 (s, 1H), 8.11-8.28 (m, 2H); ESI-MS m/z [M+H]$^+$ calc'd for C$_{18}$H$_{18}$F$_3$N$_5$O$_2$, 394.1. found 394.2.

Example 278

1-methyl-5-(6-(trifluoromethyl)-1H-indazol-4-yl)pyrimidine-2,4(1H,3H)-dione

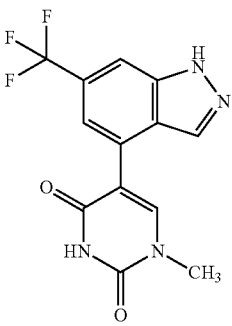 [SMILES: Cn1cc(-c2cc(C(F)(F)F)cc3[nH]ncc23)c(=O)[nH]c1=O]

The title compound was prepared in a manner similar to EXAMPLE 265 using 5-bromo-1-methylpyrimidine-2,4(1H,3H)-dione in place of methyl 5-iodo-6-oxo-1,6-dihydropyridine-3-carboxylate. $^1$H NMR (400 MHz, CD$_3$OD) δ ppm 8.18 (s, 1H), 7.97 (s, 1H), 7.86 (s, 1H), 7.48 (s, 1H), 3.46 (s, 3H); ESI-MS m/z [M+H]$^+$ calc'd for C$_{13}$H$_9$F$_3$N$_4$O$_2$, 311.1. found 311.2.

Example 279

N-(2-hydroxyethyl)-2-(3-methyl-4-(6-(trifluoromethyl)-1H-indazol-4-yl)-1H-pyrazol-1-yl)acetamide

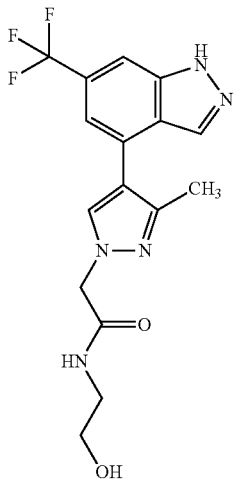 [SMILES: Cc1nn(CC(=O)NCCO)cc1-c1cc(C(F)(F)F)cc2[nH]ncc12]

A TFA salt of the title compound was prepared in a manner similar to EXAMPLE 257 using 2-(4-bromo-3-methyl-1H-pyrazol-1-yl)acetamide in place of N-(5-bromo-6-methylpyridin-2-yl)methanesulfonamide. $^1$H NMR (400 MHz, DMSO-d$_6$) δ ppm 2.31 (s, 3H), 3.18 (q, J=5.89 Hz, 2H), 3.44 (q, J=5.73 Hz, 2H), 4.65-4.86 (m, 3H), 7.28 (s, 1H), 7.81 (s, 1H), 8.06-8.31 (m, 3H), 13.62 (s, 1H); ESI-MS m/z [M+H]$^+$ calc'd for C$_{16}$H$_{16}$F$_3$N$_5$O$_2$, 368.1. found 368.

Example 280

N,N-dimethyl-2-(4-(6-(trifluoromethyl)-1H-indazol-4-yl)phenoxy)ethanamine

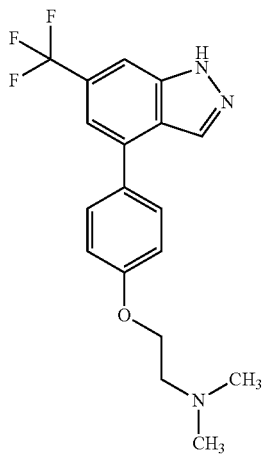

A TFA salt of the title compound was prepared in a manner similar to EXAMPLE 247 using N,N-dimethyl-2-(4-(4,4,5,5-tetramethyl-1,3,2-dioxaborolan-2-yl)phenoxy)ethanamine in place of N,N-dimethyl-5-(4,4,5,5-tetramethyl-1,3,2-dioxaborolan-2-yl)pyrimidin-2-amine. $^1$H NMR (400 MHz, DMSO-d$_6$) δ ppm 2.83-2.96 (m, 6H), 3.58 (d, J=4.55 Hz, 2H), 4.31-4.48 (m, 2H), 7.12-7.30 (m, 2H), 7.41 (d, J=1.26 Hz, 1H), 7.71-7.86 (m, 2H), 7.91 (s, 1H), 8.32 (d, J=0.76 Hz, 1H), 9.78 (br s, 1H); ESI-MS m/z [M+H]$^+$ calc'd for C$_{18}$H$_{18}$F$_3$N$_3$O, 350.1. found 350.

Example 281

4-(2-(4-(6-(trifluoromethyl)-1H-indazol-4-yl)phenoxy)ethyl)morpholine

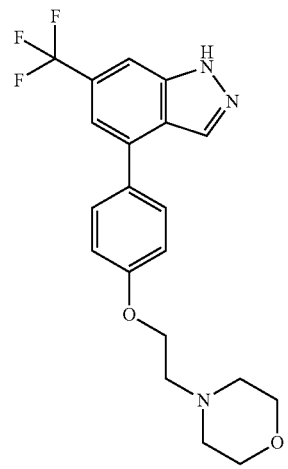 [SMILES: FC(F)(F)c1cc(-c2ccc(OCCN3CCOCC3)cc2)c2cn[nH]c2c1]

A TFA salt of the title compound was prepared in a manner similar to EXAMPLE 247 using 4-(2-(4-(4,4,5,5-tetramethyl-1,3,2-dioxaborolan-2-yl)phenoxy)ethyl)morpholine in place of N,N-dimethyl-5-(4,4,5,5-tetramethyl-1,3,2-dioxaborolan-2-yl)pyrimidin-2-amine. $^1$H NMR (400 MHz, DMSO-d$_6$) δ ppm 3.26 (br s, 2H), 3.57 (d, J=12.13 Hz, 2H), 3.61-3.69 (m, 2H), 3.74 (t, J=11.24 Hz, 2H), 4.02 (d, J=11.87 Hz, 2H), 4.36-4.54 (m, 2H), 7.11-7.29 (m, 2H), 7.41 (d, J=1.01 Hz, 1H), 7.72-7.86 (m, 2H), 7.91 (s, 1H), 8.32 (d, J=1.01 Hz, 1H), 10.27 (br s, 1H); ESI-MS m/z [M+H]$^+$ calc'd for C$_{20}$H$_{20}$F$_3$N$_3$O$_2$, 392.2. found 392.

Example 282

(2-amino-5-(6-(trifluoromethyl)-1H-indazol-4-yl)pyridin-3-yl)(4-methylpiperazin-1-yl)methanone

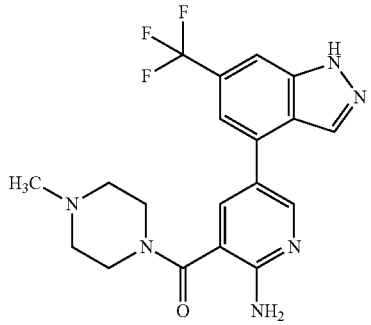 [SMILES: CN1CCN(C(=O)c2cc(-c3cc(C(F)(F)F)cc4[nH]ncc34)cnc2N)CC1]

4-(4,4,5,5-Tetramethyl-1,3,2-dioxaborolan-2-yl)-6-(trifluoromethyl)-1H-indazole (20 mg, 0.064 mmol), (2-amino-5-bromopyridin-3-yl)(4-methylpiperazin-1-yl)methanone (PREPARATION x56, 1 mL, 0.096 mmol), sodium carbonate (27.2 mg, 0.256 mmol), and PdCl$_2$(dppf)CH$_2$Cl$_2$ (5.23 mg, 6.41 μmol) were sealed in a vial, which was heated to 135° C. for 30 minutes in a microwave reactor. The reaction mixture was purified by preparative HPLC, eluting with ACN/H$_2$O (containing 0.05% TFA). The product-containing fractions were dried to give a TFA salt of the title compound as a tan solid (9.73 mg). ESI-MS m/z [M+H]$^+$ calc'd for C$_{19}$H$_{19}$F$_3$N$_6$O, 405.2. found 405.3.

Example 283

4-(6-(trifluoromethyl)-1H-indazol-4-yl)picolinamide

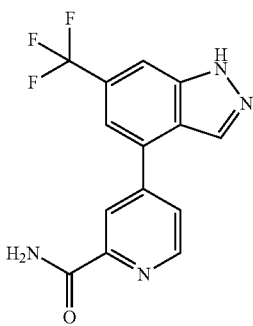

To a mixture of 4-(6-(trifluoromethyl)-1H-indazol-4-yl)picolinic acid (0.028 g, 0.091 mmol) in DMF (3 mL) were added ammonium chloride (0.024 g, 0.456 mmol), HOBt (0.018 g, 0.137 mmol), and EDC (0.028 g, 0.146 mmol), followed by N-ethyl-N-isopropylpropan-2-amine (0.079 mL, 0.456 mmol). The reaction mixture was stirred for 18 hours at room temperature. The crude reaction mixture was subsequently purified by preparative HPLC, eluting with a gradient of 30-35% acetonitrile (containing 0.035% TFA) in H$_2$O (containing 0.05% TFA) over a period of 6.5 minutes. The product-containing fractions were combined and the solvent removed in vacuo to give a TFA salt of the title compound as an off white solid (0.012 g, 43%). $^1$H NMR (400 MHz, DMSO-d$_6$) δ ppm 7.68 (s, 1H), 7.80 (br s, 1H), 7.95-8.15 (m, 2H), 8.27 (br s, 1H), 8.32-8.47 (m, 2H), 8.81 (d, J=5.05 Hz, 1H), 13.89 (br s, 1H); ESI-MS m/z [M+H]$^+$ calc'd for C$_{14}$H$_9$F$_3$N$_4$O, 307.1. found 307.11.

Example 284

(4-methylpiperazin-1-yl)(4-(6-(trifluoromethyl)-1H-indazol-4-yl)pyridin-2-yl)methanone

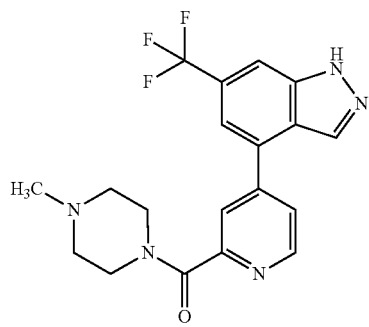 [SMILES: CN1CCN(C(=O)c2cc(-c3cc(C(F)(F)F)cc4[nH]ncc34)ccn2)CC1]

A TFA salt of the title compound was prepared in a manner similar to EXAMPLE 283 using 1-methylpiperazine in place of ammonium chloride. $^1$H NMR (400 MHz, DMSO-d$_6$) δ ppm 2.79-2.90 (m, 3H), 3.08-3.24 (m, 2H), 3.33-3.53 (m, 3H), 3.58 (d, J=11.12 Hz, 1H), 4.12 (d, J=15.16 Hz, 1H), 4.64 (d, J=12.13 Hz, 1H), 7.59-7.74 (m, 1H), 7.95-8.07 (m, 2H), 8.11 (s, 1H), 8.40-8.48 (m, 1H), 8.69-8.85 (m, 1H), 9.96 (br s, 1H); ESI-MS m/z [M+H]$^+$ calc'd for C$_{19}$H$_{18}$F$_3$N$_5$O, 390.1. found 390.25.

Example 285

N-(2-hydroxyethyl)-2-methoxy-5-(6-(trifluoromethyl)-1H-indazol-4-yl)nicotinamide

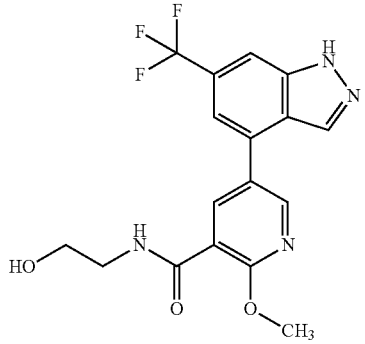 [SMILES: COc1ncc(-c2cc(C(F)(F)F)cc3[nH]ncc23)cc1C(=O)NCCO]

A TFA salt of the title compound was prepared in a manner similar to EXAMPLE 282 using 5-bromo-N-(2-hydroxyethyl)-2-methoxynicotinamide (PREPARATION x59) in place of (2-amino-5-bromopyridin-3-yl)(4-methylpiperazin-1-yl)methanone. ESI-MS m/z [M+H]$^+$ calc'd for C$_{17}$H$_{15}$F$_3$N$_4$O$_3$, 381.1. found 381.2.

Example 286

N-(2-hydroxyethyl)-5-(6-(trifluoromethyl)-1H-indazol-4-yl)pyrimidine-2-carboxamide

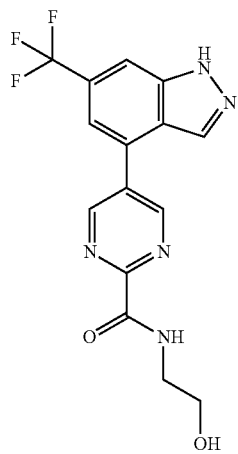 [SMILES: O=C(NCCO)c1ncc(-c2cc(C(F)(F)F)cc3[nH]ncc23)cn1]

A TFA salt of the title compound was prepared in a manner similar to EXAMPLE 257 using 5-bromo-N-(2-hydroxyethyl)pyrimidine-2-carboxamide in place of N-(5- bromo-6-methylpyridin-2-yl)methanesulfonamide. $^{1}$H NMR (400 MHz, DMSO-$d_6$) δ ppm 3.44 (q, J=6.06 Hz, 2H), 3.50-3.63 (m, 2H), 3.67-3.79 (m, 1H), 4.58 (t, J=5.31 Hz, 1H), 7.71-7.85 (m, 1H), 8.10 (s, 1H), 8.50 (s, 1H), 8.90 (t, J=5.94 Hz, 1H), 9.35-9.44 (m, 2H); ESI-MS m/z [M+H]$^+$ calc'd for $C_{15}H_{12}F_3N_5O_2$, 352.1. found 352.19.

Example 287

(4-methylpiperazin-1-yl)(5-(6-(trifluoromethyl)-1H-indazol-4-yl)pyridin-3-yl)methanone

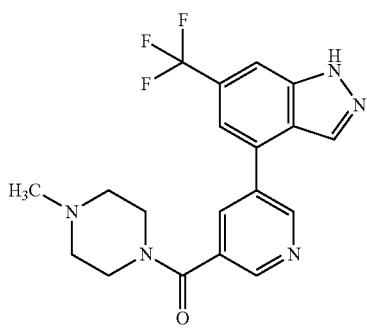 [SMILES: CN1CCN(C(=O)c2cncc(-c3cc(C(F)(F)F)cc4[nH]ncc34)c2)CC1]

A TFA salt of the title compound was prepared in a manner similar to EXAMPLE 282 using (5-bromopyridin-3-yl)(4-methylpiperazin-1-yl)methanone (PREPARATION x54) in place of (2-amino-5-bromopyridin-3-yl)(4-methylpiperazin-1-yl)methanone. ESI-MS m/z [M+H]$^+$ calc'd for $C_{19}H_{18}F_3N_5O$, 390.1. found 390.3.

Example 288

(2-methoxy-5-(6-(trifluoromethyl)-1H-indazol-4-yl)pyridin-3-yl)(4-methylpiperazin-1-yl)methanone

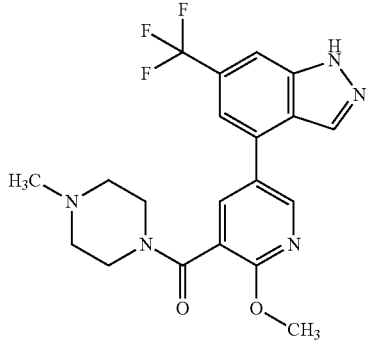 [SMILES: COc1ncc(-c2cc(C(F)(F)F)cc3[nH]ncc23)cc1C(=O)N1CCN(C)CC1]

A TFA salt of the title compound was prepared in a manner similar to EXAMPLE 282 using (5-bromo-2-methoxypyridin-3-yl)(4-methylpiperazin-1-yl)methanone (PREPARATION x55) in place of (2-amino-5-bromopyridin-3-yl)(4-methylpiperazin-1-yl)methanone. ESI-MS m/z [M+H]$^+$ calc'd for $C_{20}H_{20}F_3N_5O_2$, 420.2. found 420.3.

Example 289

(2-fluoro-5-(6-(trifluoromethyl)-1H-indazol-4-yl)pyridin-3-yl)(4-methylpiperazin-1-yl)methanone

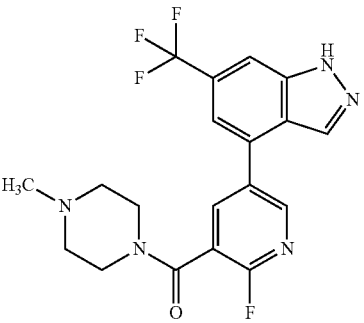 [SMILES: CN1CCN(C(=O)c2cc(-c3cc(C(F)(F)F)cc4[nH]ncc34)cnc2F)CC1]

A TFA salt of the title compound was prepared in a manner similar to EXAMPLE 282 using (5-bromo-2-fluoropyridin-3-yl)(4-methylpiperazin-1-yl)methanone (PREPARATION x57) in place of (2-amino-5-bromopyridin-3-yl)(4-methylpiperazin-1-yl)methanone. ESI-MS m/z [M+H]$^+$ calc'd for $C_{19}H_{17}F_4N_5O$, 408.1. found 408.2.

Example 290

N-(2-hydroxyethyl)-5-(6-(trifluoromethyl)-1H-indazol-4-yl)nicotinamide

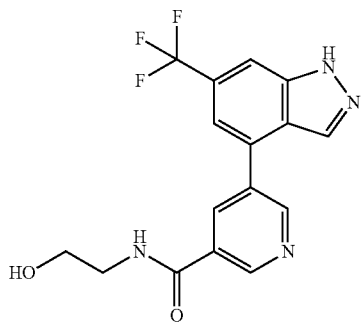 [SMILES: O=C(NCCO)c1cncc(-c2cc(C(F)(F)F)cc3[nH]ncc23)c1]

A TFA salt of the title compound was prepared in a manner similar to EXAMPLE 282 using 5-bromo-N-(2-hydroxyethyl)nicotinamide (PREPARATION x58) in place of (2-amino-5-bromopyridin-3-yl)(4-methylpiperazin-1-yl)methanone. ESI-MS m/z [M+H]$^+$ calc'd for $C_{16}H_{13}F_3N_4O_2$, 351.1. found 351.2.

Example 291

4-(7-methoxy-1H-pyrrolo[2,3-c]pyridin-4-yl)-6-(trifluoromethyl)-1H-indazole

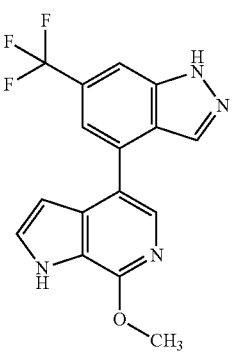 [SMILES: COc1ncc(-c2cc(C(F)(F)F)cc3[nH]ncc23)c2cc[nH]c12]

A TFA salt of the title compound was prepared in a manner similar to EXAMPLE 247 using (1-acetyl-7-methoxy-1H-pyrrolo[2,3-c]pyridin-4-yl)boronic acid in place of N,N-dimethyl-5-(4,4,5,5-tetramethyl-1,3,2-dioxaborolan-2-yl)pyrimidin-2-amine. $^1$H NMR (400 MHz, DMSO-d$_6$) δ ppm 4.12 (s, 3H), 6.28-6.50 (m, 1H), 7.51 (d, J=1.01 Hz, 1H), 7.58 (t, J=2.78 Hz, 1H), 7.86-8.03 (m, 2H), 8.14 (d, J=0.76 Hz, 1H), 12.11 (br s, 1H); ESI-MS m/z [M+H]$^+$ calc'd for C$_{16}$H$_{11}$F$_3$N$_4$O, 333.1. found 333.19.

Example 292

4-(7-methyl-1H-pyrrolo[2,3-c]pyridin-4-yl)-6-(trifluoromethyl)-1H-indazole

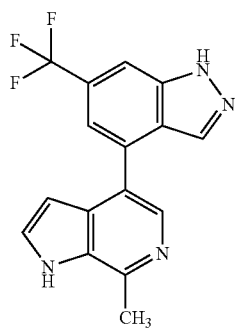 [SMILES: Cc1ncc(-c2cc(C(F)(F)F)cc3[nH]ncc23)c2cc[nH]c12]

A TFA salt of the title compound was prepared in a manner similar to EXAMPLE 247 using 1-(7-methyl-4-(4,4,5,5-tetramethyl-1,3,2-dioxaborolan-2-yl)-1H-pyrrolo[2,3-c]pyridin-1-yl)ethanone in place of N,N-dimethyl-5-(4,4,5,5-tetramethyl-1,3,2-dioxaborolan-2-yl)pyrimidin-2-amine. $^1$H NMR (400 MHz, DMSO-d$_6$) δ ppm 3.03 (s, 3H), 6.57 (br s, 1H), 6.71 (d, J=1.26 Hz, 1H), 7.64 (s, 1H), 8.12 (d, J=9.85 Hz, 1H), 8.33 (br s, 1H), 8.52 (s, 1H), 13.36 (br s, 1H), 13.91 (br s, 1H); ESI-MS m/z [M+H]$^+$ calc'd for C$_{16}$H$_{11}$F$_3$N$_4$, 317.1. found 317.16.

Example 293

N-(2-methoxyethyl)-5-(6-(trifluoromethyl)-1H-indazol-4-yl)pyrimidin-2-amine

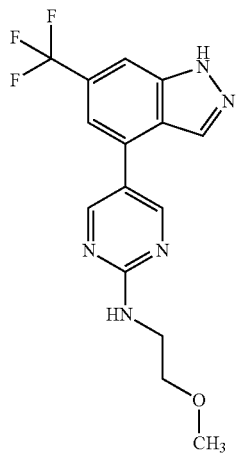 [SMILES: COCCNc1ncc(-c2cc(C(F)(F)F)cc3[nH]ncc23)cn1]

A TFA salt of the title compound was prepared in a manner similar to EXAMPLE 257 using 5-bromo-N-(2-methoxyethyl)pyrimidin-2-amine in place of N-(5-bromo-6-methylpyridin-2-yl)methanesulfonamide. $^1$H NMR (400 MHz, DMSO-d$_6$) δ ppm 3.29 (s, 3H), 3.44-3.60 (m, 4H), 7.48 (d, J=1.01 Hz, 1H), 7.61 (br s, 1H), 7.89 (s, 1H), 8.40 (d, J=1.01 Hz, 1H), 8.76 (s, 2H); ESI-MS m/z [M+H]$^+$ calc'd for C$_{15}$H$_{14}$F$_3$N$_5$O, 338.1. found 338.2.

Example 294 morpholino(5-(6-(trifluoromethyl)-1H-indazol-4-yl)pyrimidin-2-yl)methanone

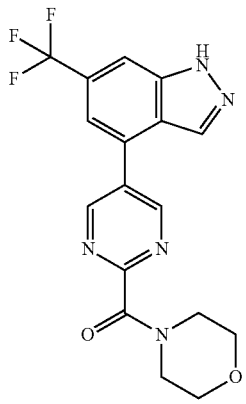 [SMILES: O=C(c1ncc(-c2cc(C(F)(F)F)cc3[nH]ncc23)cn1)N1CCOCC1]

A TFA salt of the title compound was prepared in a manner similar to EXAMPLE 257 using (5-bromopyrimidin-2-yl)(morpholino)methanone in place of N-(5-bromo-6-methylpyridin-2-yl)methanesulfonamide. $^1$H NMR (400 MHz, DMSO-d$_6$) δ ppm 3.24-3.37 (m, 2H), 3.53-3.64 (m, 2H), 3.71 (s, 4H), 7.74 (d, J=1.01 Hz, 1H), 8.08 (s, 1H), 8.52 (d, J=0.76 Hz, 1H), 9.33 (s, 2H); ESI-MS m/z [M+H]$^+$ calc'd for C$_{17}$H$_{14}$F$_3$N$_5$O$_2$, 378.1. found 378.21.

Example 295

5-(6-(trifluoromethyl)-1H-indazol-4-yl)pyrimidine-2-carboxamide

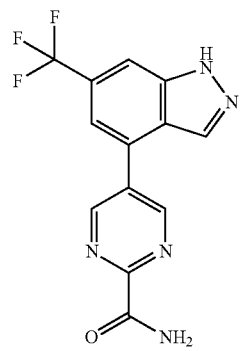 [SMILES: NC(=O)c1ncc(-c2cc(C(F)(F)F)cc3[nH]ncc23)cn1]

A TFA salt of the title compound was prepared in a manner similar to EXAMPLE 257 using 5-bromopyrimidine-2-carboxamide in place of N-(5-bromo-6-methylpyridin-2-yl)methanesulfonamide. $^1$H NMR (400 MHz, DMSO-d$_6$) δ ppm 7.77 (s, 1H), 7.91 (br s, 1H), 8.09 (s, 1H), 8.32 (br s, 1H), 8.49 (s, 1H), 9.37 (s, 2H), 13.87 (br s, 1H); ESI-MS m/z [M+H]$^+$ calc'd for C$_{13}$H$_8$F$_3$N$_5$O, 308.1. found 308.11.

Example 296

4-methyl-6-(6-(trifluoromethyl)-1H-indazol-4-yl)-2H-benzo[b][1,4]oxazin-3(4H)-one

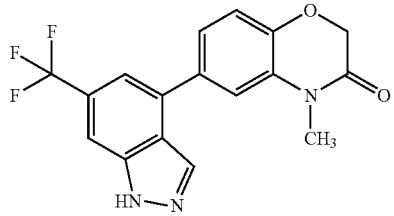 [SMILES: CN1C(=O)COc2ccc(-c3cc(C(F)(F)F)cc4[nH]ncc34)cc21]

A TFA salt of the title compound was prepared in a manner similar to EXAMPLE 247 using 4-methyl-6-(4,4,5,5-tetramethyl-1,3,2-dioxaborolan-2-yl)-2H-benzo[b][1,4]oxazin-3(4H)-one in place of N,N-dimethyl-5-(4,4,5,5-tetramethyl-1,3,2-dioxaborolan-2-yl)pyrimidin-2-amine. $^1$H NMR (400 MHz, DMSO-d$_6$) δ ppm 3.41 (s, 3H), 4.75 (s, 2H), 7.18 (d, J=8.34 Hz, 1H), 7.36-7.59 (m, 3H), 7.92 (s, 1H), 8.39 (s, 1H), 13.71 (br s, 1H); ESI-MS m/z [M+H]$^+$ calc'd for C$_{17}$H$_{12}$F$_3$N$_3$O$_2$, 348.1. found 348.16.

Example 297

5-(4-methylpiperazine-1-carbonyl)-3-(6-(trifluoromethyl)-1H-indazol-4-yl)pyridin-2(1H)-one

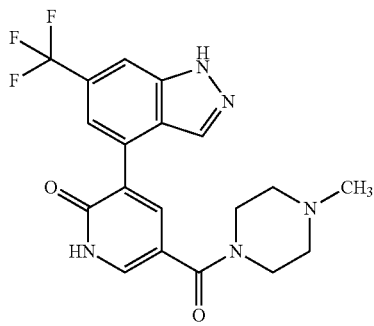 [SMILES: CN1CCN(C(=O)c2c[nH]c(=O)c(-c3cc(C(F)(F)F)cc4[nH]ncc34)c2)CC1]

A TFA salt of the title compound was prepared in a manner similar to EXAMPLE 265 using 3-bromo-5-(4-methylpiperazine-1-carbonyl)pyridin-2(1H)-one in place of methyl 5-iodo-6-oxo-1,6-dihydropyridine-3-carboxylate. $^1$H NMR (400 MHz, CD$_3$OD) δ ppm 8.15 (s, 1H), 7.95 (d, J=4.0 Hz, 1H), 7.92 (s, 1H), 7.87 (d, J=4.0 Hz, 1H), 7.60 (s, 1H), 4.35-4.58 (m, 2H), 3.38-3.66 (m, 4H), 3.08-3.25 (m, 2H), 2.94 (s, 3H); ESI-MS m/z [M+H]$^+$ calc'd for C$_{19}$H$_{18}$F$_3$N$_5$O$_2$, 406.1. found 406.4.

Example 298

5-(morpholine-4-carbonyl)-3-(6-(trifluoromethyl)-1H-indazol-4-yl)pyridin-2(1H)-one

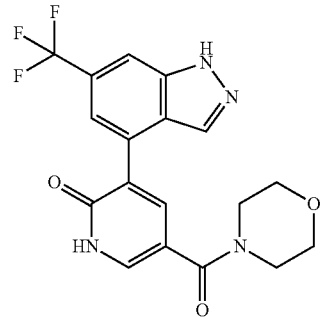 [SMILES: O=C(c1c[nH]c(=O)c(-c2cc(C(F)(F)F)cc3[nH]ncc23)c1)N1CCOCC1]

The title compound was prepared in a manner similar to EXAMPLE 265 using 3-bromo-5-(morpholine-4-carbonyl)pyridin-2(1H)-one in place of methyl 5-iodo-6-oxo-1,6-dihydropyridine-3-carboxylate. $^1$H NMR (400 MHz, CD$_3$OD) δ ppm 8.16 (s, 1H), 7.92 (d, J=4.0 Hz, 1H), 7.91 (s, 1H), 7.80 (d, J=4.0 Hz, 1H), 7.60 (s, 1H), 3.71 (br s, 8H); ESI-MS m/z [M+H]$^+$ calc'd for C$_{18}$H$_{15}$F$_3$N$_4$O$_3$, 393.1. found 393.3.

Example 299

N-(2-hydroxyethyl)-6-oxo-5-(6-(trifluoromethyl)-1H-indazol-4-yl)-1,6-dihydropyridine-3-carboxamide

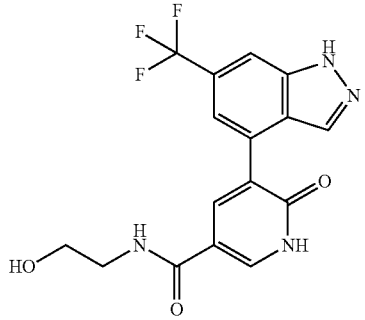 [SMILES: O=C(NCCO)c1c[nH]c(=O)c(-c2cc(C(F)(F)F)cc3[nH]ncc23)c1]

The title compound was prepared in a manner similar to EXAMPLE 265 using 5-bromo-N-(2-hydroxyethyl)-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.30 (d, J=2.0 Hz, 1H), 8.18 (d, J=2.0 Hz, 1H), 8.15 (s, 1H), 7.91 (s, 1H), 7.60 (s, 1H), 3.70 (t, J=4.0, 8.0 Hz, 2H), 3.48 (t, J=4.0, 8.0 Hz, 2H); ESI-MS m/z [M+H]$^+$ calc'd for C$_{16}$H$_{13}$F$_3$N$_4$O$_3$, 367.1. found 367.3.

Example 300

2-(3-methyl-2,6-dioxo-5-(6-(trifluoromethyl)-1H-indazol-4-yl)-2,3-dihydropyrimidin-1(6H)-yl)acetamide

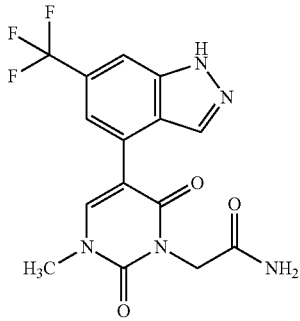 [SMILES: Cn1cc(-c2cc(C(F)(F)F)cc3[nH]ncc23)c(=O)n(CC(N)=O)c1=O]

The title compound was prepared in a manner similar to EXAMPLE 265 using 2-(5-bromo-3-methyl-2,6-dioxo-2,3-dihydropyrimidin-1(6H)-yl)acetamide in place of methyl 5-iodo-6-oxo-1,6-dihydropyridine-3-carboxylate. $^1$H NMR (400 MHz, CD$_3$OD) δ ppm 8.15 (s, 1H), 8.00 (s, 1H), 7.86 (s, 1H), 7.48 (s, 1H), 4.72 (s, 2H), 3.51 (s, 3H); ESI-MS m/z [M+H]$^+$ calc'd for C$_{15}$H$_{12}$F$_3$N$_5$O$_3$, 368.1. found 368.3.

Example 301

N-methyl-2-(3-methyl-2,6-dioxo-5-(6-(trifluoromethyl)-1H-indazol-4-yl)-2,3-dihydropyrimidin-1(6H)-yl)acetamide

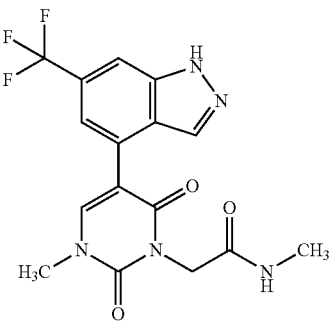 [SMILES: CNC(=O)Cn1c(=O)c(-c2cc(C(F)(F)F)cc3[nH]ncc23)cn(C)c1=O]

The title compound was prepared in a manner similar to EXAMPLE 265 using 2-(5-bromo-3-methyl-2,6-dioxo-2,3-dihydropyrimidin-1(6H)-yl)-N-methylacetamide in place of methyl 5-iodo-6-oxo-1,6-dihydropyridine-3-carboxylate. $^1$H NMR (400 MHz, CD$_3$OD) δ ppm 8.15 (s, 1H), 8.01 (s, 1H), 7.86 (s, 1H), 7.48 (s, 1H), 4.69 (s, 2H), 3.51 (s, 3H), 2.78 (s, 3H); ESI-MS m/z [M+H]$^+$ calc'd for C$_{16}$H$_{14}$F$_3$N$_5$O$_3$, 382.1. found 382.3.

Example 302

N-ethyl-2-(3-methyl-2,6-dioxo-5-(6-(trifluoromethyl)-1H-indazol-4-yl)-2,3-dihydropyrimidin-1(6H)-yl)acetamide

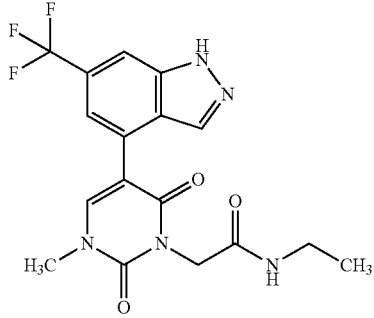 [SMILES: CCNC(=O)Cn1c(=O)c(-c2cc(C(F)(F)F)cc3[nH]ncc23)cn(C)c1=O]

The title compound was prepared in a manner similar to EXAMPLE 265 using 2-(5-bromo-3-methyl-2,6-dioxo-2,3-dihydropyrimidin-1(6H)-yl)-N-ethylacetamide in place of methyl 5-iodo-6-oxo-1,6-dihydropyridine-3-carboxylate. $^1$H NMR (400 MHz, CD$_3$OD) δ ppm 8.15 (s, 1H), 8.01 (s, 1H), 7.86 (s, 1H), 7.48 (s, 1H), 4.68 (s, 2H), 3.26 (q, J=4.0, 8.0 Hz, 2H), 1.15 (t, J=8.0, 8.0 Hz, 3H); ESI-MS m/z [M+H]$^+$ calc'd for C$_{17}$H$_{16}$F$_3$N$_5$O$_3$, 396.1. found 396.3.

Example 303

3-(2-hydroxyethyl)-1-methyl-5-(6-(trifluoromethyl)-1H-indazol-4-yl)pyrimidine-2,4(1H,3H)-dione

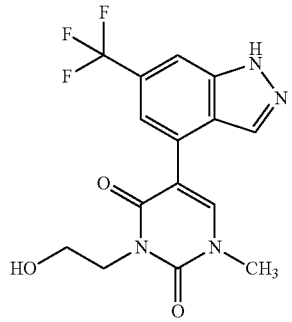 [SMILES: Cn1cc(-c2cc(C(F)(F)F)cc3[nH]ncc23)c(=O)n(CCO)c1=O]

The title compound was prepared in a manner similar to EXAMPLE 265 using 5-bromo-3-(2-hydroxyethyl)-1-methylpyrimidine-2,4(1H,3H)-dione in place of methyl 5-iodo-6-oxo-1,6-dihydropyridine-3-carboxylate. $^1$H NMR (400 MHz, CD$_3$OD) δ ppm 8.15 (s, 1H), 7.98 (s, 1H), 7.86 (s, 1H), 7.47 (s, 1H), 4.71 (t, J=4.0, 8.0 Hz, 1H), 4.44 (t, J=4.0, 8.0 Hz, 1H), 4.22 (t, J=4.0, 8.0 Hz, 1H), 3.81 (t, J=8.0, 8.0 Hz, 1H), 3.49 (s, 3H); ESI-MS m/z [M+H]$^+$ calc'd for C$_{15}$H$_{13}$F$_3$N$_4$O$_3$, 355.1. found 355.3.

Example 304

3-methoxy-N-methyl-4-(6-(trifluoromethyl)-1H-indazol-4-yl)benzamide

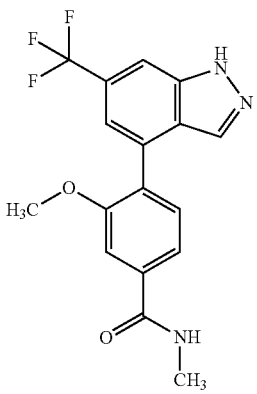 [SMILES: CNC(=O)c1ccc(-c2cc(C(F)(F)F)cc3[nH]ncc23)c(OC)c1]

A 20 mL vial was charged with 3-methoxy-4-(6-(trifluoromethyl)-1H-indazol-4-yl)benzoic acid (0.04 g, 0.119 mmol), EDC (0.034 g, 0.178 mmol), HOBt (0.027 g, 0.178 mmol), methanamine (0.178 mL, 0.357 mmol), DMA (1 mL), and DIPEA (0.062 mL, 0.357 mmol). The vial was capped and the reaction mixture was stirred at room temperature for 2 days. The reaction mixture was subsequently diluted with methanol and purified via preparative HPLC, eluting with a gradient of 35-55% ACN (containing 0.1% formic acid) in H$_2$O (containing 0.1% formic acid). The product fractions were collected and dried in vacuo to give a formic acid salt of the title compound as a white solid (23.6 mg, 56.8%). $^1$H NMR (400 MHz, DMSO-d$_6$) δ ppm 2.84 (d, J=4.29 Hz, 3H), 3.83 (s, 3H), 7.37 (s, 1H), 7.49-7.56 (m, 1H), 7.56-7.62 (m, 1H), 7.65 (s, 1H), 7.94 (s, 1H), 7.97 (s, 1H), 8.60 (d, J=4.55 Hz, 1H), 13.61 (br s, 1H); ESI-MS m/z [M+H]$^+$ calc'd for C$_{17}$H$_{14}$F$_3$N$_3$O$_2$, 350.1. found 350.2.

Example 305

N-(2-hydroxyethyl)-3-methoxy-4-(6-(trifluoromethyl)-1H-indazol-4-yl)benzamide

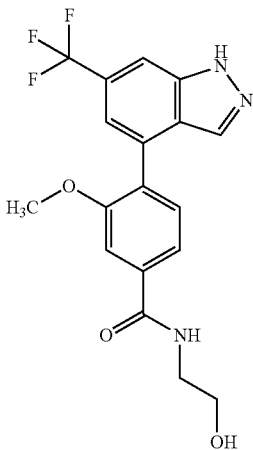 [SMILES: COc1cc(C(=O)NCCO)ccc1-c1cc(C(F)(F)F)cc2[nH]ncc12]

A formic acid salt of the title compound was prepared in a manner similar to EXAMPLE 304 using ethanolamine in place of methanamine. $^1$H NMR (400 MHz, DMSO-d$_6$) δ ppm 3.37-3.43 (m, 2H), 3.56 (q, J=5.89 Hz, 2H), 3.83 (s, 3H), 7.36 (s, 1H), 7.53 (d, J=7.83 Hz, 1H), 7.58-7.65 (m, 1H), 7.67 (s, 1H), 7.94 (s, 1H), 7.97 (s, 1H), 8.62 (t, J=5.56 Hz, 1H); ESI-MS m/z [M+H]$^+$ calc'd for C$_{18}$H$_{16}$F$_3$N$_3$O$_3$, 380.1. found 380.3.

Example 306

3-methoxy-4-(6-(trifluoromethyl)-1H-indazol-4-yl)benzamide

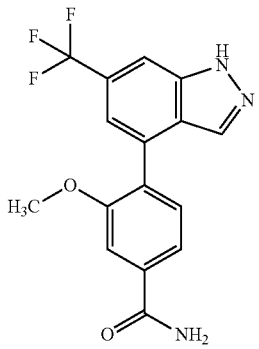 [SMILES: COc1cc(C(N)=O)ccc1-c1cc(C(F)(F)F)cc2[nH]ncc12]

A formic acid salt of the title compound was prepared in a manner similar to EXAMPLE 304 using ammonium chloride in place of methanamine. $^1$H NMR (400 MHz, DMSO-d$_6$) δ ppm 3.83 (s, 3H), 7.37 (s, 1H), 7.52 (d, J=7.83 Hz, 2H), 7.60-7.67 (m, 1H), 7.69 (s, 1H), 7.94 (s, 1H), 7.97 (s, 1H), 8.14 (s, 1H), 13.60 (br s, 1H); ESI-MS m/z [M+H]$^+$ calc'd for C$_{16}$H$_{12}$F$_3$N$_3$O$_2$, 336.1. found 336.2.

Example 307

N-(2-hydroxyethyl)-4-methyl-5-(6-(trifluoromethyl)-1H-indazol-4-yl)picolinamide

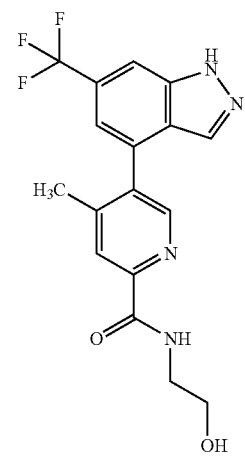 [SMILES: Cc1cc(C(=O)NCCO)ncc1-c1cc(C(F)(F)F)cc2[nH]ncc12]

A TFA salt of the title compound was prepared in a manner similar to EXAMPLE 270 using methyl 4-methyl-5-(6-(trifluoromethyl)-1H-indazol-4-yl)picolinate in place of methyl 5-(6-(trifluoromethyl)-1H-indazol-4-yl)picolinate. $^1$H NMR (400 MHz, CD$_3$OD) δ ppm 2.29 (br s, 3H), 3.57 (br s, 2H), 3.72-3.78 (m, 2H), 7.27-7.40 (m, 1H), 7.91 (br s, 1H), 8.00 (br s, 1H), 8.12 (br s, 1H), 8.60 (s, 1H); ESI-MS m/z [M+H]$^+$ calc'd for C$_{17}$H$_{15}$F$_3$N$_4$O$_2$, 365.1. found 365.

Example 308

N-(2-hydroxyethyl)-4-(6-(trifluoromethyl)-1H-indazol-4-yl)picolinamide

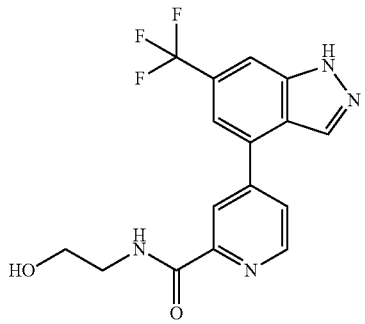 [SMILES: O=C(NCCO)c1cc(-c2cc(C(F)(F)F)cc3[nH]ncc23)ccn1]

A TFA salt of the title compound was prepared in a manner similar to EXAMPLE 257 using 4-bromo-N-(2-hydroxyethyl)picolinamide in place of N-(5-bromo-6-methylpyridin-2-yl)methanesulfonamide. $^1$H NMR (400 MHz, DMSO-d$_6$) δ ppm 3.44 (q, J=5.98 Hz, 2H), 3.57 (t, J=6.06 Hz, 2H), 7.69 (d, J=1.01 Hz, 1H), 8.00-8.14 (m, 2H), 8.30-8.46 (m, 2H), 8.74-8.91 (m, 2H); ESI-MS m/z [M+H]$^+$ calc'd for C$_{16}$H$_{13}$F$_3$N$_4$O$_2$, 351.1. found 351.16.

Example 309

N,N-dimethyl-2-(3-methyl-2,6-dioxo-5-(6-(trifluoromethyl)-1H-indazol-4-yl)-2,3-dihydropyrimidin-1(6H)-yl)acetamide

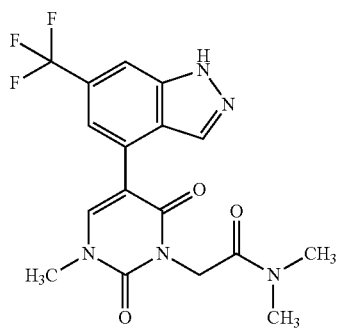 [SMILES: CN(C)C(=O)Cn1c(=O)c(-c2cc(C(F)(F)F)cc3[nH]ncc23)cn(C)c1=O]

The title compound was prepared in a manner similar to EXAMPLE 265 using 2-(5-bromo-3-methyl-2,6-dioxo-2,3-dihydropyrimidin-1(6H)-yl)-N,N-dimethylacetamide in place of methyl 5-iodo-6-oxo-1,6-dihydropyridine-3-carboxylate. $^1$H NMR (400 MHz, CD$_3$OD) δ ppm 8.15 (s, 1H), 8.02 (s, 1H), 7.87 (s, 1H), 7.49 (s, 1H), 4.92 (s, 2H), 3.57-3.79 (m, 8H), 3.51 (s, 3H); ESI-MS m/z [M+H]$^+$ calc'd for C$_{17}$H$_{16}$F$_3$N$_5$O$_3$, 396.1. found 396.3.

Example 310

1-methyl-3-(2-morpholino-2-oxoethyl)-5-(6-(trifluoromethyl)-1H-indazol-4-yl)pyrimidine-2,4(1H,3H)-dione

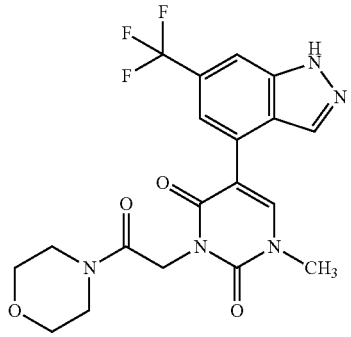 [SMILES: Cn1cc(-c2cc(C(F)(F)F)cc3[nH]ncc23)c(=O)n(CC(=O)N2CCOCC2)c1=O]

The title compound was prepared in a manner similar to EXAMPLE 265 using 5-bromo-1-methyl-3-(2-morpholino-2-oxoethyl)pyrimidine-2,4(1H,3H)-dione in place of methyl 5-iodo-6-oxo-1,6-dihydropyridine-3-carboxylate. $^1$H NMR (400 MHz, CD$_3$OD) δ ppm 8.15 (s, 1H), 8.02 (s, 1H), 7.87 (s, 1H), 7.49 (s, 1H), 4.92 (s, 2H), 3.57-3.79 (m, 8H), 3.51 (s, 3H); ESI-MS m/z [M+H]$^+$ calc'd for C$_{19}$H$_{18}$F$_3$N$_5$O$_4$, 438.1. found 438.4.

Example 311

3-(4-fluorobenzyl)-1-methyl-5-(6-(trifluoromethyl)-1H-indazol-4-yl)pyrimidine-2,4(1H,3H)-dione

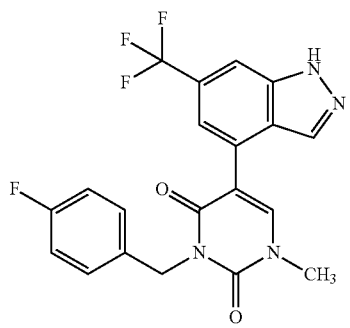 [SMILES: Cn1cc(-c2cc(C(F)(F)F)cc3[nH]ncc23)c(=O)n(Cc2ccc(F)cc2)c1=O]

The title compound was prepared in a manner similar to EXAMPLE 265 using 5-bromo-3-(4-fluorobenzyl)-1-methylpyrimidine-2,4(1H,3H)-dione in place of methyl 5-iodo-6-oxo-1,6-dihydropyridine-3-carboxylate. $^1$H NMR (400 MHz, CD$_3$OD) δ ppm 8.09 (s, 1H), 7.97 (s, 1H), 7.86 (s, 1H), 7.46-7.52 (m, 2H), 7.00-7.06 (m, 2H), 5.19 (s, 2H), 3.49 (s, 3H); ESI-MS m/z [M+H]$^+$ calc'd for C$_{20}$H$_{14}$F$_4$N$_4$O$_2$, 419.1. found 419.3.

Example 312

2-(3-methyl-2,6-dioxo-5-(6-(trifluoromethyl)-1H-indazol-4-yl)-2,3-dihydropyrimidin-1(6H)-yl)acetonitrile

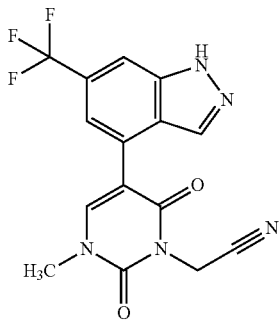 [SMILES: Cn1cc(-c2cc(C(F)(F)F)cc3[nH]ncc23)c(=O)n(CC#N)c1=O]

The title compound was prepared in a manner similar to EXAMPLE 265 using 2-(5-bromo-3-methyl-2,6-dioxo-2,3-dihydropyrimidin-1(6H)-yl)acetonitrile in place of methyl 5-iodo-6-oxo-1,6-dihydropyridine-3-carboxylate. $^1$H NMR (400 MHz, CD$_3$OD) δ ppm 8.17 (s, 1H), 8.04 (s, 1H), 7.88 (s, 1H), 7.51 (s, 1H), 4.99 (s, 2H), 3.53 (s, 3H); ESI-MS m/z [M+H]$^+$ calc'd for C$_{15}$H$_{10}$F$_3$N$_5$O$_2$, 350.1. found 350.3.

Example 313

1-methyl-3-(2-morpholinoethyl)-5-(6-(trifluoromethyl)-1H-indazol-4-yl)pyrimidine-2,4(1H,3H)-dione

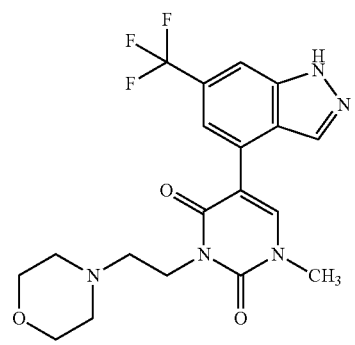 [SMILES: Cn1cc(-c2cc(C(F)(F)F)cc3[nH]ncc23)c(=O)n(CCN2CCOCC2)c1=O]

The title compound was prepared in a manner similar to EXAMPLE 265 using 5-bromo-1-methyl-3-(2-morpholinoethyl)pyrimidine-2,4(1H,3H)-dione in place of methyl 5-iodo-6-oxo-1,6-dihydropyridine-3-carboxylate. $^1$H NMR (400 MHz, CD$_3$OD) δ ppm 8.21 (s, 1H), 8.03 (s, 1H), 7.88 (s, 1H), 7.48 (s, 1H), 4.46 (t, J=8.0, 8.0 Hz, 2H), 4.00-4.13 (m, 2H), 3.69-3.89 (m, 4H), 3.57 (t, J=8.0, 8.0 Hz, 2H), 3.52 (s, 3H), 3.13-3.27 (m, 2H); ESI-MS m/z [M+H]$^+$ calc'd for C$_{19}$H$_{20}$F$_3$N$_5$O$_3$, 424.2. found 424.4.

Example 314

1-methyl-5-(morpholine-4-carbonyl)-3-(6-(trifluoromethyl)-1H-indazol-4-yl)pyridin-2(1H)-one

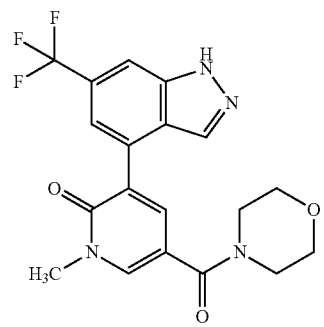 [SMILES: Cn1cc(C(=O)N2CCOCC2)cc(-c2cc(C(F)(F)F)cc3[nH]ncc23)c1=O]

The title compound was prepared in a manner similar to EXAMPLE 265 using 3-bromo-1-methyl-5-(morpholine-4-carbonyl)pyridin-2(1H)-one in place of methyl 5-iodo-6-oxo-1,6-dihydropyridine-3-carboxylate. $^1$H NMR (400 MHz, CD$_3$OD) δ ppm 8.12 (s, 1H), 8.09 (d, J=4.0 Hz, 1H), 7.90 (s, 1H), 7.86 (d, J=4.0 Hz, 1H), 7.58 (s, 1H), 3.71 (br s, 11H); ESI-MS m/z [M+H]$^+$ calc'd for C$_{19}$H$_{17}$F$_3$N$_4$O$_3$, 407.1. found 407.4.

Example 315

N-(2-hydroxyethyl)-1-methyl-6-oxo-5-(6-(trifluoromethyl)-1H-indazol-4-yl)-1,6-dihydropyridine-3-carboxamide

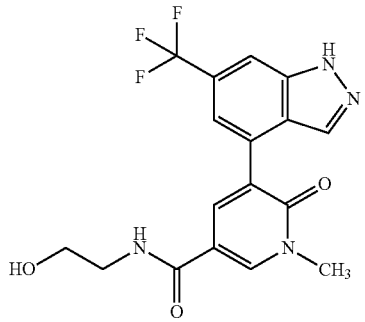 [SMILES: Cn1cc(C(=O)NCCO)cc(-c2cc(C(F)(F)F)cc3[nH]ncc23)c1=O]

The title compound was prepared in a manner similar to EXAMPLE 265 using 5-bromo-N-(2-hydroxyethyl)-1-methyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.44 (d, J=4.0 Hz, 1H), 8.22 (d, J=4.0 Hz, 1H), 8.12 (s, 1H), 7.90 (s, 1H), 7.57 (s, 1H), 3.73 (s, 3H), 3.70 (t, J=8.0, 8.0 Hz, 2H), 3.48 (t, J=8.0, 8.0 Hz, 2H); ESI-MS m/z [M+H]$^+$ calc'd for C$_{17}$H$_{15}$F$_3$N$_4$O$_3$, 381.1. found 381.3.

Example 316

2-(4-methoxy-3-(6-(trifluoromethyl)-1H-indazol-4-yl)phenyl)-1-morpholinoethanone

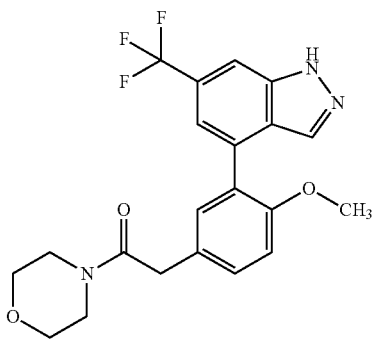 [SMILES: COc1ccc(CC(=O)N2CCOCC2)cc1-c1cc(C(F)(F)F)cc2[nH]ncc12]

To a 20 mL vial charged with a solution of morpholine (0.096 g, 1.098 mmol) in dioxane (5 mL) was added trimethylaluminum (0.549 mL, 1.098 mmol) in toluene dropwise at room temperature. After stirring for 15 minutes at room temperature, methyl 2-(4-methoxy-3-(6-(trifluoromethyl)-1H-indazol-4-yl)phenyl)acetate (0.1 g, 0.274 mmol) was added. The reaction mixture was heated at 110° C. for 1 hour in a microwave reactor and was subsequently transferred to a round bottom flask where the reaction was quenched with concentrated HCl. The mixture was concentrated and the crude residue was purified by preparative HPLC, eluting with 35% acetonitrile (containing 0.035% TFA) in $H_2O$ (containing 0.05% TFA) over a period of 10 minutes. The product-containing fractions were combined and the volatiles were removed in vacuo to give a TFA salt of the title compound as a light yellow solid (0.038 g, 33%). $^1$H NMR (400 MHz, $CD_3OD$) δ ppm 3.51-3.68 (m, 8H), 3.74-3.85 (m, 5H), 7.15 (d, J=8.34 Hz, 1H), 7.28-7.40 (m, 3H), 7.85 (s, 1H), 7.93 (d, J=0.76 Hz, 1H); ESI-MS m/z [M+H]$^+$ calc'd for $C_{21}H_{20}F_3N_3O_3$, 420.1. found 420.2.

Example 317

2-(3,5-dimethyl-4-(6-(trifluoromethyl)-1H-indazol-4-yl)-1H-pyrazol-1-yl)-1-morpholinoethanone

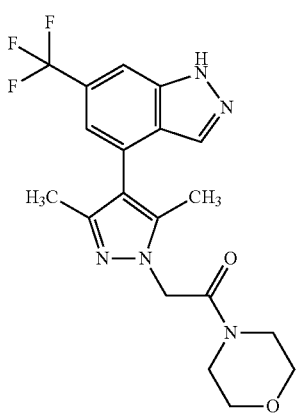 [SMILES: Cc1nn(CC(=O)N2CCOCC2)c(C)c1-c1cc(C(F)(F)F)cc2[nH]ncc12]

A TFA salt of the title compound was prepared in a manner similar to EXAMPLE 283 using 2-(3,5-dimethyl-4-(6-(trifluoromethyl)-1H-indazol-4-yl)-1H-pyrazol-1-yl)acetic acid in place of 4-(6-(trifluoromethyl)-1H-indazol-4-yl)picolinic acid. $^1$H NMR (400 MHz, $CD_3OD$) δ ppm 2.17 (d, J=2.53 Hz, 6H), 3.59-3.67 (m, 4H), 3.67-3.74 (m, 2H), 3.74-3.81 (m, 2H), 5.18 (s, 2H), 7.24 (d, J=1.26 Hz, 1H), 7.88 (s, 1H), 8.00 (d, J=1.01 Hz, 1H); ESI-MS m/z [M+H]$^+$ calc'd for $C_{19}H_{20}F_3N_5O_2$, 408.2. found 408.21.

Example 318

(3-methoxy-4-(6-(trifluoromethyl)-1H-indazol-4-yl)phenyl)(morpholino)methanone

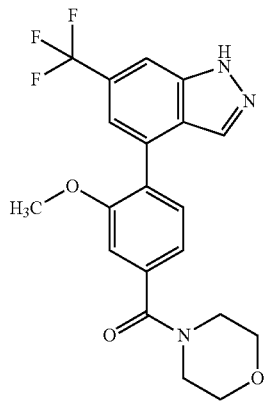 [SMILES: COc1cc(C(=O)N2CCOCC2)ccc1-c1cc(C(F)(F)F)cc2[nH]ncc12]

The title compound was prepared in a manner similar to EXAMPLE 283 using 3-methoxy-4-(6-(trifluoromethyl)-1H-indazol-4-yl)benzoic acid in place of 4-(6-(trifluoromethyl)-1H-indazol-4-yl)picolinic acid. $^1$H NMR (400 MHz, $CDCl_3$) δ ppm 3.58 (d, J=8.34 Hz, 1H), 3.63-3.92 (m, 10H), 7.07-7.17 (m, 2H), 7.38-7.51 (m, 2H), 7.77-7.83 (m, 1H), 7.99 (br s, 1H); ESI-MS m/z [M+H]$^+$ calc'd for $C_{20}H_{18}F_3N_3O_3$, 406.1. found 406.21.

Example 319

3-(2-(dimethylamino)ethyl)-1-methyl-5-(6-(trifluoromethyl)-1H-indazol-4-yl)pyrimidine-2,4(1H,3H)-dione

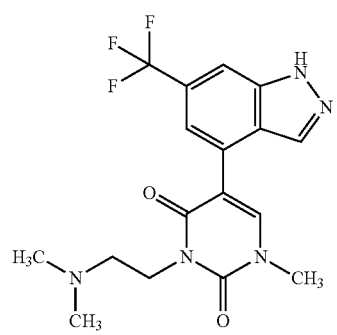 [SMILES: CN(C)CCn1c(=O)c(-c2cc(C(F)(F)F)cc3[nH]ncc23)cn(C)c1=O]

A TFA salt of the title compound was prepared in a manner similar to EXAMPLE 265 using 5-bromo-3-(2-(dimethylamino)ethyl)-1-methylpyrimidine-2,4(1H,3H)-dione in place of methyl 5-iodo-6-oxo-1,6-dihydropyridine-3-carboxylate. $^1$H NMR (400 MHz, CD$_3$OD) δ ppm 8.19 (s, 1H), 8.04 (s, 1H), 7.89 (s, 1H), 7.50 (s, 1H), 4.44 (t, J=4.0, 8.0 Hz, 2H), 3.49-3.54 (m, 5H), 3.02 (s, 6H); ESI-MS m/z [M+H]$^+$ calc'd for C$_{17}$H$_{18}$F$_3$N$_5$O$_2$, 382.1. found 382.4.

Example 320

N-(2-hydroxyethyl)-2-(4-methoxy-3-(6-(trifluoromethyl)-1H-indazol-4-yl)phenyl)acetamide

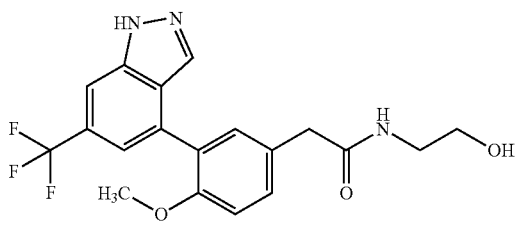 [SMILES: COc1ccc(CC(=O)NCCO)cc1-c1cc(C(F)(F)F)cc2[nH]ncc12]

A TFA salt of the title compound was prepared in a manner similar to EXAMPLE 316 using 2-aminoethanol in place of morpholine. $^1$H NMR (400 MHz, CD$_3$OD) δ ppm 3.49-3.63 (m, 4H), 3.78 (d, J=1.26 Hz, 3H), 4.43 (t, J=5.31 Hz, 1H), 7.08-7.17 (m, 1H), 7.32-7.43 (m, 3H), 7.84 (s, 1H), 7.93 (dd, J=6.82, 1.01 Hz, 1H); ESI-MS m/z [M+H]$^+$ calc'd for C$_{19}$H$_{18}$F$_3$N$_3$O$_3$, 394.1. found 394.21.

Example 321

3-fluoro-4-(6-(trifluoromethyl)-1H-indazol-4-yl)benzamide

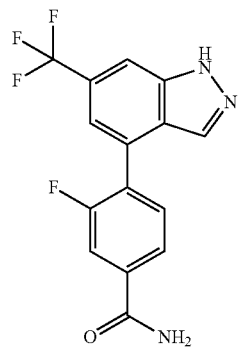

To a 20 mL vial charged with ammonium chloride (0.127 g, 2.365 mmol) in dioxane (8 mL) was added trimethylaluminum (1.183 mL, 2.365 mmol) in toluene dropwise at room temperature. After stirring for 10 minutes at room temperature, methyl 3-fluoro-4-(6-(trifluoromethyl)-1H-indazol-4-yl)benzoate (0.2 g, 0.591 mmol) was added. The mixture was heated at 110° C. for 1 hour in a microwave reactor. The reaction mixture was transferred to a round bottom flask and was quenched with concentrated HCl. The mixture was subsequently concentrated and the crude residue was purified by preparative HPLC, eluting with 35% acetonitrile (containing 0.035% TFA) in H$_2$O (containing 0.05% TFA) over a period of 6.5 minutes. The product-containing fractions were combined and the volatiles were removed in vacuo to give a TFA salt of the title compound as an off white solid (0.019 g, 9.9%). $^1$H NMR (400 MHz, DMSO-d$_6$) δ ppm 7.49 (s, 1H), 7.64 (s, 1H), 7.73-7.86 (m, 1H), 7.86-7.96 (m, 2H), 8.04 (s, 1H), 8.14 (s, 1H), 8.20 (s, 1H); ESI-MS m/z [M+H]$^+$ calc'd for C$_{15}$H$_9$F$_4$N$_3$O, 324.1. found 324.11.

Example 322

3-fluoro-N-(2-hydroxyethyl)-4-(6-(trifluoromethyl)-1H-indazol-4-yl)benzamide

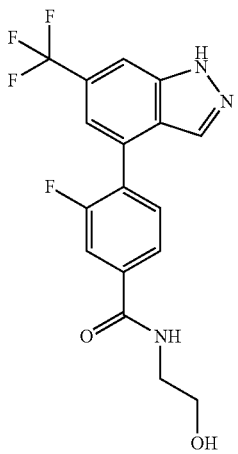 [SMILES: O=C(NCCO)c1ccc(-c2cc(C(F)(F)F)cc3[nH]ncc23)c(F)c1]

A TFA salt of the title compound was prepared in a manner similar to EXAMPLE 321 using 2-aminoethanol HCl in place of ammonium chloride. $^1$H NMR (400 MHz, DMSO-d$_6$) δ ppm 3.38-3.46 (m, 2H), 3.48-3.62 (m, 2H), 4.78 (br s, 1H), 7.49 (s, 1H), 7.74-7.84 (m, 1H), 7.89 (d, J=9.35 Hz, 2H), 8.04 (s, 1H), 8.13 (s, 1H), 8.69 (t, J=5.56 Hz, 1H), 13.77 (s, 1H); ESI-MS m/z [M+H]$^+$ calc'd for C$_{17}$H$_{13}$F$_4$N$_3$O$_2$, 368.1. found 368.16.

Example 323

4-(5-(methoxymethyl)-3-methyl-1H-pyrazol-4-yl)-6-(trifluoromethyl)-1H-indazole

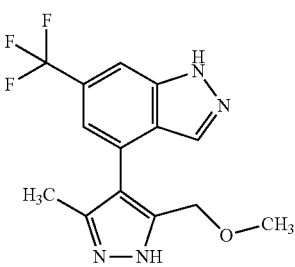 [SMILES: COCc1[nH]nc(C)c1-c1cc(C(F)(F)F)cc2[nH]ncc12]

A TFA salt of the title compound was prepared in a manner similar to EXAMPLE 257 using 4-bromo-5-(methoxymethyl)-3-methyl-1H-pyrazole in place of N-(5-bromo-6-methylpyridin-2-yl)methanesulfonamide. $^1$H NMR (400 MHz, CD$_3$OD) δ ppm 2.27 (s, 3H), 3.29 (s, 3H), 4.35 (s, 2H), 7.33 (d, J=1.26 Hz, 1H), 7.89 (s, 1H), 8.01 (d, J=1.01 Hz, 1H); ESI-MS m/z [M+H]$^+$ calc'd for C$_{14}$H$_{13}$F$_3$N$_4$O, 311.1. found 311.15.

Example 324

1-(3,5-dimethyl-4-(6-(trifluoromethyl)-1H-indazol-4-yl)-1H-pyrazol-1-yl)propan-2-one

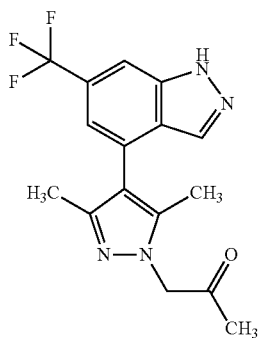

A TFA salt of the title compound was prepared in a manner similar to EXAMPLE 257 using 1-(4-bromo-3,5-dimethyl-1H-pyrazol-1-yl)propan-2-one in place of N-(5-bromo-6-methylpyridin-2-yl)methanesulfonamide. $^1$H NMR (400 MHz, DMSO-$d_6$) δ ppm 2.08 (d, J=8.59 Hz, 6H), 2.18 (s, 3H), 5.12 (s, 2H), 7.17 (d, J=1.26 Hz, 1H), 7.87 (s, 1H), 7.96 (d, J=0.76 Hz, 1H); ESI-MS m/z [M+H]$^+$ calc'd for $C_{16}H_{15}F_3N_4O$, 337.1. found 337.2.

Example 325

4-(4-methoxy-3-(6-(trifluoromethyl)-1H-indazol-4-yl)benzoyl)-1-methylpiperazin-2-one

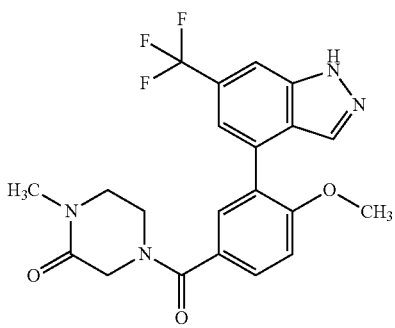

To a vial containing 1-methylpiperazin-2-one HCl (0.172 g, 1.142 mmol) in dioxane (5 mL) was added trimethylaluminum (0.571 mL, 1.142 mmol) in toluene dropwise at room temperature. After stirring for 15 minutes at room temperature, methyl 4-methoxy-3-(6-(trifluoromethyl)-1H-indazol-4-yl)benzoate (0.1 g, 0.285 mmol) was added. The mixture was heated at 110° C. for 1 hour in a microwave reactor and was subsequently transferred to a round bottom flask. The reaction mixture was quenched with concentrated HCl and concentrated. The crude residue was purified by preparative HPLC, eluting with 35% acetonitrile (containing 0.035% TFA) in H$_2$O (containing 0.05% TFA) over a period of 5 minutes. The product-containing fractions were combined and the volatiles removed in vacuo to give a TFA salt of the title compound as light brown semisolid (0.024 g, 19%). $^1$H NMR (400 MHz, DMSO-$d_6$) δ ppm 2.86 (s, 3H), 3.37 (t, J=5.43 Hz, 2H), 3.70-3.86 (m, 5H), 4.12 (s, 2H), 7.29 (d, J=8.59 Hz, 1H), 7.37 (d, J=1.01 Hz, 1H), 7.52 (d, J=2.02 Hz, 1H), 7.61 (dd, J=8.59, 2.27 Hz, 1H), 7.94 (s, 1H), 7.99 (d, J=0.76 Hz, 1H); ESI-MS m/z [M+H]$^+$ calc'd for $C_{21}H_{19}F_3N_4O_3$, 433.1. found 433.22.

Example 326

4-fluoro-3-(6-(trifluoromethyl)-1H-indazol-4-yl)benzamide

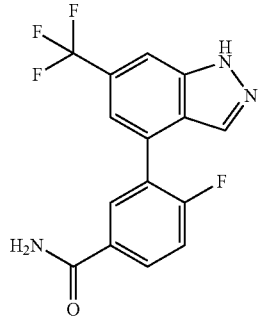 [SMILES: NC(=O)c1ccc(F)c(-c2cc(C(F)(F)F)cc3[nH]ncc23)c1]

A TFA salt of the title compound was prepared in a manner similar to EXAMPLE 247 using (5-carbamoyl-2-fluorophenyl)boronic acid in place of N,N-dimethyl-5-(4,4,5,5-tetramethyl-1,3,2-dioxaborolan-2-yl)pyrimidin-2-amine. $^1$H NMR (400 MHz, DMSO-$d_6$) δ ppm 7.47-7.58 (m, 3H), 7.96-8.11 (m, 2H), 8.11-8.24 (m, 3H), 13.75 (s, 1H); ESI-MS m/z [M+H]$^+$ calc'd for $C_{15}H_9F_4N_3O$, 324.1. found 324.11.

Example 327

1,3-dimethyl-4-(6-(trifluoromethyl)-1H-indazol-4-yl)-1H-pyrazole-5-carboxamide

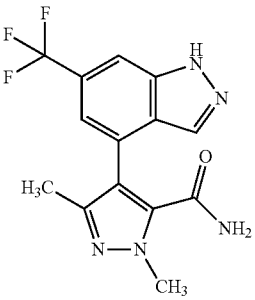 [SMILES: Cc1nn(C)c(C(N)=O)c1-c1cc(C(F)(F)F)cc2[nH]ncc12]

A TFA salt of the title compound was prepared in a manner similar to EXAMPLE 257 using 4-bromo-1,3-dimethyl-1H-pyrazole-5-carboxamide in place of N-(5-bromo-6-methylpyridin-2-yl)methanesulfonamide. $^1$H NMR (400 MHz, CD$_3$OD) δ ppm 2.18 (s, 3H), 4.03 (s, 3H), 7.33 (d, J=1.01 Hz, 1H), 7.84-7.93 (m, 1H), 7.96 (d, J=1.01 Hz, 1H); ESI-MS m/z [M+H]$^+$ calc'd for $C_{14}H_{12}F_3N_5O$, 324.1. found 324.15.

Example 328

(3-hydroxyazetidin-1-yl)(4-methoxy-3-(6-(trifluoromethyl)-1H-indazol-4-yl)phenyl)methanone

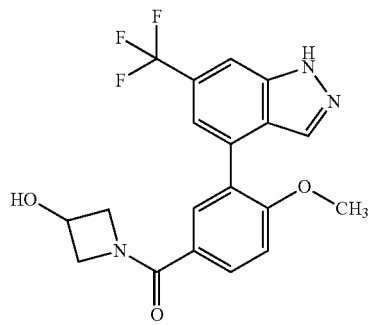 [SMILES: COc1ccc(C(=O)N2CC(O)C2)cc1-c1cc(C(F)(F)F)cc2[nH]ncc12]

A TFA salt of the title compound was prepared in a manner similar to EXAMPLE 325 using azetidin-3-ol HCl in place of 1-methylpiperazin-2-one HCl. $^1$H NMR (400 MHz, DMSO-d$_6$) δ ppm 3.82 (s, 4H), 4.09 (br s, 1H), 4.24 (br s, 1H), 4.50 (d, J=4.29 Hz, 2H), 5.75 (d, J=5.81 Hz, 1H), 7.27 (d, J=8.84 Hz, 1H), 7.35 (d, J=1.01 Hz, 1H), 7.65 (d, J=2.27 Hz, 1H), 7.77 (dd, J=8.59, 2.27 Hz, 1H), 7.96 (s, 1H), 7.93 (s, 1H), 13.60 (s, 1H); ESI-MS m/z [M+H]$^+$ calc'd for C$_{19}$H$_{16}$F$_3$N$_3$O$_3$, 392.1. found 392.21.

Example 329

3-(6-(trifluoromethyl)-1H-indazol-4-yl)benzenesulfonamide

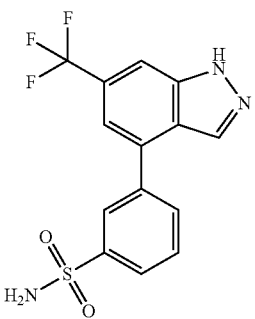 [SMILES: NS(=O)(=O)c1cccc(-c2cc(C(F)(F)F)cc3[nH]ncc23)c1]

4-Bromo-6-(trifluoromethyl)-1H-indazole (40 mg, 0.151 mmol), (3-sulfamoylphenyl)boronic acid (45.5 mg, 0.226 mmol), PdCl$_2$(dppf) (11.04 mg, 0.015 mmol), sodium bicarbonate (323 μL, 0.604 mmol), and dioxane were mixed in a 10 mL vial to give an orange suspension. The vial was sealed and then heated to 140° C. for 20 minutes in a microwave reactor. The reaction mixture was subsequently filtered and the product was purified by preparative HPLC, eluting with a gradient of 35-70% ACN in H$_2$O (containing 10 mM NH$_4$HCO$_3$). The pure fractions were lyophilized to give the title compound as a white solid (35.8 mg, 69.5%). $^1$H NMR (400 MHz, DMSO-d$_6$) δ ppm 7.50 (s, 2H), 7.53 (s, 1H), 7.75-7.80 (m, 1H), 7.92-7.94 (m, 1H), 8.02 (s, 1H), 8.06 (dt, J=8.02, 1.29 Hz, 1H), 8.21 (t, J=1.64 Hz, 1H), 8.40 (s, 1H); ESI-MS m/z [M+H]$^+$ calc'd for C$_{14}$H$_{10}$F$_3$N$_3$O$_2$S, 342.0. found 342.2.

Example 330

N-(2-hydroxyethyl)-3-methyl-4-(6-(trifluoromethyl)-1H-indazol-4-yl)benzamide

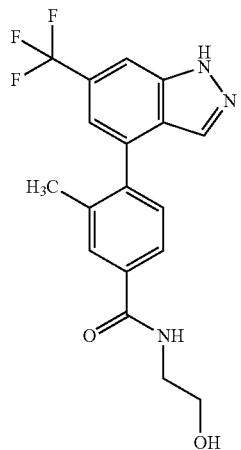 [SMILES: Cc1cc(C(=O)NCCO)ccc1-c1cc(C(F)(F)F)cc2[nH]ncc12]

A TFA salt of the title compound was prepared in a manner similar to EXAMPLE 270 using methyl 3-methyl-4-(6-(trifluoromethyl)-1H-indazol-4-yl)benzoate in place of methyl 5-(6-(trifluoromethyl)-1H-indazol-4-yl)picolinate. $^1$H NMR (400 MHz, CD$_3$OD) δ ppm 2.23 (s, 3H), 3.55 (t, J=5.94 Hz, 2H), 3.75 (t, J=5.81 Hz, 2H), 7.26 (d, J=1.01 Hz, 1H), 7.42 (d, J=7.83 Hz, 1H), 7.75-7.85 (m, 2H), 7.85-7.92 (m, 1H), 7.94 (s, 1H); ESI-MS m/z [M+H]$^+$ calc'd for C$_{18}$H$_{16}$F$_3$N$_3$O$_2$, 364.1. found 364.19.

Example 331

3-chloro-N-(2-hydroxyethyl)-4-(6-(trifluoromethyl)-1H-indazol-4-yl)benzamide

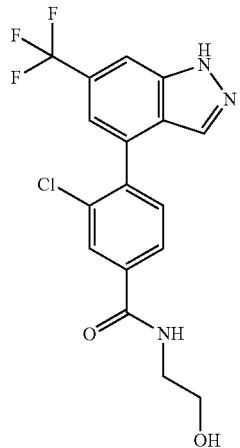 [SMILES: O=C(NCCO)c1ccc(-c2cc(C(F)(F)F)cc3[nH]ncc23)c(Cl)c1]

A TFA salt of the title compound was prepared in a manner similar to EXAMPLE 270 using methyl 3-chloro-4-(6-(trifluoromethyl)-1H-indazol-4-yl)benzoate in place of methyl 5-(6-(trifluoromethyl)-1H-indazol-4-yl)picolinate. $^1$H NMR (400 MHz, CD$_3$OD) δ ppm 3.47-3.60 (m, 1H), 3.70-3.84 (m, 2H), 4.60 (t, J=5.31 Hz, 1H), 7.35-7.40 (m, 1H), 7.55-7.69 (m, 1H), 7.84-8.02 (m, 3H), 8.04-8.16 (m, 1H); ESI-MS m/z [M+H]$^+$ calc'd for $C_{17}H_{13}ClF_3N_3O_2$, 384.1. found 384.18.

Example 332

N-cyclopropyl-6-oxo-5-(6-(trifluoromethyl)-1H-indazol-4-yl)-1,6-dihydropyridine-3-carboxamide

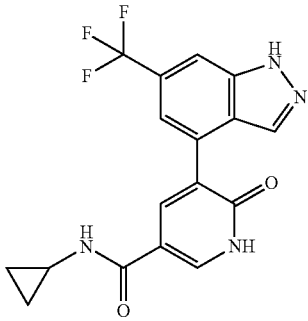 [SMILES: O=C(NC1CC1)c1c[nH]c(=O)c(-c2cc(C(F)(F)F)cc3[nH]ncc23)c1]

The title compound was prepared in a manner similar to EXAMPLE 265 using 5-bromo-N-cyclopropyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.26 (d, J=2.0 Hz, 1H), 8.15 (d, J=2.0 Hz, 1H), 8.12 (s, 1H), 7.91 (s, 1H), 7.59 (s, 1H), 2.79-2.87 (m, 1H), 0.76-0.83 (m, 2H), 0.59-0.65 (m, 1H); ESI-MS m/z [M+H]$^+$ calc'd for $C_{17}H_{13}F_3N_4O_2$, 363.1. found 363.3.

Example 333

N-(cyanomethyl)-6-oxo-5-(6-(trifluoromethyl)-1H-indazol-4-yl)-1,6-dihydropyridine-3-carboxamide

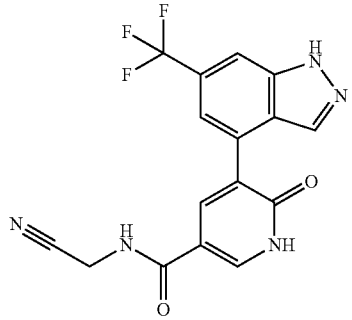 [SMILES: N#CCNC(=O)c1c[nH]c(=O)c(-c2cc(C(F)(F)F)cc3[nH]ncc23)c1]

The title compound was prepared in a manner similar to EXAMPLE 265 using 5-bromo-N-(cyanomethyl)-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.26 (d, J=4.0 Hz, 1H), 8.21 (d, J=4.0 Hz, 1H), 8.14 (s, 1H), 7.92 (s, 1H), 7.61 (s, 1H), 4.31 (s, 2H); ESI-MS m/z [M+H]$^+$ calc'd for $C_{16}H_{10}F_3N_5O_2$, 362.1. found 362.3.

Example 334

N,N-dimethyl-6-oxo-5-(6-(trifluoromethyl)-1H-indazol-4-yl)-1,6-dihydropyridine-3-carboxamide

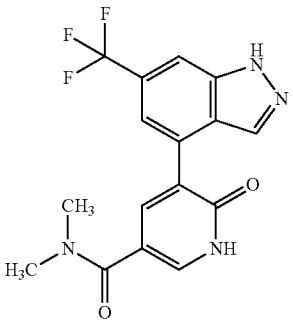 [SMILES: CN(C)C(=O)c1c[nH]c(=O)c(-c2cc(C(F)(F)F)cc3[nH]ncc23)c1]

The title compound was prepared in a manner similar to EXAMPLE 265 using 5-bromo-N,N-dimethyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.16 (s, 1H), 7.95 (d, J=4.0 Hz, 1H), 7.91 (1H), 7.81 (d, J=4.0 Hz, 1H), 7.60 (s, 1H), 3.08-3.21 (br s, 6H); ESI-MS m/z [M+H]$^+$ calc'd for $C_{16}H_{13}F_3N_4O_2$, 351.1. found 351.3.

Example 335

(S)—N-(2-hydroxypropyl)-6-oxo-5-(6-(trifluoromethyl)-1H-indazol-4-yl)-1,6-dihydropyridine-3-carboxamide

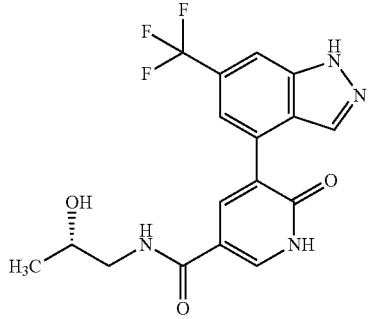 [SMILES: C[C@H](O)CNC(=O)c1c[nH]c(=O)c(-c2cc(C(F)(F)F)cc3[nH]ncc23)c1]

The title compound was prepared in a manner similar to EXAMPLE 265 using (S)-5-bromo-N-(2-hydroxypropyl)-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.30 (d, J=4.0 Hz, 1H), 8.18 (d, J=4.0 Hz, 1H), 8.14 (s, 1H), 7.91 (s, 1H), 7.60 (s, 1H), 3.89-32.99 (m, 1H), 3.23-3.44 (m, 2H), 1.19 (d, J=8.0 Hz, 3H); ESI-MS m/z [M+H]$^+$ calc'd for $C_{17}H_{15}F_3N_4O_3$, 381.1. found 381.3.

Example 336

(R)—N-(2-hydroxypropyl)-6-oxo-5-(6-(trifluoromethyl)-1H-indazol-4-yl)-1,6-dihydropyridine-3-carboxamide

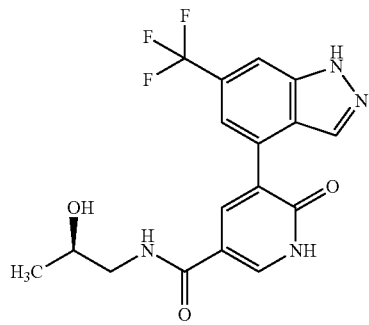 [SMILES: C[C@@H](O)CNC(=O)c1c[nH]c(=O)c(-c2cc(C(F)(F)F)cc3[nH]ncc23)c1]

The title compound was prepared in a manner similar to EXAMPLE 265 using (R)-5-bromo-N-(2-hydroxypropyl)-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.30 (d, J=4.0 Hz, 1H), 8.18 (d, J=4.0 Hz, 1H), 8.14 (s, 1H), 7.91 (s, 1H), 7.60 (s, 1H), 3.90-3.99 (m, 1H), 3.23-3.44 (m, 2H), 1.19 (d, J=8.0 Hz, 3H); ESI-MS m/z [M+H]$^+$ calc'd for C$_{17}$H$_{15}$F$_3$N$_4$O$_3$, 381.1. found 381.3.

Example 337

N-(2,3-dihydroxypropyl)-6-oxo-5-(6-(trifluoromethyl)-1H-indazol-4-yl)-1,6-dihydropyridine-3-carboxamide

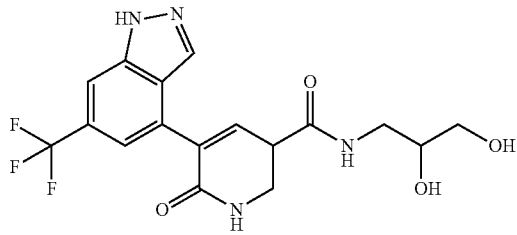 [SMILES: O=C1NCC(C(=O)NCC(O)CO)C=C1c1cc(C(F)(F)F)cc2[nH]ncc12]

The title compound was prepared in a manner similar to EXAMPLE 265 using 5-bromo-N-(2,3-dihydroxypropyl)-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.29 (d, J=4.0 Hz, 1H), 8.18 (d, J=4.0 Hz, 1H), 8.14 (s, 1H), 7.91 (s, 1H), 7.60 (s, 1H), 3.75-3.86 (m, 1H), 3.47-3.59 (m, 4H), 3.33-3.43 (m, 1H); ESI-MS m/z [M+H]$^+$ calc'd for C$_{17}$H$_{15}$F$_3$N$_4$O$_4$, 397.1. found 397.3.

Example 338

N-(2,2-difluoroethyl)-6-oxo-5-(6-(trifluoromethyl)-1H-indazol-4-yl)-1,6-dihydropyridine-3-carboxamide

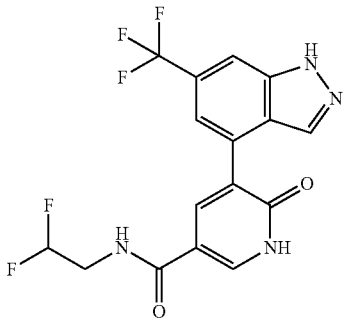 [SMILES: O=C(NCC(F)F)c1c[nH]c(=O)c(-c2cc(C(F)(F)F)cc3[nH]ncc23)c1]

The title compound was prepared in a manner similar to EXAMPLE 265 using 5-bromo-N-(2,2-difluoroethyl)-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.29 (d, J=4.0 Hz, 1H), 8.19 (d, J=4.0 Hz, 1H), 8.14 (s, 1H), 7.91 (s, 1H), 7.60 (s, 1H), 5.83-6.16 (m, 1H), 3.66-3.77 (m, 2H); ESI-MS m/z [M+H]$^+$ calc'd for C$_{16}$H$_{11}$F$_5$N$_4$O$_2$, 387.1. found 387.3.

Example 339

4-(3-fluoro-1H-pyrrolo[2,3-b]pyridin-5-yl)-6-(trifluoromethyl)-1H-indazole

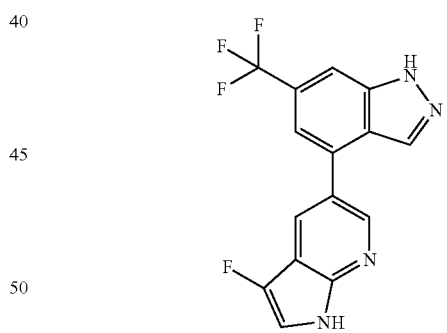

A 20 mL microwave vial was charged with a mixture of 4-bromo-6-(trifluoromethyl)-1H-indazole (60 mg, 0.226 mmol), (3-fluoro-1H-pyrrolo[2,3-b]pyridin-5-yl)boronic acid (61.1 mg, 0.340 mmol) and PdCl$_2$(dppf)CH$_2$Cl$_2$ (9.31 mg, 0.011 mmol) in dioxane (4 mL) and aqueous saturated NaHCO$_3$ (2 mL). The resulting brown suspension was heated at 130° C. for 30 minutes in microwave reactor. The reaction mixture was subsequently purified by preparative HPLC, eluting with a gradient of 65-80% acetonitrile (containing 0.035% TFA) in H$_2$O (containing 0.05% TFA). The product fractions were collected and dried to give a TFA salt of the title compound as a dark purple solid (13.1 mg, 18.1%). $^1$H NMR (400 MHz, CD$_3$OD) δ ppm 7.34 (d, J=2.27 Hz, 1H), 7.50 (d, J=1.01 Hz, 1H), 7.92 (s, 1H), 8.29

(d, J=1.01 Hz, 1H), 8.36 (d, J=2.02 Hz, 1H), 8.62 (d, J=2.02 Hz, 1H); ESI-MS m/z [M+H]+ calc'd for $C_{15}H_8F_4N_4$, 321.1. found 321.2.

Example 340

4-(3-methyl-1H-pyrrolo[2,3-b]pyridin-5-yl)-6-(trifluoromethyl)-1H-indazole

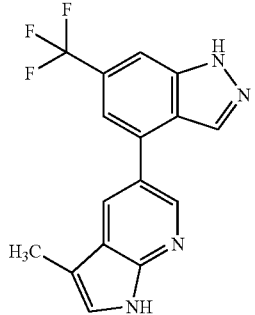 [SMILES: Cc1c[nH]c2ncc(-c3cc(C(F)(F)F)cc4[nH]ncc34)cc12]

A TFA salt of the title compound was prepared in a manner similar to EXAMPLE 339 using (3-methyl-1H-pyrrolo[2,3-b]pyridin-5-yl)boronic acid in place of (3-fluoro-1H-pyrrolo[2,3-b]pyridin-5-yl)boronic acid. $^1$H NMR (400 MHz, $CD_3OD$) δ ppm 2.43 (d, J=1.26 Hz, 3H), 7.40 (d, J=1.01 Hz, 1H), 7.56 (d, J=1.26 Hz, 1H), 7.96 (s, 1H), 8.33 (d, J=1.01 Hz, 1H), 8.60 (d, J=2.02 Hz, 1H), 8.63 (d, J=1.77 Hz, 1H); ESI-MS m/z [M+H]+ calc'd for $C_{16}H_{11}F_3N_4$, 317.1. found 317.3.

Example 341

2-methyl-6-(6-(trifluoromethyl)-1H-indazol-4-yl)-3H-imidazo[4,5-b]pyridine

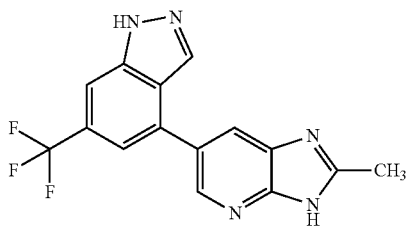 [SMILES: Cc1nc2cc(-c3cc(C(F)(F)F)cc4[nH]ncc34)cnc2[nH]1]

A TFA salt of the title compound was prepared in a manner similar to EXAMPLE 339 using 1-(2-methyl-6-(4,4,5,5-tetramethyl-1,3,2-dioxaborolan-2-yl)-1H-imidazo[4,5-b]pyridin-1-yl)ethanone in place of (3-fluoro-1H-pyrrolo[2,3-b]pyridin-5-yl)boronic acid. $^1$H NMR (400 MHz, $CD_3OD$) δ ppm 2.93 (s, 3H), 7.61 (d, J=1.01 Hz, 1H), 8.02 (d, J=1.01 Hz, 1H), 8.33 (d, J=1.01 Hz, 1H), 8.54 (d, J=2.02 Hz, 1H), 8.97 (d, J=2.02 Hz, 1H); ESI-MS m/z [M+H]+ calc'd for $C_{15}H_{10}F_3N_5$, 318.1. found 318.3.

Example 342

3-fluoro-4-(6-(trifluoromethyl)-1H-indazol-4-yl)benzenesulfonamide

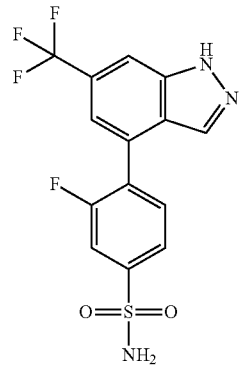 [SMILES: NS(=O)(=O)c1ccc(-c2cc(C(F)(F)F)cc3[nH]ncc23)c(F)c1]

To a 5 mL vial equipped with a magnetic stir bar were added 4-(4,4,5,5-tetramethyl-1,3,2-dioxaborolan-2-yl)-6-(trifluoromethyl)-1H-indazole (40 mg, 0.128 mmol), 4-bromo-3-fluorobenzenesulfonamide (39.1 mg, 0.154 mmol), aqueous saturated sodium bicarbonate (0.274 mL, 0.513 mmol), $PdCl_2$(dppf) (9.38 mg, 0.013 mmol), and dioxane (2 mL) to give an orange suspension. The vial was sealed and then heated in a microwave reactor at 140° C. for 30 minutes. The reaction mixture was subsequently filtered and the product was purified by preparative HPLC, eluting with a gradient of 35-60% ACN (containing 0.035% TFA) in $H_2O$ (containing 0.05% TFA). The pure fractions were lyophilized to give a TFA salt of the title compound as a white solid (13.7 mg, 22.6%). $^1$H NMR (400 MHz, DMSO-$d_6$) δ ppm 7.50 (s, 2H), 7.53 (s, 1H), 7.75-7.80 (m, 1H), 7.92-7.94 (m, 1H), 8.02 (s, 1H), 8.06 (dt, J=8.02, 1.29 Hz, 1H), 8.21 (t, J=1.64 Hz, 1H), 8.40 (s, 1H); ESI-MS m/z [M+H]+ calc'd for $C_{14}H_9F_4N_3O_2S$, 360.0. found 360.1.

Example 343

2-chloro-4-(6-(trifluoromethyl)-1H-indazol-4-yl)benzenesulfonamide

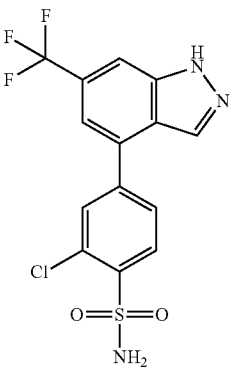 [SMILES: NS(=O)(=O)c1ccc(-c2cc(C(F)(F)F)cc3[nH]ncc23)cc1Cl]

A TFA salt of the title compound was prepared in a manner similar to EXAMPLE 342 using 4-bromo-2-chlorobenzenesulfonamide in place of 4-bromo-3-fluorobenzenesulfonamide. ¹H NMR (400 MHz, CD₃OD) δ ppm 1.22-1.26 (m, 2H), 2.00-2.04 (m, 2H), 4.10 (q, J=7.07 Hz, 1H), 7.54 (d, J=1.01 Hz, 1H), 7.86 (dd, J=8.08, 1.77 Hz, 1H), 7.97 (d, J=1.52 Hz, 1H), 7.99 (s, 1H), 8.26 (d, J=8.34 Hz, 1H), 8.30 (d, J=1.01 Hz, 1H ESI-MS m/z [M+H]⁺ calc'd for C₁₄H₉ClF₃N₃O₂S, 376.0. found 376.1.

Example 344

2-fluoro-4-(6-(trifluoromethyl)-1H-indazol-4-yl)benzenesulfonamide

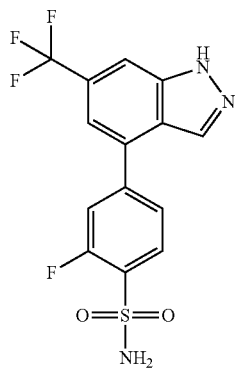

A TFA salt of the title compound was prepared in a manner similar to EXAMPLE 342 using 4-bromo-2-fluorobenzenesulfonamide in place of 4-bromo-3-fluorobenzenesulfonamide. ¹H NMR (400 MHz, CD₃OD) δ ppm 7.54 (d, J=1.01 Hz, 1H), 7.71 (dd, J=5.81, 1.26 Hz, 1H), 7.73-7.74 (m, 1H), 7.99 (s, 1H), 8.04-8.09 (m, 1H), 8.32 (d, J=1.01 Hz, 1H); ESI-MS m/z [M+H]⁺ calc'd for C₁₄H₉F₄N₃O₂S, 360.0. found 360.2.

Example 345

5-(6-(trifluoromethyl)-1H-indazol-4-yl)pyridine-2-sulfonamide

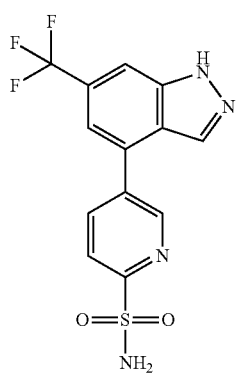 [SMILES: NS(=O)(=O)c1ccc(-c2cc(C(F)(F)F)cc3[nH]ncc23)cn1]

4-(4,4,5,5-Tetramethyl-1,3,2-dioxaborolan-2-yl)-6-(trifluoromethyl)-1H-indazole (39.5 mg, 0.127 mmol), 5-bromopyridine-2-sulfonamide (45 mg, 0.190 mmol), PdCl₂(dppf) (9.26 mg, 0.013 mmol), sodium bicarbonate (0.271 mL, 0.506 mmol), and dioxane (2 mL) were mixed in a 10 mL vial to give an orange suspension. The vial was sealed and then heated to 140° C. for 20 minutes in a microwave reactor. The reaction mixture was subsequently filtered and the product was purified by preparative HPLC, eluting with a gradient of 35-60% ACN (containing 0.035% TFA) in H₂O (containing 0.05% TFA). The pure fractions were lyophilized to give a TFA salt of the title compound as a white solid (9.9 mg, 17%). ¹H NMR (400 MHz, CD₃OD) δ ppm 2.01 (s, 1H), 7.61 (d, J=1.26 Hz, 1H), 8.03 (s, 1H), 8.17-8.21 (m, 1H), 8.34 (d, J=1.01 Hz, 1H), 8.43 (dd, J=8.08, 2.27 Hz, 1H), 9.07 (dd, J=2.27, 0.76 Hz, 1H); ESI-MS m/z [M+H]⁺ calc'd for C₁₃H₉F₃N₄O₂S, 343.0. found 343.2.

Example 346

5-(6-(trifluoromethyl)-1H-indazol-4-yl)pyridine-3-sulfonamide

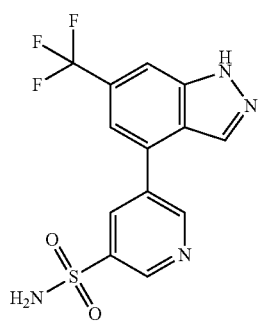 [SMILES: NS(=O)(=O)c1cncc(-c2cc(C(F)(F)F)cc3[nH]ncc23)c1]

A TFA salt of the title compound was prepared in a manner similar to EXAMPLE 342 using 5-bromopyridine-3-sulfonamide in place of 4-bromo-3-fluorobenzenesulfonamide. ¹H NMR (400 MHz, CD₃OD) δ ppm 7.61 (d, J=1.26 Hz, 1H), 8.04 (d, J=1.01 Hz, 1H), 8.34 (d, J=1.01 Hz, 1H), 8.63 (t, J=2.15 Hz, 1H), 9.13 (d, J=2.27 Hz, 1H), 9.16 (d, J=2.02 Hz, 1H); ESI-MS m/z [M+H]⁺ calc'd for C₁₃H₉F₃N₄O₂S, 343.0. found 343.2.

Example 347

4-(4-(methylsulfonyl)phenyl)-6-(trifluoromethyl)-1H-indazole

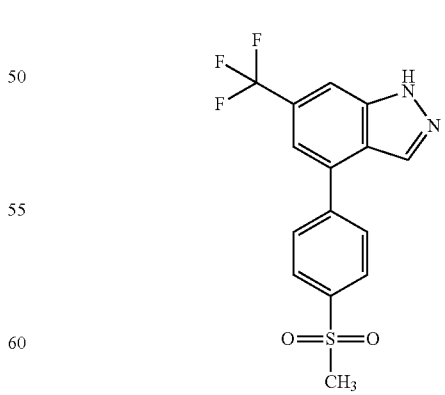

A TFA salt of the title compound was prepared in a manner similar to EXAMPLE 342 using 1-bromo-4-(methylsulfonyl)benzene in place of 4-bromo-3-fluorobenzenesulfonamide. ¹H NMR (400 MHz, CD₃OD) δ ppm 3.21 (s, 3H), 7.55 (d, J=1.01 Hz, 1H), 7.98 (s, 1H), 8.01-8.05 (m, 2H), 8.14-8.18 (m, 2H), 8.32 (d, J=1.01 Hz, 1H); ESI-MS m/z [M+H]+ calc'd for $C_{15}H_{11}F_3N_2O_2S$, 341.0. found 341.2.

Example 348

4-(1-(difluoromethyl)-3,5-dimethyl-1H-pyrazol-4-yl)-6-(trifluoromethyl)-1H-indazole

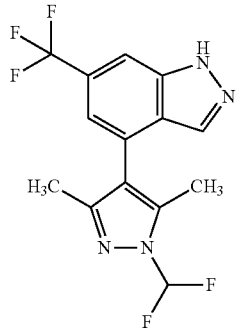 [SMILES: Cc1nn(C(F)F)c(C)c1-c1cc(C(F)(F)F)cc2[nH]ncc12]

A TFA salt of the title compound was prepared in a manner similar to EXAMPLE 257 using 4-bromo-1-(difluoromethyl)-3,5-dimethyl-1H-pyrazole in place of N-(5-bromo-6-methylpyridin-2-yl)methanesulfonamide. $^1$H NMR (400 MHz, CD$_3$OD) δ ppm 2.16 (s, 3H), 2.35 (s, 3H), 7.24 (d, J=1.01 Hz, 1H), 7.50 (s, 1H), 7.88-8.01 (m, 2H); ESI-MS m/z [M+H]+ calc'd for $C_{14}H_{11}F_5N_4$, 331.1. found 331.15.

Example 349

2-(4-(6-(trifluoromethyl)-1H-indazol-4-yl)-1H-pyrazol-1-yl)ethanol

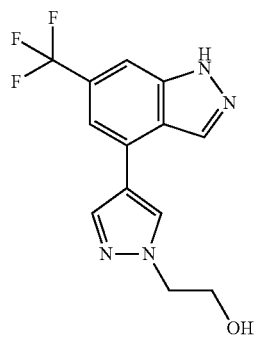 [SMILES: OCCn1cc(-c2cc(C(F)(F)F)cc3[nH]ncc23)cn1]

A TFA salt of the title compound was prepared in a manner similar to EXAMPLE 257 using 2-(4-bromo-1H-pyrazol-1-yl)ethanol in place of N-(5-bromo-6-methylpyridin-2-yl)methanesulfonamide. $^1$H NMR (400 MHz, CD$_3$OD) δ ppm 3.97 (t, J=5.43 Hz, 2H), 4.35 (t, J=5.31 Hz, 2H), 7.52 (d, J=1.01 Hz, 1H), 7.75 (s, 1H), 8.09 (d, J=0.76 Hz, 1H), 8.32 (s, 1H), 8.45 (d, J=1.01 Hz, 1H); ESI-MS m/z [M+H]+ calc'd for $C_{13}H_{11}F_3N_4O$, 297.1. found 297.14.

Example 350

2-(4-methoxy-3-(6-(trifluoromethyl)-1H-indazol-4-yl)phenyl)acetamide

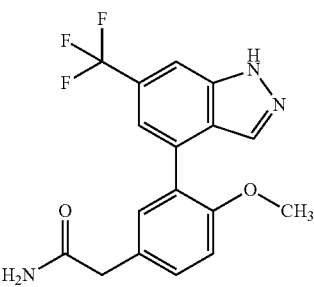 [SMILES: COc1ccc(CC(N)=O)cc1-c1cc(C(F)(F)F)cc2[nH]ncc12]

A TFA salt of the title compound was prepared in a manner similar to EXAMPLE 316 using ammonium chloride in place of morpholine. $^1$H NMR (400 MHz, CD$_3$OD) δ ppm 3.53 (s, 2H), 3.79 (s, 3H), 7.14 (d, J=8.84 Hz, 1H), 7.32-7.44 (m, 3H), 7.84 (s, 1H), 7.94 (d, J=0.76 Hz, 1H); ESI-MS m/z [M+H]+ calc'd for $C_{17}H_{14}F_3N_3O_2$, 350.1. found 350.16.

Example 351

3-chloro-4-(6-(trifluoromethyl)-1H-indazol-4-yl)benzenesulfonamide

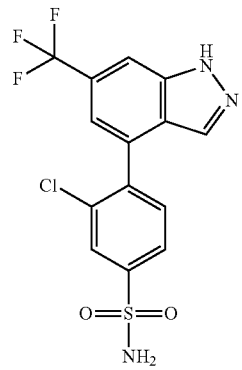 [SMILES: NS(=O)(=O)c1ccc(-c2cc(C(F)(F)F)cc3[nH]ncc23)c(Cl)c1]

A TFA salt of the title compound was prepared in a manner similar to EXAMPLE 342 using 4-bromo-3-chlorobenzenesulfonamide in place of 4-bromo-3-fluorobenzenesulfonamide. $^1$H NMR (400 MHz, CD$_3$OD) δ ppm 2.04 (s, 1H), 7.39 (s, 1H), 7.70 (d, J=8.34 Hz, 1H), 7.91 (s, 1H), 7.96-8.01 (m, 2H), 8.13 (d, J=1.52 Hz, 1H); ESI-MS m/z [M+H]+ calc'd for $C_{14}H_9ClF_3N_3O_2S$, 376.0. found 376.1.

Example 352

2-(3,5-dimethyl-4-(6-(trifluoromethyl)-1H-indazol-4-yl)-1H-pyrazol-1-yl)-N-isopropylacetamide

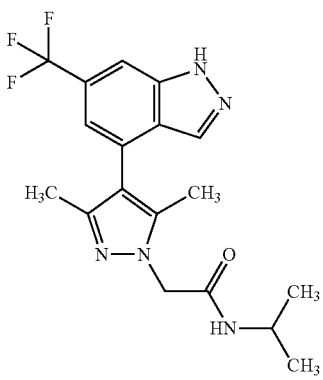 [SMILES: Cc1nn(CC(=O)NC(C)C)c(C)c1-c1cc(C(F)(F)F)cc2[nH]ncc12]

4-(4,4,5,5-Tetramethyl-1,3,2-dioxaborolan-2-yl)-6-(trifluoromethyl)-1H-indazole (58.3 mg, 0.187 mmol), 2-(4-bromo-3,5-dimethyl-1H-pyrazol-1-yl)-N-isopropylacetamide (77 mg, 0.28 mmol), PdCl$_2$(dppf) (13.66 mg, 0.019 mmol), sodium bicarbonate (0.399 mL, 0.747 mmol), and dioxane (2 mL) were mixed in a 10 mL vial to give an orange suspension. The vial was sealed and then heated to 140° C. for 45 minutes in a microwave reactor. The reaction mixture was subsequently filtered and the product was purified by preparative HPLC, eluting with a gradient of 35-55% ACN (containing 0.035% TFA) in H$_2$O (containing 0.05% TFA). The pure fractions were lyophilized to give a TFA salt of the title compound as a white solid (10.2 mg, 11.1%). $^1$H NMR (400 MHz, CD$_3$OD) δ ppm 1.20 (d, J=6.57 Hz, 6H), 2.15 (s, 3H), 2.19 (s, 3H), 2.66 (s, 1H), 7.23 (s, 1H), 7.87 (s, 1H), 8.00 (d, J=1.01 Hz, 1H); ESI-MS m/z [M+H]$^+$ calc'd for C$_{18}$H$_{20}$F$_3$N$_5$O, 380.2. found 380.3.

Example 353

N,N,1-trimethyl-6-oxo-5-(6-(trifluoromethyl)-1H-indazol-4-yl)-1,6-dihydropyridine-3-carboxamide

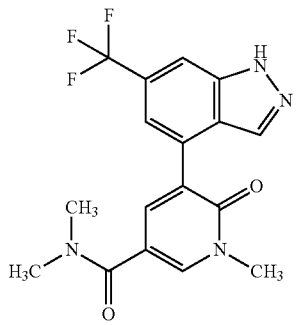 [SMILES: CN(C)C(=O)c1cc(-c2cc(C(F)(F)F)cc3[nH]ncc23)c(=O)n(C)c1]

The title compound was prepared in a manner similar to EXAMPLE 265 using 5-bromo-N,N,1-trimethyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.14 (s, 1H), 8.11 (d, J=4.0 Hz, 1H), 7.88-7.92 (m, 2H), 7.58 (s, 1H), 3.71 (s, 3H), 3.02-3.23 (br s, 6H); ESI-MS m/z [M+H]$^+$ calc'd for C$_{17}$H$_{15}$F$_3$N$_4$O$_2$, 365.1. found 365.3.

Example 354

N-(cyanomethyl)-1-methyl-6-oxo-5-(6-(trifluoromethyl)-1H-indazol-4-yl)-1,6-dihydropyridine-3-carboxamide

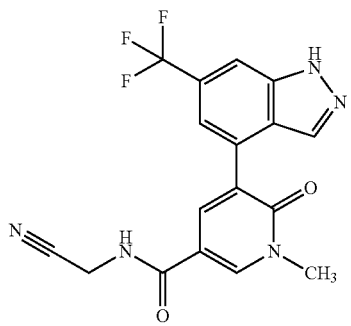 [SMILES: Cn1cc(C(=O)NCC#N)cc(-c2cc(C(F)(F)F)cc3[nH]ncc23)c1=O]

The title compound was prepared in a manner similar to EXAMPLE 265 using 5-bromo-N-(cyanomethyl)-1-methyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.48 (d, J=4.0 Hz, 1H), 8.19 (d, J=4.0 Hz, 1H), 8.12 (s, 1H), 7.91 (s, 1H), 7.58 (s, 1H), 4.31 (s, 2H), 3.74 (s, 3H); ESI-MS m/z [M+H]$^+$ calc'd for C$_{17}$H$_{12}$F$_3$N$_5$O$_2$, 376.1. found 376.3.

Example 355

N-(2,2-difluoroethyl)-1-methyl-6-oxo-5-(6-(trifluoromethyl)-1H-indazol-4-yl)-1,6-dihydropyridine-3-carboxamide

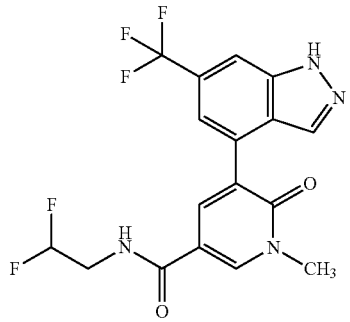 [SMILES: Cn1cc(C(=O)NCC(F)F)cc(-c2cc(C(F)(F)F)cc3[nH]ncc23)c1=O]

The title compound was prepared in a manner similar to EXAMPLE 265 using 5-bromo-N-(2,2-difluoroethyl)-1-methyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.46 (d, J=4.0 Hz, 1H), 8.22 (d, J=4.0 Hz, 1H), 8.11 (s, 1H), 7.91 (s, 1H), 7.58 (s, 1H), 5.80-6.17 (m, 1H), 3.66-3.78 (m, 5H); ESI-MS m/z [M+H]$^+$ calc'd for C$_{17}$H$_{13}$F$_5$N$_4$O$_2$, 401.1. found 401.3.

Example 356

N-(2,3-dihydroxypropyl)-1-methyl-6-oxo-5-(6-(trifluoromethyl)-1H-indazol-4-yl)-1,6-dihydropyridine-3-carboxamide

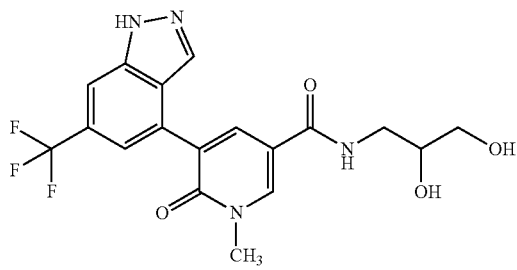 [SMILES: Cn1cc(C(=O)NCC(O)CO)cc(-c2cc(C(F)(F)F)cc3[nH]ncc23)c1=O]

The title compound was prepared in a manner similar to EXAMPLE 265 using 5-bromo-N-(2,3-dihydroxypropyl)-1-methyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.45 (d, J=4.0 Hz, 1H), 8.22 (d, J=4.0 Hz, 1H), 8.11 (s, 1H), 7.90 (s, 1H), 7.58 (s, 1H), 3.77-3.86 (m, 1H), 3.49-3.59 (m, 3H), 3.34-3.42 (m, 1H); ESI-MS m/z [M+H]$^+$ calc'd for C$_{18}$H$_{17}$F$_3$N$_4$O$_4$, 411.1. found 411.

Example 357

N-cyclopropyl-1-methyl-6-oxo-5-(6-(trifluoromethyl)-1H-indazol-4-yl)-1,6-dihydropyridine-3-carboxamide

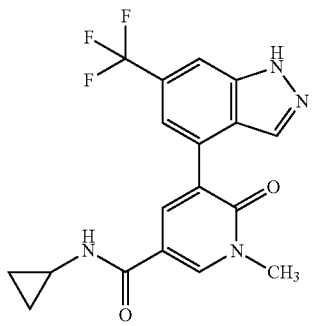 [SMILES: Cn1cc(C(=O)NC2CC2)cc(-c2cc(C(F)(F)F)cc3[nH]ncc23)c1=O]

The title compound was prepared in a manner similar to EXAMPLE 265 using 5-bromo-N-cyclopropyl-1-methyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.42 (d, J=4.0 Hz, 1H), 8.19 (d, J=4.0 Hz, 1 h), 8.10 (s, 1H), 7.91 (s, 1H), 7.56 (s, 1H), 3.72 (s, 2H), 2.78-2.87 (m, 1H), 0.74-0.84 (m, 2H), 0.59-0.65 (m, 2H); ESI-MS m/z [M+H]$^+$ calc'd for C$_{18}$H$_{15}$F$_3$N$_4$O$_2$, 377.1. found 377.3.

Example 358

(R)—N-(2-hydroxypropyl)-1-methyl-6-oxo-5-(6-(trifluoromethyl)-1H-indazol-4-yl)-1,6-dihydropyridine-3-carboxamide

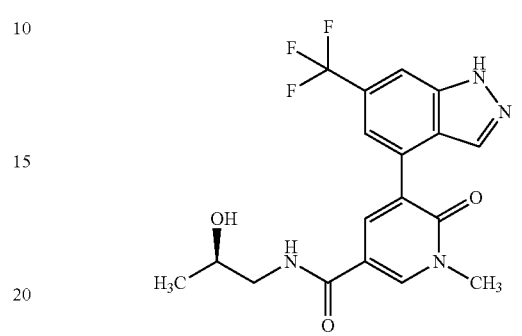

The title compound was prepared in a manner similar to EXAMPLE 265 using (R)-5-bromo-N-(2-hydroxypropyl)-1-methyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.44 (d, J=4.0 Hz, 1H), 8.23 (d, J=4.0 Hz, 1H), 8.11 (s, 1H), 7.91 (s, 1H), 7.57 (s, 1H), 3.89-3.99 (m, 1H), 3.73 (s, 3H), 3.24-3.44 (m, 2H), 1.19 (d, J=8.0 Hz, 3H); ESI-MS m/z [M+H]$^+$ calc'd for C$_{18}$H$_{17}$F$_3$N$_4$O$_3$, 395.1. found 395.3.

Example 359

(S)—N-(2-hydroxypropyl)-1-methyl-6-oxo-5-(6-(trifluoromethyl)-1H-indazol-4-yl)-1,6-dihydropyridine-3-carboxamide

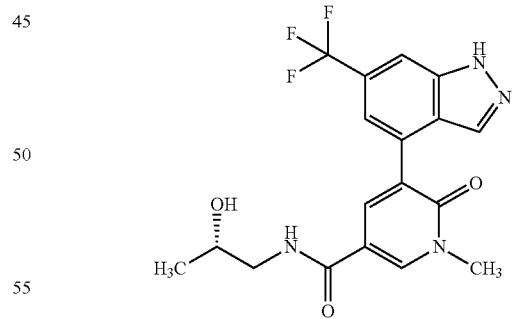

The title compound was prepared in a manner similar to EXAMPLE 265 using (S)-5-bromo-N-(2-hydroxypropyl)-1-methyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.44 (d, J=4.0 Hz, 1H), 8.23 (d, J=4.0 Hz, 1H), 8.11 (s, 1H), 7.90 (s, 1H), 7.57 (s, 1H), 3.89-3.99 (m, 1H), 3.73 (s, 3H), 3.24-3.44 (m, 2H), 1.19 (d, J=8.0 Hz, 3H); ESI-MS m/z [M+H]$^+$ calc'd for C$_{15}$H$_{17}$F$_3$N$_4$O$_3$, 395.1. found 395.3.

Example 360

4-fluoro-N-(2-hydroxyethyl)-3-(6-(trifluoromethyl)-1H-indazol-4-yl)benzamide

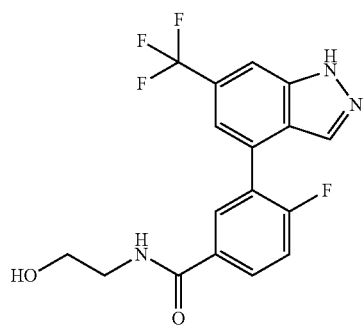

A TFA salt of the title compound was prepared in a manner similar to EXAMPLE 270 using ethyl 4-fluoro-3-(6-(trifluoromethyl)-1H-indazol-4-yl)benzoate in place of methyl 5-(6-(trifluoromethyl)-1H-indazol-4-yl)picolinate. $^1$H NMR (400 MHz, DMSO-$d_6$) δ ppm 3.34-3.38 (m, 2H), 3.52 (q, J=5.89 Hz, 2H), 4.75 (t, J=5.68 Hz, 1H), 7.40-7.64 (m, 2H), 7.92-8.09 (m, 2H), 8.09-8.21 (m, 2H), 8.62 (t, J=5.43 Hz, 1H), 13.76 (s, 1H); ESI-MS m/z [M+H]$^+$ calc'd for $C_{17}H_{13}F_4N_3O_2$, 368.1. found 368.16.

Example 361

(3-hydroxyazetidin-1-yl)(3-methyl-4-(6-(trifluoromethyl)-1H-indazol-4-yl)phenyl)methanone

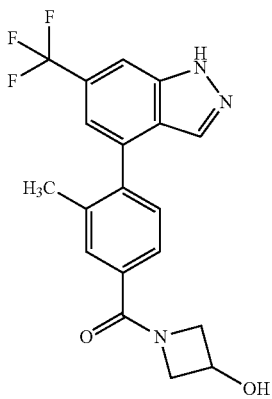 [SMILES: Cc1cc(C(=O)N2CC(O)C2)ccc1-c1cc(C(F)(F)F)cc2[nH]ncc12]

To a solution of azetidin-3-ol (0.262 g, 3.59 mmol) in dioxane (8 mL) was added trimethylaluminum (1.795 mL, 3.59 mmol) in toluene dropwise at room temperature. After stirring for 10 minutes at room temperature, methyl 3-methyl-4-(6-(trifluoromethyl)-1H-indazol-4-yl)benzoate (0.2 g, 0.598 mmol) was added. The reaction mixture was heated at 110° C. for 1 hour in a microwave reactor and then transferred to a round bottom flask. The reaction was quenched with concentrated HCl and the mixture concentrated. The residue was purified by preparative HPLC, eluting with 35% acetonitrile (containing 0.035% TFA) in H$_2$O (containing 0.05% TFA) over a period of 5.5 minutes. The product-containing fractions were combined and the volatiles removed in vacuo to give a TFA salt of the title compound as light brown solid (0.032 g, 14%). $^1$H NMR (400 MHz, CD$_3$OD) δ ppm 2.13-2.30 (m, 3H), 3.99 (dd, J=10.74, 3.41 Hz, 1H), 4.18-4.29 (m, 1H), 4.43 (dd, J=10.36, 6.82 Hz, 1H), 4.56-4.74 (m, 2H), 7.26 (d, J=1.01 Hz, 1H), 7.43 (d, J=7.83 Hz, 1H), 7.59 (dd, J=7.96, 1.39 Hz, 1H), 7.67 (s, 1H), 7.84 (s, 1H), 7.94 (s, 1H); ESI-MS m/z [M+H]$^+$ calc'd for $C_{19}H_{16}F_3N_3O_2$, 376.1. found 376.21.

Example 362

4-(6-(2-methoxyethoxy)-2-methylpyridin-3-yl)-6-(trifluoromethyl)-1H-indazole

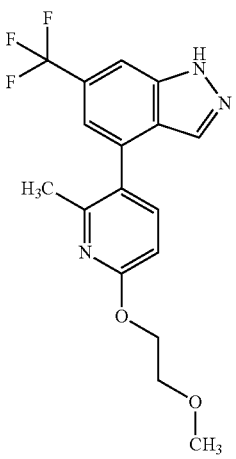 [SMILES: COCCOc1ccc(-c2cc(C(F)(F)F)cc3[nH]ncc23)c(C)n1]

A TFA salt of the title compound was prepared in a manner similar to EXAMPLE 257 using 3-bromo-6-(2-methoxyethoxy)-2-methylpyridine in place of N-(5-bromo-6-methylpyridin-2-yl)methanesulfonamide. $^1$H NMR (400 MHz, DMSO-$d_6$) δ ppm 2.28 (s, 3H), 3.33 (s, 3H), 3.63-3.74 (m, 2H), 4.35-4.53 (m, 2H), 6.80 (d, J=8.34 Hz, 1H), 7.29 (s, 1H), 7.70 (d, J=8.34 Hz, 1H), 7.96 (d, J=8.08 Hz, 2H); ESI-MS m/z [M+H]$^+$ calc'd for $C_{17}H_{16}F_3N_3O_2$, 352.1. found 352.2.

Example 363

2-(3,5-dimethyl-4-(6-(trifluoromethyl)-1H-indazol-4-yl)-1H-pyrazol-1-yl)-N,N-dimethylacetamide

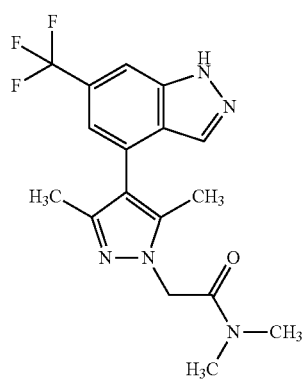 [SMILES: Cc1nn(CC(=O)N(C)C)c(C)c1-c1cc(C(F)(F)F)cc2[nH]ncc12]

A TFA salt of the title compound was prepared in a manner similar to EXAMPLE 257 using 2-(4-bromo-3,5-dimethyl-1H-pyrazol-1-yl)-N,N-dimethylacetamide in place of N-(5-bromo-6-methylpyridin-2-yl)methanesulfonamide. ¹H NMR (400 MHz, CD₃OD) δ ppm 2.17 (d, J=4.29 Hz, 6H), 3.02 (s, 3H), 3.18 (s, 3H), 5.16 (s, 2H), 7.24 (d, J=1.26 Hz, 1H), 7.88 (s, 1H), 8.01 (d, J=1.01 Hz, 1H); ESI-MS m/z [M+H]⁺ calc'd for $C_{17}H_{18}F_3N_5O$, 366.1. found 366.2.

Example 364

(5S)-5-((3,5-dimethyl-4-(6-(trifluoromethyl)-1H-indazol-4-yl)-1H-pyrazol-1-yl)methyl)pyrrolidin-2-one

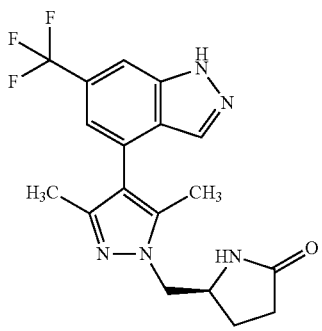 [SMILES: Cc1nn(C[C@@H]2CCC(=O)N2)c(C)c1-c1cc(C(F)(F)F)cc2[nH]ncc12]

4-(4,4,5,5-Tetramethyl-1,3,2-dioxaborolan-2-yl)-6-(trifluoromethyl)-1H-indazole, (S)-5-((4-bromo-3,5-dimethyl-1H-pyrazol-1-yl)methyl)pyrrolidin-2-one, PdCl₂(dppf), sodium bicarbonate, and dioxane (2 mL) were mixed in a 10 mL vial to give an orange suspension. The vial was sealed and then heated to 140° C. for 45 minutes in a microwave reactor. The reaction mixture was subsequently filtered and the product was purified by preparative HPLC, eluting with a gradient of 35-55% ACN (containing 0.035% TFA) in H₂O (containing 0.05% TFA). The pure fractions were lyophilized to give a TFA salt of the title compound as a white solid (8 mg). ¹H NMR (400 MHz, DMSO-d₆) δ ppm 1.98 (s, 3H), 2.10 (s, 3H), 2.16 (s, 3H), 4.09 (d, J=5.31 Hz, 2H), 7.16 (s, 1H), 7.81 (s, 1H), 7.86 (s, 1H), 8.03 (s, 1H); ESI-MS m/z [M+H]⁺ calc'd for $C_{18}H_{18}F_3N_5O$, 378.1. found 378.3.

Example 365

4-(2-(methylsulfonyl)phenyl)-6-(trifluoromethyl)-1H-indazole

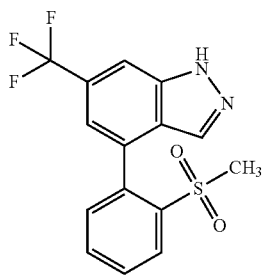 [SMILES: CS(=O)(=O)c1ccccc1-c1cc(C(F)(F)F)cc2[nH]ncc12]

A TFA salt of the title compound was prepared in a manner similar to EXAMPLE 342 using 1-bromo-2-(methylsulfonyl)benzene in place of 4-bromo-3-fluorobenzenesulfonamide. ¹H NMR (400 MHz, DMSO-d₆) δ ppm 2.86 (s, 3H), 7.42 (d, J=1.01 Hz, 1H), 7.55 (dd, J=7.33, 1.26 Hz, 1H), 7.79-7.87 (m, 4H), 8.01 (s, 1H), 8.18 (dd, J=7.83, 1.52 Hz, 1H); ESI-MS m/z [M+H]⁺ calc'd for $C_{15}H_{11}F_3N_2O_2S$, 341.0. found 341.2.

Example 366

2-(3,5-dimethyl-4-(6-(trifluoromethyl)-1H-indazol-4-yl)-1H-pyrazol-1-yl)-1-(3-hydroxyazetidin-1-yl)ethanone

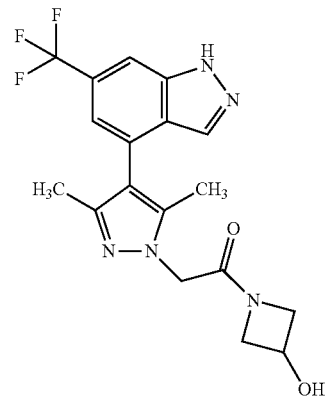 [SMILES: Cc1nn(CC(=O)N2CC(O)C2)c(C)c1-c1cc(C(F)(F)F)cc2[nH]ncc12]

A TFA salt of the title compound was prepared in a manner similar to EXAMPLE 257 using 2-(4-bromo-3,5-dimethyl-1H-pyrazol-1-yl)-1-(3-hydroxyazetidin-1-yl)ethanone in place of N-(5-bromo-6-methylpyridin-2-yl)methanesulfonamide. ¹H NMR (400 MHz, CD₃OD) δ ppm 2.19 (s, 3H), 2.16 (s, 3H), 3.85 (dd, J=10.99, 3.92 Hz, 1H), 4.06 (ddd, J=9.47, 4.29, 1.14 Hz, 1H), 4.29 (dd, J=10.61, 6.82 Hz, 1H), 4.43-4.55 (m, 1H), 4.65 (tt, J=6.82, 4.42 Hz, 1H), 7.22 (d, J=1.26 Hz, 1H), 7.88 (s, 1H), 7.98 (d, J=1.01 Hz, 1H); ESI-MS m/z [M+H]⁺ calc'd for $C_{18}H_{18}F_3N_5O_2$, 394.1. found 394.21.

Example 367

2-(3,5-dimethyl-4-(6-(trifluoromethyl)-1H-indazol-4-yl)-1H-pyrazol-1-yl)-N-methylacetamide

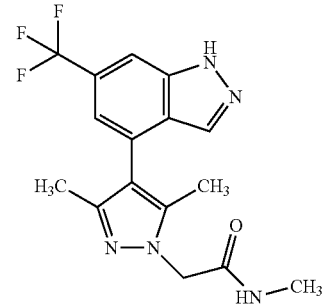 [SMILES: CNC(=O)Cn1nc(C)c(-c2cc(C(F)(F)F)cc3[nH]ncc23)c1C]

A TFA salt of the title compound was prepared in a manner similar to EXAMPLE 257 using 2-(4-bromo-3,5- dimethyl-1H-pyrazol-1-yl)-N-methylacetamide in place of N-(5-bromo-6-methylpyridin-2-yl)methanesulfonamide. ¹H NMR (400 MHz, CD₃OD) δ ppm 2.20 (s, 3H), 2.17 (s, 3H), 2.81 (s, 3H), 4.85 (s, 2H), 7.24 (d, J=1.26 Hz, 1H), 7.88 (s, 1H), 8.00 (d, J=1.01 Hz, 1H); ESI-MS m/z [M+H]⁺ calc'd for C₁₆H₁₆F₃N₅O, 352.1. found 352.16.

Example 368

N-(2-hydroxyethyl)-4-methyl-3-(6-(trifluoromethyl)-1H-indazol-4-yl)benzamide

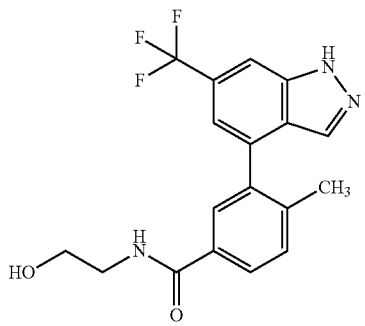 [SMILES: Cc1ccc(C(=O)NCCO)cc1-c1cc(C(F)(F)F)cc2[nH]ncc12]

A TFA salt of the title compound was prepared in a manner similar to EXAMPLE 270 using methyl 4-methyl-3-(6-(trifluoromethyl)-1H-indazol-4-yl)benzoate in place of methyl 5-(6-(trifluoromethyl)-1H-indazol-4-yl)picolinate. ¹H NMR (400 MHz, DMSO-d₆) δ ppm 2.18 (s, 3H), 3.49 (q, J=6.06 Hz, 2H), 4.71 (t, J=5.68 Hz, 1H), 7.29 (s, 1H), 7.49 (d, J=8.08 Hz, 1H), 7.76-7.93 (m, 3H), 7.99 (s, 1H), 8.47 (t, J=5.43 Hz, 1H), 13.72 (br s, 1H); ESI-MS m/z [M+H]⁺ calc'd for C₁₈H₁₆F₃N₃O₂, 364.1. found 364.2.

Example 369

(3-hydroxyazetidin-1-yl)(4-methyl-3-(6-(trifluoromethyl)-1H-indazol-4-yl)phenyl)methanone

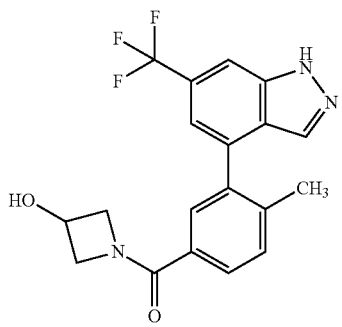 [SMILES: Cc1ccc(C(=O)N2CC(O)C2)cc1-c1cc(C(F)(F)F)cc2[nH]ncc12]

A TFA salt of the title compound was prepared in a manner similar to EXAMPLE 361 using methyl 4-methyl-3-(6-(trifluoromethyl)-1H-indazol-4-yl)benzoate in place of methyl 3-methyl-4-(6-(trifluoromethyl)-1H-indazol-4-yl)benzoate. ¹H NMR (400 MHz, DMSO-d₆) δ ppm 2.19 (s, 3H), 3.78 (d, J=9.85 Hz, 1H), 4.06 (br s, 1H), 4.24 (br s, 1H), 4.42-4.57 (m, 2H), 5.74 (d, J=5.81 Hz, 1H), 7.29 (s, 1H), 7.43-7.61 (m, 2H), 7.64 (dd, J=7.83, 1.77 Hz, 1H), 7.91 (s, 1H), 7.98 (s, 1H), 13.73 (br s, 1H); ESI-MS m/z [M+H]⁺ calc'd for C₁₉H₁₆F₃N₃O₂, 376.1. found 376.21.

Example 370

(3-hydroxypyrrolidin-1-yl)(4-methyl-3-(6-(trifluoromethyl)-1H-indazol-4-yl)phenyl)methanone

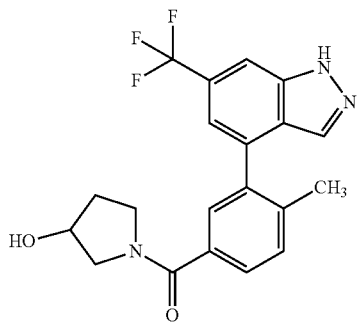 [SMILES: Cc1ccc(C(=O)N2CCC(O)C2)cc1-c1cc(C(F)(F)F)cc2[nH]ncc12]

To a microwave vial charged with pyrrolidin-3-ol (0.109 g, 1.256 mmol) in dioxane (8 mL) was added trimethylaluminum (0.628 mL, 1.256 mmol) in toluene dropwise at room temperature. After stirring for 5 minutes at room temperature, methyl 4-methyl-3-(6-(trifluoromethyl)-1H-indazol-4-yl)benzoate (0.07 g, 0.209 mmol) was added. The reaction mixture was heated at 110° C. for 1 hour in a microwave reactor and then transferred to a round bottom flask. The reaction was quenched with concentrated HCl and the mixture concentrated. The residue was purified by preparative HPLC, eluting with 35% acetonitrile (containing 0.035% TFA) in H₂O (containing 0.05% TFA) over a period of 5 minutes. The product-containing fractions were combined and the volatiles removed in vacuo to give a TFA salt of the title compound as a clear film. ESI-MS m/z [M+H]⁺ calc'd for C₂₀H₁₈F₃N₃O₂, 390.1. found 390.21.

Example 371

(3-(hydroxymethyl)pyrrolidin-1-yl)(4-methyl-3-(6-(trifluoromethyl)-1H-indazol-4-yl)phenyl)methanone

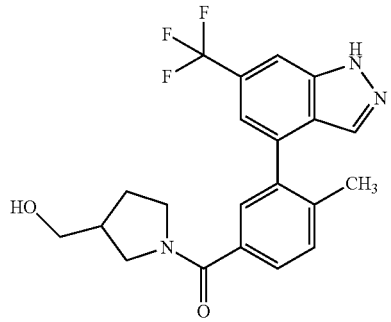 [SMILES: Cc1ccc(C(=O)N2CCC(CO)C2)cc1-c1cc(C(F)(F)F)cc2[nH]ncc12]

A TFA salt of the title compound was prepared in a manner similar to EXAMPLE 370 using pyrrolidin-3-ylmethanol in place of pyrrolidin-3-ol. ¹H NMR (400 MHz, DMSO-d₆) δ ppm 1.53-1.72 (m, 1H), 1.79-1.98 (m, 2H), 2.12-2.22 (m, 4H), 2.26-2.38 (m, 2H), 7.29 (s, 1H), 7.37-7.50 (m, 2H), 7.50-7.60 (m, 1H), 7.90 (s, 1H), 7.97 (s, 1H), 13.71 (br s, 1H); ESI-MS m/z [M+H]+ calc'd for C21H20F3N3O2, 404.2. found 404.21.

Example 372

(4-hydroxypiperidin-1-yl)(4-methyl-3-(6-(trifluoromethyl)-1H-indazol-4-yl)phenyl)methanone

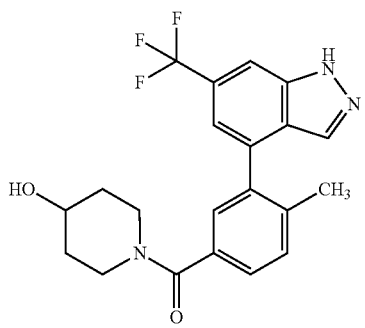 [SMILES: Cc1ccc(C(=O)N2CCC(O)CC2)cc1-c1cc(C(F)(F)F)cc2[nH]ncc12]

A TFA salt of the title compound was prepared in a manner similar to EXAMPLE 370 using piperidin-4-ol in place of pyrrolidin-3-ol. ¹H NMR (400 MHz, DMSO-d6) δ ppm 1.36 (br s, 1H), 1.65-1.80 (m, 2H), 1.96 (d, J=14.40 Hz, 1H), 2.19 (s, 3H), 3.46 (br s, 1H), 3.61 (br s, 1H), 3.72 (br s, 1H), 5.21-5.30 (m, 1H), 7.25-7.34 (m, 1H), 7.34-7.54 (m, 3H), 7.82-7.94 (m, 1H), 7.97 (s, 1H); ESI-MS m/z [M+H]+ calc'd for C21H20F3N3O2, 404.2. found 404.21.

Example 373

1-methyl-5-(6-(trifluoromethyl)-1H-indazol-4-yl)pyridin-2(1H)-one

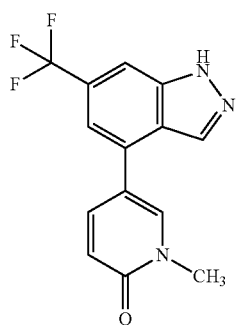 [SMILES: Cn1cc(-c2cc(C(F)(F)F)cc3[nH]ncc23)ccc1=O]

The title compound was prepared in a manner similar to EXAMPLE 265 using 5-bromo-1-methylpyridin-2(1H)-one in place of methyl 5-iodo-6-oxo-1,6-dihydropyridine-3-carboxylate. ¹H NMR (400 MHz, CD3OD) δ ppm 8.34 (s, 1H), 8.14 (d, J=4.0 Hz, 1H), 7.98 (dd, J=4.0, 8.0 Hz, 1H), 7.87 (s, 1H), 7.42 (s, 1H), 6.73 (d, J=8.0 Hz, 1H), 3.70 (s, 3H); ESI-MS m/z [M+H]+ calc'd for C14H10F3N3O, 294.1. found 294.2.

Example 374

2-(2-oxo-5-(6-(trifluoromethyl)-1H-indazol-4-yl)pyridin-1(2H)-yl)acetic acid

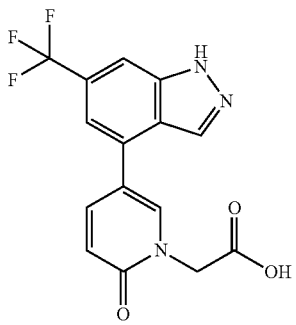 [SMILES: O=C(O)Cn1cc(-c2cc(C(F)(F)F)cc3[nH]ncc23)ccc1=O]

The title compound was prepared in a manner similar to EXAMPLE 265 using methyl 2-(5-bromo-2-oxopyridin-1(2H)-yl)acetate in place of methyl 5-iodo-6-oxo-1,6-dihydropyridine-3-carboxylate. ¹H NMR (400 MHz, CD3OD) δ ppm 8.34 (s, 1H), 8.13 (d, J=4.0 Hz, 1H), 8.01 (dd, J=4.0, 8.0 Hz, 1H), 7.88 (s, 1H), 7.43 (s, 1H), 6.76 (d, J=8.0 Hz, 1H); ESI-MS m/z [M+H]+ calc'd for C15H10F3N3O3, 338.1. found 338.2.

Example 375

1-methyl-5-(4-methylpiperazine-1-carbonyl)-3-(6-(trifluoromethyl)-1H-indazol-4-yl)pyridin-2(1H)-one

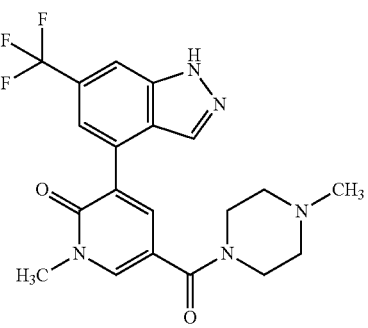 [SMILES: CN1CCN(C(=O)c2cc(-c3cc(C(F)(F)F)cc4[nH]ncc34)c(=O)n(C)c2)CC1]

The title compound was prepared in a manner similar to EXAMPLE 265 using 3-iodo-1-methyl-5-(4-methylpiperazine-1-carbonyl)pyridin-2(1H)-one in place of methyl 5-iodo-6-oxo-1,6-dihydropyridine-3-carboxylate. ¹H NMR (400 MHz, CD3OD) δ ppm 8.12 (s, 1H), 8.08 (d, J=4.0 Hz, 1H), 7.90 (s, 1H), 7.85 (d, J=4.0 Hz, 1H), 7.58 (s, 1H), 3.67-3.77 (m, 7H), 2.46-2.54 (m, 4H), 2.33 (s, 3H); ESI-MS m/z [M+H]+ calc'd for C20H20F3N5O2, 420.2. found 420.4.

Example 376

2,5-difluoro-4-(6-(trifluoromethyl)-1H-indazol-4-yl)benzenesulfonamide

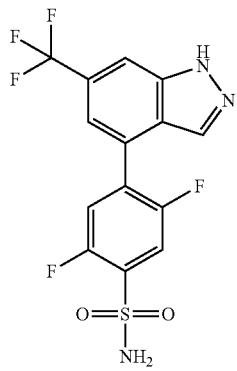 [SMILES: NS(=O)(=O)c1cc(F)c(-c2cc(C(F)(F)F)cc3[nH]ncc23)cc1F]

A TFA salt of the title compound was prepared in a manner similar to EXAMPLE 342 using 4-bromo-2,5-difluorobenzenesulfonamide in place of 4-bromo-3-fluorobenzenesulfonamide. $^1$H NMR (400 MHz, DMSO-d$_6$) δ ppm 7.57 (s, 1H), 7.74-7.79 (m, 1H), 7.86 (dd, J=10.23, 5.68 Hz, 1H), 7.96 (s, 1H), 8.08 (s, 1H), 8.20 (s, 1H); ESI-MS m/z [M+H]$^+$ calc'd for $C_{14}H_8F_5N_3O_2S$, 378.0. found 378.2.

Example 377

6-methyl-5-(6-(trifluoromethyl)-1H-indazol-4-yl)picolinonitrile

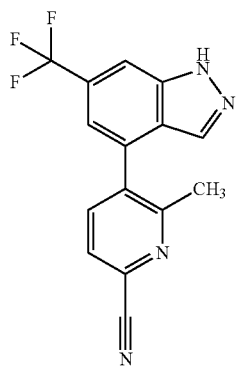 [SMILES: Cc1nc(C#N)ccc1-c1cc(C(F)(F)F)cc2[nH]ncc12]

A mixture of 4-(6-chloro-2-methylpyridin-3-yl)-6-(trifluoromethyl)-1H-indazole (0.97 g, 3.11 mmol), dicyanozinc (1.462 g, 12.45 mmol), and tetrakis(triphenylphoshine)palladium(0) (0.360 g, 0.311 mmol) in DMF (15 mL) was thoroughly degassed by nitrogen and stirred at 120° C. for 24 hours. The reaction mixture was subsequently cooled and diluted with EtOAc then washed with brine. The organic layer was dried over Na$_2$SO$_4$ and concentrated in vacuo. The residue was purified by CombiFlash® chromatography, eluting with a gradient of 0-100% EtOAc in hexane. The product-containing fractions were combined and concentrated in vacuo to give the title compound as a white solid (0.32 g, 34%). $^1$H NMR (400 MHz, DMSO-d$_6$) δ ppm 2.39 (s, 3H), 7.45 (d, J=1.01 Hz, 1H), 7.90-8.16 (m, 4H), 13.81 (s, 1H); ESI-MS m/z [M+H]$^+$ calc'd for $C_{15}H_9F_3N_4$, 303.1. found 303.18.

Example 378

N-(2-hydroxyethyl)-5-(6-(trifluoromethyl)-1H-indazol-4-yl)pyridine-2-sulfonamide

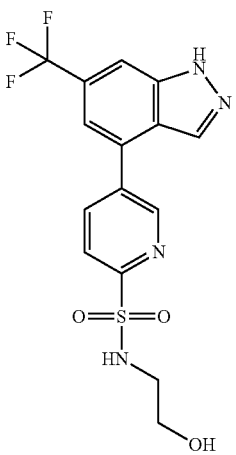 [SMILES: O=S(=O)(NCCO)c1ccc(-c2cc(C(F)(F)F)cc3[nH]ncc23)cn1]

4-(4,4,5,5-Tetramethyl-1,3,2-dioxaborolan-2-yl)-6-(trifluoromethyl)-1H-indazole (40 mg, 0.128 mmol), 5-bromo-N-(2-hydroxyethyl)pyridine-2-sulfonamide (43.2 mg, 0.154 mmol), PdCl$_2$(dppf) (9.38 mg, 0.013 mmol), sodium bicarbonate (0.274 mL, 0.513 mmol), and dioxane (2 mL) were mixed in a 10 mL vial to give an orange suspension. The vial was sealed and then heated to 140° C. for 20 minutes in a microwave reactor. The reaction mixture was subsequently filtered and the product was purified by preparative HPLC, eluting with a gradient of 25-50% ACN (containing 0.035% TFA) in H$_2$O (containing 0.05% TFA). The pure fractions were lyophilized to give a TFA salt of the title compound as a white solid (16.4 mg, 25.6%). $^1$H NMR (400 MHz, DMSO-d$_6$) δ ppm 3.05 (q, J=6.48 Hz, 2H), 3.40-3.46 (m, 7H), 7.70 (d, J=1.01 Hz, 1H), 7.96 (t, J=5.81 Hz, 1H), 8.08 (dd, J=8.21, 0.88 Hz, 2H), 8.45 (s, 1H), 8.51 (dd, J=8.21, 2.40 Hz, 1H), 9.15 (dd, J=2.27, 1.01 Hz, 1H); ESI-MS m/z [M+H]$^+$ calc'd for $C_{15}H_{13}F_3N_4O_3S$, 387.1. found 387.2.

Example 379

6-methyl-5-(6-(trifluoromethyl)-1H-indazol-4-yl)picolinamide

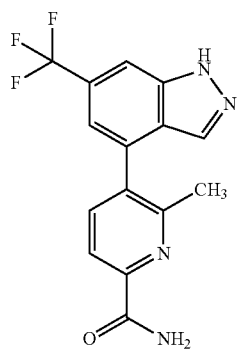 [SMILES: Cc1nc(C(N)=O)ccc1-c1cc(C(F)(F)F)cc2[nH]ncc12]

6-Methyl-5-(6-(trifluoromethyl)-1H-indazol-4-yl)picolinonitrile (0.02 g, 0.066 mmol) in acetic acid (2 mL) and H₂SO₄ (2 mL) was stirred at room temperature for 18 hours. The reaction mixture was subsequently poured into a conical flask containing ice and was carefully neutralized with NaHCO₃ and extracted into DCM. The organic layer was dried over Na₂SO₄ and concentrated in vacuo. The residue was purified by preparative HPLC (Waters SunFire C18, 5 μm, 30 mm ID×75 mm column) eluting with a gradient of 45-55% ACN (containing 0.035% TFA) in water (containing 0.05% TFA) to give the title compound as white solid (0.32 g, 34%). ¹H NMR (400 MHz, DMSO-d₆) δ ppm 2.42 (s, 3H), 7.42 (d, J=1.26 Hz, 1H), 7.73 (br s, 1H), 7.90-8.08 (m, 3H), 8.14 (br s, 1H); ESI-MS m/z [M+H]⁺ calc'd for C₁₅H₁₁F₃N₄O, 321.1. found 321.2.

Example 380

4-(3,5-dimethyl-1-((3-methyloxetan-3-yl)methyl)-1H-pyrazol-4-yl)-6-(trifluoromethyl)-1H-indazole

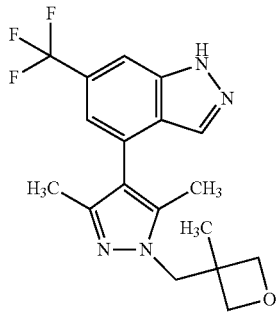 [SMILES: Cc1nn(CC2(C)COC2)c(C)c1-c1cc(C(F)(F)F)cc2[nH]ncc12]

To a 5 mL vial equipped with a magnetic stir bar were added 4-(4,4,5,5-tetramethyl-1,3,2-dioxaborolan-2-yl)-6-(trifluoromethyl)-1H-indazole (41.6 mg, 0.133 mmol), 4-bromo-3,5-dimethyl-1-((3-methyloxetan-3-yl)methyl)-1H-pyrazole (51.8 mg, 0.2 mmol), sodium bicarbonate (0.285 mL, 0.533 mmol), PdCl₂(dppf) (9.76 mg, 0.013 mmol), and dioxane (3 mL). The contents of the vial were stirred to give an orange suspension. The vial was sealed and then heated in a microwave reactor at 140° C. for 90 minutes. The reaction mixture was subsequently filtered and the product was purified by preparative HPLC, eluting with a gradient of 25-50% ACN (containing 0.035% TFA) in H₂O (containing 0.05% TFA). The pure fractions were lyophilized to give a TFA salt of the title compound as a clear glass (6.9 mg, 11%). ¹H NMR (400 MHz, CD₃OD) δ ppm 1.46 (s, 3H), 2.37 (s, 6H), 3.71 (s, 2H), 4.31 (d, J=11.37 Hz, 2H), 4.58 (d, J=11.37 Hz, 2H), 7.39 (d, J=1.01 Hz, 1H), 8.04-8.06 (m, 1H), 8.07 (d, J=0.76 Hz, 1H); ESI-MS m/z [M+H]⁺ calc'd for C₁₈H₁₉F₃N₄O, 365.2. found 365.3.

Example 381

1,5-dimethyl-4-(6-(trifluoromethyl)-1H-indazol-4-yl)-1H-pyrazol-3-amine

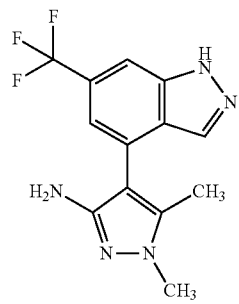

A TFA salt of the title compound was prepared in a manner similar to EXAMPLE 342 using 4-bromo-1,5-dimethyl-1H-pyrazol-3-amine in place of 4-bromo-3-fluorobenzenesulfonamide. ¹H NMR (400 MHz, CD₃OD) δ ppm 2.24 (s, 3H), 3.81 (s, 3H), 7.32 (d, J=1.01 Hz, 1H), 7.92-7.94 (m, 1H), 8.06 (d, J=1.01 Hz, 1H); ESI-MS m/z [M+H]⁺ calc'd for C₁₃H₁₂F₃N₅, 296.1. found 296.2.

Example 382

5-methyl-6-(6-(trifluoromethyl)-1H-indazol-4-yl)-3H-imidazo[4,5-b]pyridin-2-ol

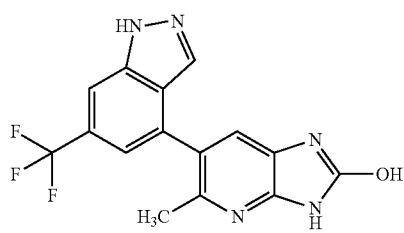 [SMILES: Cc1nc2[nH]c(O)nc2cc1-c1cc(C(F)(F)F)cc2[nH]ncc12]

A TFA salt of the title compound was prepared in a manner similar to EXAMPLE 257 using 6-bromo-5-methyl-3H-imidazo[4,5-b]pyridin-2-ol in place of N-(5-bromo-6-methylpyridin-2-yl)methanesulfonamide. ¹H NMR (400 MHz, Dioxane) δ ppm 2.23 (s, 3H), 7.15 (s, 1H), 7.29 (s, 1H), 7.95 (d, J=9.60 Hz, 2H), 10.81 (s, 1H), 11.37 (s, 1H), 13.67 (s, 1H); ESI-MS m/z [M+H]⁺ calc'd for C₁₅H₁₀F₃N₅O, 334.1. found 334.3.

Example 383

4-(2-methyl-6-(4H-1,2,4-triazol-4-yl)pyridin-3-yl)-6-(trifluoromethyl)-1H-indazole

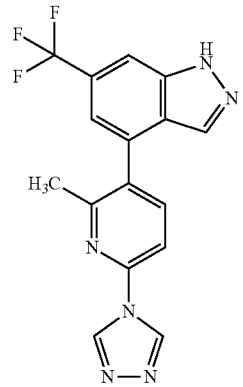 [SMILES: Cc1nc(-n2cnnc2)ccc1-c1cc(C(F)(F)F)cc2[nH]ncc12]

A TFA salt of the title compound was prepared in a manner similar to EXAMPLE 265 using 3-bromo-2-methyl-6-(4H-1,2,4-triazol-4-yl)pyridine in place of methyl 5-iodo-6-oxo-1,6-dihydropyridine-3-carboxylate. ¹H NMR (400 MHz, CD₃OD) δ ppm 9.48 (s, 2H), 7.99-8.04 (m, 2H), 7.94 (s, 1H), 7.79 (d, J=8.0 Hz, 1H), 7.38 (s, 1H), 2.47 (s, 3H); ESI-MS m/z [M+H]⁺ calc'd for C₁₆H₁₁F₃N₆, 345.1. found 345.3.

Example 384

4-(2-methyl-6-(pyrrolidin-1-yl)pyridin-3-yl)-6-(trifluoromethyl)-1H-indazole

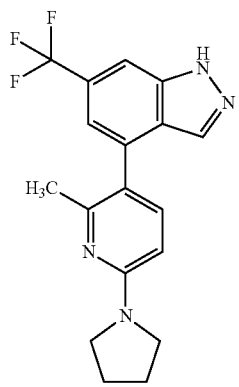 [SMILES: Cc1nc(N2CCCC2)ccc1-c1cc(C(F)(F)F)cc2[nH]ncc12]

A TFA salt of the title compound was prepared in a manner similar to EXAMPLE 265 using 3-bromo-2-methyl-6-(pyrrolidin-1-yl)pyridine in place of methyl 5-iodo-6-oxo-1,6-dihydropyridine-3-carboxylate. $^1$H NMR (400 MHz, CD$_3$OD) δ ppm 7.91-8.04 (m, 3H), 7.37 (s, 1H), 7.07 (d, J=8.0 Hz, 1H), 3.67-3.77 (m, 4H), 2.45 (s, 3H), 2.15-2.27 (m, 4H); ESI-MS m/z [M+H]$^+$ calc'd for C$_{18}$H$_{17}$F$_3$N$_4$, 347.1. found 347.4.

Example 385

(3-hydroxyazetidin-1-yl)(4-(6-(trifluoromethyl)-1H-indazol-4-yl)pyridin-2-yl)methanone

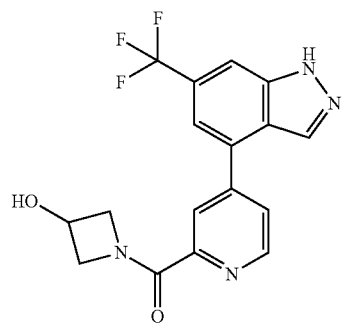 [SMILES: O=C(c1cc(-c2cc(C(F)(F)F)cc3[nH]ncc23)ccn1)N1CC(O)C1]

A TFA salt of the title compound was prepared in a manner similar to EXAMPLE 283 using azetidin-3-ol HCl in place of ammonium chloride. $^1$H NMR (400 MHz, DMSO-d$_6$) δ ppm 3.85 (dd, J=10.74, 4.17 Hz, 1H), 4.22-4.43 (m, 2H), 4.48-4.60 (m, 1H), 4.72-4.87 (m, 1H), 7.62-7.69 (m, 1H), 7.98 (dd, J=5.05, 1.77 Hz, 1H), 8.08 (s, 1H), 8.26 (s, 1H), 8.39 (s, 1H), 8.79 (d, J=4.80 Hz, 1H); ESI-MS m/z [M+H]$^+$ calc'd for C$_{17}$H$_{13}$F$_3$N$_4$O$_2$, 363.1. found 363.14.

Example 386

2-(3,5-dimethyl-4-(6-(trifluoromethyl)-1H-indazol-4-yl)-1H-pyrazol-1-yl)-N-(2-hydroxyethyl)acetamide

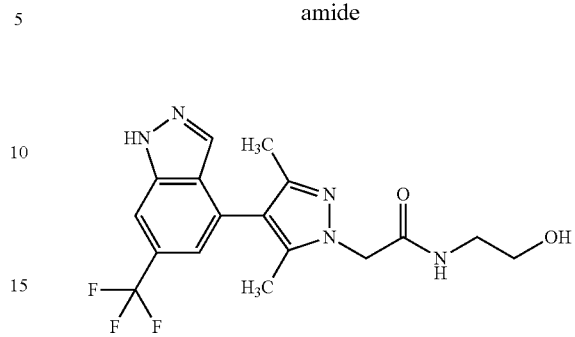

To a mixture of 4-(4,4,5,5-tetramethyl-1,3,2-dioxaborolan-2-yl)-6-(trifluoromethyl)-1H-indazole (0.1 g, 0.320 mmol), 2-(4-bromo-3,5-dimethyl-1H-pyrazol-1-yl)-N-(2-hydroxyethyl)acetamide (0.133 g, 0.481 mmol) and PdCl$_2$(dppf) (0.012 g, 0.016 mmol) in dioxane (10 mL) was added aqueous saturated NaHCO$_3$ (3 mL). The resulting light yellow suspension was heated at 140° C. for 60 minutes in a microwave reactor. The reaction mixture was subsequently concentrated and the residue was purified by preparative HPLC, eluting with a gradient of 25-30% acetonitrile (containing 0.035% TFA) in H$_2$O (containing 0.05% TFA) over a period of 5.5 minutes. The product-containing fractions were combined and solvent removed by rotary evaporation. The product was lyophilized and then dissolved in MeOH (4 mL). Aqueous NaOH (1N, 0.3 mL) was added and the mixture was stirred for 1 hour at room temperature. The mixture was acidified with concentrated HCl. The solution was concentrated by rotary evaporation and then diluted with EtOAc and water. The organic layer was concentrated to give an HCl salt of the title compound as a light yellow solid (6.8 mg, 5.6%). $^1$H NMR (400 MHz, DMSO-d$_6$) δ ppm 2.09 (s, 3H), 2.15 (s, 3H), 3.19 (q, J=5.73 Hz, 2H), 3.39-3.48 (m, 2H), 4.77 (s, 2H), 7.14 (d, J=1.26 Hz, 1H), 7.87 (s, 1H), 7.96 (s, 1H), 8.12-8.24 (m, 1H); ESI-MS m/z [M+H]$^+$ calc'd for C$_{17}$H$_{18}$F$_3$N$_5$O$_2$, 382.1. found 382.21.

Example 387

N-(2-hydroxyethyl)-6-methyl-5-(6-(trifluoromethyl)-1H-indazol-4-yl)picolinamide

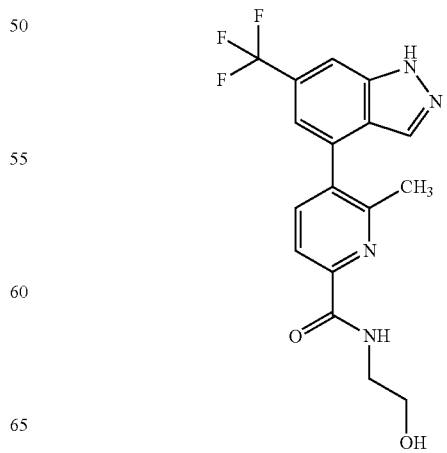

To 6-methyl-5-(6-(trifluoromethyl)-1H-indazol-4-yl)picolinic acid (1.6 g, 4.98 mmol) in DMF (20 mL) were added HOBt (0.942 g, 6.97 mmol), EDC (1.432 g, 7.47 mmol), 2-aminoethanol (0.913 g, 14.94 mmol), followed by N-ethyl-N-isopropylpropan-2-amine (4.34 mL, 24.90 mmol). The reaction mixture was stirred for 16 hours at room temperature, was subsequently diluted with EtOAc and was washed with brine. Volatiles were evaporated from the organic phase and the residue was purified by Combi-Flash® chromatography, eluting with a gradient of 0-20% MeOH in DCM. The product-containing fractions were combined and concentrated in vacuo to give the title compound as a white solid (0.658 g, 36.3%). ¹H NMR (400 MHz, DMSO-d₆) δ ppm 2.43 (s, 3H), 3.44 (q, J=5.98 Hz, 2H), 3.57 (t, J=5.94 Hz, 2H), 7.38-7.44 (m, 1H), 7.90-8.07 (m, 4H), 8.70 (t, J=5.81 Hz, 1H); ESI-MS m/z [M+H]⁺ calc'd for C₁₇H₁₅F₃N₄O₂, 365.1. found 365.2.

Example 388

4-(7-methylimidazo[1,5-a]pyridin-6-yl)-6-(trifluoromethyl)-1H-indazole

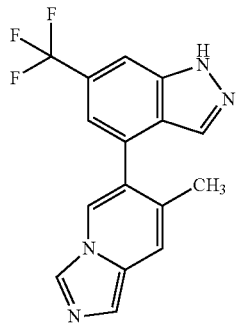 [SMILES: Cc1cc2cncn2cc1-c1cc(C(F)(F)F)cc2[nH]ncc12]

A TFA salt of the title compound was prepared in a manner similar to EXAMPLE 257 using 6-bromo-7-methylimidazo[1,5-a]pyridine in place of N-(5-bromo-6-methylpyridin-2-yl)methanesulfonamide. ¹H NMR (400 MHz, CD₃OD) δ ppm 2.37 (s, 3H), 7.48 (d, J=1.26 Hz, 1H), 7.94 (s, 1H), 8.02 (d, J=1.01 Hz, 1H), 8.04 (d, J=2.02 Hz, 1H), 8.07-8.11 (m, 1H), 8.17 (d, J=1.77 Hz, 1H), 8.85 (s, 1H); ESI-MS m/z [M+H]⁺ calc'd for C₁₆H₁₁F₃N₄, 317.1. found 317.3.

Example 389

6-methyl-5-(6-(trifluoromethyl)-1H-indazol-4-yl)pyridin-2(1H)-one

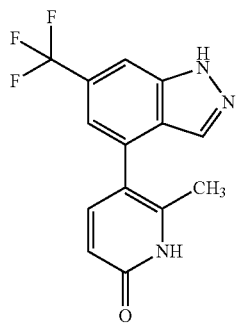 [SMILES: Cc1[nH]c(=O)ccc1-c1cc(C(F)(F)F)cc2[nH]ncc12]

A TFA salt of the title compound was prepared in a manner similar to EXAMPLE 257 using 5-bromo-6-methylpyridin-2-ol in place of N-(5-bromo-6-methylpyridin-2-yl)methanesulfonamide. ¹H NMR (400 MHz, CD₃OD) δ ppm 2.23 (s, 3H), 6.55 (d, J=9.35 Hz, 1H), 7.29 (d, J=1.26 Hz, 1H), 7.65 (d, J=9.35 Hz, 1H), 7.93 (s, 1H), 8.00 (d, J=1.01 Hz, 1H); ESI-MS m/z [M+H]⁺ calc'd for C₁₄H₁₀F₃N₃O, 294.1. found 294.3.

Example 390

4-methyl-5-(6-(trifluoromethyl)-1H-indazol-4-yl)pyridin-2(1H)-one

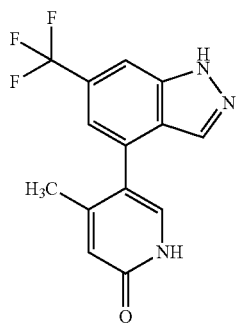 [SMILES: Cc1cc(=O)[nH]cc1-c1cc(C(F)(F)F)cc2[nH]ncc12]

A TFA salt of the title compound was prepared in a manner similar to EXAMPLE 257 using 5-bromo-4-methylpyridin-2-ol in place of N-(5-bromo-6-methylpyridin-2-yl)methanesulfonamide. ¹H NMR (400 MHz, CD₃OD) δ ppm 2.06 (d, J=1.01 Hz, 3H), 6.55 (d, J=0.76 Hz, 1H), 7.18 (d, J=1.01 Hz, 1H), 7.32 (s, 1H), 7.87 (dd, J=5.43, 0.88 Hz, 2H); ESI-MS m/z [M+H]⁺ calc'd for C₁₄H₁₀F₃N₃O, 294.1. found 294.3.

Example 391

6-methoxy-5-(6-(trifluoromethyl)-1H-indazol-4-yl)picolinamide

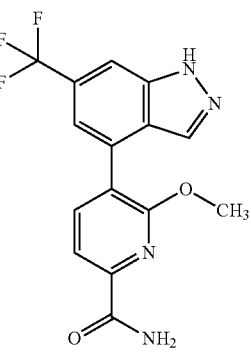

To 6-methoxy-5-(6-(trifluoromethyl)-1H-indazol-4-yl)picolinic acid (0.020 g, 0.059 mmol) in DMF (3 mL) were added ammonium chloride (0.016 g, 0.297 mmol), HOBt (0.011 g, 0.083 mmol), and EDC (0.017 g, 0.089 mmol), followed by N-ethyl-N-isopropylpropan-2-amine (0.052 mL, 0.297 mmol). The reaction mixture was stirred for 1 hour at room temperature. The crude reaction mixture was

Example 392

4-(6-chloro-2-methoxypyridin-3-yl)-6-(trifluoromethyl)-1H-indazole

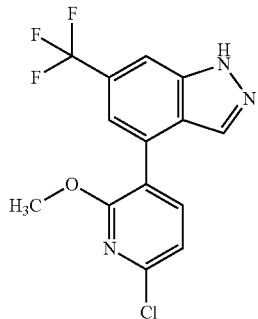 [SMILES: COc1nc(Cl)ccc1-c1cc(C(F)(F)F)cc2[nH]ncc12]

A TFA salt of the title compound was prepared in a manner similar to EXAMPLE 247 using (6-chloro-2-methoxypyridin-3-yl)boronic acid in place of N,N-dimethyl-5-(4,4,5,5-tetramethyl-1,3,2-dioxaborolan-2-yl)pyrimidin-2-amine. ESI-MS m/z [M+H]$^+$ calc'd for $C_{14}H_9ClF_3N_3O$, 328.0. found 328.11.

Example 393

5-methyl-6-(6-(trifluoromethyl)-1H-indazol-4-yl)-[1,2,4]triazolo[1,5-a]pyridine

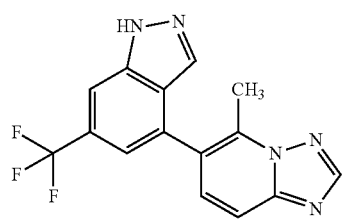 [SMILES: Cc1c(-c2cc(C(F)(F)F)cc3[nH]ncc23)ccc2ncnn12]

A TFA salt of the title compound was prepared in a manner similar to EXAMPLE 257 using 6-bromo-5-methyl-[1,2,4]triazolo[1,5-a]pyridine in place of N-(5-bromo-6-methylpyridin-2-yl)methanesulfonamide. $^1$H NMR (400 MHz, CD$_3$OD) δ ppm 2.74 (s, 3H), 7.44-7.47 (m, 1H), 7.89 (br s, 2H), 7.96-8.08 (m, 3H); ESI-MS m/z [M+H]$^+$ calc'd for $C_{15}H_{10}F_3N_5$, 318.1. found 318.4.

Example 394

N-(2-hydroxyethyl)-6-methoxy-5-(6-(trifluoromethyl)-1H-indazol-4-yl)picolinamide

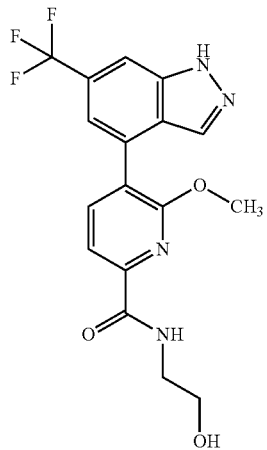 [SMILES: COc1nc(C(=O)NCCO)ccc1-c1cc(C(F)(F)F)cc2[nH]ncc12]

The title compound was prepared in a manner similar to EXAMPLE 391 using 2-aminoethanol in place of ammonium chloride. $^1$H NMR (400 MHz, CD$_3$OD) δ ppm 3.61 (t, J=5.68 Hz, 2H), 3.77 (t, J=5.68 Hz, 2H), 4.06 (s, 3H), 7.47 (d, J=1.01 Hz, 1H), 7.88 (d, J=7.58 Hz, 1H), 7.94 (s, 1H), 8.02 (t, J=7.33 Hz, 2H); ESI-MS m/z [M+H]$^+$ calc'd for $C_{17}H_{15}F_3N_4O_3$, 381.1. found 381.21.

Example 395

(3-hydroxyazetidin-1-yl)(6-methoxy-5-(6-(trifluoromethyl)-1H-indazol-4-yl)pyridin-2-yl)methanone

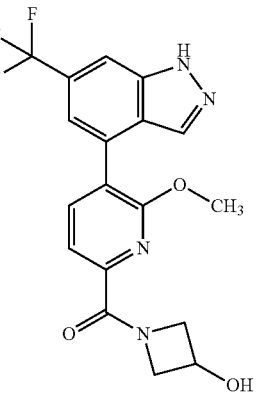

A TFA salt of the title compound was prepared in a manner similar to EXAMPLE 391 using azetidin-3-ol in place of ammonium chloride. ESI-MS m/z [M+H]$^+$ calc'd for $C_{18}H_{15}F_3N_4O_3$, 393.1. found 393.22.

--- purified by preparative HPLC, eluting with a gradient of 30-40% acetonitrile (containing 0.035% TFA) in H$_2$O (containing 0.05% TFA) over a period of 7 minutes. The product-containing fractions were combined and the volatiles removed in vacuo to give a TFA salt of the title compound as white solid (0.012 g, 60%). $^1$H NMR (400 MHz, DMSO-d$_6$) δ ppm 3.99 (s, 3H), 7.45-7.51 (m, 1H), 7.70-7.83 (m, 1H), 7.98 (s, 1H), 8.03-8.12 (m, 2H), 8.13 (s, 1H); ESI-MS m/z [M+H]$^+$ calc'd for $C_{15}H_{11}F_3N_4O_2$, 337.1. found 337.15.

(Note: The above paragraph belongs at the top of column 213, before Example 392.)

Example 396

6-methoxy-5-(6-(trifluoromethyl)-1H-indazol-4-yl)picolinonitrile

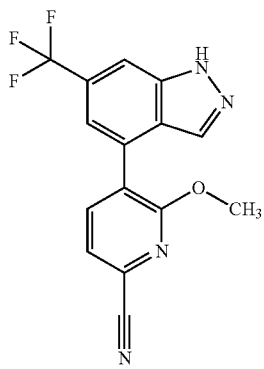

A mixture of 4-(6-chloro-2-methoxypyridin-3-yl)-6-(trifluoromethyl)-1H-indazole (0.71 g, 2.167 mmol), dicyanozinc (1.018 g, 8.67 mmol) and tetrakis(triphenylphoshine)palladium(0) (0.250 g, 0.217 mmol) in DMF (15 mL) was thoroughly degassed with nitrogen and stirred at 100° C. overnight. The reaction mixture was subsequently cooled, diluted with EtOAc, and washed with brine. The organic layer was dried over $Na_2SO_4$ and the volatiles removed by rotary evaporation. The crude residue was purified by preparative HPLC, eluting with a gradient of 60-65% acetonitrile (containing 0.035% TFA) in $H_2O$ (containing 0.05% TFA) over a period of 5 minutes. The product-containing fractions were combined and concentrated to give a TFA salt of the title compound as white solid. $^1$H NMR (400 MHz, $CD_3OD$) δ ppm 3.99 (s, 3H), 7.48 (s, 1H), 7.63 (d, J=7.58 Hz, 1H), 7.96 (s, 1H), 8.00-8.07 (m, 2H); ESI-MS m/z $[M+H]^+$ calc'd for $C_{15}H_9F_3N_4O$, 319.1. found 319.21.

Example 397

(3-hydroxyazetidin-1-yl)(6-methyl-2-(methylamino)-5-(6-(trifluoromethyl)-1H-indazol-4-yl)pyridin-3-yl)methanone

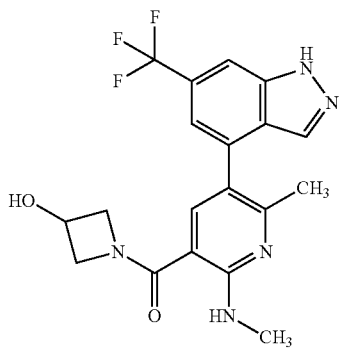 [SMILES: CNc1nc(C)c(-c2cc(C(F)(F)F)cc3[nH]ncc23)cc1C(=O)N1CC(O)C1]

A TFA salt of the title compound was prepared in a manner similar to EXAMPLE 257 using (5-bromo-6-methyl-2-(methylamino)pyridin-3-yl)(3-hydroxyazetidin-1-yl)methanone in place of N-(5-bromo-6-methylpyridin-2-yl)methanesulfonamide. $^1$H NMR (400 MHz, $CD_3OD$) δ ppm 2.42 (s, 3H), 3.18 (s, 3H), 4.03-4.12 (m, 2H), 4.48-4.68 (m, 3H), 7.31-7.39 (m, 1H), 7.91 (s, 1H), 7.96-8.05 (m, 2H); ESI-MS m/z $[M+H]^+$ calc'd for $C_{19}H_{18}F_3N_5O_2$, 406.1. found 406.22.

Example 398

5-methyl-6-(6-(trifluoromethyl)-1H-indazol-4-yl)tetrazolo[1,5-a]pyridine

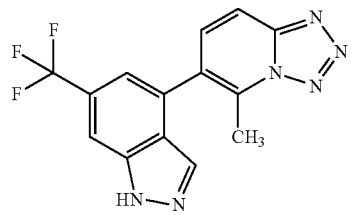 [SMILES: Cc1c(-c2cc(C(F)(F)F)cc3[nH]ncc23)ccc2nnnn12]

To a 20 mL microwave vial was added a mixture of 4-(4,4,5,5-tetramethyl-1,3,2-dioxaborolan-2-yl)-6-(trifluoromethyl)-1H-indazole (50 mg, 0.160 mmol), 6-bromo-5-methyltetrazolo[1,5-a]pyridine (34.1 mg, 0.160 mmol), and $PdCl_2$(dppf) (6.59 mg, 8.01 μmol) in dioxane (4 mL) and aqueous saturated $NaHCO_3$ (2 mL). The resulting yellow suspension was heated at 130° C. for 30 minutes in a microwave reactor. The reaction mixture was subsequently purified by preparative HPLC, eluting with a gradient of 45-65% acetonitrile in $H_2O$ (containing 10 mM $NH_4HCO_3$). The product fractions were combined and dried to give the title compound. $^1$H NMR (400 MHz, $CD_3OD$) δ ppm 2.83 (s, 3H), 7.51 (d, J=1.01 Hz, 1H), 7.91 (d, J=9.09 Hz, 1H), 8.04 (s, 1H), 8.06 (s, 1H), 8.10 (dd, J=9.09, 0.76 Hz, 1H); ESI-MS m/z $[M+H]^+$ calc'd for $C_{14}H_9F_3N_6$, 319.1. found 319.3.

Example 399

4-(6-methyl-5-(6-(trifluoromethyl)-1H-indazol-4-yl)pyridin-2-yl)morpholine

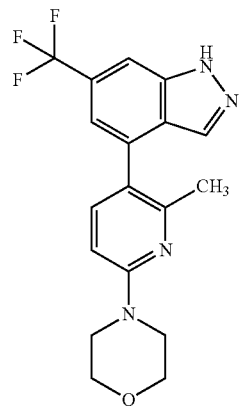 [SMILES: Cc1nc(N2CCOCC2)ccc1-c1cc(C(F)(F)F)cc2[nH]ncc12]

A TFA salt of the title compound was prepared in a manner similar to EXAMPLE 398 using 4-(5-bromo-6-methylpyridin-2-yl)morpholine in place of 6-bromo-5-methyltetrazolo[1,5-a]pyridine (34.1 mg, 0.160 mmol). $^1$H NMR (400 MHz, CD₃OD) δ ppm 2.46 (s, 3H), 3.75-3.82 (m, 4H), 3.86-3.95 (m, 4H), 7.32 (d, J=9.09 Hz, 1H), 7.38 (d, J=1.26 Hz, 1H), 7.99 (d, J=0.76 Hz, 1H), 8.00-8.05 (m, 2H); ESI-MS m/z [M+H]⁺ calc'd for $C_{18}H_{17}F_3N_4O$, 363.1. found 363.3.

Example 400

4-(2-methyl-6-(4-methylpiperazin-1-yl)pyridin-3-yl)-6-(trifluoromethyl)-1H-indazole

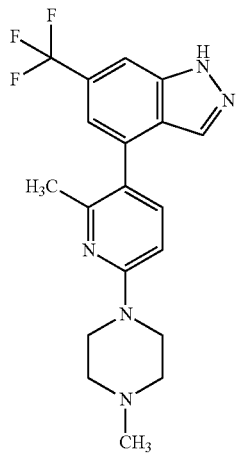 [SMILES: Cc1nc(N2CCN(C)CC2)ccc1-c1cc(C(F)(F)F)cc2[nH]ncc12]

A mixture of 4-(6-chloro-2-methylpyridin-3-yl)-6-(trifluoromethyl)-1H-indazole (20 mg, 0.064 mmol) and 1-methylpiperazine (19.28 mg, 0.192 mmol) in DMF (3 mL) was heated in a microwave reactor at 180° C. for 50 minutes. The reaction mixture was subsequently purified via preparative HPLC, eluting with 20-40% ACN (containing 0.035% TFA) in H₂O (containing 0.05% TFA) to give a TFA salt of the title compound. ¹H NMR (400 MHz, CD₃OD) δ ppm 7.93 (s, 1H), 7.89 (s, 1H), 7.75 (d, J=8.0 Hz, 1H), 7.27 (s, 1H), 7.03 (d, J=8.0 Hz, 1H), 3.00-3.54 (br, 8H), 2.69, (s, 3H), 2.35 (s, 3H); ESI-MS m/z [M+H]⁺ calc'd for $C_{19}H_{20}F_3N_5$, 376.2. found 376.4.

Example 401

1,6-dimethyl-5-(4-methylpiperazine-1-carbonyl)-3-(6-(trifluoromethyl)-1H-indazol-4-yl)pyridin-2(1H)-one

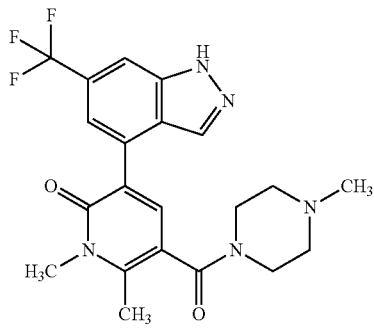 [SMILES: Cc1c(C(=O)N2CCN(C)CC2)cc(-c2cc(C(F)(F)F)cc3[nH]ncc23)c(=O)n1C]

A TFA salt of the title compound was prepared in a manner similar to EXAMPLE 265 using 3-bromo-1,6-dimethyl-5-(4-methylpiperazine-1-carbonyl)pyridin-2(1H)-one in place of methyl 5-iodo-6-oxo-1,6-dihydropyridine-3-carboxylate. ¹H NMR (400 MHz, CD₃OD) δ ppm 8.08 (s, 1H), 7.89 (s, 1H), 7.71 (s, 1H), 7.54 (s, 1H), 3.04-3.83 (br peak, 8H), 3.71 (s, 3H), 2.93 (s, 3H), 2.51 (s, 3H); ESI-MS m/z [M+H]⁺ calc'd for $C_{21}H_{22}F_3N_5O_2$, 434.2. found 434.4.

Example 402

1,6-dimethyl-5-(6-(trifluoromethyl)-1H-indazol-4-yl)pyridin-2(1H)-one

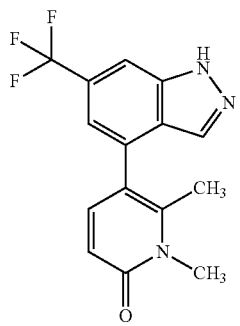 [SMILES: Cc1c(-c2cc(C(F)(F)F)cc3[nH]ncc23)ccc(=O)n1C]

The title compound was prepared in a manner similar to EXAMPLE 265 using 5-bromo-1,6-dimethylpyridin-2(1H)-one in place of methyl 5-iodo-6-oxo-1,6-dihydropyridine-3-carboxylate. ¹H NMR (400 MHz, CD₃OD) δ ppm 7.99 (s, 1H), 7.93 (s, 1H), 7.53 (d, J=8.0 Hz, 1H), 7.27 (s, 1H), 6.61 (d, J=8.0 Hz, 1H), 3.71 (s, 3H), 2.32 (s, 3H); ESI-MS m/z [M+H]⁺ calc'd for $C_{15}H_{12}F_3N_3O$, 308.1. found 308.3.

Example 403

1,4-dimethyl-5-(6-(trifluoromethyl)-1H-indazol-4-yl)pyridin-2(1H)-one

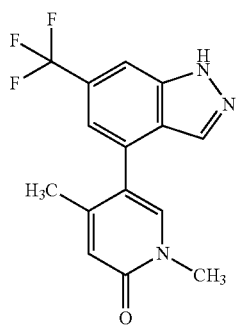 [SMILES: Cc1cc(=O)n(C)cc1-c1cc(C(F)(F)F)cc2[nH]ncc12]

The title compound was prepared in a manner similar to EXAMPLE 265 using 5-bromo-1,4-dimethylpyridin-2(1H)-one in place of methyl 5-iodo-6-oxo-1,6-dihydropyridine-3-carboxylate. ¹H NMR (400 MHz, CD₃OD) δ ppm 8.02 (s, 1H), 7.94 (s, 1H), 7.72 (s, 1H), 7.30 (s, 1H), 6.58 (s, 1, 1H), 3.61 (s, 3H), 2.07 (s, 3H); ESI-MS m/z [M+H]⁺ calc'd for $C_{15}H_{12}F_3N_3O$, 308.1. found 308.3.

Example 404

N-(2-hydroxyethyl)-1,2-dimethyl-6-oxo-5-(6-(trifluoromethyl)-1H-indazol-4-yl)-1,6-dihydropyridine-3-carboxamide

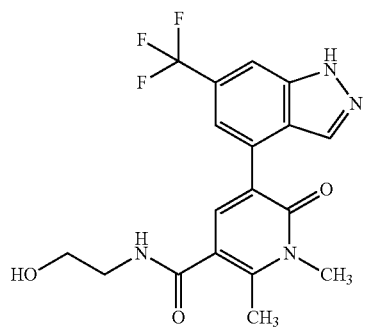 [SMILES: Cc1c(C(=O)NCCO)cc(-c2cc(C(F)(F)F)cc3[nH]ncc23)c(=O)n1C]

The title compound was prepared in a manner similar to EXAMPLE 265 using 5-bromo-N-(2-hydroxyethyl)-1,2-dimethyl-6-oxo-1,6-dihydropyridine-3-carboxamide in place of methyl 5-iodo-6-oxo-1,6-dihydropyridine-3-carboxylate. $^1$H NMR (400 MHz, CD$_3$OD) δ ppm 8.12 (s, 1H), 7.88 (s, 1H), 7.83 (s, 1H), 7.56 (s, 1H), 3.67-3.75 (m, 5H), 3.47 (t, J=4.0, 8.0 Hz, 2H), 2.63 (s, 3H); ESI-MS m/z [M+H]$^+$ calc'd for C$_{18}$H$_{17}$F$_3$N$_4$O$_3$, 395.1. found 395.3.

Example 405

2-(6-methyl-2-oxo-5-(6-(trifluoromethyl)-1H-indazol-4-yl)pyridin-1(2H)-yl)acetonitrile

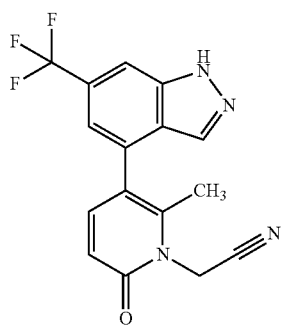 [SMILES: Cc1c(-c2cc(C(F)(F)F)cc3[nH]ncc23)ccc(=O)n1CC#N]

The title compound was prepared in a manner similar to EXAMPLE 265 using 2-(5-bromo-6-methyl-2-oxopyridin-1(2H)-yl)acetonitrile in place of methyl 5-iodo-6-oxo-1,6-dihydropyridine-3-carboxylate. $^1$H NMR (400 MHz, CD$_3$OD) δ ppm 8.02 (s, 1H), 7.93 (s, 1H), 7.55 (d, J=8.0 Hz, 1H), 7.31 (s, 1H), 6.60 (d, J=8.0 Hz, 1H), 4.99 (s, 2H), 2.24 (s, 3H); ESI-MS m/z [M+H]$^+$ calc'd for C$_{16}$H$_{11}$F$_3$N$_4$O, 333.1. found 333.3.

Example 406

4-methyl-1-(pyridin-2-ylmethyl)-5-(6-(trifluoromethyl)-1H-indazol-4-yl)pyridin-2(1H)-one

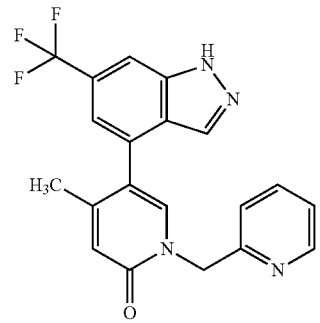 [SMILES: Cc1cc(=O)n(Cc2ccccn2)cc1-c1cc(C(F)(F)F)cc2[nH]ncc12]

A TFA salt of the title compound was prepared in a manner similar to EXAMPLE 265 using 5-bromo-4-methyl-1-(pyridin-2-ylmethyl)pyridin-2(1H)-one in place of methyl 5-iodo-6-oxo-1,6-dihydropyridine-3-carboxylate. $^1$H NMR (400 MHz, CD$_3$OD) δ ppm 8.71 (d, J=4.0 Hz, 1H), 8.29 (t, J=8.0, 8.0 Hz, 1H), 8.09 (s, 1H), 7.96 (s, 1H), 7.92 (s, 1H), 7.71-7.79 (m, 2H), 7.37 (s, 1H), 6.61 (s, 1H), 5.46 (s, 2H), 2.11 (s, 3H); ESI-MS m/z [M+H]$^+$ calc'd for C$_{20}$H$_{15}$F$_3$N$_4$O, 385.1. found 385.4.

Example 407

6-methyl-1-(pyridin-2-ylmethyl)-5-(6-(trifluoromethyl)-1H-indazol-4-yl)pyridin-2(1H)-one

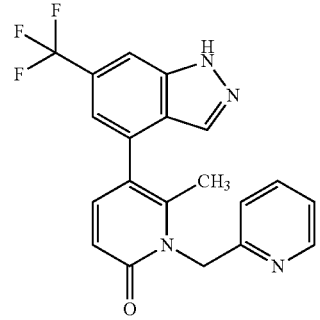 [SMILES: Cc1c(-c2cc(C(F)(F)F)cc3[nH]ncc23)ccc(=O)n1Cc1ccccn1]

A TFA salt of the title compound was prepared in a manner similar to EXAMPLE 265 using 5-bromo-6-methyl-1-(pyridin-2-ylmethyl)pyridin-2(1H)-one in place of methyl 5-iodo-6-oxo-1,6-dihydropyridine-3-carboxylate. $^1$H NMR (400 MHz, CD$_3$OD) δ ppm 8.66 (d, J=4.0 Hz, 1H), 8.15 (d, J=8.0 Hz, 1H), 8.04 (s, 1H), 7.95 (s, 1H), 7.57-7.65 (m, 3H), 7.34 (s, 1H), 6.66 (d, J=8.0 Hz, 1H), 5.68 (s, 2H), 2.33 (s, 3H); ESI-MS m/z [M+H]$^+$ calc'd for C$_{20}$H$_{15}$F$_3$N$_4$O, 385.1. found 385.4.

Example 408

2-(4-methyl-2-oxo-5-(6-(trifluoromethyl)-1H-indazol-4-yl)pyridin-1(2H)-yl)acetonitrile

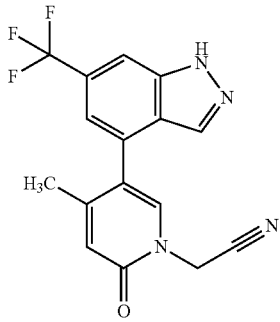 [SMILES: Cc1cc(=O)n(CC#N)cc1-c1cc(C(F)(F)F)cc2[nH]ncc12]

A TFA salt of the title compound was prepared in a manner similar to EXAMPLE 265 using 2-(5-bromo-4-methyl-2-oxopyridin-1(2H)-yl)acetonitrile in place of methyl 5-iodo-6-oxo-1,6-dihydropyridine-3-carboxylate. $^1$H NMR (400 MHz, CD$_3$OD) δ ppm 8.07 (s, 1H), 7.95 (s, 1H), 7.77 (s, 1H), 7.33 (s, 1H), 6.60 (s, 1H), 5.02 (s, 2H), 2.08 (s, 3H); ESI-MS m/z [M+H]$^+$ calc'd for C$_{16}$H$_{11}$F$_3$N$_4$O, 333.1. found 333.3.

Example 409

4-(2-methyl-6-(2-(methylsulfonyl)ethyl)pyridin-3-yl)-6-(trifluoromethyl)-1H-indazole

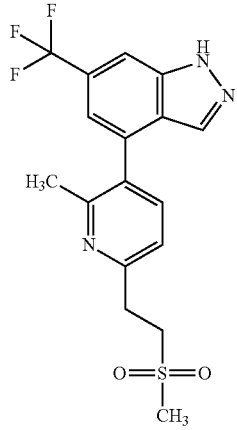 [SMILES: Cc1nc(CCS(C)(=O)=O)ccc1-c1cc(C(F)(F)F)cc2[nH]ncc12]

STEP A: 4-(6-chloro-2-methylpyridin-3-yl)-6-(trifluoromethyl)-1H-indazole

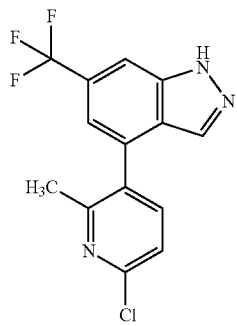

The reaction was carried out in eight microwave vials. To each vial were added 4-bromo-6-(trifluoromethyl)-1H-indazole (0.5 g, 1.886 mmol), (6-chloro-2-methylpyridin-3-yl)boronic acid (0.3875 g, 2.264 mmol) and PdCl$_2$(dppf) (0.069 g, 0.0944 mmol) in dioxane (12 mL) and aqueous saturated NaHCO$_3$ (3 mL). The resulting light-brown suspensions were each heated at 140° C. for 60 minutes in a microwave reactor. The reaction mixtures were combined and concentrated and the crude residue was diluted with EtOAc and washed with water. The volatiles were removed via rotary evaporation and the product purified by CombiFlash® chromatography, eluting with a gradient of 0-100% EtOAc in heptane over a period of 180 minutes. The product-containing fractions were combined and the volatiles removed via rotary evaporation to give the title compound (3.56 g, 76%). ESI-MS m/z [M+H]$^+$ calc'd for C$_{14}$H$_9$ClF$_3$N$_3$, 312.05. found 311.89.

STEP B: 4-(2-methyl-6-(2-(methylsulfonyl)ethyl)pyridin-3-yl)-6-(trifluoromethyl)-1H-indazole To a microwave vial were added of 4-(6-chloro-2-methylpyridin-3-yl)-6-(trifluoromethyl)-1H-indazole (0.33 g, 1.059 mmol), potassium vinyl trifluoroborate (0.312 g, 2.329 mmol), Et$_3$N (0.298 mL, 2.117 mmol) and PdCl$_2$(dppf) (0.077 g, 0.106 mmol) in IPA (12 mL) to give a light-brown suspension. The mixture was bubbled with nitrogen and heated at 100° C. for 30 minutes in a microwave reactor. Sodium methanesulfinate (0.540 g, 5.29 mmol) and acetic acid (0.606 mL, 10.59 mmol) were added and the reaction mixture was stirred at 60° C. for 18 hours and then cooled. The volatiles were evaporated, and the resulting crude residue was purified by LCMS, eluting with 40% ACN in H$_2$O (containing 10 mM NH$_4$HCO$_3$) over a period of 8 minutes. The product-containing fractions were combined and the volatiles were evaporated using a GeneVac™ to give the title compound as white solid (0.192 g, 47.3%). $^1$H NMR (400 MHz, CD$_3$OD) δ ppm 2.41 (s, 3H), 3.05 (s, 3H), 3.35-3.43 (m, 2H), 3.59-3.72 (m, 2H), 7.32 (s, 1H), 7.40 (d, J=7.83 Hz, 1H), 7.75 (d, J=7.83 Hz, 1H), 7.89 (s, 1H), 7.98 (s, 1H); ESI-MS m/z [M+H]$^+$ calc'd for C$_{17}$H$_{16}$F$_3$N$_3$O$_2$S, 384.1. found 384.09.

Example 410

(3-methyl-1-((1-methyl-1H-pyrazol-4-yl)methyl)-4-(6-(trifluoromethyl)-1H-indazol-4-yl)-1H-pyrazol-5-yl)methanol

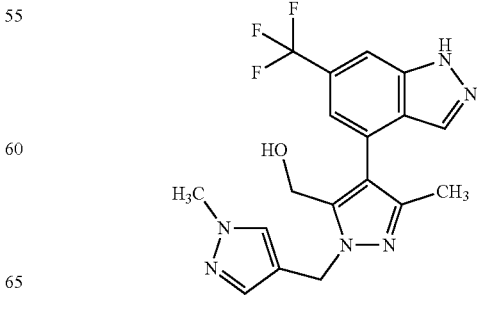

STEP A: ethyl 4-bromo-3-methyl-1-((1-methyl-1H-pyrazol-4-yl)methyl)-1H-pyrazole-5-carboxylate

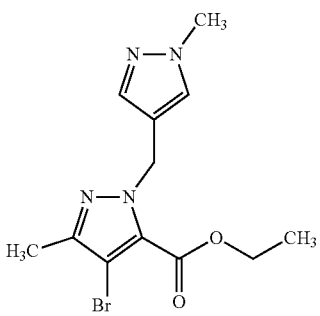 [SMILES: CCOC(=O)c1c(Br)c(C)nn1Cc1cnn(C)c1]

To ethyl 4-bromo-3-methyl-1H-pyrazole-5-carboxylate (2.56 g, 10.98 mmol) in DMF (30 mL) were added Cs$_2$CO$_3$ (8.94 g, 27.4 mmol) and 4-(chloromethyl)-1-methyl-1H-pyrazole, HCl (2.2 g, 13.17 mmol). The reaction mixture was stirred at room temperature for 20 hours and then diluted with water. The product was extracted into EtOAc. The organic phase was dried over Na$_2$SO$_4$ and concentrated. The crude residue was purified by CombiFlash® chromatography (120 g, column) eluting with a gradient of 10-100% EtOAc in heptane over a period of 180 minutes. The product-containing fractions were combined and concentrated to give the title compound (0.82 g, 23%) and a regioisomer, ethyl 4-bromo-5-methyl-1-((1-methyl-1H-pyrazol-4-yl)methyl)-1H-pyrazole-3-carboxylate (1.32 g, 36.8%).

STEP B: ethyl 3-methyl-1-((1-methyl-1H-pyrazol-4-yl)methyl)-4-(1-(tetrahydro-2H-pyran-2-yl)-6-(trifluoromethyl)-1H-indazol-4-yl)-1H-pyrazole-5-carboxylate

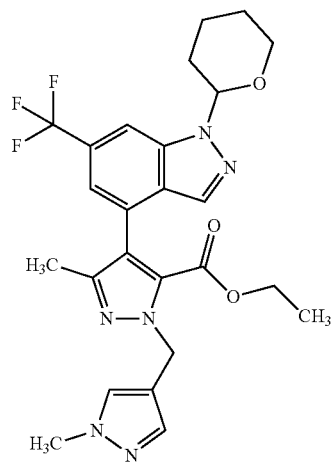 [SMILES: CCOC(=O)c1c(-c2cc(C(F)(F)F)cc3c2cnn3C2CCCCO2)c(C)nn1Cc1cnn(C)c1]

To a microwave vial were added 1-(tetrahydro-2H-pyran-2-yl)-4-(4,4,5,5-tetramethyl-1,3,2-dioxaborolan-2-yl)-6-(trifluoromethyl)-1H-indazole (0.993 g, 2.506 mmol), ethyl 4-bromo-3-methyl-1-((1-methyl-1H-pyrazol-4-yl)methyl)-1H-pyrazole-5-carboxylate (0.82 g, 2.506 mmol), and PdCl$_2$(dppf) (0.092 g, 0.125 mmol) in dioxane (25 mL) and aqueous saturated NaHCO$_3$ (6 mL). The mixture was bubbled with nitrogen to give a light yellow suspension, which was heated at 140° C. for 60 minutes in a microwave reactor. The reaction mixture was subsequently diluted with EtOAc, washed with water and brine, dried over Na$_2$SO$_4$, and concentrated. The crude residue was purified by CombiFlash® chromatography (120 g column) eluting with a gradient of 10-100% EtOAc in heptane over a period of 180 minutes. The product-containing fractions were combined and concentrated to give the title compound as an off white solid (0.745 g, 57.5%). ESI-MS m/z [M+H]$^+$ calc'd for C$_{25}$H$_{27}$F$_3$N$_6$O$_3$, 517.22. found 517.20.

STEP C: (3-methyl-1-((1-methyl-1H-pyrazol-4-yl)methyl)-4-(6-(trifluoromethyl)-1H-indazol-4-yl)-1H-pyrazol-5-yl)methanol A 100 mL round bottom flask was charged with ethyl 3-methyl-1-((1-methyl-1H-pyrazol-4-yl)methyl)-4-(1-(tetrahydro-2H-pyran-2-yl)-6-(trifluoromethyl)-1H-indazol-4-yl)-1H-pyrazole-5-carboxylate (0.745 g, 1.442 mmol) in THF (10 mL). The mixture was cooled to 0° C. A 1M solution of lithium aluminum hydride (4.33 mL, 4.33 mmol) in ether was added, and the reaction mixture was stirred at 0° C. for 1 hour. The reaction was quenched with 1N HCl (6 mL) at 0° C. and the product was extracted into EtOAc. The organic phase was washed with brine and dried over Na$_2$SO$_4$. The volatiles were removed by evaporation. The crude residue was dissolved in MeOH (5 mL). HCl (0.5 mL) was added and the mixture was stirred for 2 hours. The product was purified by LCMS, eluting with 30% ACN in H$_2$O (containing 10 mM NH$_4$HCO$_3$) over a period of 10 minutes. The product-containing fractions were combined and the volatiles were evaporated using a GeneVac™ to give the title compound (0.178 g, 31.6%). $^1$H NMR (400 MHz, CD$_3$OD) δ ppm 2.27 (s, 3H), 3.88 (s, 3H), 4.51 (s, 2H), 5.30 (s, 2H), 7.37 (d, J=1.26 Hz, 1H), 7.52 (s, 1H), 7.65 (s, 1H), 7.88 (s, 1H), 7.94-8.02 (m, 1H); ESI-MS m/z [M+H]$^+$ calc'd for C$_{18}$H$_{17}$F$_3$N$_6$O, 391.15. found 391.13.

Example 411

(5-methyl-1-((3-methylisoxazol-5-yl)methyl)-4-(6-(trifluoromethyl)-1H-indazol-4-yl)-1H-pyrazol-3-yl)methanol

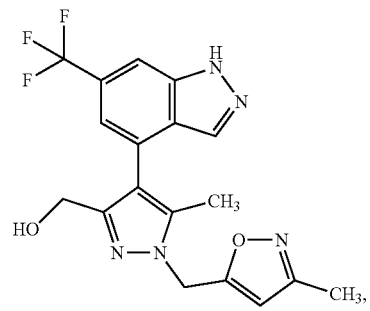 [SMILES: Cc1cc(Cn2nc(CO)c(-c3cc(C(F)(F)F)cc4[nH]ncc34)c2C)on1]

and

Example 412

(3-methyl-1-((3-methylisoxazol-5-yl)methyl)-4-(6-(trifluoromethyl)-1H-indazol-4-yl)-1H-pyrazol-5-yl)methanol

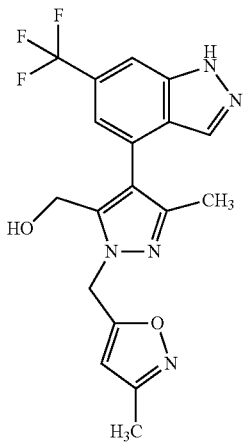 [SMILES: Cc1cc(Cn2nc(C)c(-c3cc(C(F)(F)F)cc4[nH]ncc34)c2CO)on1]

STEP A: ethyl 4-bromo-5-methyl-1-((3-methylisoxazol-5-yl)methyl)-1H-pyrazole-3-carboxylate and ethyl 4-bromo-3-methyl-1-((3-methylisoxazol-5-yl)methyl)-1H-pyrazole-5-carboxylate

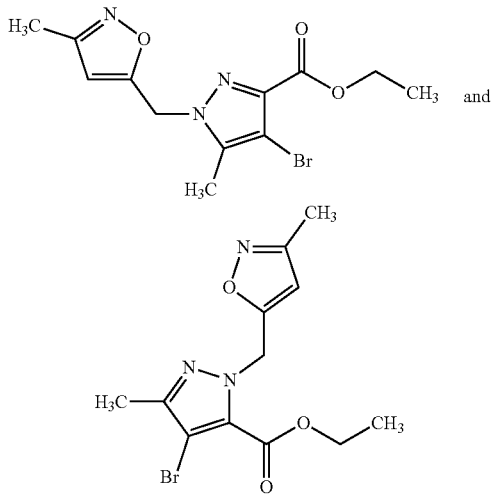

To a mixture of ethyl 4-bromo-3-methyl-1H-pyrazole-5-carboxylate (0.331 g, 1.420 mmol) in DMF (10 mL) were added $Cs_2CO_3$ (1.157 g, 3.55 mmol) and 5-(bromomethyl)-3-methylisoxazole (0.5 g, 2.84 mmol). The reaction mixture was stirred at room temperature for 20 hours and then diluted with water. The product was extracted into EtOAc. The organic phase was dried over $Na_2SO_4$ and concentrated to give the title compounds as a crude mixture that was used without further purification (0.24 g).

STEP B: ethyl 5-methyl-1-((3-methylisoxazol-5-yl)methyl)-4-(6-(trifluoromethyl)-1H-indazol-4-yl)-1H-pyrazole-3-carboxylate and ethyl 3-methyl-1-((3-methylisoxazol-5-yl)methyl)-4-(6-(trifluoromethyl)-1H-indazol-4-yl)-1H-pyrazole-5-carboxylate

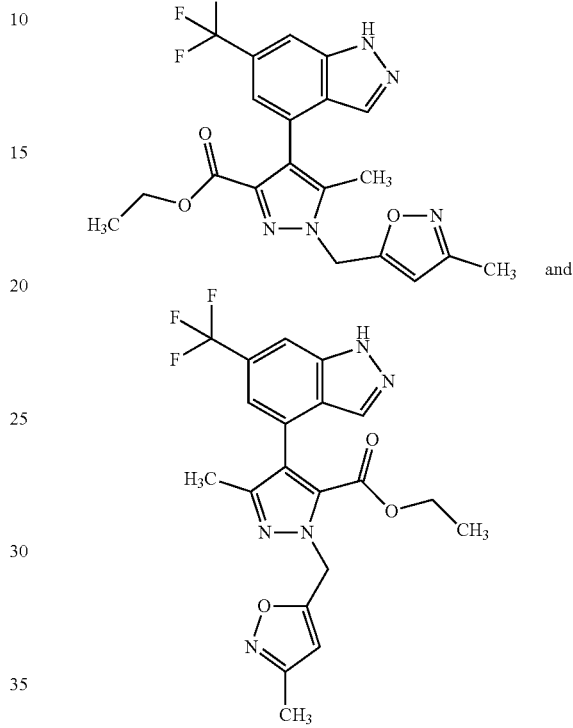

A microwave vial was charged with (6-(trifluoromethyl)-1H-indazol-4-yl)boronic acid (0.168 g, 0.731 mmol), a mixture of ethyl 4-bromo-3-methyl-1-((3-methylisoxazol-5-yl)methyl)-1H-pyrazole-5-carboxylate and ethyl 4-bromo-5-methyl-1-((3-methylisoxazol-5-yl)methyl)-1H-pyrazole-3-carboxylate (0.240 g), and $PdCl_2(dppf)$ (0.027 g, 0.037 mmol) in dioxane (12 mL) and aqueous saturated $NaHCO_3$ (3 mL). The solution was bubbled with nitrogen to give a light yellow suspension, which was heated at 140° C. for 60 minutes in a microwave reactor. The reaction mixture was subsequently concentrated to give the title compounds as a crude mixture that was used without further purification (0.21 g).

STEP C: (5-methyl-1-((3-methylisoxazol-5-yl)methyl)-4-(6-(trifluoromethyl)-1H-indazol-4-yl)-1H-pyrazol-3-yl)methanol and (3-methyl-1-((3-methylisoxazol-5-yl)methyl)-4-(6-(trifluoromethyl)-1H-indazol-4-yl)-1H-pyrazol-5-yl)methanol A 40 ml, vial was charged with a mixture of ethyl 3-methyl-1-((3-methylisoxazol-5-yl)methyl)-4-(6-(trifluoromethyl)-1H-indazol-4-yl)-1H-pyrazole-5-carboxylate and ethyl 5-methyl-1-((3-methylisoxazol-5-yl)methyl)-4-(6-(trifluoromethyl)-1H-indazol-4-yl)-1H-pyrazole-3-carboxylate (0.210 g) in THF (6 mL). The mixture was cooled to 0° C. A 1M solution of lithium aluminum hydride (1.454 mL, 1.454 mmol) in ether was added and the reaction mixture was stirred for 30 minutes at room temperature. The reaction was quenched with 1N HCl (2 mL) at 0° C. The mixture was allowed to warm to room temperature and the product was extracted into EtOAc. The organic phase was washed with brine and dried over Na$_2$SO$_4$. The volatiles were evaporated and the crude residue was purified by LCMS, eluting with 35% ACN in H$_2$O (containing 10 mM NH$_4$HCO$_3$) over a period of 10 minutes. The product-containing fractions were combined and the volatiles evaporated using a GeneVac™ to give the title compounds. The later-eluting peak was assigned to the regioisomer of EXAMPLE 411 (3.3 mg). $^1$H NMR (400 MHz, CD$_3$OD) δ ppm 2.19 (s, 3H), 2.30 (s, 3H), 4.59 (s, 2H), 5.63 (s, 2H), 6.26 (s, 1H), 7.31 (d, J=1.26 Hz, 1H), 7.92 (s, 1H), 8.04 (d, J=0.76 Hz, 1H); ESI-MS m/z [M+H]$^+$ calc'd for C$_{18}$H$_{16}$F$_3$N$_5$O$_2$, 392.13. found 392.21. The earlier-eluting peak was assigned to the regioisomer of EXAMPLE 412 (2.8 mg). $^1$H NMR (400 MHz, CD$_3$OD) δ ppm 2.30 (s, 3H), 2.31 (s, 3H), 4.50 (s, 2H), 5.55 (s, 2H), 6.28 (s, 1H), 7.34-7.43 (m, 1H), 7.90 (s, 1H), 7.96-8.05 (m, 1H); ESI-MS m/z [M+H]$^+$ calc'd for C$_{18}$H$_{16}$F$_3$N$_5$O$_2$, 392.13. found 392.21.

Example 413

(R)-1-(4-methyl-5-(6-(trifluoromethyl)-1H-indazol-4-yl)pyrimidin-2-yl)pyrrolidin-3-ol

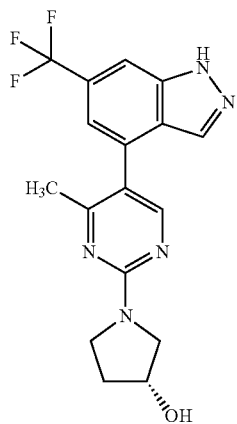 [SMILES: Cc1nc(N2CC[C@@H](O)C2)ncc1-c1cc(C(F)(F)F)cc2[nH]ncc12]

STEP A: (R)-1-(5-bromo-4-methylpyrimidin-2-yl)pyrrolidin-3-ol

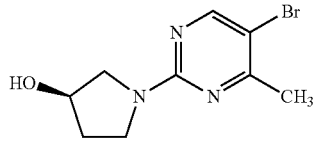

In a 500 mL pear flask equipped with a magnetic stir bar were mixed (R)-pyrrolidin-3-ol hydrochloride (8.94 g, 72.3 mmol), 5-bromo-2-chloro-4-methylpyrimidine (15 g, 72.3 mmol), DIPEA (31.6 mL, 181 mmol), and EtOH (150 mL). The resulting yellow suspension was heated in a sand bath to 70° C. for 18 hours. At this time about half of the solvent was evaporated. Water (250 mL) was added to the flask while rapidly stirring the solution. An off-white precipitate formed and was filtered off, washed with water (100 mL) and dried to give the title compound (16.7 g, 89.5%).

STEP B: (R)-1-(4-methyl-5-(6-(trifluoromethyl)-1H-indazol-4-yl)pyrimidin-2-yl)pyrrolidin-3-ol A 350 mL glass bomb was charged with 4-(4,4,5,5-tetramethyl-1,3,2-dioxaborolan-2-yl)-6-(trifluoromethyl)-1H-indazole (15 g, 48.1 mmol) (R)-1-(5-bromo-4-methyl-pyrimidin-2-yl)pyrrolidin-3-ol (10.34 g, 40.1 mmol) and PdCl$_2$(dppf) (1.465 g, 2.003 mmol) in dioxane (150 mL) and aqueous saturated NaHCO$_3$ (60 mL). The resulting light yellow suspension was purged with N$_2$ and the glass bomb was sealed. The mixture was heated at 110° C. for 24 hours in an oil bath. The reaction mixture was then cooled, poured into water (250 mL), and extracted with EtOAc (2×400 mL). The combined organic layers were washed with brine (100 mL), dried over Na$_2$SO$_4$, and filtered. The solvent was evaporated to yield a residue which was purified via flash chromatography (330 g column) in two batches, each eluting with a gradient of 0-20% MeOH in DCM. The pure fractions were combined and concentrated to yield product as a rusty solid. The solid was dissolved in THF (250 mL) and treated with Si-Thiol (20 g, 1.28 mmol/g, Silicycle® lot 22477). The mixture was stirred overnight at RT and was then filtered through a pad of Celite. The filtrate was concentrated and the product was purified by preparative HPLC, eluting with a gradient of 20-45% ACN in H$_2$O (containing 0.1% formic acid). The pure fractions were concentrated to about 1 L of solvent. The resulting white slurry was neutralized with aqueous saturated NaHCO$_3$ and extracted with EtOAc (3×800 mL). The combined organic layers were washed with water (800 mL), dried over Na$_2$SO$_4$, filtered, and concentrated. When the volume of EtOAc was about 300 mL, MeOH (300 mL) was added and the solvent was evaporated to yield a free flowing white solid. The solid was dried in a vacuum oven for 2 days at 50° C. to give the title compound (5.85 g, 40.2%). $^1$H NMR (400 MHz, DMSO-d$_6$) δ ppm 1.88-1.95 (m, 1H), 2.03 (dt, J=12.95, 4.14 Hz, 1H), 2.22 (s, 3H), 3.33 (s, 2H), 3.50-3.70 (m, 4H), 4.41 (br s, 1H), 4.98 (br s, 1H), 7.28 (d, J=1.26 Hz, 1H), 7.92 (s, 1H), 8.04 (s, 1H), 8.29 (s, 1H), 13.67 (s, 1H); ESI-MS m/z [M+H]$^+$ calc'd for C$_{17}$H$_{16}$F$_3$N$_5$O, 364.1. found 364.4.

Example 414

(R)-4-(2-methyl-6-(3-methylpiperazin-1-yl)pyridin-3-yl)-6-(trifluoromethyl)-1H-indazole

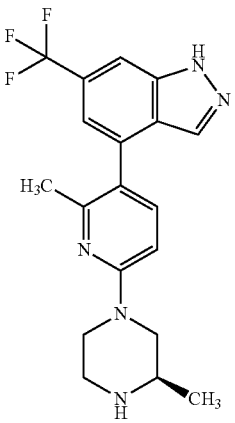 [SMILES: Cc1nc(N2CCN[C@H](C)C2)ccc1-c1cc(C(F)(F)F)cc2[nH]ncc12]

229

STEP A: (R)-1-(5-bromo-6-methylpyridin-2-yl)-3-methylpiperazine

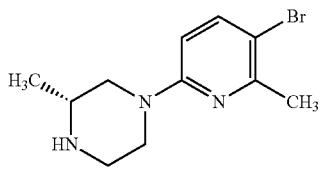

In a 10 mL microwave vial equipped with a magnetic stir bar were mixed 3-bromo-6-chloro-2-methylpyridine (515 mg, 2.496 mmol), (R)-2-methylpiperazine (250 mg, 2.496 mmol), and Et$_3$N (1.044 mL, 7.49 mmol) in DMF (4 mL). The resulting yellow suspension was heated in a microwave reactor to 165° C. for 4 hours. The reaction mixture was subsequently partitioned between 0.25N HCl (40 mL) and EtOAc (40 mL). The phases were separated and the aqueous layer was back-extracted with EtOAc (40 mL). The organic layers were combined, washed with brine (20 mL), dried over Na$_2$SO$_4$, filtered, and concentrated. The residue was purified using flash chromatography (12 g column) eluting with a gradient of 0-100% EtOAc in heptanes and then 0-20% MeOH in DCM. The pure fractions were combined and concentrated to give the title compound as a clear syrup (240 mg, 35.6%).

STEP B: (R)-4-(2-methyl-6-(3-methylpiperazin-1-yl)pyridin-3-yl)-6-(trifluoromethyl)-1H-indazole In a 10 mL microwave vial were mixed (R)-1-(5-bromo-6-methylpyridin-2-yl)-3-methylpiperazine (120 mg, 0.444 mmol), (6-(trifluoromethyl)-1H-indazol-4-yl)boronic acid (133 mg, 0.577 mmol), PdCl$_2$(dppf) (32.5 mg, 0.044 mmol), and aqueous NaHCO$_3$ (0.950 mL, 1.777 mmol) in dioxane (10 mL) to give an orange suspension. The vial was sealed and heated in a microwave reactor to 145° C. for 45 minutes. The reaction mixture was then filtered and the product was purified by preparative HPLC, eluting with a gradient of 15-40% ACN (containing 0.035% TFA) in H$_2$O (containing 0.05% TFA). The pure fractions were lyophilized to give a TFA salt of the title compound as a white solid (31.6 mg, 14.5%). $^1$H NMR (400 MHz, DMSO-d$_6$) δ ppm 1.31 (d, J=6.57 Hz, 3H), 2.27 (s, 3H), 2.95 (dd, J=14.02, 10.48 Hz, 1H), 3.05-3.21 (m, 2H), 3.36 (d, J=7.33 Hz, 1H), 3.44 (d, J=11.62 Hz, 1H), 4.44 (d, J=13.14 Hz, 2H), 6.94 (d, J=8.59 Hz, 1H), 7.24 (d, J=1.52 Hz, 1H), 7.64 (d, J=8.59 Hz, 1H), 7.92-7.94 (m, 1H), 7.95 (d, J=1.01 Hz, 1H), 8.77 (d, J=8.59 Hz, 1H), 9.10 (d, J=8.34 Hz, 1H); ESI-MS m/z [M+H]$^+$ calc'd for C$_{19}$H$_{20}$F$_3$N$_5$, 376.2. found 376.4.

Example 415

(1R,5S)-3-(4-methyl-5-(6-(trifluoromethyl)-1H-indazol-4-yl)pyrimidin-2-yl)-3-azabicyclo[3.1.0]hexane-2-carboxamide

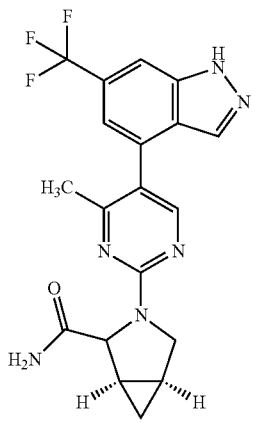 [SMILES: Cc1nc(N2C[C@H]3C[C@H]3C2C(N)=O)ncc1-c1cc(C(F)(F)F)cc2[nH]ncc12]

230

STEP A: (1R,5S)-3-(5-bromo-4-methylpyrimidin-2-yl)-3-azabicyclo[3.1.0]hexane-2-carboxylic acid

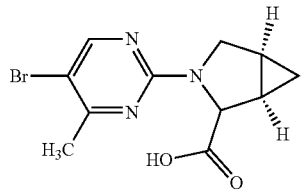 [SMILES: Cc1nc(N2C[C@H]3C[C@H]3C2C(=O)O)ncc1Br]

In a 40 mL vial were mixed 5-bromo-2-chloro-4-methylpyrimidine (438 mg, 2.109 mmol), (1R,5S)-3-azabicyclo[3.1.0]hexane-2-carboxylic acid (295 mg, 2.320 mmol), and Et$_3$N (0.882 mL, 6.33 mmol) in EtOH (90 mL). The resulting yellow solution was stirred at 75° C. for 3 days. The reaction mixture was subsequently partitioned between 1N HCl (40 mL) and EtOAc (40 mL). The phases were separated and the aqueous layer was back-extracted with EtOAc (75 mL). The organic layers were combined, washed with brine (40 mL), dried over Na$_2$SO$_4$, filtered, and concentrated to give the title compound as a white solid, which was used without further purification (660 mg).

STEP B: (1R,5S)-3-(4-methyl-5-(6-(trifluoromethyl)-1H-indazol-4-yl)pyrimidin-2-yl)-3-azabicyclo[3.1.0]hexane-2-carboxylic acid

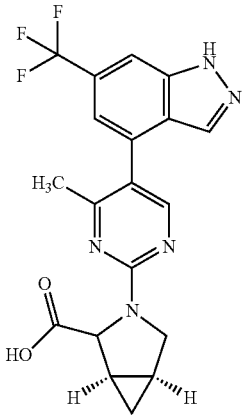 [SMILES: Cc1nc(N2C[C@H]3C[C@H]3C2C(=O)O)ncc1-c1cc(C(F)(F)F)cc2[nH]ncc12]

In a 10 mL microwave vial were mixed (1R,5S)-3-(5-bromo-4-methylpyrimidin-2-yl)-3-azabicyclo[3.1.0]hexane-2-carboxylic acid (200 mg, 0.671 mmol), (6-(trifluoromethyl)-1H-indazol-4-yl)boronic acid (201 mg, 0.872 mmol), PdCl$_2$(dppf) (49.1 mg, 0.067 mmol), and aqueous NaHCO$_3$ (1.435 mL, 2.68 mmol) in dioxane (10 mL) to give an orange suspension. The vial was sealed and heated in a microwave reactor to 140° C. for 40 minutes. Additional (6-(trifluoromethyl)-1H-indazol-4-yl)boronic acid (201 mg, 0.872 mmol) and PdCl$_2$(dppf) (49.1 mg, 0.067 mmol) were added and heating was continued for 45 minutes. The reaction mixture was subsequently partitioned between water (50 mL) and EtOAc (50 mL). The phases were separated. The organic layer was discarded and the aqueous layer was acidified with 1N HCl and extracted with EtOAc (2×75 mL). The organic layers were combined, washed with brine (50 mL), dried over Na$_2$SO$_4$, filtered, and concentrated to give the title compound as a tan glass, which was used without further purification (170 mg, 62.8%).

STEP C: (1R,5S)-3-(4-methyl-5-(6-(trifluoromethyl)-1H-indazol-4-yl)pyrimidin-2-yl)-3-azabicyclo[3.1.0]hexane-2-carboxamide In a 4 mL vial equipped with a magnetic stir bar were mixed (1R,5S)-3-(4-methyl-5-(6-(trifluoromethyl)-1H-indazol-4-yl)pyrimidin-2-yl)-3-azabicyclo[3.1.0]hexane-2-carboxylic acid (80 mg, 0.198 mmol), $NH_4Cl$ (21.22 mg, 0.397 mmol), HATU (90 mg, 0.238 mmol) and $Et_3N$ (0.083 mL, 0.595 mmol) in DMF (2 mL). The resulting brown solution was stirred overnight. The product was purified by preparative HPLC, eluting with a gradient of 25-50% ACN (containing 0.035% TFA) in $H_2O$ (containing 0.05% TFA). The pure fractions were lyophilized to give a TFA salt of the title compound as a white solid (3.3 mg, 3.2%). $^1$H NMR (400 MHz, $CD_3OD$) δ ppm 0.78-0.86 (m, 2H), 1.88 (ddd, J=12.06, 7.26, 4.67 Hz, 1H), 2.09-2.15 (m, 1H), 2.25-2.29 (m, 3H), 3.82 (dd, J=10.61, 5.05 Hz, 1H), 3.92-3.96 (m, 1H), 4.61 (d, J=5.31 Hz, 1H), 7.28 (d, J=1.01 Hz, 1H), 7.93-7.95 (m, 2H), 8.27 (s, 1H); ESI-MS m/z $[M+H]^+$ calc'd for $C_{19}H_{17}F_3N_6O$, 403.2. found 403.4.

TABLE 1 lists MetAP2 inhibition data for many of the compounds described in the examples, where larger $pIC_{50}$ values represent higher potency. The compounds were tested in accordance with the enzyme assay described on page 32 of the specification in which the MetAP2 enzyme is complexed with cobalt or manganese ions.

TABLE 1

MetAP2 Inhibition ($pIC_{50}$) for Example (Ex) Compounds

| Ex | MetAP2 Co $pIC_{50}$ | MetAP2 Mn $pIC_{50}$ |
|---|---|---|
| 1 | 6.5 | 7.7 |
| 2 | 7.4 | 8.0 |
| 3 | 7.4 | 8.4 |
| 4 | 7.6 | 8.2 |
| 5 | 6.7 | 8.5 |
| 6 | 6.6 | 8.2 |
| 7 | 7.6 | 8.3 |
| 8 | 7.4 | 8.5 |
| 9 | 7.3 | 8.4 |
| 10 | 5.9 | 7.5 |
| 11 | 7.5 | 8.5 |
| 12 | 7.4 | 8.5 |
| 13 | 6.4 | 8.0 |
| 14 | 7.0 | 8.0 |
| 15 | 8.0 | 8.2 |
| 16 | 7.5 | 8.3 |
| 17 | 7.7 | 8.1 |
| 18 | 7.6 | 8.5 |
| 19 | 7.2 | 8.5 |
| 20 | 7.1 | 8.1 |
| 21 | 7.0 | 8.1 |
| 22 | 7.4 | 8.3 |
| 23 | 7.0 | 8.2 |
| 24 | 7.5 | 7.9 |
| 25 | 7.3 | 8.1 |
| 26 | 7.2 | 7.9 |
| 27 | 6.9 | 7.8 |
| 28 | 6.8 | 7.6 |
| 29 | 7.1 | 8.2 |
| 30 | 7.1 | 7.6 |
| 31 | 6.7 | 7.8 |
| 32 | 7.4 | 7.7 |
| 33 | 7.0 | 8.0 |
| 34 | 6.5 | 7.5 |
| 35 | 7.6 | 8.1 |
| 36 | 7.6 | 8.2 |
| 37 | 7.4 | 8.1 |
| 38 | 7.3 | 8.0 |
| 39 | 7.5 | 7.9 |
| 40 | 7.4 | 8.0 |
| 41 | 7.6 | 8.2 |
| 42 | 7.2 | 8.2 |
| 43 | 7.1 | 8.2 |
| 44 | 7.3 | 8.3 |
| 45 | 7.3 | 8.1 |
| 46 | 7.2 | 8.3 |
| 47 | 6.3 | 7.3 |
| 48 | 7.3 | 8.3 |
| 49 | 6.7 | 7.8 |
| 50 | 7.5 | 8.3 |
| 51 | 5.6 | 7.0 |
| 52 | 6.9 | 7.9 |
| 53 | 7.4 | 8.3 |
| 54 | 6.4 | 8.2 |
| 55 | 7.1 | 8.3 |
| 56 | 7.4 | 7.9 |
| 57 | 7.2 | 7.6 |
| 58 | 6.9 | 7.9 |
| 59 | 7.1 | 7.9 |
| 60 | 6.0 | 7.3 |
| 61 | 6.8 | 7.4 |
| 62 | 7.0 | 7.9 |
| 63 | 7.2 | 7.8 |
| 64 | 7.5 | 8.0 |
| 65 | 7.8 | 7.9 |
| 66 | 7.1 | 7.8 |
| 67 | 7.7 | 8.4 |
| 68 | 7.6 | 7.9 |
| 69 | 6.8 | 8.2 |
| 70 | 7.4 | 8.2 |
| 71 | 7.0 | 7.6 |
| 72 | 7.6 | 8.6 |
| 73 | 6.7 | 7.1 |
| 74 | 7.3 | 8.4 |
| 75 | 6.8 | 8.1 |
| 76 | 6.4 | 7.4 |
| 77 | 7.1 | 8.2 |
| 78 | 7.0 | 8.3 |
| 79 | 7.6 | 8.0 |
| 80 | 7.1 | 8.1 |
| 81 | 7.4 | 7.8 |
| 82 | 6.3 | 8.0 |
| 83 | 7.4 | 7.7 |
| 84 | 7.7 | 8.5 |
| 85 | 7.1 | 8.2 |
| 86 | 7.8 | 8.5 |
| 87 | 6.9 | 8.1 |
| 88 | 7.1 | 8.4 |
| 89 | 7.7 | 8.4 |
| 90 | 7.5 | 8.5 |
| 91 | 6.7 | 8.2 |
| 92 | 7.3 | 8.4 |
| 93 | 7.3 | 8.0 |
| 94 | 7.2 | 8.5 |
| 95 | 7.7 | 8.5 |
| 96 | 7.4 | 8.3 |
| 97 | 7.3 | 8.6 |
| 98 | 7.4 | 7.8 |
| 99 | 6.2 | 7.4 |
| 100 | 6.7 | 7.8 |
| 101 | 7.5 | 8.0 |
| 102 | 6.2 | 7.1 |
| 103 | 7.3 | 8.2 |
| 104 | 6.5 | 7.4 |
| 105 | 6.5 | 8.0 |
| 106 | 6.8 | 7.9 |
| 107 | 7.5 | 8.3 |
| 108 | 7.1 | 7.9 |
| 109 | 7.3 | 8.5 |
| 110 | 7.2 | 8.4 |
| 111 | 7.3 | 7.8 |
| 112 | 7.3 | 7.9 |
| 113 | 7.7 | 8.1 |
| 114 | 7.3 | 8.2 |
| 115 | 6.8 | 8.0 |

TABLE 1-continued

MetAP2 Inhibition (pIC$_{50}$) for Example (Ex) Compounds

| Ex | MetAP2 Co pIC$_{50}$ | MetAP2 Mn pIC$_{50}$ |
|---|---|---|
| 116 | 7.4 | 8.1 |
| 117 | 7.8 | 8.5 |
| 118 | 7.4 | 8.2 |
| 119 | 7.0 | 8.1 |
| 120 | 7.2 | 7.8 |
| 121 | 7.2 | 8.2 |
| 122 | 7.4 | 7.9 |
| 123 | 7.2 | 7.5 |
| 124 | 7.2 | 7.8 |
| 125 | 6.8 | 7.5 |
| 126 | 7.3 | 8.1 |
| 127 | 7.8 | 7.9 |
| 128 | 7.4 | 7.9 |
| 129 | 8.0 | 8.4 |
| 130 | 8.1 | 8.8 |
| 131 | 7.1 | 8.1 |
| 132 | 7.3 | 8.3 |
| 133 | 7.2 | 8.0 |
| 134 | 7.0 | 7.6 |
| 135 | 6.8 | 8.0 |
| 136 | 6.8 | 7.9 |
| 137 | 6.8 | 8.0 |
| 138 | 7.4 | 8.0 |
| 139 | 7.4 | 8.0 |
| 140 | 7.5 | 8.4 |
| 141 | 7.9 | 8.3 |
| 142 | 7.6 | 8.1 |
| 143 | 7.2 | 7.8 |
| 144 | 6.7 | 7.7 |
| 145 | 5.4 | 6.2 |
| 146 | 6.1 | 7.0 |
| 147 | 5.3 | 6.9 |
| 148 | 7.0 | 7.6 |
| 149 | 6.3 | 7.2 |
| 150 | 6.1 | 6.6 |
| 151 | 6.7 | 8.2 |
| 152 | 5.7 | 6.9 |
| 153 | 6.7 | 7.6 |
| 154 | 7.0 | 7.8 |
| 155 | 7.2 | 7.8 |
| 156 | 6.3 | 7.5 |
| 157 | 6.6 | 7.9 |
| 158 | 6.5 | 7.1 |
| 159 | 5.8 | 6.8 |
| 160 | 7.1 | 7.4 |
| 161 | 6.6 | 7.9 |
| 162 | 6.5 | 8.2 |
| 163 | 6.1 | 7.9 |
| 164 | 7.8 | 8.4 |
| 165 | 6.0 | 7.2 |
| 166 | 6.1 | 7.4 |
| 167 | 6.8 | 8.4 |
| 168 | 7.6 | 8.2 |
| 169 | 6.6 | 7.7 |
| 170 | 7.0 | 7.7 |
| 171 | 7.2 | 8.3 |
| 172 | 7.3 | 8.1 |
| 173 | 7.5 | 7.8 |
| 174 | 7.2 | 7.9 |
| 175 | 7.4 | 8.0 |
| 176 | 7.4 | 7.9 |
| 177 | 7.3 | 8.4 |
| 178 | 7.5 | 8.1 |
| 179 | 7.6 | 8.0 |
| 180 | 6.0 | 7.4 |
| 181 | 7.8 | 8.3 |
| 182 | 6.1 | 7.6 |
| 183 | 6.5 | 7.4 |
| 184 | 6.3 | 7.7 |
| 185 | 7.8 | 8.4 |
| 186 | 7.7 | 8.1 |
| 187 | 7.1 | 8.1 |
| 188 | 5.8 | 7.1 |
| 189 | 7.3 | 8.3 |
| 190 | 6.7 | 7.4 |
| 191 | 6.1 | 7.6 |
| 192 | 5.3 | 7.0 |
| 193 | 7.2 | 8.2 |
| 194 | 6.8 | 8.0 |
| 195 | 7.6 | 8.2 |
| 196 | 7.2 | 8.2 |
| 197 | 7.2 | 8.2 |
| 198 | 6.2 | 7.9 |
| 199 | 6.3 | 6.8 |
| 200 | 6.5 | 7.3 |
| 201 | 6.1 | 7.7 |
| 202 | 6.3 | 7.6 |
| 203 | 5.4 | 7.1 |
| 204 | 6.1 | 7.8 |
| 205 | 5.9 | 7.9 |
| 206 | 7.1 | 8.1 |
| 207 | 7.1 | 8.1 |
| 208 | 7.1 | 8.2 |
| 209 | 7.1 | 8.2 |
| 210 | 6.2 | 7.9 |
| 211 | 7.6 | 8.2 |
| 212 | 6.7 | 8.0 |
| 213 | 6.2 | 7.1 |
| 214 | 6.3 | 7.8 |
| 215 | 7.3 | 8.1 |
| 216 | 6.4 | 8.0 |
| 217 | 6.8 | 8.0 |
| 218 | 5.7 | 6.6 |
| 219 | 7.3 | 7.9 |
| 220 | 7.1 | 8.2 |
| 221 | 7.2 | 8.0 |
| 222 | 6.6 | 7.8 |
| 223 | 6.9 | 8.1 |
| 224 | 7.4 | 8.6 |
| 225 | 7.0 | 8.1 |
| 226 | | |
| 227 | 6.9 | 8.1 |
| 228 | 6.8 | 8.3 |
| 229 | 7.2 | 8.2 |
| 230 | 6.8 | 8.1 |
| 231 | 6.8 | 8.2 |
| 232 | 7.2 | 8.2 |
| 233 | 7.0 | 8.1 |
| 234 | 7.7 | 8.4 |
| 235 | 7.9 | 8.4 |
| 236 | 7.2 | 8.2 |
| 237 | 7.9 | 8.6 |
| 238 | 7.4 | 8.2 |
| 239 | 7.8 | 8.3 |
| 240 | 6.8 | 8.3 |
| 241 | 7.8 | 8.7 |
| 242 | 7.3 | 8.2 |
| 243 | 7.4 | 8.3 |
| 244 | 7.5 | 8.3 |
| 245 | 5.8 | 7.5 |
| 246 | 7.0 | 8.5 |
| 247 | 7.3 | 8.4 |
| 248 | 7.2 | 8.3 |
| 249 | 7.1 | 7.9 |
| 250 | 7.1 | 8.2 |
| 251 | 7.2 | 8.3 |
| 252 | 5.8 | 7.0 |
| 253 | 7.2 | 8.0 |
| 254 | 6.1 | 7.5 |
| 255 | 7.6 | 8.1 |
| 256 | 6.9 | 8.0 |
| 257 | 7.3 | 8.1 |
| 258 | 7.6 | 8.1 |
| 259 | 7.5 | 8.1 |
| 260 | 7.0 | 8.2 |
| 261 | 6.0 | 7.4 |
| 262 | 6.7 | 8.0 |
| 263 | 7.7 | 7.8 |
| 264 | 7.0 | 8.2 |
| 265 | 7.0 | 8.0 |

TABLE 1-continued

MetAP2 Inhibition (pIC$_{50}$) for Example (Ex) Compounds

| Ex | MetAP2 Co pIC$_{50}$ | MetAP2 Mn pIC$_{50}$ |
|---|---|---|
| 266 | 7.2 | 7.9 |
| 267 | 7.4 | 8.0 |
| 268 | 7.4 | 7.8 |
| 269 | 7.2 | 8.4 |
| 270 | 7.4 | 8.5 |
| 271 | 6.5 | 7.9 |
| 272 | 7.4 | 8.0 |
| 273 | 7.7 | 8.4 |
| 274 | 7.2 | 8.4 |
| 275 | 6.9 | 8.3 |
| 276 | 6.4 | 7.4 |
| 277 | 7.2 | 8.3 |
| 278 | 6.2 | 8.0 |
| 279 | 7.3 | 8.3 |
| 280 | 7.5 | 8.2 |
| 281 | 7.2 | 8.1 |
| 282 | 7.3 | 8.2 |
| 283 | 7.2 | 8.4 |
| 284 | 7.1 | 8.1 |
| 285 | 7.3 | 8.4 |
| 286 | 6.7 | 8.1 |
| 287 | 7.2 | 8.4 |
| 288 | 7.5 | 8.3 |
| 289 | 7.0 | 8.2 |
| 290 | 6.6 | 8.1 |
| 291 | 7.2 | 8.0 |
| 292 | 7.4 | 8.2 |
| 293 | 7.0 | 8.2 |
| 294 | 5.8 | 7.5 |
| 295 | 6.7 | 8.2 |
| 296 | 7.7 | 8.2 |
| 297 | 6.8 | 8.2 |
| 298 | 6.4 | 8.0 |
| 299 | 6.4 | 8.1 |
| 300 | 6.4 | 7.9 |
| 301 | 6.0 | 7.8 |
| 302 | 6.3 | 8.2 |
| 303 | 6.0 | 7.9 |
| 304 | 7.8 | 8.1 |
| 305 | 7.6 | 7.9 |
| 306 | 7.8 | 8.2 |
| 307 | 7.2 | 7.7 |
| 308 | 7.1 | 8.2 |
| 309 | 6.0 | 7.7 |
| 310 | 6.0 | 7.7 |
| 311 | 6.0 | 7.2 |
| 312 | 6.0 | 7.6 |
| 313 | 5.8 | 7.6 |
| 314 | 6.2 | 7.7 |
| 315 | 6.5 | 8.0 |
| 316 | 7.3 | 8.0 |
| 317 | 7.2 | 7.7 |
| 318 | 7.4 | 7.9 |
| 319 | 5.9 | 7.4 |
| 320 | 7.6 | 7.8 |
| 321 | 7.7 | 7.8 |
| 322 | 7.9 | 8.4 |
| 323 | 8.0 | 7.9 |
| 324 | 7.2 | 7.5 |
| 325 | 7.2 | 7.6 |
| 326 | 7.5 | 7.9 |
| 327 | 6.2 | 7.2 |
| 328 | 7.9 | 7.9 |
| 329 | 7.4 | 7.8 |
| 330 | 7.9 | 8.0 |
| 331 | 7.8 | 8.0 |
| 332 | 6.5 | 7.9 |
| 333 | 6.6 | 7.9 |
| 334 | 6.1 | 7.7 |
| 335 | 6.2 | 7.8 |
| 336 | 6.2 | 8.0 |
| 337 | 6.4 | 7.8 |
| 338 | 6.4 | 8.0 |
| 339 | 6.9 | 7.7 |
| 340 | 7.0 | 7.8 |
| 341 | 7.8 | 8.1 |
| 342 | 7.4 | 8.2 |
| 343 | 7.0 | 8.2 |
| 344 | 7.0 | 8.2 |
| 345 | 7.0 | 8.3 |
| 346 | 7.0 | 8.3 |
| 347 | 7.2 | 8.2 |
| 348 | 7.1 | 7.9 |
| 349 | 7.0 | 8.2 |
| 350 | 7.5 | 8.1 |
| 351 | 7.4 | 7.9 |
| 352 | 7.4 | 7.7 |
| 353 | 6.1 | 7.8 |
| 354 | 6.5 | 8.2 |
| 355 | 6.5 | 8.3 |
| 356 | 6.5 | 8.2 |
| 357 | 6.7 | 8.1 |
| 358 | 6.3 | 8.0 |
| 359 | 6.3 | 8.0 |
| 360 | 7.4 | 8.1 |
| 361 | 7.8 | 8.0 |
| 362 | 7.4 | 7.8 |
| 363 | 7.1 | 7.8 |
| 364 | 7.1 | 7.7 |
| 365 | 5.8 | 7.1 |
| 366 | 7.3 | 7.8 |
| 367 | 7.3 | 7.8 |
| 368 | 7.5 | 7.9 |
| 369 | 7.5 | 8.0 |
| 370 | 6.9 | 7.5 |
| 371 | 7.3 | 7.8 |
| 372 | 7.0 | 7.5 |
| 373 | 6.9 | 8.2 |
| 374 | 5.8 | 7.2 |
| 375 | 6.9 | 8.0 |
| 376 | 7.3 | 8.3 |
| 377 | 7.3 | 8.3 |
| 378 | 7.2 | 8.3 |
| 379 | 7.4 | 8.2 |
| 380 | 6.4 | 7.6 |
| 381 | 7.4 | 8.2 |
| 382 | 7.9 | 8.2 |
| 383 | 7.7 | 8.3 |
| 384 | 7.1 | 7.8 |
| 385 | 7.1 | 8.3 |
| 386 | 7.2 | 7.9 |
| 387 | 7.6 | 8.2 |
| 388 | 7.2 | 8.1 |
| 389 | 7.3 | 8.4 |
| 390 | 7.4 | 8.2 |
| 391 | 7.4 | 8.3 |
| 392 | 6.7 | 7.9 |
| 393 | 7.3 | 8.2 |
| 394 | 7.5 | 8.3 |
| 395 | 7.5 | 8.2 |
| 396 | 6.9 | 7.9 |
| 397 | 7.8 | 8.4 |
| 398 | 6.9 | 8.4 |
| 399 | 7.6 | 8.1 |
| 400 | 7.9 | 8.1 |
| 401 | 6.7 | 8.2 |
| 402 | 7.4 | 8.5 |
| 403 | 7.2 | 8.0 |
| 404 | 6.6 | 7.9 |
| 405 | 7.1 | 8.0 |
| 406 | 7.1 | 7.8 |
| 407 | 7.1 | 7.9 |
| 408 | 7.1 | 8.4 |
| 409 | 7.8 | 8.4 |
| 410 | 7.8 | 8.2 |
| 411 | 8.2 | 8.1 |
| 412 | 7.8 | 8.4 |
| 413 | 7.8 | 8.3 |

TABLE 1-continued

MetAP2 Inhibition (pIC$_{50}$) for Example (Ex) Compounds

| Ex | MetAP2 Co pIC$_{50}$ | MetAP2 Mn pIC$_{50}$ |
|---|---|---|
| 414 | 8.0 | 8.4 |
| 415 | 8.0 | 8.1 |

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. It is to be understood that the above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all cited articles and references, including patents, patent applications and publications, are herein incorporated by reference in their entirety and for all purposes.

What is claimed is:

1. A compound of Formula 1,

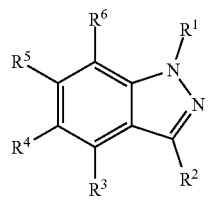

or a pharmaceutically acceptable salt thereof, wherein:
$R^1$ is hydrogen;
$R^2$ is selected from hydrogen, —OH, chloro, fluoro, —CN, methyl, and hydroxymethyl;
$R^3$ is selected from $C_{6-14}$ aryl, $C_{1-9}$ heteroaryl, and $C_{2-6}$ heterocyclyl, each optionally substituted with from one to five substituents independently selected from halo, oxo, —CN, $R^7$, and $R^8$;
$R^4$ is hydrogen;
$R^5$ is $C_{1-3}$ haloalkyl;
$R^6$ is selected from hydrogen, —OH, —NH$_2$, chloro, fluoro, and methyl;
each $R^7$ is independently selected from —OR$^9$, —N(R$^9$)R$^{10}$, —NR$^9$C(O)R$^{10}$, —NHC(O)NR$^9$R$^{10}$, —NR$^9$C(O)NHR$^{10}$, —C(O)R$^9$, —C(O)OR$^9$, —C(O)N(R$^9$)R$^{10}$, —C(O)N(R$^9$)OR$^{10}$, —C(O)N(R$^9$)S(O)$_2$R$^8$, —N(R$^9$)S(O)$_2$R$^8$, —SR$^9$, —S(O)R$^8$, —S(O)$_2$R$^8$, and —S(O)$_2$N(R$^9$)R$^{10}$;
each $R^8$ is independently selected from
(a) $C_{1-6}$ alkyl, $C_{2-6}$ alkenyl, and $C_{2-6}$ alkynyl, each optionally substituted with from one to five substituents independently selected from halo, oxo, —CN, and $R^{11}$; and
(b) $C_{3-8}$ cycloalkyl-(CH$_2$)$_m$—, $C_{2-6}$ heterocyclyl-(CH$_2$)$_m$—, $C_{6-14}$ aryl-(CH$_2$)$_m$—, and $C_{1-9}$ heteroaryl-(CH$_2$)$_m$—, each optionally substituted with from one to five substituents independently selected from halo, oxo, —CN, $R^{11}$, and $C_{1-6}$ alkyl optionally substituted with from one to five substituents independently selected from halo, oxo, —CN, and $R^{11}$;
each $R^9$ and $R^{10}$ is independently selected from
(a) hydrogen;
(b) $C_{1-6}$ alkyl, $C_{2-6}$ alkenyl, and $C_{2-6}$ alkynyl, each optionally substituted with from one to five substituents independently selected from halo, oxo, —CN, and $R^{11}$; and
(c) $C_{3-8}$ cycloalkyl-(CH$_2$)$_m$—, $C_{2-6}$ heterocyclyl-(CH$_2$)$_m$—, $C_{6-14}$ aryl-(CH$_2$)$_m$—, and $C_{1-9}$ heteroaryl-(CH$_2$)$_m$—, each optionally substituted with from one to five substituents independently selected from halo, oxo, —CN, $R^{11}$, and $C_{1-6}$ alkyl optionally substituted with from one to five substituents independently selected from halo, oxo, —CN, and $R^{11}$;
each $R^{11}$ is independently selected from —OR$^{12}$, —N(R$^{12}$)R$^{13}$, —N(R$^{12}$)C(O)R$^{13}$, —NHC(O)NR$^{12}$R$^{13}$, —NR$^{12}$C(O)NHR$^{13}$, —C(O)R$^{12}$, —C(O)OR$^{12}$, —C(O)N(R$^{12}$)R$^{13}$, —C(O)N(R$^{12}$)OR$^{13}$, —C(O)N(R$^{12}$)S(O)$_2$R$^{14}$, —NR$^{12}$S(O)$_2$R$^{14}$, —SR$^{12}$, —S(O)R$^{14}$, —S(O)$_2$R$^{14}$, and —S(O)$_2$N(R$^{12}$)R$^{13}$;
each $R^{12}$ and $R^{13}$ is independently selected from
(a) hydrogen; and
(b) $C_{1-6}$ alkyl and $C_{3-8}$ cycloalkyl-(CH$_2$)$_m$—, each optionally substituted with from one to five substituents independently selected from halo, oxo, —CN, —OH, and —NH$_2$;
each $R^{14}$ is independently selected from $C_{1-6}$ alkyl and $C_{3-8}$ cycloalkyl-(CH$_2$)$_m$—, each optionally substituted with from one to five substituents independently selected from halo, oxo, —CN, —OH, and —NH$_2$; and
each m is independently selected from 0, 1, 2, 3, and 4;
wherein each heteroaryl and heterocyclyl moiety has from one to four heteroatoms independently selected from N, O, and S.

2. A compound or pharmaceutically acceptable salt according to claim 1, wherein $R^3$ is selected from phenyl, naphthalenyl, fluorenyl, pyrrolyl, furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl, benzofuranyl, isobenzofuranyl, benzothiopheneyl, benzo[c]thiopheneyl, 1H-indolyl, 3H-indolyl, isoindolyl, 1H-isoindolyl, indolinyl, isoindolinyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]

pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, oxiranyl, thiiranyl, aziridinyl, oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, and 1,2-dihydropyrazolo[1,5-d][1,2,4]triazinyl, each optionally substituted with from one to five substituents independently selected from halo, oxo, —CN, $R^7$, and $R^8$.

3. A compound or pharmaceutically acceptable salt according to claim 1, wherein $R^3$ is selected from phenyl, pyridinyl, pyrimidinyl, pyridazinyl, pyrazinyl, 1,2-dihydropyridinyl, 1,6-dihydropyrimidinyl, 1,2,3,4-tetrahydropyrimidinyl, imidazolyl, pyrazolyl, tetrazolyl, thiazolyl, isoxazolyl, quinolinyl, isoquinolinyl, 1,7-naphthyridinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 1H-indolyl, indolinyl, isoindolinyl, benzimidazolyl, 2,3-dihydro-1H-benzo[d]imidazolyl, benzo[d]thiazolyl, 1H-pyrrolo[2,3-b]pyridinyl, 1H-pyrrolo[2,3-c]pyridinyl, imidazo[1,2-a]pyridinyl, pyrazolo[1,5-a]pyridinyl, 2,3-dihydro-1H-pyrrolo[2,3-b]pyridinyl, 3H-imidazo[4,5-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, and 1,2-dihydropyrazolo[1,5-d][1,2,4]triazinyl, each optionally substituted with from one to five substituents independently selected from halo, oxo, —CN, $R^7$, and $R^8$.

4. A compound or pharmaceutically acceptable salt according to claim 1, wherein $R^3$ is selected from phenyl, pyridinyl, 1,2-dihydropyridinyl, pyrimidinyl, 1,2,3,4-tetrahydropyrimidinyl, pyrazolyl, and 3H-imidazo[4,5-b]pyridinyl, each optionally substituted with from one to five substituents independently selected from halo, oxo, —CN, $R^7$, and $R^8$.

5. A compound or pharmaceutically acceptable salt according to claim 1, wherein $R^3$ is phenyl, which is optionally substituted with from one to five substituents independently selected from halo, oxo, —CN, $R^7$, and $R^8$.

6. A compound or pharmaceutically acceptable salt according to claim 1, wherein $R^3$ is pyridinyl, which is optionally substituted with from one to four substituents independently selected from halo, oxo, —CN, $R^7$, and $R^8$.

7. A compound or pharmaceutically acceptable salt according to claim 1, wherein $R^3$ is 1,2-dihydropyridinyl, which is optionally substituted with from one to five substituents independently selected from halo, oxo, —CN, $R^7$, and $R^8$.

8. A compound or pharmaceutically acceptable salt according to claim 1, wherein $R^3$ is pyrimidinyl, which is optionally substituted with from one to three substituents independently selected from halo, oxo, —CN, $R^7$, and $R^8$.

9. A compound or pharmaceutically acceptable salt according to claim 1, wherein $R^3$ is pyrazolyl, which is optionally substituted with from one to three substituents independently selected from halo, oxo, —CN, $R^7$, and $R^8$.

10. A compound or pharmaceutically acceptable salt according to claim 1, wherein $R^3$ is 3H-imidazo[4,5-b]pyridinyl, which is optionally substituted with from one to four substituents independently selected from halo, oxo, —CN, $R^7$, and $R^8$.

11. A compound or pharmaceutically acceptable salt according to claim 1, wherein $R^2$ is hydrogen.

12. A compound or pharmaceutically acceptable salt according to claim 1, wherein $R^5$ is trifluoromethyl.

13. A compound or pharmaceutically acceptable salt according to claim 1, wherein $R^6$ is hydrogen.

14. A compound according to claim 1, which is selected from the following compounds:
   4-phenyl-6-(trifluoromethyl)-1H-indazole;
   4-(3-methylpyridin-4-yl)-6-(trifluoromethyl)-1H-indazole;
   4-(imidazo[1,2-a]pyridin-6-yl)-6-(trifluoromethyl)-1H-indazole;
   7-(6-(trifluoromethyl)-1H-indazol-4-yl)-3,4-dihydro-2H-pyrido[3,2-b][1,4]oxazine;
   5-(6-(trifluoromethyl)-1H-indazol-4-yl)nicotinonitrile;
   4-(pyrimidin-5-yl)-6-(trifluoromethyl)-1H-indazole;
   4-(6-(trifluoromethyl)-1H-indazol-4-yl)benzamide;
   (3-(6-(trifluoromethyl)-1H-indazol-4-yl)phenyl)methanol;
   5-(6-(trifluoromethyl)-1H-indazol-4-yl)pyrimidin-2-amine;
   2-(6-(trifluoromethyl)-1H-indazol-4-yl)benzamide;
   (4-(6-(trifluoromethyl)-1H-indazol-4-yl)phenyl)methanol;
   (2-(6-(trifluoromethyl)-1H-indazol-4-yl)phenyl)methanol;
   4-(1H-pyrazol-3-yl)-6-(trifluoromethyl)-1H-indazole;
   4-(pyridin-4-yl)-6-(trifluoromethyl)-1H-indazole;
   2'-methyl-6-(trifluoromethyl)-1H,2'H-4,4'-biindazole;
   5-(6-(trifluoromethyl)-1H-indazol-4-yl)pyridin-2-amine;
   4-(1H-benzo[d]imidazol-5-yl)-6-(trifluoromethyl)-1H-indazole;
   3-(6-(trifluoromethyl)-1H-indazol-4-yl)benzamide;
   4-(pyridin-3-yl)-6-(trifluoromethyl)-1H-indazole;
   4-(1-methyl-1H-pyrazol-5-yl)-6-(trifluoromethyl)-1H-indazole;
   4-(3-methyl-1H-pyrazol-4-yl)-6-(trifluoromethyl)-1H-indazole;
   4-(1H-pyrazol-4-yl)-6-(trifluoromethyl)-1H-indazole;
   1'-methyl-6-(trifluoromethyl)-1H,1'H-4,6'-biindazole;
   4-(6-(trifluoromethyl)-1H-indazol-4-yl)benzenesulfonamide;
   7-(6-(trifluoromethyl)-1H-indazol-4-yl)isoquinoline;
   4-(benzo[d][1,3]dioxol-4-yl)-6-(trifluoromethyl)-1H-indazole;
   N-isobutyl-3-(6-(trifluoromethyl)-1H-indazol-4-yl)benzamide;
   (5-(6-(trifluoromethyl)-1H-indazol-4-yl)pyridin-3-yl)methanol;
   4-(4-methoxypyridin-3-yl)-6-(trifluoromethyl)-1H-indazole;
   8-(6-(trifluoromethyl)-1H-indazol-4-yl)quinoline;
   N,N-diethyl-3-(6-(trifluoromethyl)-1H-indazol-4-yl)benzamide;
   3-(6-(trifluoromethyl)-1H-indazol-4-yl)benzonitrile;
   N-benzyl-3-(6-(trifluoromethyl)-1H-indazol-4-yl)benzamide;
   N-cyclopropyl-4-(6-(trifluoromethyl)-1H-indazol-4-yl)benzamide;

1'-methyl-6-(trifluoromethyl)-1H,1'H-4,5'-biindazole;
2-methyl-5-(3-(6-(trifluoromethyl)-1H-indazol-4-yl)phenyl)-1,3,4-oxadiazole;
2-(3-(6-(trifluoromethyl)-1H-indazol-4-yl)phenyl)acetamide;
4-(1,3-dimethyl-1H-pyrazol-4-yl)-6-(trifluoromethyl)-1H-indazole;
2,4-dimethyl-5-(6-(trifluoromethyl)-1H-indazol-4-yl)thiazole;
4-(pyrazolo[1,5-a]pyridin-3-yl)-6-(trifluoromethyl)-1H-indazole;
4-(5-methoxypyridin-3-yl)-6-(trifluoromethyl)-1H-indazole;
4-(1-(pyridin-4-ylmethyl)-1H-pyrazol-4-yl)-6-(trifluoromethyl)-1H-indazole;
N-(2-(6-(trifluoromethyl)-1H-indazol-4-yl)phenyl)methanesulfonamide;
4-(3-methoxypyridin-4-yl)-6-(trifluoromethyl)-1H-indazole;
4-(3-fluoropyridin-4-yl)-6-(trifluoromethyl)-1H-indazole;
N,N-dimethyl-2-(6-(trifluoromethyl)-1H-indazol-4-yl)benzamide;
4-(4-(methoxymethyl)phenyl)-6-(trifluoromethyl)-1H-indazole;
4-(3-chloropyridin-4-yl)-6-(trifluoromethyl)-1H-indazole;
4-(2-methylpyridin-3-yl)-6-(trifluoromethyl)-1H-indazole;
4-(1-methyl-1H-indol-2-yl)-6-(trifluoromethyl)-1H-indazole;
2-(6-(trifluoromethyl)-1H-indazol-4-yl)benzonitrile;
4-(2-methoxypyridin-3-yl)-6-(trifluoromethyl)-1H-indazole;
5-(6-(trifluoromethyl)-1H-indazol-4-yl)pyrimidine-2,4(1H,3H)-dione;
4-(2,6-dimethoxypyridin-3-yl)-6-(trifluoromethyl)-1H-indazole;
N-(4-(6-(trifluoromethyl)-1H-indazol-4-yl)phenyl)methanesulfonamide;
4-(3-(6-(trifluoromethyl)-1H-indazol-4-yl)phenyl)morpholine;
4-(6-(cyclopropylmethoxy)pyridin-3-yl)-6-(trifluoromethyl)-1H-indazole;
4-(1H-pyrrolo[2,3-b]pyridin-5-yl)-6-(trifluoromethyl)-1H-indazole;
4-(4-(6-(trifluoromethyl)-1H-indazol-4-yl)thiazol-2-yl)morpholine;
4-(3-(1H-pyrazol-3-yl)phenyl)-6-(trifluoromethyl)-1H-indazole;
4-(4-(1H-pyrazol-5-yl)phenyl)-6-(trifluoromethyl)-1H-indazole;
2-chloro-5-(6-(trifluoromethyl)-1H-indazol-4-yl)benzamide;
4-(1-methyl-1H-benzo[d]imidazol-6-yl)-6-(trifluoromethyl)-1H-indazole;
4-(3-fluoro-4-(6-(trifluoromethyl)-1H-indazol-4-yl)pyridin-2-yl)morpholine;
4-(5-fluoro-1H-pyrrolo[2,3-b]pyridin-4-yl)-6-(trifluoromethyl)-1H-indazole;
1',3'-dimethyl-6-(trifluoromethyl)-1H,1'H-4,6'-biindazole;
4-(3-(1H-pyrazol-1-yl)phenyl)-6-(trifluoromethyl)-1H-indazole;
4-(5-methyl-1-phenyl-1H-pyrazol-4-yl)-6-(trifluoromethyl)-1H-indazole;
4-(1-(pyridin-2-ylmethyl)-1H-pyrazol-4-yl)-6-(trifluoromethyl)-1H-indazole;
N-(3-(6-(trifluoromethyl)-1H-indazol-4-yl)pyridin-2-yl)pivalamide;
4-(2-(4-(6-(trifluoromethyl)-1H-indazol-4-yl)-1H-pyrazol-1-yl)ethyl)morpholine;
5-fluoro-2-(6-(trifluoromethyl)-1H-indazol-4-yl)benzonitrile;
4-(1H-indol-7-yl)-6-(trifluoromethyl)-1H-indazole;
4-(1-methyl-1H-indol-4-yl)-6-(trifluoromethyl)-1H-indazole;
3-(6-(trifluoromethyl)-1H-indazol-4-yl)pyridin-2-amine;
4-(1,5-dimethyl-1H-pyrazol-4-yl)-6-(trifluoromethyl)-1H-indazole;
3,5-dimethyl-4-(6-(trifluoromethyl)-1H-indazol-4-yl)isoxazole;
4-(1H-indol-4-yl)-6-(trifluoromethyl)-1H-indazole;
1,3-dimethyl-5-(6-(trifluoromethyl)-1H-indazol-4-yl)pyrimidine-2,4(1H,3H)-dione;
4-(3,5-dimethyl-1H-pyrazol-4-yl)-6-(trifluoromethyl)-1H-indazole;
(4-methylpiperazin-1-yl)(3-(6-(trifluoromethyl)-1H-indazol-4-yl)phenyl)methanone;
pyrrolidin-1-yl(3-(6-(trifluoromethyl)-1H-indazol-4-yl)phenyl)methanone;
4-(2,5-dimethoxyphenyl)-6-(trifluoromethyl)-1H-indazole;
4-(2,3-dimethoxyphenyl)-6-(trifluoromethyl)-1H-indazole;
N-ethyl-3-(6-(trifluoromethyl)-1H-indazol-4-yl)benzamide;
4-(5-(6-(trifluoromethyl)-1H-indazol-4-yl)pyridin-2-yl)morpholine;
2-(3-(6-(trifluoromethyl)-1H-indazol-4-yl)phenyl)acetonitrile;
4-(6-methoxypyridin-2-yl)-6-(trifluoromethyl)-1H-indazole;
2-fluoro-N-methyl-4-(6-(trifluoromethyl)-1H-indazol-4-yl)benzamide;
2-(2-(6-(trifluoromethyl)-1H-indazol-4-yl)phenoxy)acetonitrile;
4-(5-(6-(trifluoromethyl)-1H-indazol-4-yl)pyrazin-2-yl)morpholine;
N-(4-(6-(trifluoromethyl)-1H-indazol-4-yl)benzyl)methanesulfonamide;
4-(1-(pyridin-3-ylmethyl)-1H-pyrazol-4-yl)-6-(trifluoromethyl)-1H-indazole;
N-methyl-5-(6-(trifluoromethyl)-1H-indazol-4-yl)picolinamide;
4-(2-(cyclopentyloxy)pyridin-3-yl)-6-(trifluoromethyl)-1H-indazole;
4-(2-(benzyloxy)pyridin-3-yl)-6-(trifluoromethyl)-1H-indazole;
4-(2-(2,2,2-trifluoroethoxy)pyridin-3-yl)-6-(trifluoromethyl)-1H-indazole;
5-(6-(trifluoromethyl)-1H-indazol-4-yl)quinoline;
4-fluoro-N-methyl-2-(6-(trifluoromethyl)-1H-indazol-4-yl)benzamide;
4-(3-(methylsulfonyl)phenyl)-6-(trifluoromethyl)-1H-indazole;
N-methyl-3-(6-(trifluoromethyl)-1H-indazol-4-yl)benzenesulfonamide;
4-(5-(methylsulfonyl)pyridin-3-yl)-6-(trifluoromethyl)-1H-indazole;
2-(3-(6-(trifluoromethyl)-1H-indazol-4-yl)phenyl)ethanol;
5-(6-(trifluoromethyl)-1H-indazol-4-yl)benzo[d]thiazole;
N,N-dimethyl-3-(6-(trifluoromethyl)-1H-indazol-4-yl)benzenesulfonamide;

2-fluoro-N-(2-hydroxyethyl)-4-(6-(trifluoromethyl)-1H-indazol-4-yl)benzamide;
2-fluoro-5-(6-(trifluoromethyl)-1H-indazol-4-yl)benzamide;
4-(6-(trifluoromethyl)-1H-indazol-4-yl)isoquinoline;
4-(6-(trifluoromethyl)-1H-indazol-4-yl)quinoline;
8-methoxy-5-(6-(trifluoromethyl)-1H-indazol-4-yl)quinoline;
4-fluoro-N-methyl-3-(6-(trifluoromethyl)-1H-indazol-4-yl)benzamide;
3-fluoro-N,N-dimethyl-5-(6-(trifluoromethyl)-1H-indazol-4-yl)benzamide;
4-(2-(pyrrolidin-1-yl)pyrimidin-5-yl)-6-(trifluoromethyl)-1H-indazole;
N-methyl-4-(6-(trifluoromethyl)-1H-indazol-4-yl)benzamide;
4-(5-(6-(trifluoromethyl)-1H-indazol-4-yl)pyrimidin-2-yl)morpholine;
N,N-dimethyl-4-(6-(trifluoromethyl)-1H-indazol-4-yl)benzamide;
2-methyl-5-(4-(6-(trifluoromethyl)-1H-indazol-4-yl)phenyl)-1,3,4-oxadiazole;
N,N-dimethyl-3-(6-(trifluoromethyl)-1H-indazol-4-yl)benzamide;
4-methyl-7-(6-(trifluoromethyl)-1H-indazol-4-yl)-3,4-dihydro-2H-pyrido[3,2-b][1,4]oxazine;
4-(2-methoxy-4-methylpyridin-3-yl)-6-(trifluoromethyl)-1H-indazole;
4-(3-chloro-2-methoxypyridin-4-yl)-6-(trifluoromethyl)-1H-indazole;
N,N,3-trimethyl-4-(6-(trifluoromethyl)-1H-indazol-4-yl)benzenesulfonamide;
4-(1,3-dimethyl-1H-pyrazol-5-yl)-6-(trifluoromethyl)-1H-indazole;
N,N,4-trimethyl-3-(6-(trifluoromethyl)-1H-indazol-4-yl)benzenesulfonamide;
(4-chloro-3-(6-(trifluoromethyl)-1H-indazol-4-yl)phenyl)methanol;
4-(6-(trifluoromethyl)-1H-indazol-4-yl)indolin-2-one;
N-(2-hydroxyethyl)-4-(6-(trifluoromethyl)-1H-indazol-4-yl)benzamide;
4-(2,4-dimethoxypyrimidin-5-yl)-6-(trifluoromethyl)-1H-indazole;
4-(2-ethoxypyridin-3-yl)-6-(trifluoromethyl)-1H-indazole;
4-(2-propoxypyridin-3-yl)-6-(trifluoromethyl)-1H-indazole;
4-(3-methylpyridin-2-yl)-6-(trifluoromethyl)-1H-indazole;
7-(6-(trifluoromethyl)-1H-indazol-4-yl)indolin-2-one;
5-chloro-3-(6-(trifluoromethyl)-1H-indazol-4-yl)pyridin-2-amine;
4-methoxy-5-(6-(trifluoromethyl)-1H-indazol-4-yl)pyrimidin-2-amine;
8-(6-(trifluoromethyl)-1H-indazol-4-yl)-2H-benzo[b][1,4]oxazin-3(4H)-one;
4-(hydroxymethyl)-3-(6-(trifluoromethyl)-1H-indazol-4-yl)benzonitrile;
4-(6-(trifluoromethyl)-1H-indazol-4-yl)isoindolin-1-one;
5-(6-(trifluoromethyl)-1H-indazol-4-yl)-1,7-naphthyridin-8-amine;
4-(2-isopropoxypyridin-3-yl)-6-(trifluoromethyl)-1H-indazole;
1-methyl-4-(6-(trifluoromethyl)-1H-indazol-4-yl)-1H-pyrazol-3-amine;
4-(1-(ethoxymethyl)-1H-imidazol-2-yl)-6-(trifluoromethyl)-1H-indazole;
4-(1,2-dimethyl-1H-imidazol-5-yl)-6-(trifluoromethyl)-1H-indazole;
4-(1-methyl-1H-imidazol-2-yl)-6-(trifluoromethyl)-1H-indazole;
4-(6-(trifluoromethyl)-1H-indazol-4-yl)-1H-pyrazole-3-carbonitrile;
4-(imidazo[1,2-a]pyridin-3-yl)-6-(trifluoromethyl)-1H-indazole;
4-(2-methylimidazo[1,2-a]pyridin-3-yl)-6-(trifluoromethyl)-1H-indazole;
3-(6-(trifluoromethyl)-1H-indazol-4-yl)imidazo[1,2-a]pyrimidine;
3-(6-(trifluoromethyl)-1H-indazol-4-yl)imidazo[1,2-a]pyrazine;
3-(6-(trifluoromethyl)-1H-indazol-4-yl)imidazo[1,2-a]pyridine-6-carbonitrile;
4-(imidazo[1,5-a]pyridin-1-yl)-6-(trifluoromethyl)-1H-indazole;
5-(6-(trifluoromethyl)-1H-indazol-4-yl)-7H-pyrrolo[2,3-d]pyrimidine;
3-(6-(trifluoromethyl)-1H-indazol-4-yl)-1H-pyrazolo[3,4-d]pyrimidin-4(5H)-one;
7-(6-(trifluoromethyl)-1H-indazol-4-yl)-5H-pyrrolo[2,3-b]pyrazine;
4-(6-(trifluoromethyl)-1H-indazol-4-yl)-1H-pyrazole-5-carbonitrile;
7-amino-3-(6-(trifluoromethyl)-1H-indazol-4-yl)pyrazolo[1,5-a]pyrimidine-6-carbonitrile;
7-methoxy-3-(6-(trifluoromethyl)-1H-indazol-4-yl)imidazo[1,2-a]pyridine-8-carbonitrile;
4-(5-methyl-1H-imidazol-4-yl)-6-(trifluoromethyl)-1H-indazole;
4-(1,5-dimethyl-1H-imidazol-2-yl)-6-(trifluoromethyl)-1H-indazole;
4-(1,4-dimethyl-1H-imidazol-2-yl)-6-(trifluoromethyl)-1H-indazole;
6-(trifluoromethyl)-4-(1,3,5-trimethyl-1H-pyrazol-4-yl)-1H-indazole;
1-methyl-4-(6-(trifluoromethyl)-1H-indazol-4-yl)-1H-pyrazol-5-amine;
5-methyl-4-(6-(trifluoromethyl)-1H-indazol-4-yl)isoxazol-3-amine;
3,7-dimethyl-8-(6-(trifluoromethyl)-1H-indazol-4-yl)-1H-purine-2,6(3H,7H)-dione;
4-(1-ethyl-3,5-dimethyl-1H-pyrazol-4-yl)-6-(trifluoromethyl)-1H-indazole;
4-(3,5-dimethyl-1-(1H-tetrazol-5-yl)-1H-pyrazol-4-yl)-6-(trifluoromethyl)-1H-indazole;
2-(3,5-dimethyl-4-(6-(trifluoromethyl)-1H-indazol-4-yl)-1H-pyrazol-1-yl)acetonitrile;
4-(1-ethyl-3-methyl-1H-pyrazol-4-yl)-6-(trifluoromethyl)-1H-indazole;
3-(3,5-dimethyl-4-(6-(trifluoromethyl)-1H-indazol-4-yl)-1H-pyrazol-1-yl)propanamide;
2-(3,5-dimethyl-4-(6-(trifluoromethyl)-1H-indazol-4-yl)-1H-pyrazol-1-yl)acetamide;
3-(3,5-dimethyl-4-(6-(trifluoromethyl)-1H-indazol-4-yl)-1H-pyrazol-1-yl)propanenitrile;
4-(1-ethyl-5-methyl-1H-pyrazol-4-yl)-6-(trifluoromethyl)-1H-indazole;
2-(3,5-dimethyl-4-(6-(trifluoromethyl)-1H-indazol-4-yl)-1H-pyrazol-1-yl)ethanamine;
4-methyl-5-(6-(trifluoromethyl)-1H-indazol-4-yl)thiazole;
N-(6-methyl-5-(6-(trifluoromethyl)-1H-indazol-4-yl)pyridin-2-yl)acetamide;

N-(4-methyl-5-(6-(trifluoromethyl)-1H-indazol-4-yl)pyridin-2-yl)acetamide;
1-morpholino-3-(2-(6-(trifluoromethyl)-1H-indazol-4-yl)phenoxy)propan-2-ol;
4-methoxy-N-methyl-3-(6-(trifluoromethyl)-1H-indazol-4-yl)benzamide;
2-(2-(6-(trifluoromethyl)-1H-indazol-4-yl)phenylsulfonyl)ethanol;
N,N-dimethyl-2-(6-(trifluoromethyl)-1H-indazol-4-yl)benzenesulfonamide;
6-methoxy-2-(6-(trifluoromethyl)-1H-indazol-4-yl)pyridin-3-amine;
(4-methoxy-3-(6-(trifluoromethyl)-1H-indazol-4-yl)phenyl)methanol;
3-methyl-4-(6-(trifluoromethyl)-1H-indazol-4-yl)benzenesulfonamide;
6-methoxy-5-(6-(trifluoromethyl)-1H-indazol-4-yl)pyridin-3-amine;
6-methyl-2-(6-(trifluoromethyl)-1H-indazol-4-yl)pyridin-3-amine;
(5-methoxy-2-(6-(trifluoromethyl)-1H-indazol-4-yl)phenyl)methanol;
4,6-dimethyl-5-(6-(trifluoromethyl)-1H-indazol-4-yl)pyrimidin-2-amine;
2-chloro-5-(6-(trifluoromethyl)-1H-indazol-4-yl)pyrimidin-4-amine;
5-(6-(trifluoromethyl)-1H-indazol-4-yl)pyrimidine-4-carboxylic acid;
5-methyl-3-(6-(trifluoromethyl)-1H-indazol-4-yl)pyridin-2-amine;
5-fluoro-3-(6-(trifluoromethyl)-1H-indazol-4-yl)pyridin-2-amine;
5-methyl-6-(6-(trifluoromethyl)-1H-indazol-4-yl)-3H-imidazo[4,5-b]pyridine;
N-methyl-5-(6-(trifluoromethyl)-1H-indazol-4-yl)pyrimidin-2-amine;
N-cyclopropyl-5-(6-(trifluoromethyl)-1H-indazol-4-yl)pyrimidin-2-amine;
5-(6-(trifluoromethyl)-1H-indazol-4-yl)pyrimidine-2-carbonitrile;
1-ethyl-5-methyl-7-(6-(trifluoromethyl)-1H-indazol-4-yl)indoline-2,3-dione;
4-(3-methoxy-6-methylpyridin-2-yl)-6-(trifluoromethyl)-1H-indazole;
6-methoxy-3-(6-(trifluoromethyl)-1H-indazol-4-yl)picolinamide;
2-(1H-1,2,4-triazol-1-yl)-N-(2-(6-(trifluoromethyl)-1H-indazol-4-yl)benzyl)acetamide;
5-fluoro-2-(6-(trifluoromethyl)-1H-indazol-4-yl)benzamide;
6-methyl-5-(6-(trifluoromethyl)-1H-indazol-4-yl)pyrimidine-2,4(1H,3H)-dione;
2-amino-1-(2-(6-(trifluoromethyl)-1H-indazol-4-yl)phenyl)ethanol;
(R)-2-(5-(6-(trifluoromethyl)-1H-indazol-4-yl)pyrimidin-2-ylamino)propan-1-ol;
(R)-1-(5-(6-(trifluoromethyl)-1H-indazol-4-yl)pyrimidin-2-ylamino)propan-2-ol;
(S)-1-(5-(6-(trifluoromethyl)-1H-indazol-4-yl)pyrimidin-2-ylamino)propan-2-ol;
2-(5-(6-(trifluoromethyl)-1H-indazol-4-yl)pyrimidin-2-ylamino)ethanol;
3-(6-(trifluoromethyl)-1H-indazol-4-yl)pyridin-2-ol;
6-methyl-3-(6-(trifluoromethyl)-1H-indazol-4-yl)pyridin-2-amine;
6-amino-5-(6-(trifluoromethyl)-1H-indazol-4-yl)nicotinonitrile;
4-(3-methoxypyridin-2-yl)-6-(trifluoromethyl)-1H-indazole;
2-(6-(trifluoromethyl)-1H-indazol-4-yl)pyridin-3-ol;
4-(2,6-dimethylpyridin-3-yl)-6-(trifluoromethyl)-1H-indazole;
5-chloro-2-(6-(trifluoromethyl)-1H-indazol-4-yl)pyridin-3-amine;
4-(2-(1H-imidazol-1-yl)pyrimidin-5-yl)-6-(trifluoromethyl)-1H-indazole;
N-(2-(6-(trifluoromethyl)-1H-indazol-4-yl)pyridin-3-yl)acetamide;
2-(3,5-dimethyl-4-(6-(trifluoromethyl)-1H-indazol-4-yl)-1H-pyrazol-1-yl)-N,N-dimethylethanamine;
(1-methyl-4-(6-(trifluoromethyl)-1H-indazol-4-yl)-1H-pyrazol-3-yl)methanol;
(6-amino-5-(6-(trifluoromethyl)-1H-indazol-4-yl)pyridin-3-yl)(4-methylpiperazin-1-yl)methanone;
2-methyl-3-(6-(trifluoromethyl)-1H-indazol-4-yl)pyrazolo[1,5-d][1,2,4]triazin-7(6H)-one;
4-(4-(1H-pyrazol-1-ylsulfonyl)phenyl)-6-(trifluoromethyl)-1H-indazole;
N-(2-hydroxyethyl)-4-(6-(trifluoromethyl)-1H-indazol-4-yl)benzenesulfonamide;
4-(4-(6-(trifluoromethyl)-1H-indazol-4-yl)phenylsulfonyl)morpholine;
4-(3-methyl-4-(6-(trifluoromethyl)-1H-indazol-4-yl)phenylsulfonyl)morpholine;
3-(4-methylpiperazine-1-carbonyl)-5-(6-(trifluoromethyl)-1H-indazol-4-yl)pyridin-2(1H)-one;
N-(2-hydroxyethyl)-2-oxo-5-(6-(trifluoromethyl)-1H-indazol-4-yl)-1,2-dihydropyridine-3-carboxamide;
N-(2-hydroxyethyl)-2-methoxy-5-(6-(trifluoromethyl)-1H-indazol-4-yl)nicotinamide;
2-amino-N-(2-hydroxyethyl)-5-(6-(trifluoromethyl)-1H-indazol-4-yl)nicotinamide;
2-oxo-5-(6-(trifluoromethyl)-1H-indazol-4-yl)-1,2-dihydropyridine-3-carboxamide;
2-methoxy-5-(6-(trifluoromethyl)-1H-indazol-4-yl)nicotinamide;
2-amino-5-(6-(trifluoromethyl)-1H-indazol-4-yl)nicotinamide;
1-methyl-5-(6-(trifluoromethyl)-1H-indazol-4-yl)indolin-2-one;
5-(6-(trifluoromethyl)-1H-indazol-4-yl)indolin-2-one;
6-(trifluoromethyl)-1H,1'H-4,5'-biindazole;
5-(6-(trifluoromethyl)-1H-indazol-4-yl)-1H-benzo[d]imidazol-2(3H)-one;
5-(6-(trifluoromethyl)-1H-indazol-4-yl)-1H-pyrrolo[2,3-b]pyridin-2(3H)-one;
6-(6-(trifluoromethyl)-1H-indazol-4-yl)indolin-2-one;
2-(6-(trifluoromethyl)-1H-indazol-4-yl)-5H-pyrrolo[2,3-b]pyrazine;
6-(6-(trifluoromethyl)-1H-indazol-4-yl)-1H-imidazo[4,5-b]pyridin-2(3H)-one;
2-(trifluoromethyl)-6-(6-(trifluoromethyl)-1H-indazol-4-yl)-3H-imidazo[4,5-b]pyridine;
5-(6-(trifluoromethyl)-1H-indazol-4-yl)-1H-pyrazolo[3,4-b]pyridine;
7-(6-(trifluoromethyl)-1H-indazol-4-yl)-3,4-dihydropyrido[2,3-b]pyrazin-2(1H)-one;
6-amino-3-methyl-5-(6-(trifluoromethyl)-1H-indazol-4-yl)pyrimidin-4(3H)-one;
4-(2-methoxypyrimidin-5-yl)-6-(trifluoromethyl)-1H-indazole;
N,N-dimethyl-5-(6-(trifluoromethyl)-1H-indazol-4-yl)pyrimidin-2-amine;

4-(3,6-dimethoxypyridazin-4-yl)-6-(trifluoromethyl)-1H-indazole;
4-(6-methoxy-2-methylpyridin-3-yl)-6-(trifluoromethyl)-1H-indazole;
(1-methyl-4-(6-(trifluoromethyl)-1H-indazol-4-yl)-1H-pyrazol-5-yl)methanol;
5-(6-(trifluoromethyl)-1H-indazol-4-yl)picolinamide;
2-methyl-3-(6-(trifluoromethyl)-1H-indazol-4-yl)pyridin-4-amine;
4-(6-methoxy-4-methylpyridin-3-yl)-6-(trifluoromethyl)-1H-indazole;
N-methyl-5-(6-(trifluoromethyl)-1H-indazol-4-yl)pyrimidine-4-carboxamide;
6-methyl-5-(6-(trifluoromethyl)-1H-indazol-4-yl)pyridin-2-amine;
2-methoxy-5-(6-(trifluoromethyl)-1H-indazol-4-yl)pyrimidin-4-amine;
N-(6-methyl-5-(6-(trifluoromethyl)-1H-indazol-4-yl)pyridin-2-yl)methanesulfonamide;
2-methoxy-N-(6-methyl-5-(6-(trifluoromethyl)-1H-indazol-4-yl)pyridin-2-yl)acetamide;
1-methyl-N-(6-methyl-5-(6-(trifluoromethyl)-1H-indazol-4-yl)pyridin-2-yl)-1H-pyrazole-4-sulfonamide;
ethyl 2-(4-(6-(trifluoromethyl)-1H-indazol-4-yl)-1H-pyrazol-1-yl)acetate;
2-(4-(6-(trifluoromethyl)-1H-indazol-4-yl)-1H-pyrazol-1-yl)acetic acid;
morpholino(5-(6-(trifluoromethyl)-1H-indazol-4-yl)pyridin-2-yl)methanone;
methyl 4-methoxy-3-(6-(trifluoromethyl)-1H-indazol-4-yl)benzoate;
2-(4-(6-(trifluoromethyl)-1H-indazol-4-yl)-1H-pyrazol-1-yl)acetamide;
methyl 6-oxo-5-(6-(trifluoromethyl)-1H-indazol-4-yl)-1,6-dihydropyridine-3-carboxylate;
(4-methoxy-3-(6-(trifluoromethyl)-1H-indazol-4-yl)phenyl)(4-methylpiperazin-1-yl)methanone;
(4-methoxy-3-(6-(trifluoromethyl)-1H-indazol-4-yl)phenyl)(morpholino)methanone;
N-(2-hydroxyethyl)-4-methoxy-3-(6-(trifluoromethyl)-1H-indazol-4-yl)benzamide;
methyl 5-(6-(trifluoromethyl)-1H-indazol-4-yl)picolinate;
N-(2-hydroxyethyl)-5-(6-(trifluoromethyl)-1H-indazol-4-yl)picolinamide;
(4-methylpiperazin-1-yl)(5-(6-(trifluoromethyl)-1H-indazol-4-yl)pyridin-2-yl)methanone;
4-methoxy-N,N-dimethyl-3-(6-(trifluoromethyl)-1H-indazol-4-yl)benzamide;
4-methoxy-3-(6-(trifluoromethyl)-1H-indazol-4-yl)benzamide;
2-(3-methyl-4-(6-(trifluoromethyl)-1H-indazol-4-yl)-1H-pyrazol-1-yl)acetamide;
6-(6-(trifluoromethyl)-1H-indazol-4-yl)pyrazolo[1,5-a]pyrimidine;
3-(6-(trifluoromethyl)-1H-indazol-4-yl)imidazo[1,2-b]pyridazine-6-carboxamide;
2-(3-methyl-4-(6-(trifluoromethyl)-1H-indazol-4-yl)-1H-pyrazol-1-yl)-1-morpholinoethanone;
1-methyl-5-(6-(trifluoromethyl)-1H-indazol-4-yl)pyrimidine-2,4(1H,3H)-dione;
N-(2-hydroxyethyl)-2-(3-methyl-4-(6-(trifluoromethyl)-1H-indazol-4-yl)-1H-pyrazol-1-yl)acetamide;
N,N-dimethyl-2-(4-(6-(trifluoromethyl)-1H-indazol-4-yl)phenoxy)ethanamine;
4-(2-(4-(6-(trifluoromethyl)-1H-indazol-4-yl)phenoxy)ethyl)morpholine;
(2-amino-5-(6-(trifluoromethyl)-1H-indazol-4-yl)pyridin-3-yl)(4-methylpiperazin-1-yl)methanone;
4-(6-(trifluoromethyl)-1H-indazol-4-yl)picolinamide;
(4-methylpiperazin-1-yl)(4-(6-(trifluoromethyl)-1H-indazol-4-yl)pyridin-2-yl)methanone;
N-(2-hydroxyethyl)-5-(6-(trifluoromethyl)-1H-indazol-4-yl)pyrimidine-2-carboxamide;
(4-methylpiperazin-1-yl)(5-(6-(trifluoromethyl)-1H-indazol-4-yl)pyridin-3-yl)methanone;
(2-methoxy-5-(6-(trifluoromethyl)-1H-indazol-4-yl)pyridin-3-yl)(4-methylpiperazin-1-yl)methanone;
(2-fluoro-5-(6-(trifluoromethyl)-1H-indazol-4-yl)pyridin-3-yl)(4-methylpiperazin-1-yl)methanone;
N-(2-hydroxyethyl)-5-(6-(trifluoromethyl)-1H-indazol-4-yl)nicotinamide;
4-(7-methoxy-1H-pyrrolo[2,3-c]pyridin-4-yl)-6-(trifluoromethyl)-1H-indazole;
4-(7-methyl-1H-pyrrolo[2,3-c]pyridin-4-yl)-6-(trifluoromethyl)-1H-indazole;
N-(2-methoxyethyl)-5-(6-(trifluoromethyl)-1H-indazol-4-yl)pyrimidin-2-amine;
morpholino(5-(6-(trifluoromethyl)-1H-indazol-4-yl)pyrimidin-2-yl)methanone;
5-(6-(trifluoromethyl)-1H-indazol-4-yl)pyrimidine-2-carboxamide;
4-methyl-6-(6-(trifluoromethyl)-1H-indazol-4-yl)-2H-benzo[b][1,4]oxazin-3(4H)-one;
5-(4-methylpiperazine-1-carbonyl)-3-(6-(trifluoromethyl)-1H-indazol-4-yl)pyridin-2(1H)-one;
5-(morpholine-4-carbonyl)-3-(6-(trifluoromethyl)-1H-indazol-4-yl)pyridin-2(1H)-one;
N-(2-hydroxyethyl)-6-oxo-5-(6-(trifluoromethyl)-1H-indazol-4-yl)-1,6-dihydropyridine-3-carboxamide;
2-(3-methyl-2,6-dioxo-5-(6-(trifluoromethyl)-1H-indazol-4-yl)-2,3-dihydropyrimidin-1(6H)-yl)acetamide;
N-methyl-2-(3-methyl-2,6-dioxo-5-(6-(trifluoromethyl)-1H-indazol-4-yl)-2,3-dihydropyrimidin-1(6H)-yl)acetamide;
N-ethyl-2-(3-methyl-2,6-dioxo-5-(6-(trifluoromethyl)-1H-indazol-4-yl)-2,3-dihydropyrimidin-1(6H)-yl)acetamide;
3-(2-hydroxyethyl)-1-methyl-5-(6-(trifluoromethyl)-1H-indazol-4-yl)pyrimidine-2,4(1H,3H)-dione;
3-methoxy-N-methyl-4-(6-(trifluoromethyl)-1H-indazol-4-yl)benzamide;
N-(2-hydroxyethyl)-3-methoxy-4-(6-(trifluoromethyl)-1H-indazol-4-yl)benzamide;
3-methoxy-4-(6-(trifluoromethyl)-1H-indazol-4-yl)benzamide;
N-(2-hydroxyethyl)-4-methyl-5-(6-(trifluoromethyl)-1H-indazol-4-yl)picolinamide;
N-(2-hydroxyethyl)-4-(6-(trifluoromethyl)-1H-indazol-4-yl)picolinamide;
N,N-dimethyl-2-(3-methyl-2,6-dioxo-5-(6-(trifluoromethyl)-1H-indazol-4-yl)-2,3-dihydropyrimidin-1(6H)-yl)acetamide;
1-methyl-3-(2-morpholino-2-oxoethyl)-5-(6-(trifluoromethyl)-1H-indazol-4-yl)pyrimidine-2,4(1H,3H)-dione;
3-(4-fluorobenzyl)-1-methyl-5-(6-(trifluoromethyl)-1H-indazol-4-yl)pyrimidine-2,4(1H,3H)-dione;
2-(3-methyl-2,6-dioxo-5-(6-(trifluoromethyl)-1H-indazol-4-yl)-2,3-dihydropyrimidin-1(6H)-yl)acetonitrile;
1-methyl-3-(2-morpholinoethyl)-5-(6-(trifluoromethyl)-1H-indazol-4-yl)pyrimidine-2,4(1H,3H)-dione;
1-methyl-5-(morpholine-4-carbonyl)-3-(6-(trifluoromethyl)-1H-indazol-4-yl)pyridin-2(1H)-one;

N-(2-hydroxyethyl)-1-methyl-6-oxo-5-(6-(trifluoromethyl)-1H-indazol-4-yl)-1,6-dihydropyridine-3-carboxamide;
2-(4-methoxy-3-(6-(trifluoromethyl)-1H-indazol-4-yl)phenyl)-1-morpholinoethanone;
2-(3,5-dimethyl-4-(6-(trifluoromethyl)-1H-indazol-4-yl)-1H-pyrazol-1-yl)-1-morpholinoethanone;
(3-methoxy-4-(6-(trifluoromethyl)-1H-indazol-4-yl)phenyl)(morpholino)methanone;
3-(2-(dimethylamino)ethyl)-1-methyl-5-(6-(trifluoromethyl)-1H-indazol-4-yl)pyrimidine-2,4(1H,3H)-dione;
N-(2-hydroxyethyl)-2-(4-methoxy-3-(6-(trifluoromethyl)-1H-indazol-4-yl)phenyl)acetamide;
3-fluoro-4-(6-(trifluoromethyl)-1H-indazol-4-yl)benzamide;
3-fluoro-N-(2-hydroxyethyl)-4-(6-(trifluoromethyl)-1H-indazol-4-yl)benzamide;
4-(5-(methoxymethyl)-3-methyl-1H-pyrazol-4-yl)-6-(trifluoromethyl)-1H-indazole;
1-(3,5-dimethyl-4-(6-(trifluoromethyl)-1H-indazol-4-yl)-1H-pyrazol-1-yl)propan-2-one;
4-(4-methoxy-3-(6-(trifluoromethyl)-1H-indazol-4-yl)benzoyl)-1-methylpiperazin-2-one;
4-fluoro-3-(6-(trifluoromethyl)-1H-indazol-4-yl)benzamide;
1,3-dimethyl-4-(6-(trifluoromethyl)-1H-indazol-4-yl)-1H-pyrazole-5-carboxamide;
(3-hydroxyazetidin-1-yl)(4-methoxy-3-(6-(trifluoromethyl)-1H-indazol-4-yl)phenyl)methanone;
3-(6-(trifluoromethyl)-1H-indazol-4-yl)benzenesulfonamide;
N-(2-hydroxyethyl)-3-methyl-4-(6-(trifluoromethyl)-1H-indazol-4-yl)benzamide;
3-chloro-N-(2-hydroxyethyl)-4-(6-(trifluoromethyl)-1H-indazol-4-yl)benzamide;
N-cyclopropyl-6-oxo-5-(6-(trifluoromethyl)-1H-indazol-4-yl)-1,6-dihydropyridine-3-carboxamide;
N-(cyanomethyl)-6-oxo-5-(6-(trifluoromethyl)-1H-indazol-4-yl)-1,6-dihydropyridine-3-carboxamide;
N,N-dimethyl-6-oxo-5-(6-(trifluoromethyl)-1H-indazol-4-yl)-1,6-dihydropyridine-3-carboxamide;
(S)—N-(2-hydroxypropyl)-6-oxo-5-(6-(trifluoromethyl)-1H-indazol-4-yl)-1,6-dihydropyridine-3-carboxamide;
(R)—N-(2-hydroxypropyl)-6-oxo-5-(6-(trifluoromethyl)-1H-indazol-4-yl)-1,6-dihydropyridine-3-carboxamide;
N-(2,3-dihydroxypropyl)-6-oxo-5-(6-(trifluoromethyl)-1H-indazol-4-yl)-1,6-dihydropyridine-3-carboxamide;
N-(2,2-difluoroethyl)-6-oxo-5-(6-(trifluoromethyl)-1H-indazol-4-yl)-1,6-dihydropyridine-3-carboxamide;
4-(3-fluoro-1H-pyrrolo[2,3-b]pyridin-5-yl)-6-(trifluoromethyl)-1H-indazole;
4-(3-methyl-1H-pyrrolo[2,3-b]pyridin-5-yl)-6-(trifluoromethyl)-1H-indazole;
2-methyl-6-(6-(trifluoromethyl)-1H-indazol-4-yl)-3H-imidazo[4,5-b]pyridine;
3-fluoro-4-(6-(trifluoromethyl)-1H-indazol-4-yl)benzenesulfonamide;
2-chloro-4-(6-(trifluoromethyl)-1H-indazol-4-yl)benzenesulfonamide;
2-fluoro-4-(6-(trifluoromethyl)-1H-indazol-4-yl)benzenesulfonamide;
5-(6-(trifluoromethyl)-1H-indazol-4-yl)pyridine-2-sulfonamide;
5-(6-(trifluoromethyl)-1H-indazol-4-yl)pyridine-3-sulfonamide;
4-(4-(methylsulfonyl)phenyl)-6-(trifluoromethyl)-1H-indazole;
4-(1-(difluoromethyl)-3,5-dimethyl-1H-pyrazol-4-yl)-6-(trifluoromethyl)-1H-indazole;
2-(4-(6-(trifluoromethyl)-1H-indazol-4-yl)-1H-pyrazol-1-yl)ethanol;
2-(4-methoxy-3-(6-(trifluoromethyl)-1H-indazol-4-yl)phenyl)acetamide;
3-chloro-4-(6-(trifluoromethyl)-1H-indazol-4-yl)benzenesulfonamide;
2-(3,5-dimethyl-4-(6-(trifluoromethyl)-1H-indazol-4-yl)-1H-pyrazol-1-yl)-N-isopropylacetamide;
N,N,1-trimethyl-6-oxo-5-(6-(trifluoromethyl)-1H-indazol-4-yl)-1,6-dihydropyridine-3-carboxamide;
N-(cyanomethyl)-1-methyl-6-oxo-5-(6-(trifluoromethyl)-1H-indazol-4-yl)-1,6-dihydropyridine-3-carboxamide;
N-(2,2-difluoroethyl)-1-methyl-6-oxo-5-(6-(trifluoromethyl)-1H-indazol-4-yl)-1,6-dihydropyridine-3-carboxamide;
N-(2,3-dihydroxypropyl)-1-methyl-6-oxo-5-(6-(trifluoromethyl)-1H-indazol-4-yl)-1,6-dihydropyridine-3-carboxamide;
N-cyclopropyl-1-methyl-6-oxo-5-(6-(trifluoromethyl)-1H-indazol-4-yl)-1,6-dihydropyridine-3-carboxamide;
(R)—N-(2-hydroxypropyl)-1-methyl-6-oxo-5-(6-(trifluoromethyl)-1H-indazol-4-yl)-1,6-dihydropyridine-3-carboxamide;
(S)—N-(2-hydroxypropyl)-1-methyl-6-oxo-5-(6-(trifluoromethyl)-1H-indazol-4-yl)-1,6-dihydropyridine-3-carboxamide;
4-fluoro-N-(2-hydroxyethyl)-3-(6-(trifluoromethyl)-1H-indazol-4-yl)benzamide;
(3-hydroxyazetidin-1-yl)(3-methyl-4-(6-(trifluoromethyl)-1H-indazol-4-yl)phenyl)methanone;
4-(6-(2-methoxyethoxy)-2-methylpyridin-3-yl)-6-(trifluoromethyl)-1H-indazole;
2-(3,5-dimethyl-4-(6-(trifluoromethyl)-1H-indazol-4-yl)-1H-pyrazol-1-yl)-N,N-dimethylacetamide;
(5S)-5-((3,5-dimethyl-4-(6-(trifluoromethyl)-1H-indazol-4-yl)-1H-pyrazol-1-yl)methyl)pyrrolidin-2-one;
4-(2-(methylsulfonyl)phenyl)-6-(trifluoromethyl)-1H-indazole;
2-(3,5-dimethyl-4-(6-(trifluoromethyl)-1H-indazol-4-yl)-1H-pyrazol-1-yl)-1-(3-hydroxyazetidin-1-yl)ethanone;
2-(3,5-dimethyl-4-(6-(trifluoromethyl)-1H-indazol-4-yl)-1H-pyrazol-1-yl)-N-methylacetamide;
N-(2-hydroxyethyl)-4-methyl-3-(6-(trifluoromethyl)-1H-indazol-4-yl)benzamide;
(3-hydroxyazetidin-1-yl)(4-methyl-3-(6-(trifluoromethyl)-1H-indazol-4-yl)phenyl)methanone;
(3-hydroxypyrrolidin-1-yl)(4-methyl-3-(6-(trifluoromethyl)-1H-indazol-4-yl)phenyl)methanone;
(3-(hydroxymethyl)pyrrolidin-1-yl)(4-methyl-3-(6-(trifluoromethyl)-1H-indazol-4-yl)phenyl)methanone;
(4-hydroxypiperidin-1-yl)(4-methyl-3-(6-(trifluoromethyl)-1H-indazol-4-yl)phenyl)methanone;
1-methyl-5-(6-(trifluoromethyl)-1H-indazol-4-yl)pyridin-2(1H)-one;
2-(2-oxo-5-(6-(trifluoromethyl)-1H-indazol-4-yl)pyridin-1(2H)-yl)acetic acid;
1-methyl-5-(4-methylpiperazine-1-carbonyl)-3-(6-(trifluoromethyl)-1H-indazol-4-yl)pyridin-2(1H)-one;
2,5-difluoro-4-(6-(trifluoromethyl)-1H-indazol-4-yl)benzenesulfonamide;
6-methyl-5-(6-(trifluoromethyl)-1H-indazol-4-yl)picolinonitrile;
N-(2-hydroxyethyl)-5-(6-(trifluoromethyl)-1H-indazol-4-yl)pyridine-2-sulfonamide;

6-methyl-5-(6-(trifluoromethyl)-1H-indazol-4-yl)picolinamide;
4-(3,5-dimethyl-1-((3-methyloxetan-3-yl)methyl)-1H-pyrazol-4-yl)-6-(trifluoromethyl)-1H-indazole;
1,5-dimethyl-4-(6-(trifluoromethyl)-1H-indazol-4-yl)-1H-pyrazol-3-amine;
5-methyl-6-(6-(trifluoromethyl)-1H-indazol-4-yl)-3H-imidazo[4,5-b]pyridin-2-ol;
4-(2-methyl-6-(4H-1,2,4-triazol-4-yl)pyridin-3-yl)-6-(trifluoromethyl)-1H-indazole;
4-(2-methyl-6-(pyrrolidin-1-yl)pyridin-3-yl)-6-(trifluoromethyl)-1H-indazole;
(3-hydroxyazetidin-1-yl)(4-(6-(trifluoromethyl)-1H-indazol-4-yl)pyridin-2-yl)methanone;
2-(3,5-dimethyl-4-(6-(trifluoromethyl)-1H-indazol-4-yl)-1H-pyrazol-1-yl)-N-(2-hydroxyethyl)acetamide;
N-(2-hydroxyethyl)-6-methyl-5-(6-(trifluoromethyl)-1H-indazol-4-yl)picolinamide;
4-(7-methylimidazo[1,5-a]pyridin-6-yl)-6-(trifluoromethyl)-1H-indazole;
6-methyl-5-(6-(trifluoromethyl)-1H-indazol-4-yl)pyridin-2(1H)-one;
4-methyl-5-(6-(trifluoromethyl)-1H-indazol-4-yl)pyridin-2(1H)-one;
6-methoxy-5-(6-(trifluoromethyl)-1H-indazol-4-yl)picolinamide;
4-(6-chloro-2-methoxypyridin-3-yl)-6-(trifluoromethyl)-1H-indazole;
5-methyl-6-(6-(trifluoromethyl)-1H-indazol-4-yl)-[1,2,4]triazolo[1,5-a]pyridine;
N-(2-hydroxyethyl)-6-methoxy-5-(6-(trifluoromethyl)-1H-indazol-4-yl)picolinamide;
(3-hydroxyazetidin-1-yl)(6-methoxy-5-(6-(trifluoromethyl)-1H-indazol-4-yl)pyridin-2-yl)methanone;
6-methoxy-5-(6-(trifluoromethyl)-1H-indazol-4-yl)picolinonitrile;
(3-hydroxyazetidin-1-yl)(6-methyl-2-(methylamino)-5-(6-(trifluoromethyl)-1H-indazol-4-yl)pyridin-3-yl)methanone;
5-methyl-6-(6-(trifluoromethyl)-1H-indazol-4-yl)tetrazolo[1,5-a]pyridine;
4-(6-methyl-5-(6-(trifluoromethyl)-1H-indazol-4-yl)pyridin-2-yl)morpholine;
4-(2-methyl-6-(4-methylpiperazin-1-yl)pyridin-3-yl)-6-(trifluoromethyl)-1H-indazole;
1,6-dimethyl-5-(4-methylpiperazine-1-carbonyl)-3-(6-(trifluoromethyl)-1H-indazol-4-yl)pyridin-2(1H)-one;
1,6-dimethyl-5-(6-(trifluoromethyl)-1H-indazol-4-yl)pyridin-2(1H)-one;
1,4-dimethyl-5-(6-(trifluoromethyl)-1H-indazol-4-yl)pyridin-2(1H)-one;
N-(2-hydroxyethyl)-1,2-dimethyl-6-oxo-5-(6-(trifluoromethyl)-1H-indazol-4-yl)-1, 6-dihydropyridine-3-carboxamide;
2-(6-methyl-2-oxo-5-(6-(trifluoromethyl)-1H-indazol-4-yl)pyridin-1 (2H)-yl)acetonitrile;
4-methyl-1-(pyridin-2-ylmethyl)-5-(6-(trifluoromethyl)-1H-indazol-4-yl)pyridin-2(1H)-one;
6-methyl-1-(pyridin-2-ylmethyl)-5-(6-(trifluoromethyl)-1H-indazol-4-yl)pyridin-2(1H)-one;
2-(4-methyl-2-oxo-5-(6-(trifluoromethyl)-1H-indazol-4-yl)pyridin-1 (2H)-yl)acetonitrile;
4-(2-methyl-6-(2-(methyl sulfonyl)ethyl)pyridin-3-yl)-6-(trifluoromethyl)-1H-indazole;
(3-methyl-1-((1-methyl-1H-pyrazol-4-yl)methyl)-4-(6-(trifluoromethyl)-1H-indazol-4-yl)-1H-pyrazol-5-yl)methanol;
(5-methyl-1-((3-methylisoxazol-5-yl)methyl)-4-(6-(trifluoromethyl)-1H-indazol-4-yl)-1H-pyrazol-3-yl)methanol;
(3-methyl-14(3-methylisoxazol-5-yl)methyl)-4-(6-(trifluoromethyl)-1H-indazol-4-yl)-1H-pyrazol-5-yl)methanol;
(R)-1-(4-methyl-5-(6-(trifluoromethyl)-1H-indazol-4-yl)pyrimidin-2-yl)pyrrolidin-3-ol;
(R)-4-(2-methyl-6-(3-methylpiperazin-1-yl)pyridin-3-yl)-6-(trifluoromethyl)-1H-indazole;
(1R,5S)-3-(4-methyl-5-(6-(trifluoromethyl)-1H-indazol-4-yl)pyrimidin-2-yl)-3-azabicyclo[3.1.0]hexane-2-carboxamide;
a stereoisomer of any one of the aforementioned compounds; and
a pharmaceutically acceptable salt of any one of the aforementioned compounds or stereoisomers.

15. A pharmaceutical composition comprising:
a compound or pharmaceutically acceptable salt as defined in any one of claims 1 to 14; and
a pharmaceutically acceptable excipient.

16. A method of treating a disease, disorder or condition in a subject, the method comprising administering to the subject an effective amount of a compound or a pharmaceutically acceptable salt as defined in any one of claims 1 to 14, wherein the disease, disorder or condition is selected from obesity, overweight, cardiovascular disease, hypertension, diabetes, hyperglycemia, insulin resistance, metabolic syndrome X, impaired glucose tolerance, non-alcoholic liver steatosis, dyslipidemia, atherosclerosis, stroke, sleep apnea, osteoarthritis, infertility, and polycystic ovary syndrome.

17. A combination comprising an effective amount of a compound or pharmaceutically acceptable salt as defined in any one of claims 1 to 14, and at least one additional pharmacologically active agent.

18. A combination according to claim 17, wherein the additional pharmacologically active agent is selected from insulin, buformin, metformin, phenformin, pioglitazone, rosiglitazone, acetohexamide, chlorpropamide, tolazamide, tolbutamide, gliclazide, glimepiride, glipizide, glyburide, nateglinide, repaglinide, acarbose, miglitol, exenatide, liraglutide, taspoglutide, alogliptin, linagliptin, saxagliptin, sitagliptin, vildagliptin, pramlinitide, orlistat, atorvastatin, fluvastatin, lovastatin, mevastatin, pitavastatin, pravastatin, rosuvastatin, simvastatin, niacin, bezafibrate, ciprofibrate, clofibrate, fenofibrate, gemfibrozil, cholestyramine, colesevelam, colestipol, and ezetimibe.

* * * * *